(12) United States Patent
Mizuki et al.

(10) Patent No.: US 9,640,773 B2
(45) Date of Patent: May 2, 2017

(54) AROMATIC AMINE DERIVATIVE AND ORGANIC ELECTROLUMINESCENCE ELEMENT USING SAME

(75) Inventors: Yumiko Mizuki, Sodegaura (JP); Hirokatsu Ito, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 472 days.

(21) Appl. No.: 14/344,941

(22) PCT Filed: Sep. 14, 2012

(86) PCT No.: PCT/JP2012/073676
§ 371 (c)(1),
(2), (4) Date: Mar. 14, 2014

(87) PCT Pub. No.: WO2013/039221
PCT Pub. Date: Mar. 21, 2013

(65) Prior Publication Data
US 2014/0346482 A1    Nov. 27, 2014

(30) Foreign Application Priority Data

Sep. 16, 2011  (JP) ................................ 2011-203853
Sep. 16, 2011  (JP) ................................ 2011-203854

(51) Int. Cl.
*H01L 51/50*     (2006.01)
*H01L 51/00*     (2006.01)
(Continued)

(52) U.S. Cl.
CPC ........ *H01L 51/5012* (2013.01); *C07D 307/91* (2013.01); *C07D 333/76* (2013.01);
(Continued)

(58) Field of Classification Search
CPC .... C07D 307/91; C07D 333/76; C09K 11/06; C09K 2211/1011; H01L 51/0052;
(Continued)

(56) References Cited

U.S. PATENT DOCUMENTS 5,153,073 A * 10/1992 Ohnuma ................ B32B 15/08
                                                        313/503
7,507,485 B2 *  3/2009 Oh ...................... H01L 51/0058
                                                        313/504
(Continued)

FOREIGN PATENT DOCUMENTS

JP       11-035532        2/1999
JP     2004-204238        7/2004
(Continued)

OTHER PUBLICATIONS

Machine translation for JP 2011-173973 A (publication date: Sep. 2011).*
(Continued)

*Primary Examiner* — Dawn Garrett
(74) *Attorney, Agent, or Firm* — Oblon, McClelland, Maier & Neustadt, L.L.P.

(57) ABSTRACT

An aromatic amine derivative is represented by the following formula (1). In the formula (1), $R_1$ to $R_{10}$ each independently represent a hydrogen atom and a substituent. In the formula (1); $R_1$ is represented by the following formula (2); any one of $R_2$ to $R_5$ and $R_7$ to $R_{10}$ is represented by the following formula (2); and $L_1$ to $L_3$ each independently represent a single bond, a divalent residue of an aryl group, or the like. In the formula (2); $Ar_1$ is a monovalent substituent having a partial structure represented by the following formula (3); X represents an oxygen atom or a sulfur atom; and A and B represent a six-membered ring. In the formula
(Continued)

(2), $Ar_2$ is an aryl group, a monovalent substituent having a partial structure represented by the formula (3), and the like.

[Formula 1]

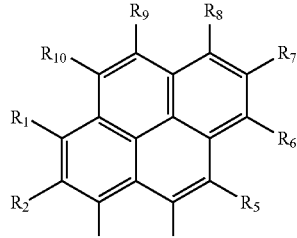

(1)

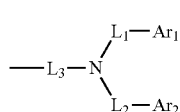

(2)

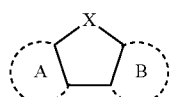

(3)

26 Claims, 1 Drawing Sheet

(51) Int. Cl.
  *C07D 333/76* (2006.01)
  *C07D 307/91* (2006.01)
  *C09K 11/06* (2006.01)
  *C09B 57/00* (2006.01)
  *C09B 1/00* (2006.01)

(52) U.S. Cl.
  CPC ............... *C09B 1/00* (2013.01); *C09B 57/00* (2013.01); *C09B 57/001* (2013.01); *C09B 57/008* (2013.01); *C09K 11/06* (2013.01); *H01L 51/006* (2013.01); *H01L 51/0054* (2013.01); *H01L 51/0061* (2013.01); *H01L 51/0073* (2013.01); *H01L 51/0074* (2013.01); *C09K 2211/1011* (2013.01); *H01L 51/0052* (2013.01); *H01L 51/0094* (2013.01)

(58) Field of Classification Search
  CPC ............... H01L 51/0054; H01L 51/006; H01L 51/0061; H01L 51/0073; H01L 51/0074; H01L 51/0094; H01L 51/5012
  See application file for complete search history.

(56) References Cited

U.S. PATENT DOCUMENTS

| | | | | |
|---|---|---|---|---|
| 8,431,250 B2* | 4/2013 | Mizuki | ............... | C07D 307/91 257/40 |
| 8,518,560 B2* | 8/2013 | Mizuki | ............... | C07D 307/91 313/504 |
| 9,166,179 B2* | 10/2015 | Mizuki | ............... | C07D 307/91 |
| 9,391,279 B2* | 7/2016 | Mizuki | ............... | C07D 307/91 |
| 2010/0295445 A1 | 11/2010 | Kuma et al. | | |
| 2010/0301319 A1 | 12/2010 | Kuma et al. | | |
| 2010/0314615 A1* | 12/2010 | Mizuki | ............... | C07D 307/91 257/40 |
| 2011/0156016 A1 | 6/2011 | Kawamura et al. | | |
| 2011/0248246 A1 | 10/2011 | Ogita et al. | | |
| 2012/0126205 A1 | 5/2012 | Kawamura et al. | | |
| 2012/0126208 A1 | 5/2012 | Kawamura et al. | | |
| 2012/0126209 A1 | 5/2012 | Kawamura et al. | | |
| 2012/0126222 A1 | 5/2012 | Ogiwara et al. | | |
| 2012/0138918 A1 | 6/2012 | Naraoka et al. | | |
| 2012/0153268 A1 | 6/2012 | Kawamura et al. | | |
| 2012/0181922 A1 | 7/2012 | Kawamura et al. | | |
| 2013/0193382 A1* | 8/2013 | Buesing | ............... | C07C 211/61 252/500 |
| 2013/0306955 A1 | 11/2013 | Mizutani et al. | | |
| 2013/0306958 A1 | 11/2013 | Ito et al. | | |
| 2014/0159023 A1 | 6/2014 | Matsumoto et al. | | |
| 2014/0217393 A1 | 8/2014 | Kato et al. | | |
| 2014/0319511 A1* | 10/2014 | Mizuki | ............... | C09K 11/06 257/40 |
| 2014/0326985 A1* | 11/2014 | Mizuki | ............... | C09K 11/06 257/40 |
| 2014/0353646 A1* | 12/2014 | Mizuki | ............... | C07D 405/14 257/40 |
| 2015/0014666 A1* | 1/2015 | Mizuki | ............... | C07D 307/91 257/40 |

FOREIGN PATENT DOCUMENTS

| | | |
|---|---|---|
| JP | 2006-298793 A | 11/2006 |
| JP | 2011-173973 | 9/2011 |
| JP | 2013-63929 A | 4/2013 |
| JP | 2013-107853 A | 6/2013 |
| KR | 10-2011-0041728 A | 4/2011 |
| KR | 10-2011-0076376 | 7/2011 |
| KR | 10-2011-0081698 A | 7/2011 |
| WO | WO 02/38524 | 5/2002 |
| WO | WO 2004/018587 | 3/2004 |
| WO | WO 2004/018588 | 3/2004 |
| WO | WO 2005/054162 | 6/2005 |
| WO | WO 2005/061656 | 7/2005 |
| WO | WO 2005/108348 | 11/2005 |
| WO | WO 2006/128800 | 12/2006 |
| WO | WO 2007/125714 | 11/2007 |
| WO | WO 2009/084512 | 7/2009 |
| WO | WO 2010/013675 | 2/2010 |
| WO | WO 2010/013676 | 2/2010 |
| WO | WO 2010/122810 | 10/2010 |
| WO | WO 2013/039184 A1 | 3/2013 |
| WO | WO 2013/039221 A1 | 3/2013 |
| WO | WO 2013/042775 A1 | 3/2013 |

OTHER PUBLICATIONS

International Preliminary Report on Patentability with Written Opinion of the International Searching Authority for corresponding International Application No. PCT/JP2012/073676, Mar. 18, 2014.
International Search Report for corresponding International Application No. PCT/JP2012/073676, Nov. 13, 2012.
Written Opinion for corresponding International Application No. PCT/JP2012/073676, Nov. 13, 2012.
Japanese Office Action issued Sep. 13, 2016 in Patent Application No. 2011-203853 (with English translation).

* cited by examiner

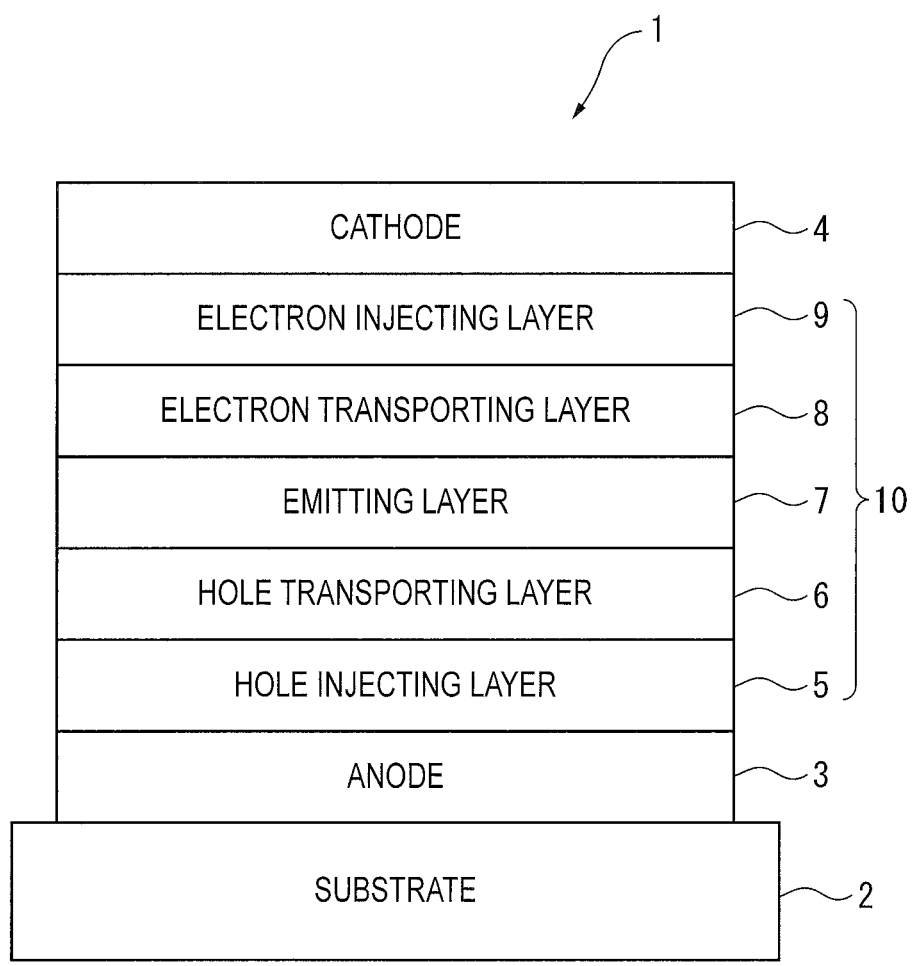

AROMATIC AMINE DERIVATIVE AND ORGANIC ELECTROLUMINESCENCE ELEMENT USING SAME

TECHNICAL FIELD

The present invention relates to an aromatic amine derivative and an organic electroluminescence device using the aromatic amine derivative.

BACKGROUND ART

An organic electroluminescence device (hereinafter, occasionally abbreviated as an organic EL device) using an organic substance is a promising component of a solid-emitting-type full-color display device of a low cost and a large area. Accordingly, various developments of the organic EL device have been made. Typically, an organic EL device is provided with an emitting layer and a pair of opposing electrodes between which the emitting layer is interposed. When an electrical field is applied to the opposing electrodes of the organic EL device, electrons are injected from a cathode and holes are injected from an anode. Further, the injected electrons and holes are recombined with the holes in the emitting layer to form excitons. Energy generated when the excitons are returned from an excited state to a ground state is irradiated as light. The organic EL device emits light in accordance with such a principle.

A typical organic EL device exhibits a higher drive voltage and lower luminescence intensity and lower luminous efficiency than those of an inorganic light-emitting diode. Moreover, since properties of the organic EL device are considerably deteriorated, the organic EL device is not in practical use. Although the organic EL device has been gradually improved in recent years, further higher luminous efficiency, longer lifetime, improvement in color reproduction and the like have been demanded.

Performance of the organic EL device has been gradually enhanced by improving an organic-EL luminescent material. In particular, improvement in color purity of a blue-emitting organic EL device (i.e., shifting emission wavelength into short wavelength) is an important technique leading to improvement in color reproduction of a display.

Patent Literature 1 discloses a luminescent material having dibenzofuran as an example of a material used in an emitting layer. Although blue emission (i.e., emission in short wavelength) is obtained, further improvement has been demanded in view of a low luminous efficiency.

Patent literatures 4 and 5 disclose a diaminopyrene derivative. Patent Literature 2 discloses a combination of an anthracene host and arylamine. Patent Literatures 3 to 5 disclose a combination of an anthracene host having a specific structure and a diaminopyrene dopant. Patent Literatures 6 to 8 disclose an anthracene host material.

Improvement in luminescence property is recognized in any materials and any combinations, but is not sufficient. A luminescent material exhibiting a high luminous efficiency and realizing short-wavelength emission has been demanded.

Patent Literature 9 discloses that an aromatic amine derivative including an arylene group at the center and a dibenzofuran ring bonded to a nitrogen atom is used as a hole transporting material. Patent Literature 10 discloses a use of an aromatic amine derivative as a hole transporting material, in which a dibenzofuran ring, dibenzothiophene ring, benzofuran ring, benzothiophene ring or the like is bonded to a nitrogen atom through an arylene group. However, Patent Literature 10 does not disclose a use of the aromatic amine derivative as a luminescent material.

Patent Literatures 11 to 13 disclose an aromatic amine derivative in which amino groups are respectively bonded to positions 1 and 6 of pyrene. In the aromatic amine derivatives of Patent Literatures 11 and 12, a dibenzofuran ring or a dibenzothiophene ring is bonded to a nitrogen atom of the amino group. Although these aromatic amine derivatives are used as a blue-emitting luminescent material, color purity and luminous efficiency need to be further improved for practical use.

CITATION LIST

Patent Literatures

Patent Literature 1: WO2006/128800
Patent Literature 2: WO2004/018588
Patent Literature 3: WO2004/018587
Patent Literature 4: JP-A-2004-204238
Patent Literature 5: WO2005/108348
Patent Literature 6: WO2005/054162
Patent Literature 7: WO2005/061656
Patent Literature 8: WO2002/038524
Patent Literature 9: JP-A-11-35532
Patent Literature 10: WO2007/125714
Patent Literature 11: International Publication No. WO2010/122810
Patent Literature 12: International Publication No. WO2009/084512
Patent Literature 13: Korean Patent Publication No. 10-2011-0076376

SUMMARY OF THE INVENTION

Problems to be Solved by the Invention

An object of the invention is to provide an organic EL device capable of providing blue emission and an aromatic amine derivative effectively usable in an organic thin-film layer of the organic EL device.

Means for Solving the Problems

According to the invention, an aromatic amine derivative and an organic EL device described below are provided.

[1] An aromatic amine derivative according to a first exemplary embodiment of the invention is represented by a formula (1) below.

[Formula 1]

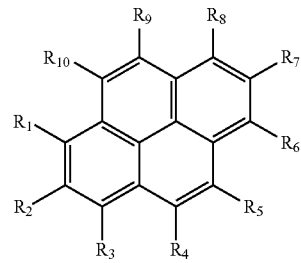

(1)

In the formula (1), $R_2$ to $R_{10}$ each independently represent: a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms.

In the formula (1), $R_1$ is represented by a formula (2) below.

In the formula (1), any one of $R_2$ to $R_5$ and $R_7$ to $R_{10}$ is represented by a formula (2) below.

[Formula 2]

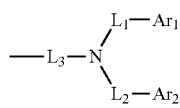

(2)

In the formula (2), $L_1$, $L_2$ and $L_3$ each independently represent a single bond, a divalent residue of a substituted or unsubstituted aryl group having 6 to 30 ring carbon atoms, or a divalent residue of a substituted or unsubstituted heterocyclic group having 5 to 30 ring atoms.

In the formula (2), $Ar_1$ is a monovalent substituent having a partial structure represented by a formula (3) below.

[Formula 3]

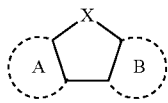

(3)

In the formula (3), X represents an oxygen atom or a sulfur atom. In the formula (3), A and B represent a six-membered ring. The six-membered ring represented by A and B may be fused with another ring.

In the formula (2), $Ar_2$ is a substituted or unsubstituted aryl group having 6 to 30 ring carbon atoms, a substituted or unsubstituted heterocyclic group having 5 to 30 ring atoms, or a monovalent substituent having a partial structure represented by the formula (3).

In the aromatic amine derivative according to the above aspect of the invention, $R_1$ and $R_3$ are represented by the formula (2).

[3] In the aromatic amine derivative according to the above aspect of the invention, $R_1$ and $R_8$ are represented by the formula (3).

[4] An aromatic amine derivative according to another aspect of the invention is represented by a formula (1a) below.

[Formula 4]

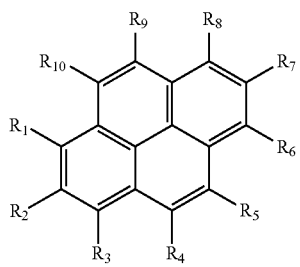

(1a)

In the formula (1a), $R_1$ and $R_3$ to $R_{10}$ each independently represent: a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms.

In the formula (1a), $R_2$ is represented by a formula (2a) below.

In the formula (1a), any one of $R_3$ to $R_{10}$ is represented by a formula (2a) below.

[Formula 5]

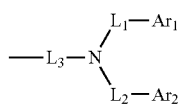

(2a)

In the formula (2a), $L_1$, $L_2$ and $L_3$ each independently represent a single bond, a divalent residue of a substituted or unsubstituted aryl group having 6 to 30 ring carbon atoms, or a divalent residue of a substituted or unsubstituted heterocyclic group having 5 to 30 ring atoms.

In the formula (2a), $Ar_1$ is a monovalent substituent having a partial structure represented by a formula (3a) below,

[Formula 6]

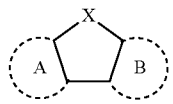

(3a)

In the formula (3a), X represents an oxygen atom or a sulfur atom. In the formula (3a), A and B represent a six-membered ring. The six-membered ring represented by A and B may be fused with another ring.

In the formula (2a), $Ar_2$ is a substituted or unsubstituted aryl group having 6 to 30 ring carbon atoms, a substituted or unsubstituted heterocyclic group having 5 to 30 ring atoms, or a monovalent substituent having a partial structure represented by the formula (3a).

[5] In the aromatic amine derivative according to any one of the above [1] to [4] aspects of the invention, the monovalent substituent having the partial structure represented by the formula (3) is a monovalent residue represented by a formula (4) below.

[Formula 7]

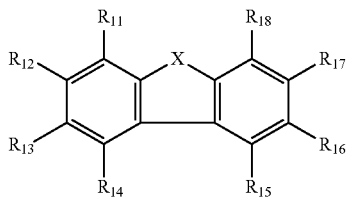

(4)

In the formula (4), X represents an oxygen atom or a sulfur atom.

In the formula (4), $R_{11}$ to $R_{18}$ each independently represent a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms.

However, in the formula (2); when $Ar_1$ is a monovalent residue of the formula (4), one of $R_{11}$ to $R_{18}$ is a single bond to be bonded to $L_1$; and when $Ar_2$ is a monovalent residue of the formula (4), one of $R_{11}$ to $R_{18}$ is a single bond to be bonded to $L_2$.

In the formula (4), at least one combination of $R_{11}$ and $R_{12}$, $R_{12}$ and $R_{13}$, $R_{13}$ and $R_{14}$, $R_{15}$ and $R_{16}$, $R_{16}$ and $R_{17}$, and $R_{17}$ and $R_{18}$ may form a saturated or unsaturated ring.

[6] According to still another aspect of the invention, an organic electroluminescence device includes: a cathode; an anode; and an organic compound layer, in which the organic compound layer includes the aromatic amine derivative according to any one of the above [1] to [5] aspects of the invention.

[7] In the organic electroluminescence device according to the above aspect of the invention, the organic compound layer includes a plurality of organic thin-film layers including an emitting layer, and at least one of the plurality of organic thin-film layers includes the aromatic amine derivative according to any one of the above [1] to [5] aspects of the invention.

[8] In the organic electroluminescence device according to the above aspect of the invention, at least one of the plurality of organic thin-film layers includes the aromatic amine derivative according to any one of the above [1] to [5] aspects of the invention and an anthracene derivative represented by a formula (20) below.

[Formula 8]

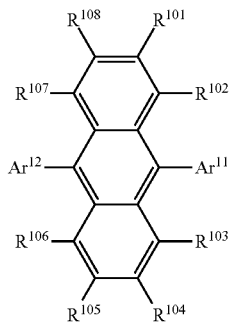

(20)

In the formula (20), $Ar^{11}$ and $Ar^{12}$ each independently represents a substituted or unsubstituted monocyclic group having 5 to 30 ring atoms, a substituted or unsubstituted fused ring group having 10 to 30 ring atoms, or a group provided by combining the monocyclic group and the fused ring group.

$R^{101}$ to $R^{108}$ each independently represent a hydrogen atom, a halogen atom, a cyano group, a substituted or unsubstituted monocyclic group having 5 to 30 ring atoms, a substituted or unsubstituted fused ring group having 10 to 30 ring atoms, a group provided by combining the monocyclic group and the fused ring group, a substituted or unsubstituted alkyl group having 1 to 30 carbon atoms, a substituted or unsubstituted cycloalkyl group having 3 to 30 ring carbon atoms, a substituted or unsubstituted alkoxy group having 1 to 30 carbon atoms, a substituted or unsubstituted aralkyl group having 7 to 30 carbon atoms, a substituted or unsubstituted aryloxy group having 6 to 30 ring carbon atoms, or a substituted or unsubstituted silyl group.

[9] In the organic electroluminescence device according to the above aspect of the invention, $Ar^{11}$ and $Ar^{12}$ in the formula (20) are each independently a substituted or unsubstituted fused ring group having 10 to 30 ring atoms.

[10] In the organic electroluminescence device according to the above aspect of the invention, in the formula (20), one of $Ar^{11}$ and $Ar^{12}$ is the substituted or unsubstituted monocyclic group having 5 to 30 ring atoms, and the other of $Ar^{11}$ and $Ar^{12}$ is the substituted or unsubstituted fused ring group having 10 to 30 ring atoms.

[11] In the organic electroluminescence device according to the above aspect of the invention, in the formula (20), $Ar^{12}$ is selected from a naphthyl group, phenanthryl group, benzoanthryl group and dibenzofuranyl group, and $Ar^{11}$ is an unsubstituted phenyl group or a phenyl group substituted by at least one of the monocyclic group and the fused ring group.

[12] In the organic electroluminescence device according to the above aspect of the invention, in the formula (20), $Ar^{12}$ is a substituted or unsubstituted fused ring group having 10 to 30 ring atoms and $Ar^{11}$ is an unsubstituted phenyl group.

[13] In the organic electroluminescence device according to the above aspect of the invention, in the formula (20), $Ar^{11}$ and $Ar^{12}$ are each independently a substituted or unsubstituted monocyclic group having 5 to 30 ring atoms.

[14] In the organic electroluminescence device according to the above aspect of the invention, in the formula (20), $Ar^{11}$ and $Ar^{12}$ are each independently a substituted or unsubstituted phenyl group.

[15] In the organic electroluminescence device according to the above aspect of the invention, in the formula (20), $Ar^{11}$ is an unsubstituted phenyl group and $Ar^{12}$ is a phenyl group having at least one of the monocyclic group and the fused ring group as a substituent.

[16] In the organic electroluminescence device according to the above aspect of the invention, in the formula (20), $Ar^{11}$ and $Ar^{12}$ are each independently a phenyl group having at least one of the monocyclic group and the fused ring group as a substituent.

The use of the aromatic amine derivative of the invention in the organic thin-film layer can provide the organic EL device capable of providing blue emission.

BRIEF DESCRIPTION OF DRAWINGS

FIG. 1 schematically shows an exemplary arrangement of an organic electroluminescence device according to an exemplary embodiment of the invention.

DESCRIPTION OF EMBODIMENTS

First Exemplary Embodiment

Aromatic Amine Derivative

An aromatic amine derivative according to a first exemplary embodiment is represented by the formula (1).

$R_2$ to $R_{10}$ in the formula (1) will be described as follows.

Examples of the aryl group having 6 to 30 ring carbon atoms in the formula (1) are a phenyl group, 1-naphthyl group, 2-naphthyl group, 1-anthryl group, 2-anthryl group, 9-anthryl group, benzanthryl group, 1-phenanthryl group, 2-phenanthryl group, 3-phenanthryl group, 4-phenanthryl group, 9-phenanthryl group, pyrenyl group, 1-chrysenyl group, 2-chrysenyl group, 3-chrysenyl group, 4-chrysenyl group, 5-chrysenyl group, 6-chrysenyl group, benzo[c]phenanthryl group, benzo[g]chrysenyl group, 1-triphenylenyl group, 2-triphenylenyl group, 1-fluorenyl group, 2-fluorenyl group, 3-fluorenyl group, 4-fluorenyl group, 9-fluorenyl group, benzofluorenyl group, dibenzofluorenyl group, 2-biphenyl group, 3-biphenyl group, 4-biphenyl group, o-terphenyl-4-yl group, o-terphenyl-3-yl group, o-terphenyl-2-yl group, m-terphenyl-4-yl group, m-terphenyl-3-yl group, m-terphenyl-2-yl group, p-terphenyl-4-yl group, p-terphenyl-3-yl group, p-terphenyl-2-yl group, m-quarterphenyl group, 3-fluoranthenyl group, 8-fluoranthenyl group, 7-fluoranthenyl group, and benzofluoranthenyl group.

The aryl group in the formula (1) preferably has 6 to 20 ring carbon atoms, more preferably 6 to 12 ring carbon atoms. Among the aryl group, a phenyl group, biphenyl group, naphthyl group, phenanthryl group, terphenyl group and fluorenyl group are particularly preferable. In a 1-fluorenyl group, 2-fluorenyl group, 3-fluorenyl group and 4-fluorenyl group, a carbon atom at a position 9 is preferably substituted by a substituted or unsubstituted alkyl group having 1 to 30 carbon atoms in the formula (1).

Examples of the heterocyclic group having 5 to 30 ring carbon atoms in the formula (1) are a pyrrolyl group, pyrazinyl group, pyridyl group, pyrimidinyl group, triazinyl group, pyridazinyl group, indolyl group, isoindolyl group, imidazolyl group, pyrazolyl group, triazolyl group, benzimidazolyl group, indazolyl group, imidazopyridinyl group, benzotriazolyl group, furyl group, benzofuranyl group, isobenzofuranyl group, dibenzofuranyl group, thienyl group, benzothiophenyl group, dibenzothiophenyl group, quinolyl group, isoquinolyl group, quinoxalinyl group, quinazolinyl group, carbazolyl group, phenantridinyl group, acridinyl group, phenanthrolinyl group, phenazinyl group, phenothiazinyl group, phenoxazinyl group, oxazolyl group, isoxazolyl group, oxadiazolyl group, benzooxazolyl group, thiazolyl group, thiadiazolyl group, isothiazolyl group, benzothiazolyl group, furazanyl group, and a group formed from a pyridine ring, pyrazine ring, pyrimidine ring, pyridazine ring, triazine ring, indole ring, quinoline ring, isoquinoline ring, quinoxaline ring, quinazoline ring, acridine ring, pirrolidine ring, dioxane ring, piperidine ring, morpholine ring, piperadine ring, carbazole ring, furan ring, thiophene ring, oxazole ring, isoxazole ring, oxadiazole ring, benzoxazole ring, thiazole ring, isothiazole ring, thiadiazole ring, benzothiazole ring, triazole ring, imidazole ring, benzimidazole ring, pyrazole ring, indazole ring, imidazopyridine ring, pyrane ring, benzofuran ring, dibenzofuran ring, benzothiophene ring and dibenzothiophene ring.

Specific examples of the heterocyclic group having 5 to 30 ring atoms are a 1-pyrrolyl group, 2-pyrrolyl group, 3-pyrrolyl group, pyrazinyl group, 2-pyridinyl group, 2-pyrimidinyl group, 4-pyrimidinyl group, 5-pyrimidinyl group, 6-pyrimidinyl group, 1,2,3-triazine-4-yl group, 1,2,4-triazine-3-yl group, 1,3,5-triazine-2-yl group, 1-imidazolyl group, 2-imidazolyl group, 1-pyrazolyl group, 1-indolidinyl group, 2-indolidinyl group, 3-indolidinyl group, 5-indolidinyl group, 6-indolidinyl group, 7-indolidinyl group, 8-indolidinyl group, 2-imidazopyridinyl group, 3-imidazopyridinyl group, 5-imidazopyridinyl group, 6-imidazopyridinyl group, 7-imidazopyridinyl group, 8-imidazopyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, azacarbazolyl-1-yl group, azacarbazolyl-2-yl group, azacarbazolyl-3-yl group, azacarbazolyl-4-yl group, azacarbazolyl-5-yl group, azacarbazolyl-6-yl group, azacarbazolyl-7-yl group, azacarbazolyl-8-yl group, azacarbazolyl-9-yl group, 1-phenanthrydinyl group, 2-phenanthrydinyl group, 3-phenanthrydinyl group, 4-phenanthrydinyl group, 6-phenanthrydinyl group, 7-phenanthrydinyl group, 8-phenanthrydinyl group, 9-phenanthrydinyl group, 10-phenanthrydinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group, 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-silafluorenyl group, 2-silafluorenyl group, 3-silafluorenyl group, 4-silafluorenyl group, 1-germafluorenyl group, 2-germafluorenyl group, 3-germafluorenyl group and 4-germafluorenyl group.

The heterocyclic group in the formula (1) preferably has 5 to 20 ring atoms, more preferably 5 to 14 ring atoms. Among the above heterocyclic group, a 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-carbazolyl group, 2-carbazolyl group, 3-carbazolyl group, 4-carbazolyl group, and 9-carbazolyl group are preferable. In 1-carbazolyl group, 2-carbazolyl group, 3-carbazolyl group and 4-carbazolyl group, a nitrogen atom at the position 9 is preferably substituted by a substituted or unsubstituted aryl group having 6 to 30 ring carbon atoms or a substituted or unsubstituted heterocyclic group having 5 to 30 ring atoms in the formula (1).

The alkyl group having 1 to 30 carbon atoms in the formula (1) may be linear, branched or cyclic. Examples of the linear or branched alkyl group are a methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, 3-methylpentyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 1,2-dinitroethyl group, 2,3-dinitro-t-butyl group, and 1,2,3-trinitropropyl group.

Examples of the cyclic alkyl group (cycloalkyl group) are a cyclopropyl group, cyclobutyl group, cyclopentyl group, cyclohexyl group, 4-methylcyclohexyl group, 1-adamantyl group, 2-adamantyl group, 1-norbornyl group and 2-norbornyl group.

The linear or branched alkyl group in the formula (1) preferably has 1 to 10 carbon atoms, more preferably 1 to 6 carbon atoms. Among the linear or branched alkyl group, a methyl group, ethyl group, propyl group, isopropyl group, n-butyl group, s-butyl group, isobutyl group, t-butyl group, n-pentyl group and n-hexyl group are preferable.

The cycloalkyl group in the formula (1) preferably has 3 to 10 ring carbon atoms, more preferably 5 to 8 ring carbon atoms. Among the cycloalkyl group, a cyclopentyl group and a cyclohexyl group are preferable.

A halogenated alkyl group provided by substituting the alkyl group with a halogen atom is exemplified by a halogenated alkyl group provided by substituting the alkyl group having 1 to 30 carbon atoms with one or more halogen groups. Specific examples of the halogenated alkyl group are a fluoromethyl group, difluoromethyl group, trifluoromethyl group, fluoroethyl group and trifluoromethylmethyl group.

The alkenyl group having 2 to 30 carbon atoms in the formula (1) may be linear, branched or cyclic. Examples of the alkenyl group are vinyl, propenyl, butenyl, oleyl, eicosapentaenyl, docosahexaenyl, styryl, 2,2-diphenylvinyl, 1,2,2-triphenylvinyl and 2-phenyl-2-propenyl, among which a vinyl group is preferable.

The alkynyl group having 2 to 30 carbon atoms in the formula (1) may be linear, branched or cyclic. Examples of the alkynyl group are ethynyl, propynyl and 2-phenylethynyl, among which an ethynyl group is preferable.

The alkylsilyl group having 3 to 30 carbon atoms in the formula (1) is exemplified by a trialkylsilyl group having the examples of the alkyl group having 1 to 30 carbon atoms. Specific examples of the alkylsilyl group are a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyldimethylsilyl group, propyldimethylsilyl group and triisopropylsilyl group. Three alkyl groups in the trialkylsilyl group may be the same or different.

Examples of the arylsilyl group having 6 to 30 ring carbon atoms in the formula (1) are a dialkylarylsilyl group, alkyldiarylsilyl group and triarylsilyl group.

The dialkylarylsilyl group is exemplified by a dialkylarylsilyl group having two of the examples of the alkyl group having 1 to 30 carbon atoms and one of the aryl group having 6 to 30 ring carbon atoms. The dialkylarylsilyl group preferably has 8 to 30 carbon atoms.

The alkyldiarylsilyl group is exemplified by an alkyldiarylsilyl group having one of the examples of the alkyl group having 1 to 30 carbon atoms and two of the aryl group having 6 to 30 ring carbon atoms. The alkyldiarylsilyl group preferably has 13 to 30 carbon atoms.

The triarylsilyl group is exemplified by a triarylsilyl group having three of the aryl group having 6 to 30 ring carbon atoms. The triarylsilyl group preferably has 18 to 30 carbon atoms.

The triarylsilyl group is exemplified by a triarylsilyl group having three of the aromatic hydrocarbon group having 6 to 30 carbon atoms.

The alkoxy group having 1 to 30 carbon atoms in the formula (1) is represented by $-OY^1$. $Y^1$ is exemplified by the alkyl group having 1 to 30 carbon atoms. Examples of the alkoxy group are a methoxy group, ethoxy group, propoxy group, butoxy group, pentyloxy group and hexyloxy group.

A halogenated alkoxy group provided by substituting the alkoxy group with a halogen atom is exemplified by a halogenated alkoxy group provided by substituting the alkoxy group having 1 to 30 carbon atoms with one or more halogen groups.

The aralkyl group having 6 to 30 ring carbon atoms in the formula (1) is represented by $-Y^2-Z^1$. $Y^2$ is exemplified by an alkylene group in relation to the alkyl group having 1 to 30 carbon atoms. $Z^1$ is exemplified by the examples of the above aryl group having 6 to 30 ring carbon atoms. This aralkyl group is preferably an aralkyl group having 7 to 30 carbon atoms, in which an aryl moiety has 6 to 30 carbon atoms, preferably 6 to 20 carbon atoms, more preferably 6 to 12 carbon atoms, and an alkyl moiety has 1 to 30 carbon atoms, preferably 1 to 20 carbon atoms, more preferably 1 to 10 carbon atoms, further preferably 1 to 6 carbon atoms. Examples of the aralkyl group are a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro-2-phenylisopropyl group.

The aryloxy group having 6 to 30 ring carbon atoms in the formula (1) is represented by $-OZ^2$. $Z^2$ is exemplified by the aryl group having 6 to 30 ring carbon atoms or later-described monocyclic group and fused cyclic group. The aryloxy group is exemplified by a phenoxy group.

Examples of the halogen atom in the formula (1) are fluorine, chlorine, bromine and iodine, among which fluorine is preferable.

In the invention, a "hydrogen atom" means isotopes having different neutron numbers and specifically encompasses protium, deuterium and tritium.

In the invention, "carbon atoms forming a ring (ring carbon atoms)" mean carbon atoms forming a saturated ring, unsaturated ring, or aromatic ring. "Atoms forming a ring (ring atoms)" mean carbon atoms and hetero atoms forming a hetero ring including a saturated ring, unsaturated ring, or aromatic ring.

Examples of the substituent meant by "substituted or unsubstituted" are a hydroxyl group, nitro group and carboxy group in addition to the above-described aryl group, heterocyclic group, alkyl group (linear or branched alkyl group, cycloalkyl group and halogenated alkyl group), alkenyl group, alkynyl group, alkylsilyl group, arylsilyl group, alkoxy group, halogenated alkoxy group, aralkyl group, aryloxy group, halogen atom, cyano group. In the above-described substituents, the aryl group, heterocyclic group, alkyl group, halogen atom, alkylsilyl group, arylsilyl group and cyano group are preferable. The preferable ones of the specific examples of each substituent are further preferable.

The phrase "unsubstituted" in "substituted or unsubstituted" means that a group is substituted by a hydrogen atom.

In a compounds or a partial structures described below thereof, the same is applied to the description of "substituted or unsubstituted."

In the formula (1), $R_1$ is represented by the formula (2). Further, in the formula (1), any one of $R_2$ to $R_5$ and $R_7$ to $R_{10}$ is represented by the formula (2).

In the formula (2), $L_1$, $L_2$ and $L_3$ each independently represent a single bond, a divalent residue of a substituted or unsubstituted aryl group having 6 to 30 ring carbon atoms, or a divalent residue of a substituted or unsubstituted heterocyclic group having 5 to 30 ring atoms.

The divalent residue of the aryl group having 6 to 30 ring carbon atoms is exemplified by a divalent group derived from an aryl group having 6 to 30 ring carbon atoms for $R_2$ to $R_{10}$ in the formula (1).

The divalent residue of the heterocyclic group having 5 to 30 ring atoms is exemplified by a divalent residue derived from a heterocyclic group having 5 to 30 ring atoms for $R_2$ to $R_{10}$ in the formula (1).

In the formula (2), $Ar_1$ is a monovalent substituent having a partial structure represented by the formula (3).

In the formula (3), X represents an oxygen atom or a sulfur atom. In the formula (3), A and B represent a six-membered ring. The six-membered ring represented by A and B may be further fused with another ring.

In the formula (2), $Ar_2$ is a substituted or unsubstituted aryl group having 6 to 30 ring carbon atoms, a substituted or unsubstituted heterocyclic group having 5 to 30 ring atoms, or a monovalent substituent having the partial structure represented by the formula (3). The aryl group and heterocyclic group for $Ar_2$ represent the same as $R_2$ to $R_{10}$ in the formula (1).

In the aromatic amine derivative according to the exemplary embodiment, the monovalent substituent having the partial structure represented by the formula (3) is preferably a monovalent residue represented by the formula (4).

In the formula (4), X represents an oxygen atom or a sulfur atom.

$R_{11}$ to $R_{18}$ in the formula (4) each independently represent the same as $R_2$ to $R_{10}$ in the formula (1). However, in the formula (2); when $Ar_1$ is a monovalent residue of the formula (4), one of $R_{11}$ to $R_{18}$ is a single bond to be bonded to $L_1$; and when $Ar_2$ is a monovalent residue of the formula (4), one of $R_{11}$ to $R_{18}$ is a single bond to be bonded to $L_2$. Thus, the structure of the formula (4) in which one of $R_{11}$ to $R_{18}$ is a single bond is exemplarily represented by the following formulae (4A) to (4D). Herein, the formula (4A) describes that $R_{11}$ in the formula (4) is a single bond, not a methyl group. The same explanation applies to the other formulae (4B) to (4D). Among these formulae, the formula (4A) in which $R_{11}$ is a single bond and the formula (4C) in which $R_{13}$ is a single bond are preferable.

[Formula 9]

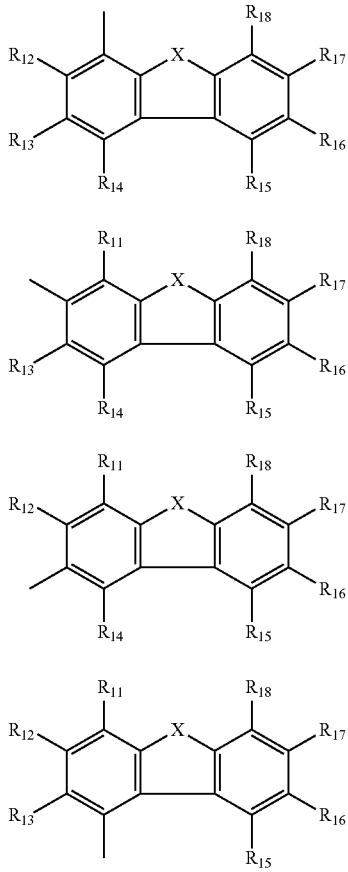

In the formula (4), at least one combination of $R_{11}$ and $R_{12}$, $R_{12}$ and $R_{13}$, $R_{13}$ and $R_{14}$, $R_{15}$ and $R_{16}$, $R_{16}$ and $R_{17}$, and $R_{17}$ and $R_{18}$ may form a saturated or unsaturated ring. An instance where such a ring may be formed in the formula (4) is exemplarily represented by the following formulae (4E), (4F) and (4G). $R_{11}$ to $R_{20}$ in the formulae (4E), (4F) and (4G) each independently represent the same as $R_2$ to $R_{10}$ in the formula (1).

[Formula 10]

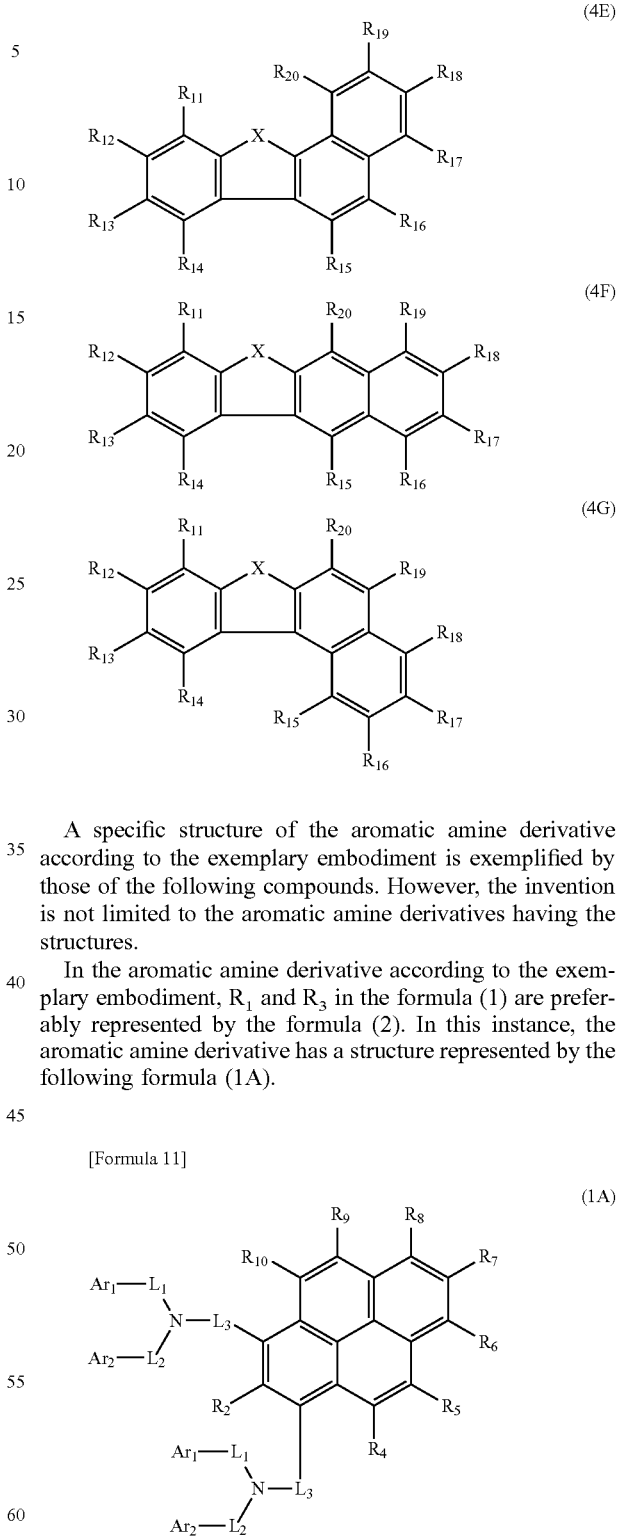

A specific structure of the aromatic amine derivative according to the exemplary embodiment is exemplified by those of the following compounds. However, the invention is not limited to the aromatic amine derivatives having the structures.

In the aromatic amine derivative according to the exemplary embodiment, $R_1$ and $R_3$ in the formula (1) are preferably represented by the formula (2). In this instance, the aromatic amine derivative has a structure represented by the following formula (1A).

[Formula 11]

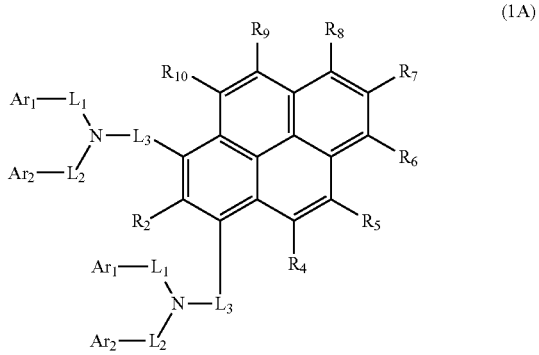

Specific examples of the aromatic amine derivative according to the exemplary embodiment are aromatic amine derivatives described in Tables 1 to 30 for $R_2$, $R_4$ to $R_{10}$, $L_1$ to $L_3$, and $Ar_1$ to $Ar_2$ in the formula (1A). Note that "—" in $L_1$ to $L_3$ of the tables represents a single bond. Moreover, in $L_1$ to $L_3$ and $Ar_1$ to $Ar_2$ in the tables, a line extending outward from the cyclic structure and having no chemical formula (e.g., $CH_3$, Ph, CN, benzene ring) at an end of the line represents a single bond, not a methyl group. For instance, in the following compound D1, $Ar_1$ has a single bond at a position 4 of a dibenzofuran ring. In short, $Ar_1$ represents a 4-dibenzofuranyl group. Likewise, $Ar_2$ represents a phenyl group.

TABLE 1

| compound | $R_2$ | $R_4$ | $R_5$ | $R_6$ | $R_7$ | $R_8$ | $R_9$ | $R_{10}$ | $L_1$ | $L_2$ | $L_3$ | $Ar_1$ | $Ar_2$ |
|---|---|---|---|---|---|---|---|---|---|---|---|---|---|
| D1 | H | H | H | H | H | H | H | H | — | — | — | 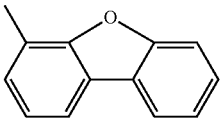 | 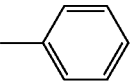 |
| D2 | H | H | H | H | H | H | H | H | — | — | — | 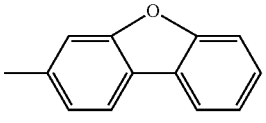 | 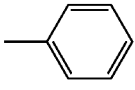 |
| D3 | H | H | H | H | H | H | H | H | — | — | — | 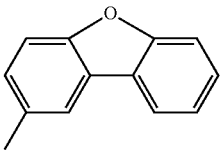 | 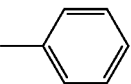 |
| D4 | H | H | H | H | H | H | H | H | — | — | — | 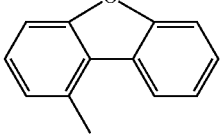 | 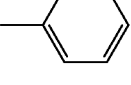 |
| D5 | H | H | H | H | H | H | H | H | — | — | — | 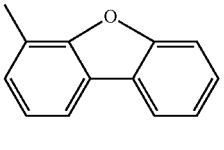 | 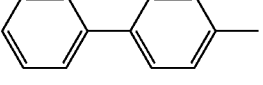 |
| D6 | H | H | H | H | H | H | H | H | — | — | — | 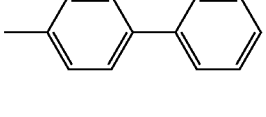 | 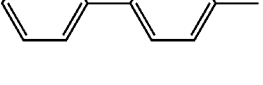 |
| D7 | H | H | H | H | H | H | H | H | — | — | — | 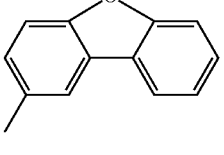 | 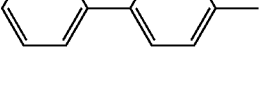 |
| D8 | H | H | H | H | H | H | H | H | — | — | — | 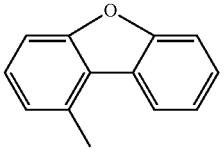 | 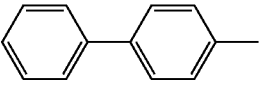 |

TABLE 2
| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D9 | H | H | H | H | H | H | H | H | — | — | — | 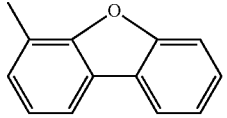 | 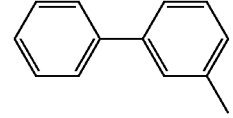 |
| D10 | H | H | H | H | H | H | H | H | — | — | — | 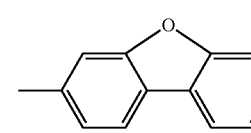 | 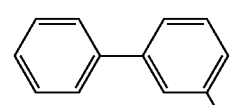 |
| D11 | H | H | H | H | H | H | H | H | — | — | — | 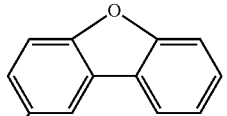 | 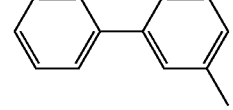 |
| D12 | H | H | H | H | H | H | H | H | — | — | — | 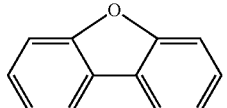 | 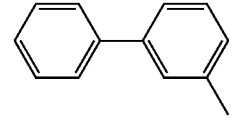 |
| D13 | H | H | H | H | H | H | H | H | — | — | — | 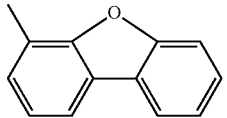 | 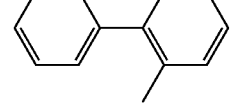 |
| D14 | H | H | H | H | H | H | H | H | — | — | — | 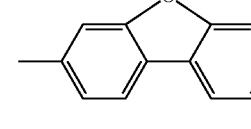 | 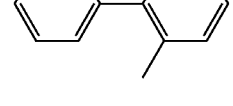 |
| D15 | H | H | H | H | H | H | H | H | — | — | — | 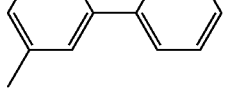 | 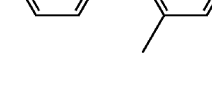 |
| D16 | H | H | H | H | H | H | H | H | — | — | — | 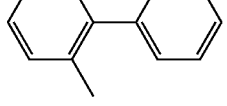 | 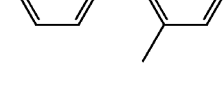 |
TABLE 3
| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D17 | H | H | H | H | H | H | H | H | — | — | — | 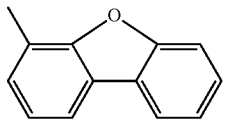 | 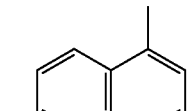 |

TABLE 3-continued
| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D18 | H | H | H | H | H | H | H | H | — | — | — | 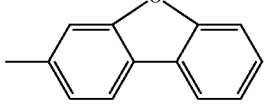 | 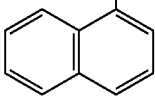 |
| D19 | H | H | H | H | H | H | H | H | — | — | — | 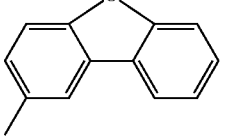 | 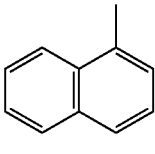 |
| D20 | H | H | H | H | H | H | H | H | — | — | — | 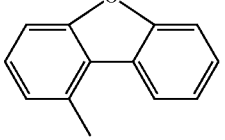 | 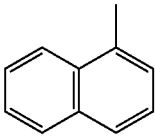 |
| D21 | H | H | H | H | H | H | H | H | — | — | — | 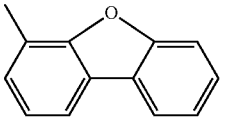 | 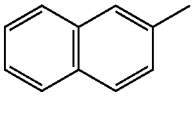 |
| D22 | H | H | H | H | H | H | H | H | — | — | — | 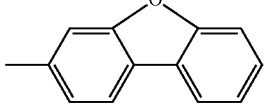 | 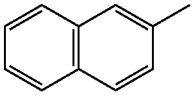 |
| D23 | H | H | H | H | H | H | H | H | — | — | — | 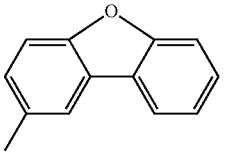 | 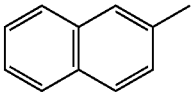 |
| D24 | H | H | H | H | H | H | H | H | — | — | — | 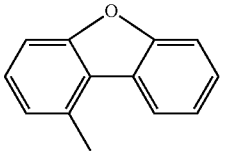 | 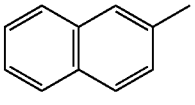 |
TABLE 4
| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D25 | H | H | H | H | H | H | H | H | — | — | — | 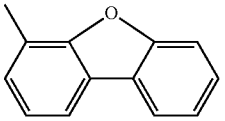 | 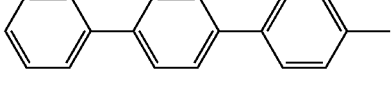 |
| D26 | H | H | H | H | H | H | H | H | — | — | — | 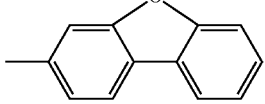 | 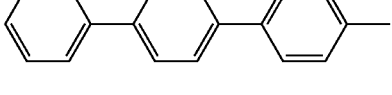 |

TABLE 4-continued
| compound | R2 | R4 | R5 | R6 | R7 | R8 | R9 | R10 | L1 | L2 | L3 | Ar1 | Ar2 |
|---|---|---|---|---|---|---|---|---|---|---|---|---|---|
| D27 | H | H | H | H | H | H | H | H | — | — | — | 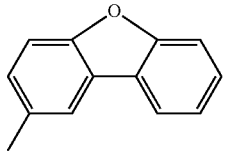 | 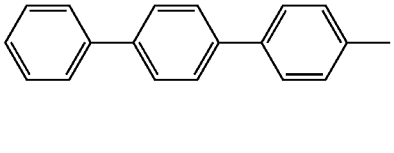 |
| D28 | H | H | H | H | H | H | H | H | — | — | — | 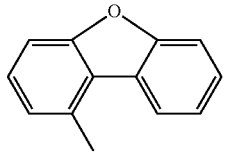 | 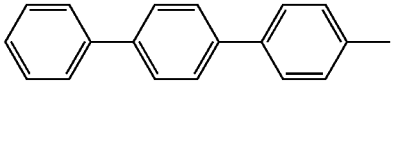 |
| D29 | H | H | H | H | H | H | H | H | — | — | — | 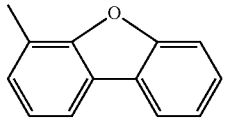 | 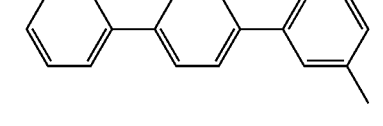 |
| D30 | H | H | H | H | H | H | H | H | — | — | — | 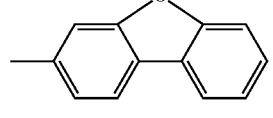 | 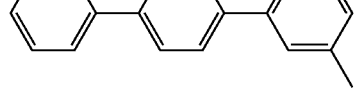 |
| D31 | H | H | H | H | H | H | H | H | — | — | — | 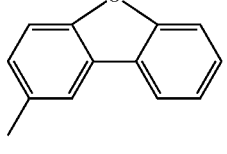 | 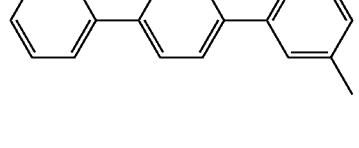 |
| D32 | H | H | H | H | H | H | H | H | — | — | — | 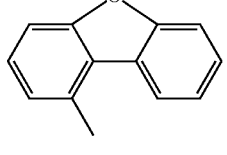 | 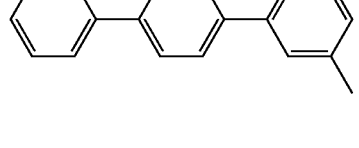 |
TABLE 5
| compound | R2 | R4 | R5 | R6 | R7 | R8 | R9 | R10 | L1 | L2 | L3 | Ar1 | Ar2 |
|---|---|---|---|---|---|---|---|---|---|---|---|---|---|
| D33 | H | H | H | H | H | H | H | H | — | — | — | 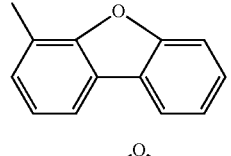 | 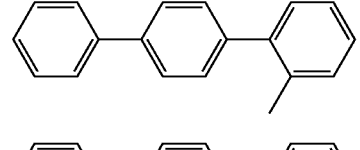 |
| D34 | H | H | H | H | H | H | H | H | — | — | — | 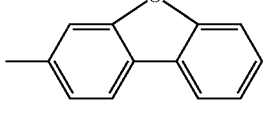 | 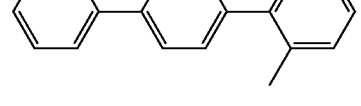 |
| D35 | H | H | H | H | H | H | H | H | — | — | — | 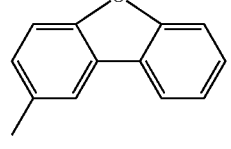 | 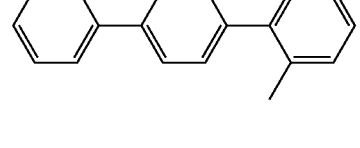 |

TABLE 5-continued
| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D36 | H | H | H | H | H | H | H | H | — | — | — | 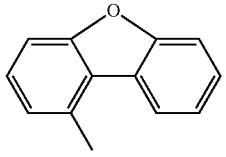 | 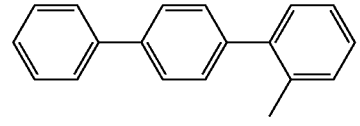 |
| D37 | H | H | H | H | H | H | H | H | — | — | — | 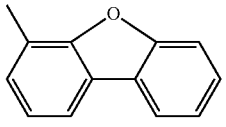 | 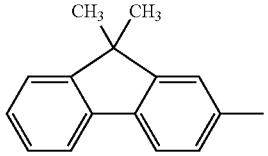 |
| D38 | H | H | H | H | H | H | H | H | — | — | — | 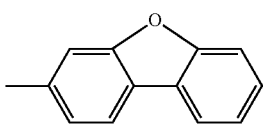 | 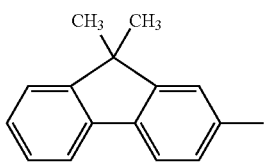 |
| D39 | H | H | H | H | H | H | H | H | — | — | — | 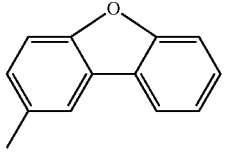 | 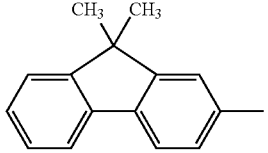 |
| D40 | H | H | H | H | H | H | H | H | — | — | — | 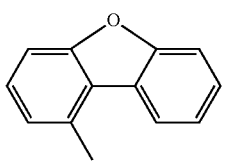 | 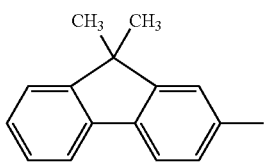 |
TABLE 6
| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D41 | H | H | H | H | H | H | H | H | — | — | — | 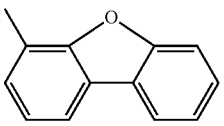 | 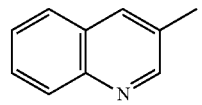 |
| D42 | H | H | H | H | H | H | H | H | — | — | — | 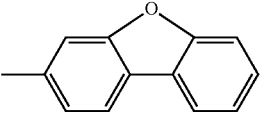 | 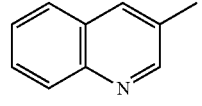 |
| D43 | H | H | H | H | H | H | H | H | — | — | — | 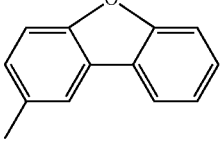 | 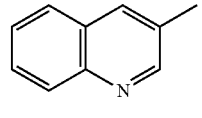 |
| D44 | H | H | H | H | H | H | H | H | — | — | — | 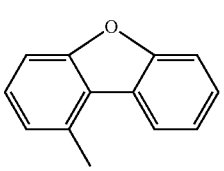 | 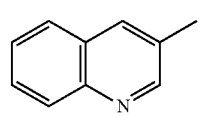 |

TABLE 6-continued
| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D45 | H | H | H | H | H | H | H | H | — | — | — | 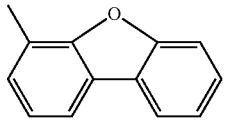 | 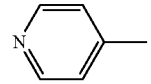 |
| D46 | H | H | H | H | H | H | H | H | — | — | — | 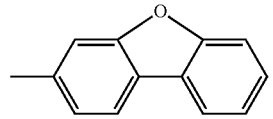 | 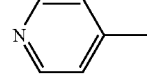 |
| D47 | H | H | H | H | H | H | H | H | — | — | — | 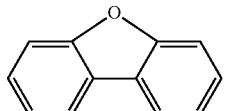 | 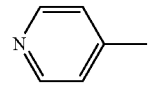 |
| D48 | H | H | H | H | H | H | H | H | — | — | — | 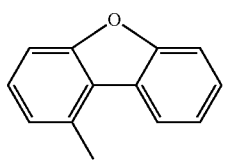 | 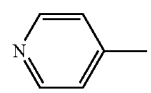 |
TABLE 7
| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D49 | H | H | H | H | H | H | H | H | — | — | — | 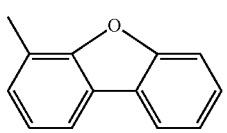 | 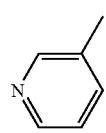 |
| D50 | H | H | H | H | H | H | H | H | — | — | — | 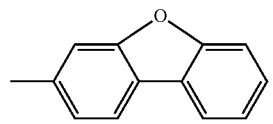 | 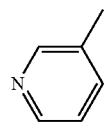 |
| D51 | H | H | H | H | H | H | H | H | — | — | — | 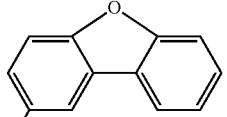 | 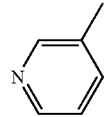 |
| D52 | H | H | H | H | H | H | H | H | — | — | — | 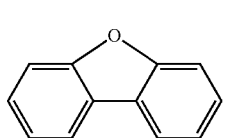 | 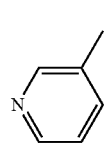 |

TABLE 8
| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D53 | H | H | H | H | H | H | H | H | — | — | — | 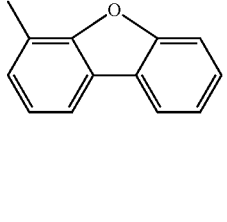 | 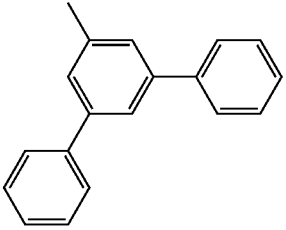 |
| D54 | H | H | H | H | H | H | H | H | — | — | — | 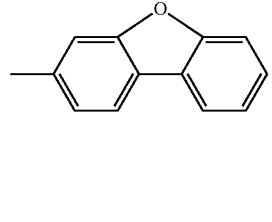 | 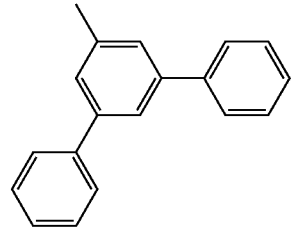 |
| D55 | H | H | H | H | H | H | H | H | — | — | — | 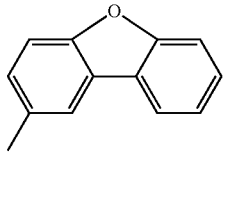 | 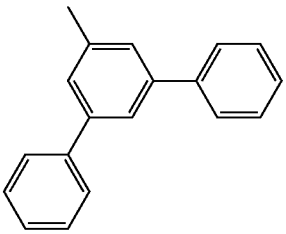 |
| D56 | H | H | H | H | H | H | H | H | — | — | — | 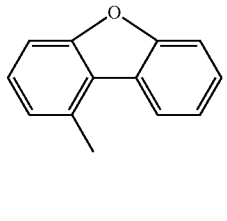 | 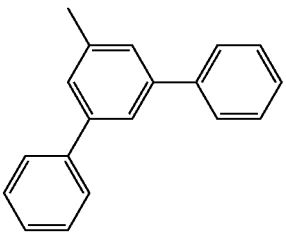 |
| D57 | H | H | H | H | H | H | H | H | — | — | — | 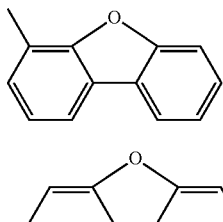 | 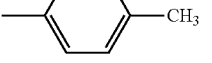 |
| D58 | H | H | H | H | H | H | H | H | — | — | — | 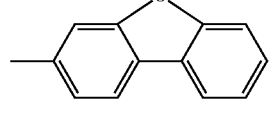 | 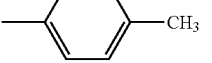 |
| D59 | H | H | H | H | H | H | H | H | — | — | — | 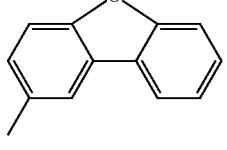 | 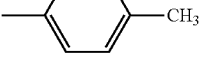 |
| D60 | H | H | H | H | H | H | H | H | — | — | — | 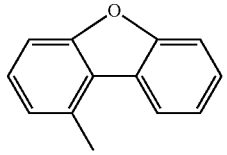 | 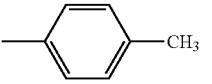 |

TABLE 9
| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D61 | H | H | H | H | H | H | H | H | — | — | — | 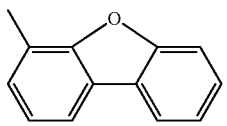 | 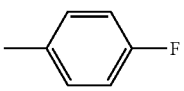 |
| D62 | H | H | H | H | H | H | H | H | — | — | — | 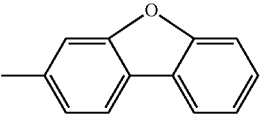 |  |
| D63 | H | H | H | H | H | H | H | H | — | — | — | 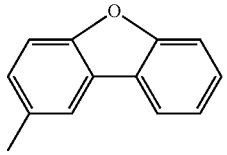 | 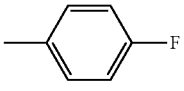 |
| D64 | H | H | H | H | H | H | H | H | — | — | — | 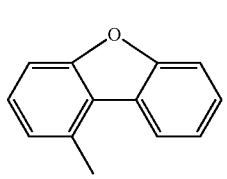 | 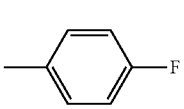 |
| D65 | H | H | H | H | H | H | H | H | — | — | — | 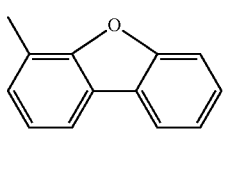 | 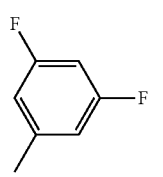 |
| D66 | H | H | H | H | H | H | H | H | — | — | — | 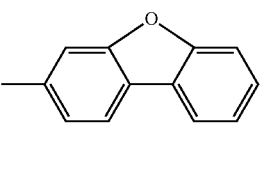 | 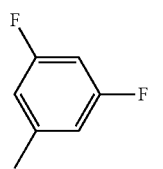 |
| D67 | H | H | H | H | H | H | H | H | — | — | — | 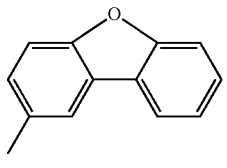 | 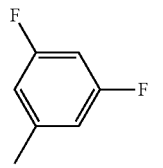 |
| D68 | H | H | H | H | H | H | H | H | — | — | — | 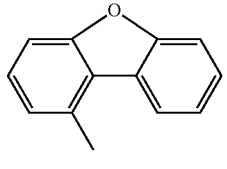 | 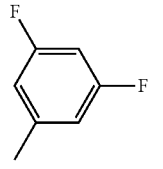 |
TABLE 10
| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D69 | H | H | H | H | H | H | H | H | — | — | — | 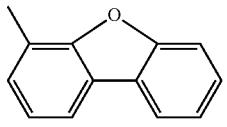 | 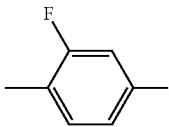 |

TABLE 10-continued

| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D70 | H | H | H | H | H | H | H | H | — | — | — | methyldibenzofuran | 2,4-difluorotolyl |
| D71 | H | H | H | H | H | H | H | H | — | — | — | methyldibenzofuran | 2,4-difluorotolyl |
| D72 | H | H | H | H | H | H | H | H | — | — | — | methyldibenzofuran | 2,4-difluorotolyl |
| D73 | H | H | H | H | H | H | H | H | — | — | — | methyldibenzofuran | 4-cyanotolyl |
| D74 | H | H | H | H | H | H | H | H | — | — | — | methyldibenzofuran | 4-cyanotolyl |
| D75 | H | H | H | H | H | H | H | H | — | — | — | methyldibenzofuran | 4-cyanotolyl |
| D76 | H | H | H | H | H | H | H | H | — | — | — | methyldibenzofuran | 4-cyanotolyl |

TABLE 11

| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D77 | H | H | H | H | H | H | H | H | — | — | — | methyldibenzofuran | 4-(trimethylsilyl)tolyl |
| D78 | H | H | H | H | H | H | H | H | — | — | — | methyldibenzofuran | 4-(trimethylsilyl)tolyl |

TABLE 11-continued
| compound | R2 | R4 | R5 | R6 | R7 | R8 | R9 | R10 | L1 | L2 | L3 | Ar1 | Ar2 |
|---|---|---|---|---|---|---|---|---|---|---|---|---|---|
| D79 | H | H | H | H | H | H | H | H | — | — | — | 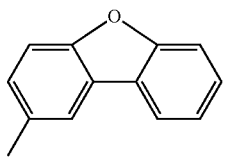 | 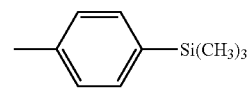 |
| D80 | H | H | H | H | H | H | H | H | — | — | — | 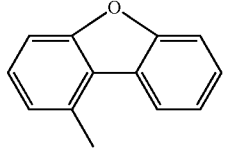 | 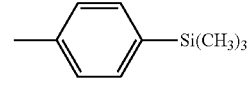 |
| D81 | H | H | H | H | H | H | H | H | — | — | — | 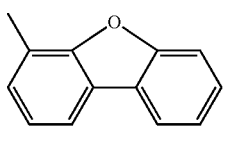 | 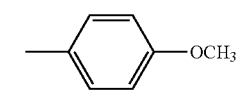 |
| D82 | H | H | H | H | H | H | H | H | — | — | — | 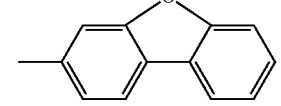 | 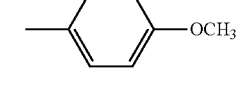 |
| D83 | H | H | H | H | H | H | H | H | — | — | — | 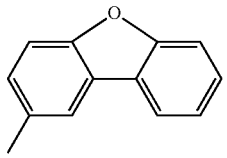 | 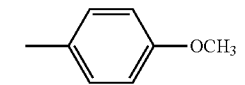 |
| D84 | H | H | H | H | H | H | H | H | — | — | — | 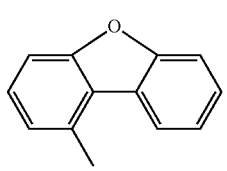 | 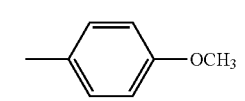 |
TABLE 12
| compound | R2 | R4 | R5 | R6 | R7 | R8 | R9 | R10 | L1 | L2 | L3 | Ar1 | Ar2 |
|---|---|---|---|---|---|---|---|---|---|---|---|---|---|
| D85 | H | H | H | H | H | H | H | H | — | — | — | 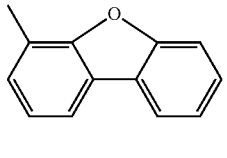 | 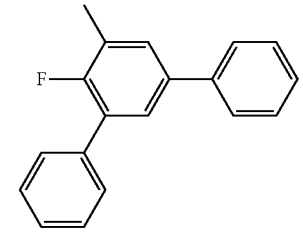 |
| D86 | H | H | H | H | H | H | H | H | — | — | — | 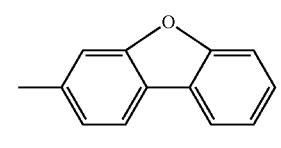 | 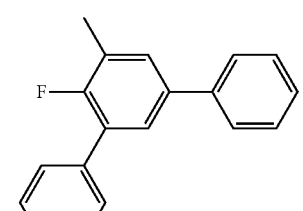 |

TABLE 12-continued
| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D87 | H | H | H | H | H | H | H | H | — | — | — | 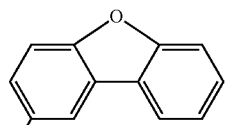 | 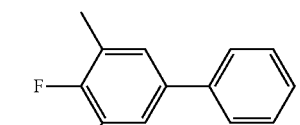 |
| D88 | H | H | H | H | H | H | H | H | — | — | — | 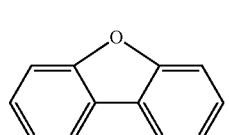 | 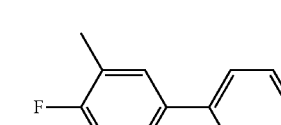 |
TABLE 13
| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D89 | H | H | H | H | H | H | H | H | — | — | — | 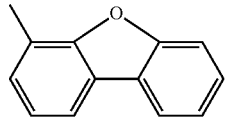 | 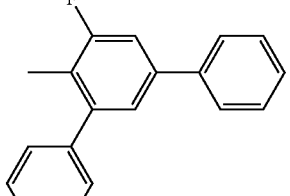 |
| D90 | H | H | H | H | H | H | H | H | — | — | — | 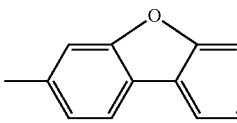 | 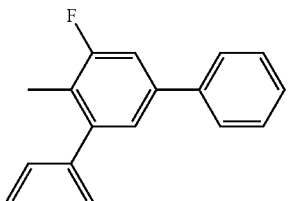 |
| D91 | H | H | H | H | H | H | H | H | — | — | — | 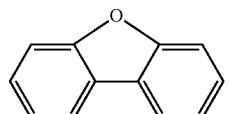 | 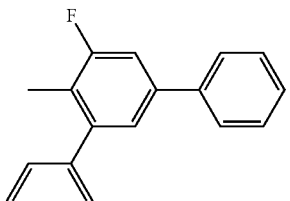 |

TABLE 13-continued
| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D92 | H | H | H | H | H | H | H | H | — | — | — | 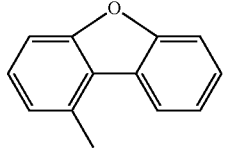 | 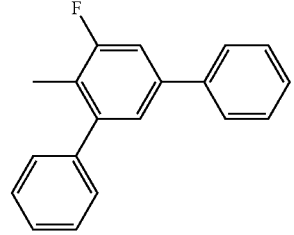 |
TABLE 14
| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D93 | H | H | H | H | H | H | H | H | — | — | — | 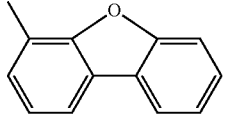 | 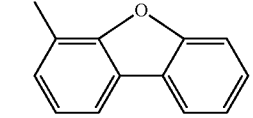 |
| D94 | H | H | H | H | H | H | H | H | — | — | — | 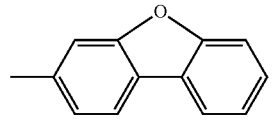 | 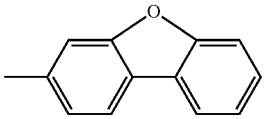 |
| D95 | H | H | H | H | H | H | H | H | — | — | — | 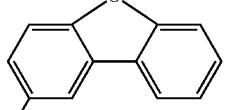 | 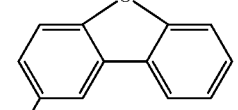 |
| D96 | H | H | H | H | H | H | H | H | — | — | — | 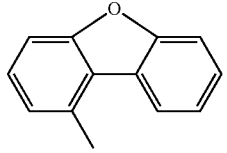 | 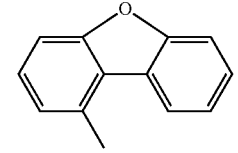 |
| D97 | H | H | H | H | H | H | H | H | — | — | — | 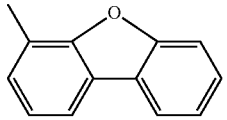 | 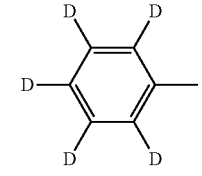 |
| D98 | H | H | H | H | H | H | H | H | — | — | — | 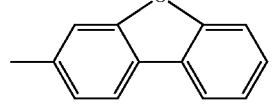 | 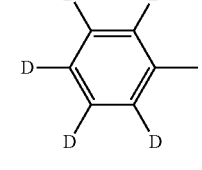 |
| D99 | H | H | H | H | H | H | H | H | — | — | — | 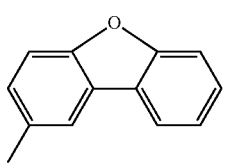 | 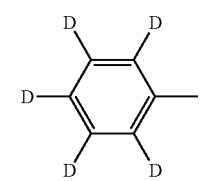 |

TABLE 14-continued
| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D100 | H | H | H | H | H | H | H | H | — | — | — | 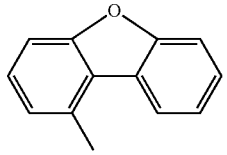 | 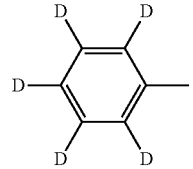 |
TABLE 15
| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D101 | H | H | H | H | H | H | H | H | — | — | — | 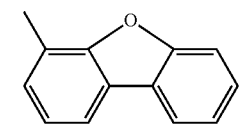 | 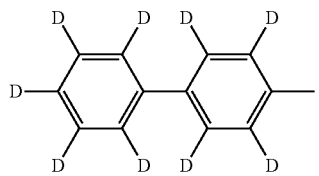 |
| D102 | H | H | H | H | H | H | H | H | — | — | — | 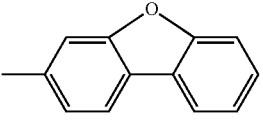 | 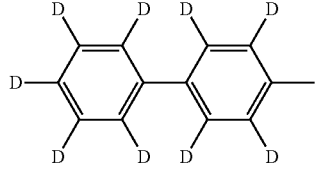 |
| D103 | H | H | H | H | H | H | H | H | — | — | — | 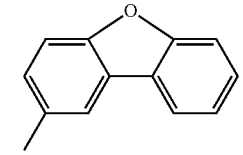 | 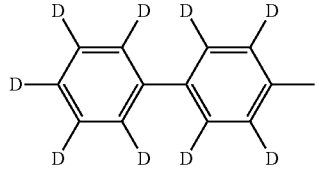 |
| D104 | H | H | H | H | H | H | H | H | — | — | — | 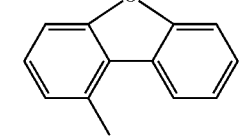 | 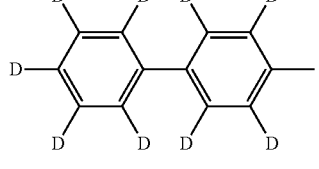 |
| D105 | H | H | H | H | H | H | H | H | — | — | — | 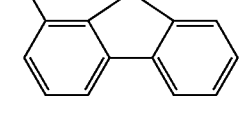 | 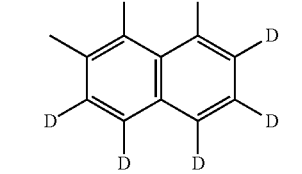 |
| D106 | H | H | H | H | H | H | H | H | — | — | — | 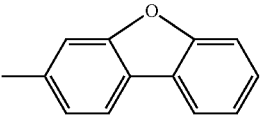 | 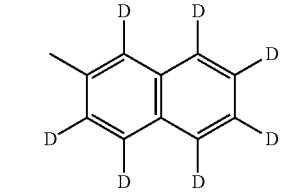 |

TABLE 15-continued
| compound | $R_2$ | $R_4$ | $R_5$ | $R_6$ | $R_7$ | $R_8$ | $R_9$ | $R_{10}$ | $L_1$ | $L_2$ | $L_3$ | $Ar_1$ | $Ar_2$ |
|---|---|---|---|---|---|---|---|---|---|---|---|---|---|
| D107 | H | H | H | H | H | H | H | H | — | — | — | 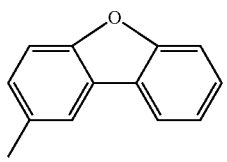 | 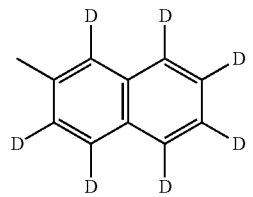 |
| D108 | H | H | H | H | H | H | H | H | — | — | — | 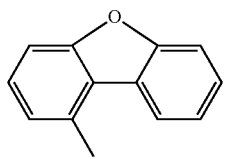 | 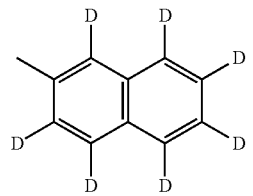 |
TABLE 16
| compound | $R_2$ | $R_4$ | $R_5$ | $R_6$ | $R_7$ | $R_8$ | $R_9$ | $R_{10}$ | $L_1$ | $L_2$ | $L_3$ | $Ar_1$ | $Ar_2$ |
|---|---|---|---|---|---|---|---|---|---|---|---|---|---|
| D109 | H | H | H | H | H | H | H | H | — | — | — | 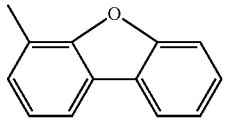 | 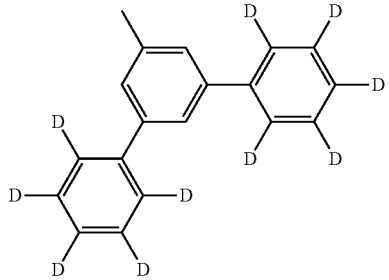 |
| D110 | H | H | H | H | H | H | H | H | — | — | — | 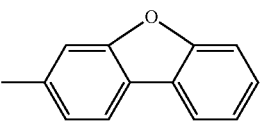 | 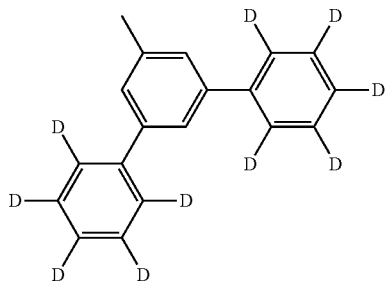 |
| D111 | H | H | H | H | H | H | H | H | — | — | — | 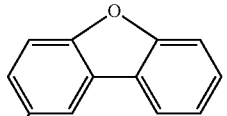 | 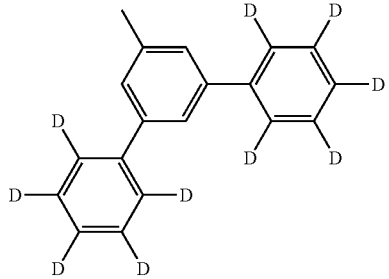 |

TABLE 16-continued

| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D112 | H | H | H | H | H | H | H | H | — | — | — | (structure) | (structure) |

TABLE 17

| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D113 | H | H | H | H | H | H | H | H | — | — | — | (structure) | (structure) |
| D114 | H | H | H | H | H | H | H | H | — | — | — | (structure) | (structure) |
| D115 | H | H | H | H | H | H | H | H | — | — | — | (structure) | (structure) |
| D116 | H | H | H | H | H | H | H | H | — | — | — | (structure) | (structure) |

TABLE 18
| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D117 | H | H | H | H | H | H | H | H | — | — | — | 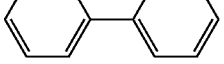 | 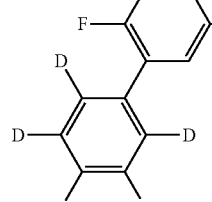 |
| D118 | H | H | H | H | H | H | H | H | — | — | — | 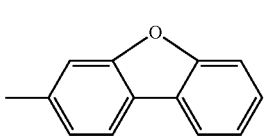 | 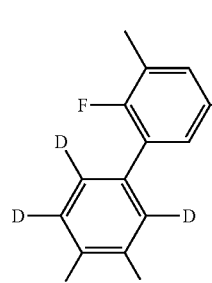 |
| D119 | H | H | H | H | H | H | H | H | — | — | — | 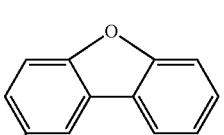 | 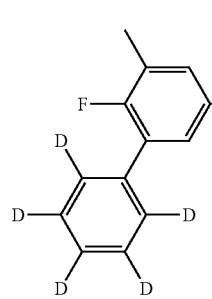 |
| D120 | H | H | H | H | H | H | H | H | — | — | — | 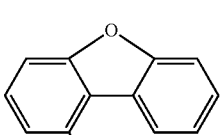 | 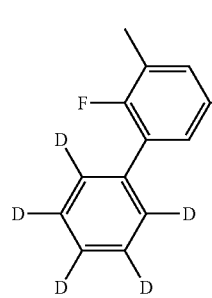 |
TABLE 19
| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D121 | H | H | H | H | H | H | H | H | — | — | — | | |

TABLE 19-continued
| compound | R2 | R4 | R5 | R6 | R7 | R8 | R9 | R10 | L1 | L2 | L3 | Ar1 | Ar2 |
|---|---|---|---|---|---|---|---|---|---|---|---|---|---|
| D122 | H | H | H | H | H | H | H | H | — | — | — | 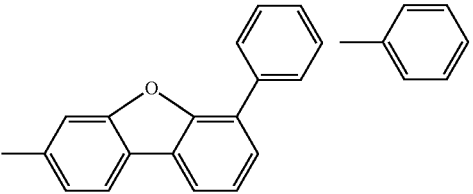 | 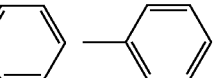 |
| D123 | H | H | H | H | H | H | H | H | — | — | — | 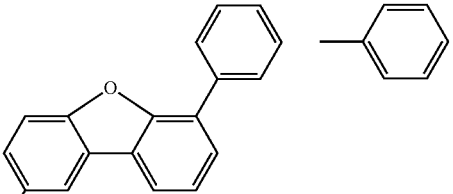 | 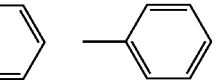 |
| D124 | H | H | H | H | H | H | H | H | — | — | — | 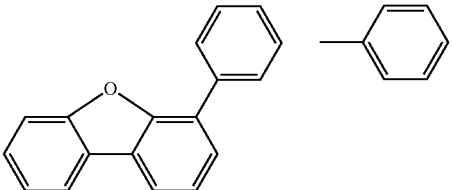 | 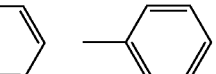 |
TABLE 20
| compound | R2 | R4 | R5 | R6 | R7 | R8 | R9 | R10 | L1 | L2 | L3 | Ar1 | Ar2 |
|---|---|---|---|---|---|---|---|---|---|---|---|---|---|
| D125 | H | H | H | H | H | H | H | H | — | — | — | 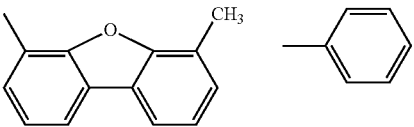 | 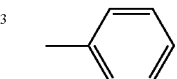 |
| D126 | H | H | H | H | H | H | H | H | — | — | — | 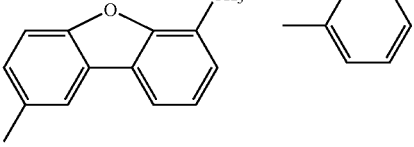 | 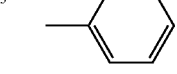 |
| D127 | H | H | H | H | H | H | H | H | — | — | — | 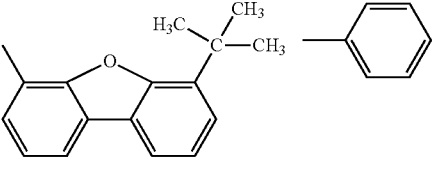 | 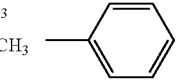 |
| D128 | H | H | H | H | H | H | H | H | — | — | — | 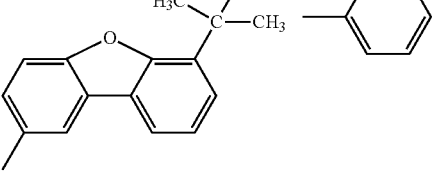 | 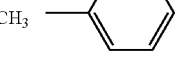 |

TABLE 21

| compound | R$_2$ | R$_4$ | R$_5$ | R$_6$ | R$_7$ | R$_8$ | R$_9$ | R$_{10}$ | L$_1$ | L$_2$ | L$_3$ | Ar$_1$ | Ar$_2$ |
|---|---|---|---|---|---|---|---|---|---|---|---|---|---|
| D129 | H | H | H | H | H | H | H | H | — | — | — | (methyl-dibenzofuran-cyclohexyl) | (phenyl) |
| D130 | H | H | H | H | H | H | H | H | — | — | — | (methyl-dibenzofuran-cyclohexyl) | (phenyl) |
| D131 | H | H | H | H | H | H | H | H | — | — | — | (methyl-dibenzofuran-Si(CH$_3$)$_3$) | (phenyl) |
| D132 | H | H | H | H | H | H | H | H | — | — | — | (methyl-dibenzofuran-Si(CH$_3$)$_3$) | (phenyl) |

TABLE 22

| compound | R$_2$ | R$_4$ | R$_5$ | R$_6$ | R$_7$ | R$_8$ | R$_9$ | R$_{10}$ | L$_1$ | L$_2$ | L$_3$ | Ar$_1$ | Ar$_2$ |
|---|---|---|---|---|---|---|---|---|---|---|---|---|---|
| D133 | H | H | H | H | H | H | H | H | — | — | — | (methyl-dibenzofuran-CN) | (phenyl) |
| D134 | H | H | H | H | H | H | H | H | — | — | — | (methyl-dibenzofuran-CN) | (phenyl) |
| D135 | H | H | H | H | H | H | H | H | — | — | — | (methyl-dibenzofuran-F) | (phenyl) |
| D136 | H | H | H | H | H | H | H | H | — | — | — | (methyl-dibenzofuran-F) | (phenyl) |

TABLE 22-continued
| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D137 | H | H | H | H | H | H | H | H | — | — | — | 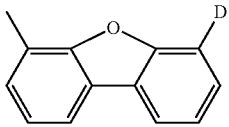 | 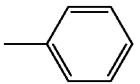 |
| D138 | H | H | H | H | H | H | H | H | — | — | — | 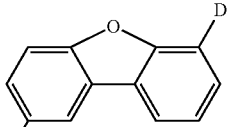 | 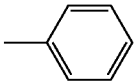 |
TABLE 23
| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D139 | H | H | H | H | H | H | H | H |  | — | — | 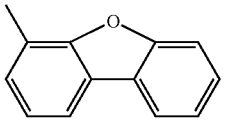 | 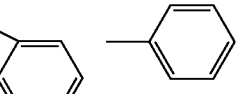 |
| D140 | H | H | H | H | H | H | H | H | 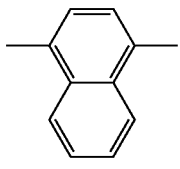 | — | — | 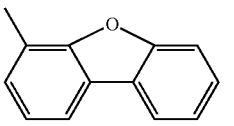 | 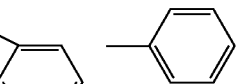 |
| D141 | H | H | H | H | H | H | H | H | 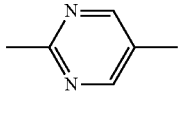 | — | — | 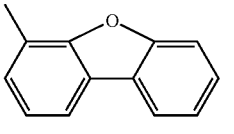 | 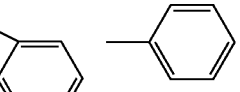 |
| D142 | H | H | H | H | H | H | H | H | 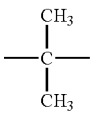 | — | — | 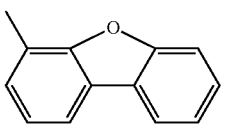 | 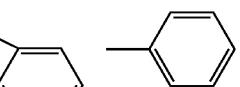 |
| D143 | H | H | H | H | H | H | H | H | — | 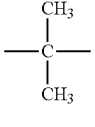 | — | 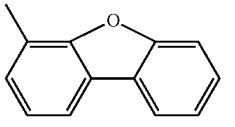 | 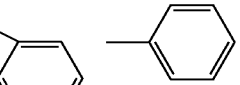 |
TABLE 24
| compound | R₂ | R₄ | R₅ | R₆ | R₇ | R₈ | R₉ | R₁₀ | L₁ | L₂ | L₃ | Ar₁ |
|---|---|---|---|---|---|---|---|---|---|---|---|---|
| D144 | H | H | H | H | H | H | H | H | — | — |  | 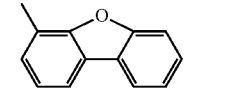 |
| D145 | H | H | H | H | H | H | H | H | — | — | 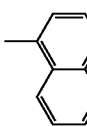 | 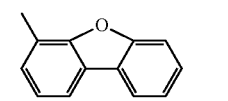 |

TABLE 24-continued
| compound | R₂ | R₄ | R₅ | R₆ | R₇ | R₈ | R₉ | R₁₀ | L₁ | L₂ | L₃ | Ar₁ |
|---|---|---|---|---|---|---|---|---|---|---|---|---|
| D146 | H | H | H | H | H | H | H | H | — | — | 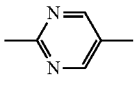 | 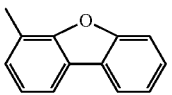 |
| D147 | H | H | H | H | H | H | H | H | 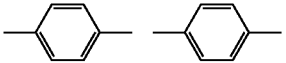 |  | — | 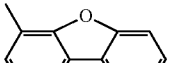 |
| D148 | H | H | H | H | H | H | H | H |  |  | — | 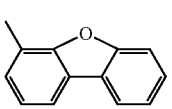 |
| D149 | H | H | H | H | H | H | H | H | — | — |  | 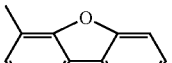 |
| D150 | H | H | H | H | H | H | H | H | — | — | — | 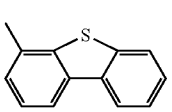 |
| compound | Ar₂ |
|---|---|
| D144 |  |
| D145 |  |
| D146 |  |
| D147 | 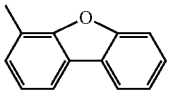 |
| D148 | 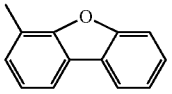 |
| D149 | 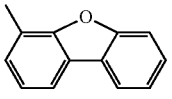 |
| D150 |  |
TABLE 25
| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D151 | H | H | H | H | H | H | H | H | — | — | — | 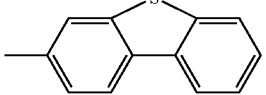 | 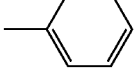 |

TABLE 25-continued
| compound | R$_2$ | R$_4$ | R$_5$ | R$_6$ | R$_7$ | R$_8$ | R$_9$ | R$_{10}$ | L$_1$ | L$_2$ | L$_3$ | Ar$_1$ | Ar$_2$ |
|---|---|---|---|---|---|---|---|---|---|---|---|---|---|
| D152 | H | H | H | H | H | H | H | H | — | — | — | 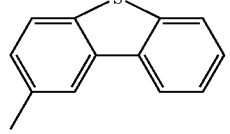 | 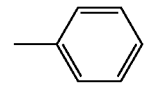 |
| D153 | H | H | H | H | H | H | H | H | — | — | — | 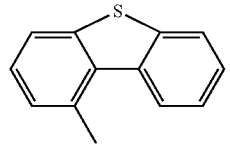 | 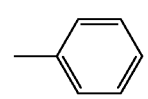 |
| D154 | H | H | H | H | H | H | H | H | — | — | — | 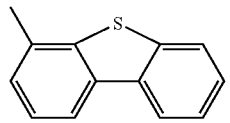 | 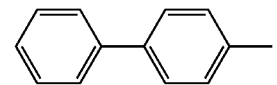 |
| D155 | H | H | H | H | H | H | H | H | — | — | — | 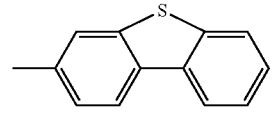 | 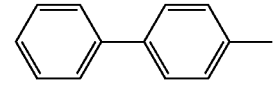 |
| D156 | H | H | H | H | H | H | H | H | — | — | — | 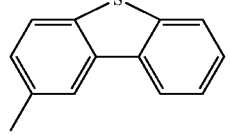 | 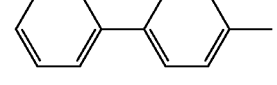 |
| D157 | H | H | H | H | H | H | H | H | — | — | — | 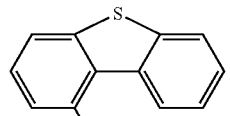 | 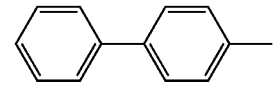 |
TABLE 26
| compound | R$_2$ | R$_4$ | R$_5$ | R$_6$ | R$_7$ | R$_8$ | R$_9$ | R$_{10}$ | L$_1$ | L$_2$ | L$_3$ | Ar$_1$ | Ar$_2$ |
|---|---|---|---|---|---|---|---|---|---|---|---|---|---|
| D158 | H | H | H | H | H | H | H | H | — | — | — | 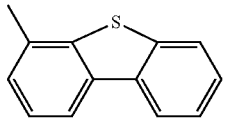 | 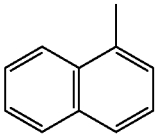 |
| D159 | H | H | H | H | H | H | H | H | — | — | — | 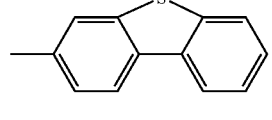 | 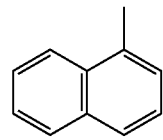 |
| D160 | H | H | H | H | H | H | H | H | — | — | — | 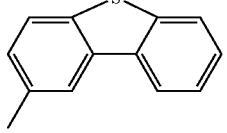 | 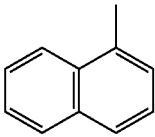 |

TABLE 26-continued
| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D161 | H | H | H | H | H | H | H | H | — | — | — | 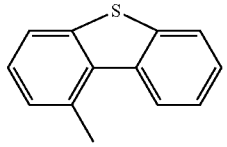 | 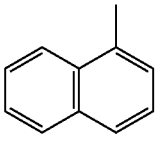 |
| D162 | H | H | H | H | H | H | H | H | — | — | — | 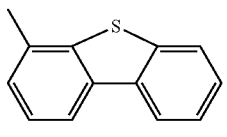 | 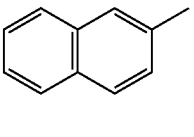 |
| D163 | H | H | H | H | H | H | H | H | — | — | — | 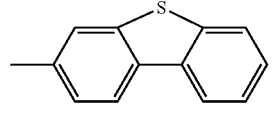 | 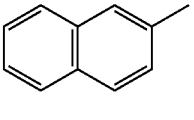 |
| D164 | H | H | H | H | H | H | H | H | — | — | — | 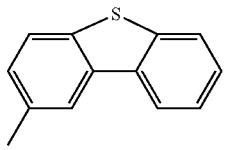 | 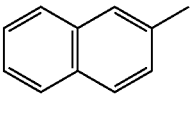 |
| D165 | H | H | H | H | H | H | H | H | — | — | — | 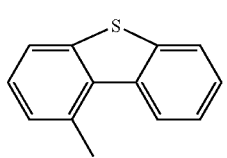 | 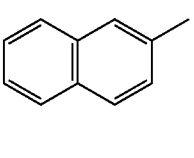 |
TABLE 27
| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D166 | H | H | H | H | H | H | H | H | — | — | — | 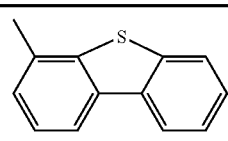 | 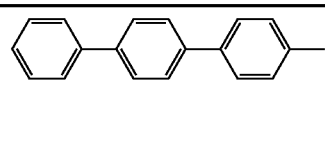 |
| D167 | H | H | H | H | H | H | H | H | — | — | — | 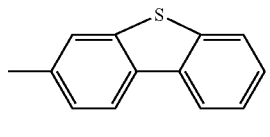 | 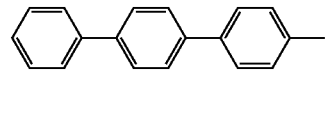 |
| D168 | H | H | H | H | H | H | H | H | — | — | — | 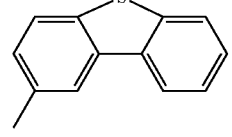 | 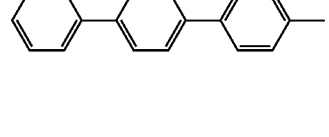 |
| D169 | H | H | H | H | H | H | H | H | — | — | — | 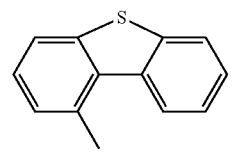 | 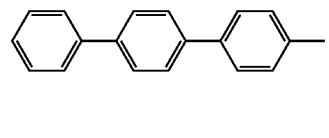 |
| D170 | H | H | H | H | H | H | H | H | — | — | — | 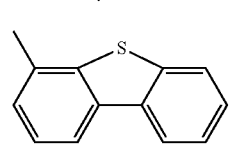 | 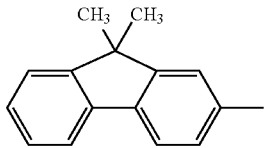 |

TABLE 27-continued
| compound | R$_2$ | R$_4$ | R$_5$ | R$_6$ | R$_7$ | R$_8$ | R$_9$ | R$_{10}$ | L$_1$ | L$_2$ | L$_3$ | Ar$_1$ | Ar$_2$ |
|---|---|---|---|---|---|---|---|---|---|---|---|---|---|
| D171 | H | H | H | H | H | H | H | H | — | — | — | 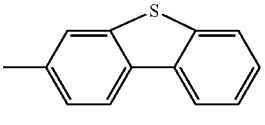 | 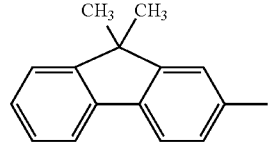 |
| D172 | H | H | H | H | H | H | H | H | — | — | — | 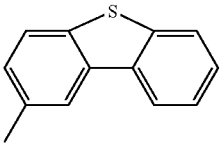 | 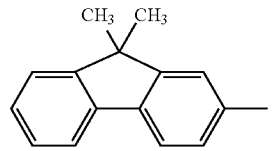 |
| D173 | H | H | H | H | H | H | H | H | — | — | — | 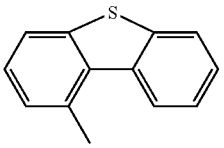 | 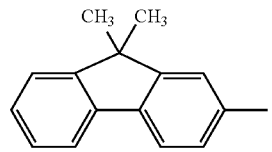 |
TABLE 28
| compound | R$_2$ | R$_4$ | R$_5$ | R$_6$ | R$_7$ | R$_8$ | R$_9$ | R$_{10}$ | L$_1$ | L$_2$ | L$_3$ | Ar$_1$ | Ar$_2$ |
|---|---|---|---|---|---|---|---|---|---|---|---|---|---|
| D174 | H | H | H | H | H | H | H | H | — | — | — | 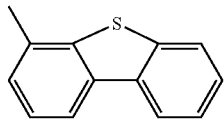 | 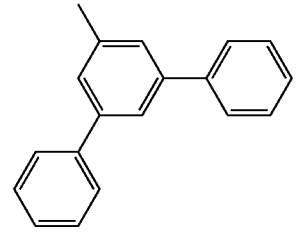 |
| D175 | H | H | H | H | H | H | H | H | — | — | — | 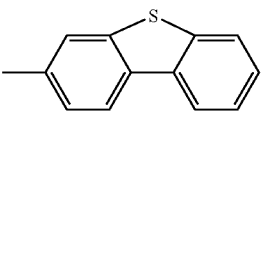 | 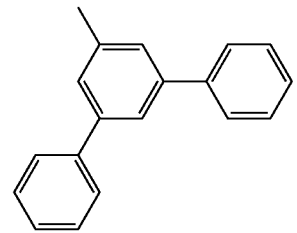 |
| D176 | H | H | H | H | H | H | H | H | — | — | — | 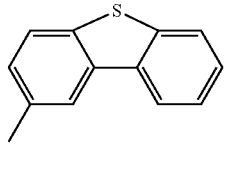 | 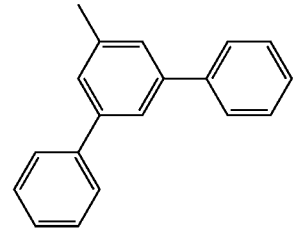 |
| D177 | H | H | H | H | H | H | H | H | — | — | — | 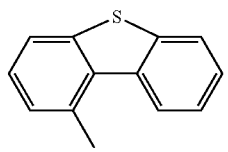 | 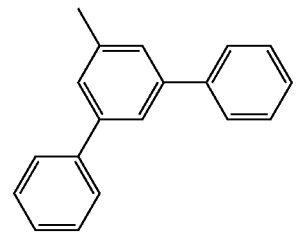 |

TABLE 29
| compound | R₂ | R₄ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D178 | H | H | H | H | H | H | H | H | — | — | — | 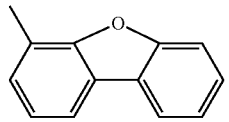 | 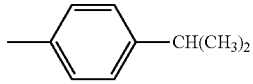 |
| D179 | H | H | H | H | H | H | H | H | — | — | — | 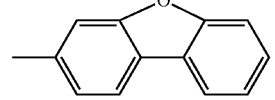 | 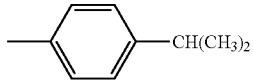 |
| D180 | H | H | H | H | H | H | H | H | — | — | — | 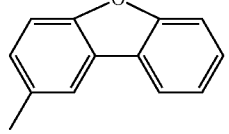 | 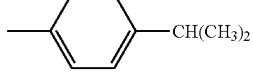 |
| D181 | H | H | H | H | H | H | H | H | — | — | — | 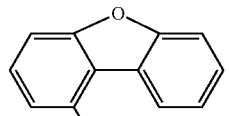 | 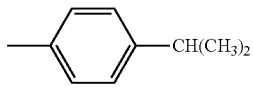 |
| D182 | H | H | H | H | H | H | H | H | — | — | — | 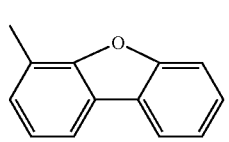 | 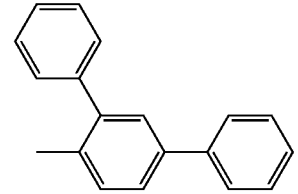 |
| D183 | H | H | H | H | H | H | H | H | — | — | — | 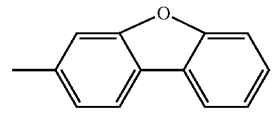 | 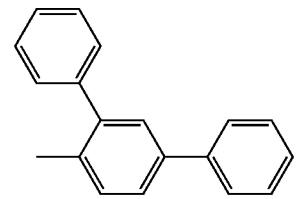 |
| D184 | H | H | H | H | H | H | H | H | — | — | — | 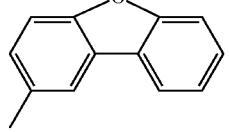 | 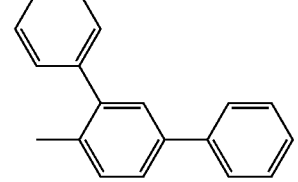 |
| D185 | H | H | H | H | H | H | H | H | — | — | — | 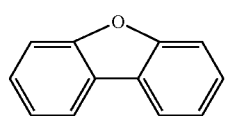 | 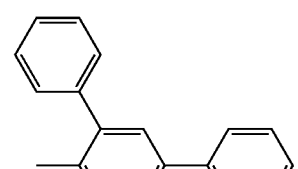 |

TABLE 30

| compound | R2 | R4 | R5 | R6 | R7 | R8 | R9 | R10 | L1 | L2 | L3 | Ar1 |
|---|---|---|---|---|---|---|---|---|---|---|---|---|
| D186 | H | H | H | phenyl | H | phenyl | H | H | — | — | — | dibenzofuranyl |
| D187 | H | H | H | phenyl | H | phenyl | H | H | — | — | — | dibenzofuranyl |
| D188 | H | H | H | phenyl | H | phenyl | H | H | — | — | — | dibenzofuranyl |
| D189 | H | H | H | phenyl | H | phenyl | H | H | — | — | — | dibenzofuranyl |
| D190 | H | H | H | naphthyl | H | naphthyl | H | H | — | — | — | dibenzofuranyl |
| D191 | H | H | H | naphthyl | H | naphthyl | H | H | — | — | — | dibenzofuranyl |
| D192 | H | H | H | naphthyl | H | naphthyl | H | H | — | — | — | dibenzofuranyl |
| D193 | H | H | H | naphthyl | H | naphthyl | H | H | — | — | — | dibenzofuranyl |

| compound | Ar2 |
|---|---|
| D186 | phenyl |
| D187 | biphenyl |
| D188 | terphenyl |
| D189 | naphthyl |
| D190 | phenyl |
| D191 | biphenyl |

TABLE 30-continued

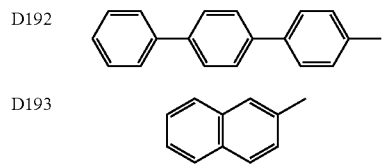

The specific examples of the aromatic amine derivative are the compounds having $R_1$ and $R_3$ in the same structure represented by the formula (2), however, not limited thereto. The aromatic amine derivative may be a compound having $R_1$ and $R_3$ in different structures.

In the aromatic amine derivative according to the exemplary embodiment, $R_1$ and $R_4$ in the formula (1) are preferably represented by the formula (2). At this instance, the aromatic amine derivative has a structure represented by the following formula (1B).

[Formula 12]

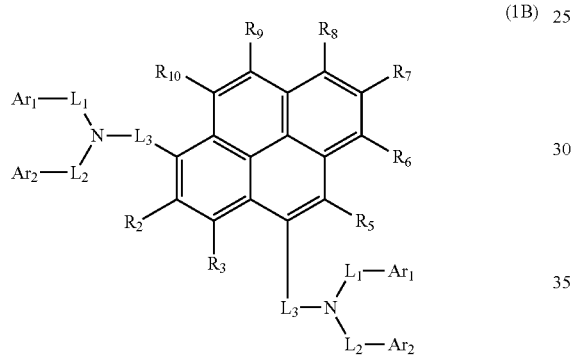

Specific examples of the aromatic amine derivative according to the exemplary embodiment are aromatic amine derivatives described in Tables 31 to 40 for $R_2$, $R_3$, $R_5$ to $R_{10}$, $L_1$ to $L_3$, and $Ar_1$ to $Ar_2$ in the formula (1B). Note that "—" in $L_1$ to $L_3$ of the tables represents a single bond. Moreover, in $L_1$ to $L_3$ and $Ar_1$ to $Ar_2$ in the tables, a line extending outward from the cyclic structure and having no chemical formula (e.g., $CH_3$, Ph, CN, benzene ring) at an end of the line represents a single bond, not a methyl group. For instance, in the following compound D501, $Ar_1$ has a single bond at a position 4 of a dibenzofuran ring. In short, $Ar_1$ represents a 4-dibenzofuranyl group. Likewise, $Ar_2$ represents a phenyl group.

TABLE 31

| compound | $R_2$ | $R_3$ | $R_5$ | $R_6$ | $R_7$ | $R_8$ | $R_9$ | $R_{10}$ | $L_1$ | $L_2$ | $L_3$ | $Ar_1$ | $Ar_2$ |
|---|---|---|---|---|---|---|---|---|---|---|---|---|---|
| D501 | H | H | H | H | H | H | H | H | — | — | — | 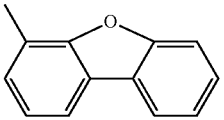 | 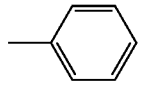 |
| D502 | H | H | H | H | H | H | H | H | — | — | — | 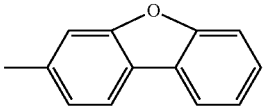 | 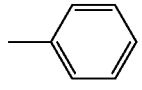 |
| D503 | H | H | H | H | H | H | H | H | — | — | — | 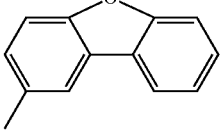 | 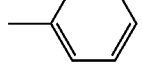 |
| D504 | H | H | H | H | H | H | H | H | — | — | — | 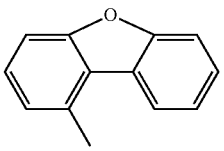 | 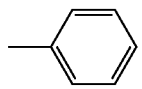 |

TABLE 31-continued
| compound | R₂ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D505 | H | H | H | H | H | H | H | H | — | — | — | 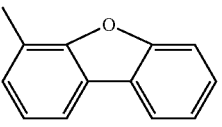 | 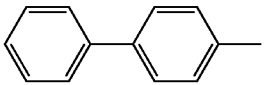 |
| D506 | H | H | H | H | H | H | H | H | — | — | — | 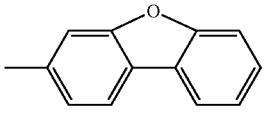 | 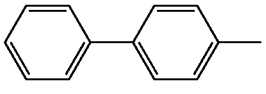 |
| D507 | H | H | H | H | H | H | H | H | — | — | — | 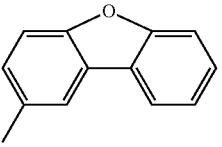 | 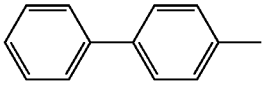 |
| D508 | H | H | H | H | H | H | H | H | — | — | — | 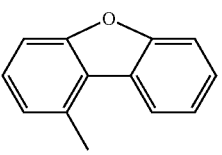 | 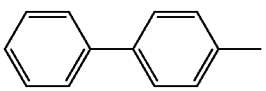 |
TABLE 32
| 化合物 | R₂ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D509 | H | H | H | H | H | H | H | H | — | — | — | 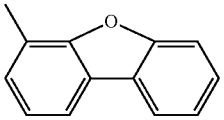 | 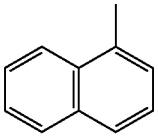 |
| D510 | H | H | H | H | H | H | H | H | — | — | — | 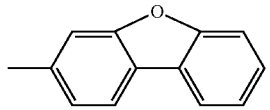 | 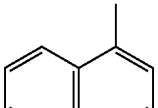 |
| D511 | H | H | H | H | H | H | H | H | — | — | — | 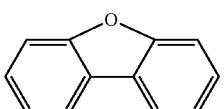 | 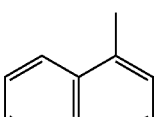 |
| D512 | H | H | H | H | H | H | H | H | — | — | — | 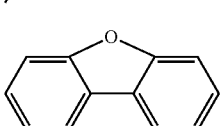 | 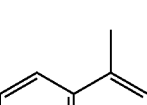 |
| D513 | H | H | H | H | H | H | H | H | — | — | — | 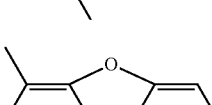 | 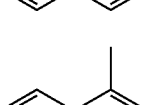 |

TABLE 32-continued
| 化合物 | R₂ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D514 | H | H | H | H | H | H | H | H | — | — | — | 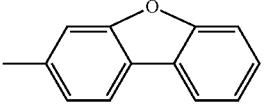 | 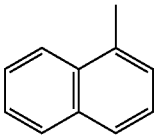 |
| D515 | H | H | H | H | H | H | H | H | — | — | — | 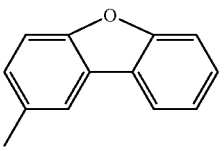 | 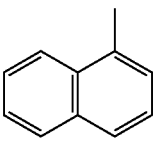 |
| D516 | H | H | H | H | H | H | H | H | — | — | — | 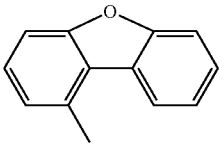 | 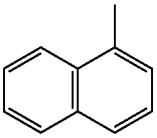 |
TABLE 33
| compound | R₂ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D517 | H | H | H | H | H | H | H | H | — | — | — | 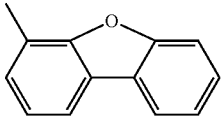 | 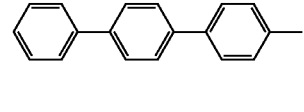 |
| D518 | H | H | H | H | H | H | H | H | — | — | — | 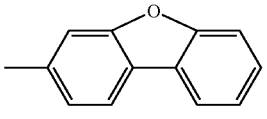 | 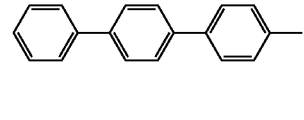 |
| D519 | H | H | H | H | H | H | H | H | — | — | — | 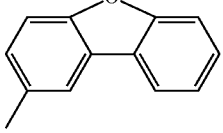 | 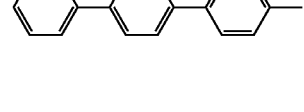 |
| D520 | H | H | H | H | H | H | H | H | — | — | — | 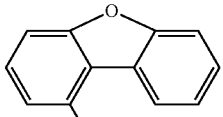 | 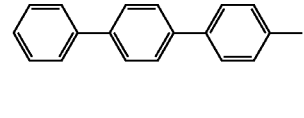 |
| D521 | H | H | H | H | H | H | H | H | — | — | — | 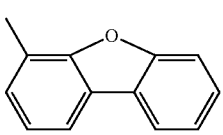 | 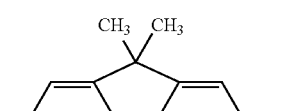 |
| D522 | H | H | H | H | H | H | H | H | — | — | — | 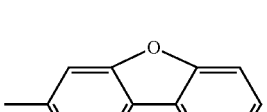 | 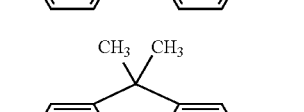 |

TABLE 33-continued
| compound | R₂ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D523 | H | H | H | H | H | H | H | H | — | — | — | 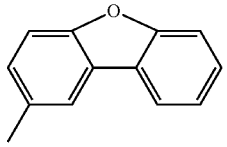 | 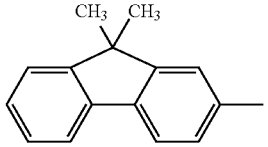 |
| D524 | H | H | H | H | H | H | H | H | — | — | — | 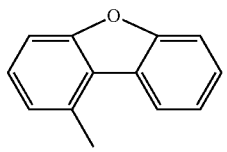 | 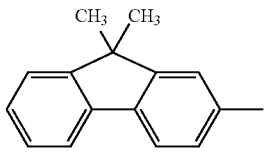 |
TABLE 34
| compound | R₂ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D525 | H | H | H | H | H | H | H | H | — | — | — | 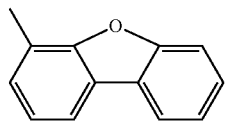 | 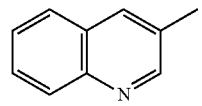 |
| D526 | H | H | H | H | H | H | H | H | — | — | — | 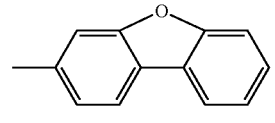 | 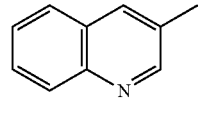 |
| D527 | H | H | H | H | H | H | H | H | — | — | — | 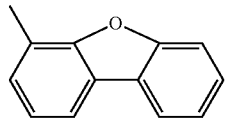 | 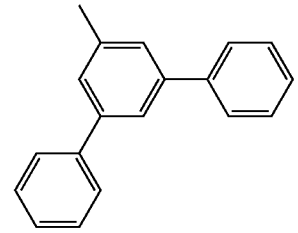 |
| D528 | H | H | H | H | H | H | H | H | — | — | — | 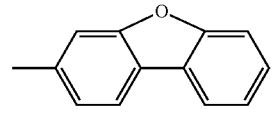 | 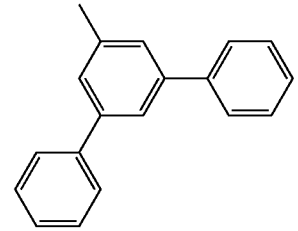 |
| D529 | H | H | H | H | H | H | H | H | — | — | — | 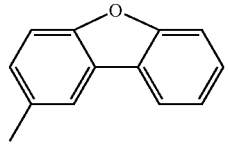 | 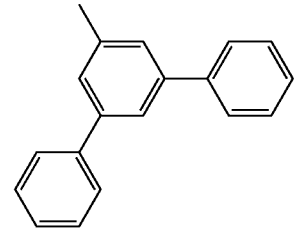 |

TABLE 34-continued
| compound | R₂ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D530 | H | H | H | H | H | H | H | H | — | — | — | 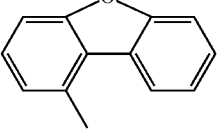 | 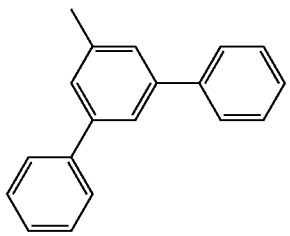 |
TABLE 35
| compound | R₂ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D531 | H | H | H | H | H | H | H | H | — | — | — | 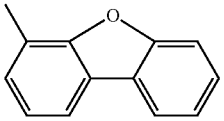 |  |
| D532 | H | H | H | H | H | H | H | H | — | — | — | 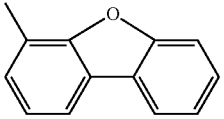 | 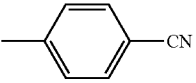 |
| D533 | H | H | H | H | H | H | H | H | — | — | — | 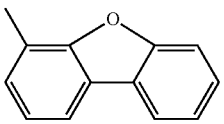 | 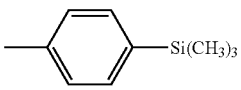 |
| D534 | H | H | H | H | H | H | H | H | — | — | — | 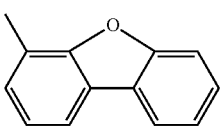 | 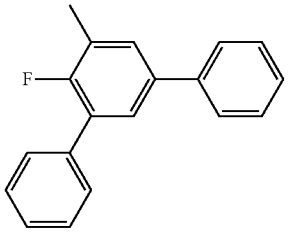 |
| D535 | H | H | H | H | H | H | H | H | — | — | — | 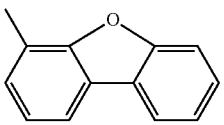 | 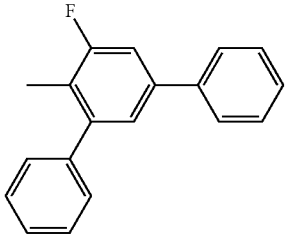 |
TABLE 36
| compound | R₂ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D536 | H | H | H | H | H | H | H | H | — | — | — | 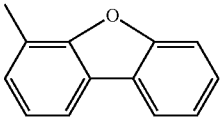 | 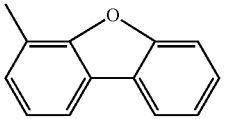 |

TABLE 36-continued
| compound | R₂ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D537 | H | H | H | H | H | H | H | H | — | — | — | 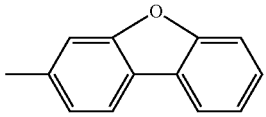 | 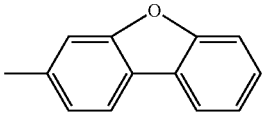 |
| D538 | H | H | H | H | H | H | H | H | — | — | — | 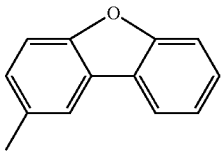 | 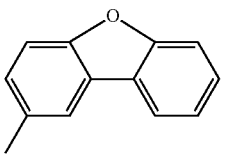 |
| D539 | H | H | H | H | H | H | H | H | — | — | — | 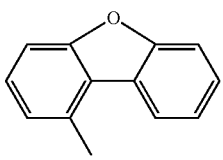 | 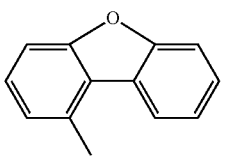 |
TABLE 37
| compound | R₂ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D540 | H | H | H | H | H | H | H | H | — | — | — | 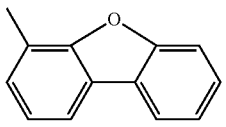 | 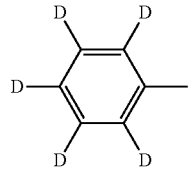 |
| D541 | H | H | H | H | H | H | H | H | — | — | — | 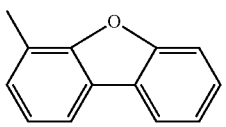 | 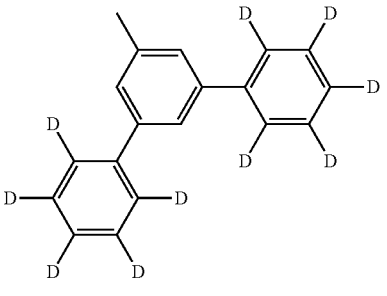 |
| D542 | H | H | H | H | H | H | H | H | — | — | — | 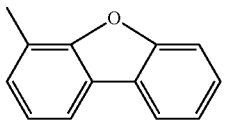 | 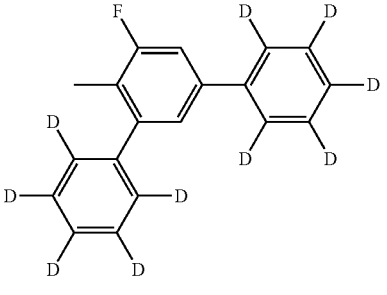 |

TABLE 37-continued
| compound | R₂ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D543 | H | H | H | H | H | H | H | H | — | — | — | 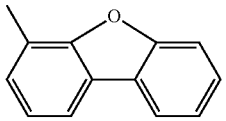 | 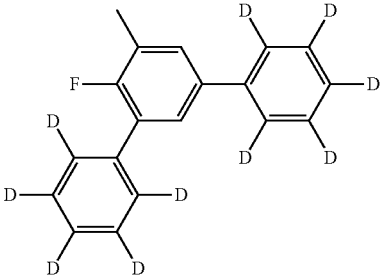 |
TABLE 38
| compound | R₂ | R₃ | R₅ | R₆ | R₇ | R₈ | R₉ | R₁₀ | L₁ | L₂ | L₃ |
|---|---|---|---|---|---|---|---|---|---|---|---|
| D544 | H | H | H | H | H | H | H | H | — | — | — |
| D545 | H | H | H | H | H | H | H | H | — | — | — |
| D546 | H | H | H | H | H | H | H | H |  | — | — |
| D547 | H | H | H | H | H | H | H | H | 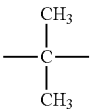 | — | — |
| D548 | H | H | H | H | H | H | H | H | — | 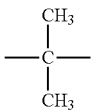 | — |
| D549 | H | H | H | H | H | H | H | H | — | — | 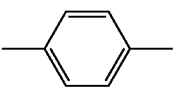 |
| D550 | H | H | H | H | H | H | H | H | 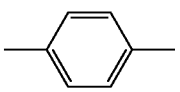 | 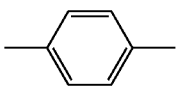 | — |
| D551 | H | H | H | H | H | H | H | H | 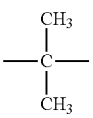 | 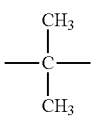 | — |
| D552 | H | H | H | H | H | H | H | H | — | — | 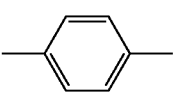 |
| compound | Ar₁ | Ar₂ |
|---|---|---|
| D544 | 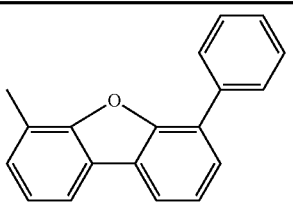 | 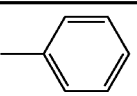 |

TABLE 38-continued

| | | |
|---|---|---|
| D545 | dibenzofuran with methyl and D substituents | methylphenyl |
| D546 | methyldibenzofuran | methylphenyl |
| D547 | methyldibenzofuran | methylphenyl |
| D548 | methyldibenzofuran | methylphenyl |
| D549 | methyldibenzofuran | methylphenyl |
| D550 | methyldibenzofuran | methyldibenzofuran |
| D551 | methyldibenzofuran | methyldibenzofuran |
| D552 | methyldibenzofuran | methyldibenzofuran |

TABLE 39

| compound | $R_2$ | $R_3$ | $R_5$ | $R_6$ | $R_7$ | $R_8$ | $R_9$ | $R_{10}$ | $L_1$ | $L_2$ | $L_3$ | $Ar_1$ | $Ar_2$ |
|---|---|---|---|---|---|---|---|---|---|---|---|---|---|
| D553 | H | H | H | H | H | H | H | H | — | — | — | methyldibenzothiophene | methylphenyl |
| D554 | H | H | H | H | H | H | H | H | — | — | — | methyldibenzothiophene | 9,9-dimethyl-methylfluorene |

TABLE 39-continued
| compound | R₂ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D555 | H | H | H | H | H | H | H | H | — | — | — | 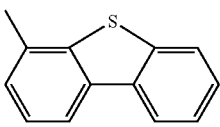 | 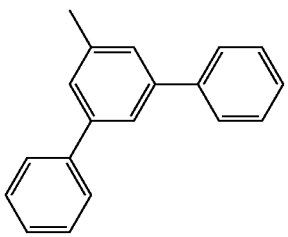 |
TABLE 40
| compound | R₂ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D556 | H | H | H | H | H | H | H | H | — | — | — | 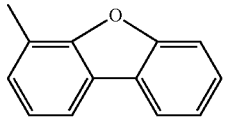 | 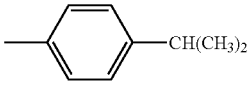 |
| D557 | H | H | H | H | H | H | H | H | — | — | — | 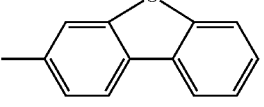 | 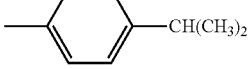 |
| D558 | H | H | H | H | H | H | H | H | — | — | — | 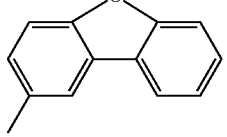 | 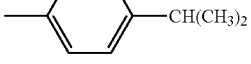 |
| D559 | H | H | H | H | H | H | H | H | — | — | — | 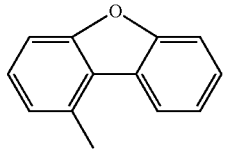 | 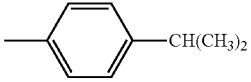 |
| D560 | H | H | H | H | H | H | H | H | — | — | — | 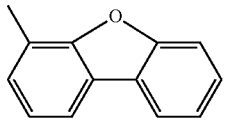 | 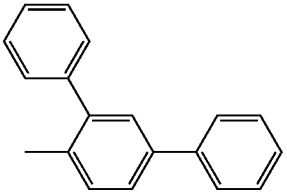 |
| D561 | H | H | H | H | H | H | H | H | — | — | — | 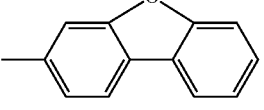 | 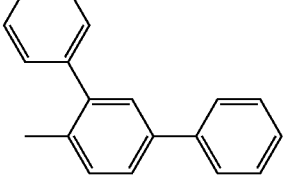 |
| D562 | H | H | H | H | H | H | H | H | — | — | — | 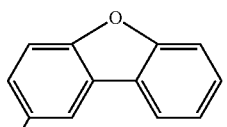 | 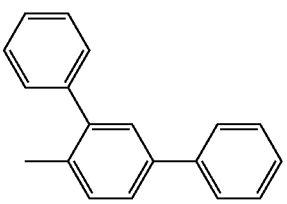 |

TABLE 40-continued

| compound | R₂ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D563 | H | H | H | H | H | H | H | H | — | — | — | 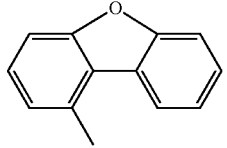 | 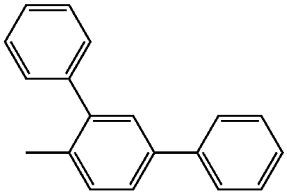 |

The specific examples of the aromatic amine derivative are the compounds having $R_1$ and $R_4$ in the same structure represented by the formula (2), however, not limited thereto. The aromatic amine derivative may be a compound having $R_1$ and $R_4$ in different structures.

In the aromatic amine derivative according to the exemplary embodiment, $R_1$ and $R_5$ in the formula (1) are preferably represented by the formula (2). At this instance, the aromatic amine derivative has a structure represented by the following formula (1C).

[Formula 13]

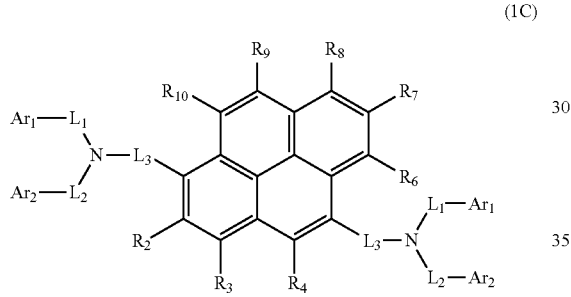

(1C)

Specific examples of the aromatic amine derivative according to the exemplary embodiment are aromatic amine derivatives described in Tables 41 to 50 for $R_2$ to $R_4$, $R_6$ to $R_{10}$, $L_1$ to $L_3$, and $Ar_1$ to $Ar_2$ in the formula (1C). Note that "—" in $L_1$ to $L_3$ of the tables represents a single bond. Moreover, in $L_1$ to $L_3$ and $Ar_1$ to $Ar_2$ in the tables, a line extending outward from the cyclic structure and having no chemical formula (e.g., $CH_3$, Ph, CN, benzene ring) at an end of the line represents a single bond, not a methyl group. For instance, in the following compound D1001, $Ar_1$ has a single bond at a position 4 of a dibenzofuran ring. In short, $Ar_1$ represents a 4-dibenzofuranyl group. Likewise, $Ar_2$ represents a phenyl group.

TABLE 41

| compound | R₂ | R₃ | R₄ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D1001 | H | H | H | H | H | H | H | H | — | — | — | 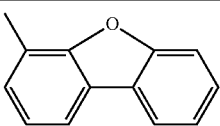 | 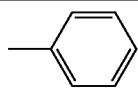 |
| D1002 | H | H | H | H | H | H | H | H | — | — | — | 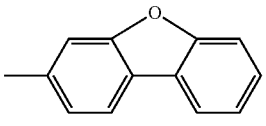 | 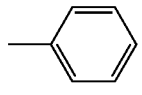 |
| D1003 | H | H | H | H | H | H | H | H | — | — | — | 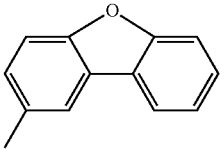 | 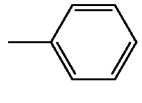 |
| D1004 | H | H | H | H | H | H | H | H | — | — | — | 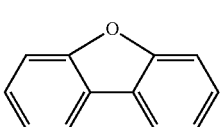 | 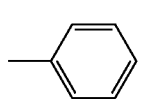 |

TABLE 41-continued
| compound | R₂ | R₃ | R₄ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D1005 | H | H | H | H | H | H | H | H | — | — | — | 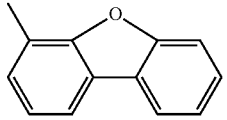 | 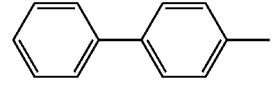 |
| D1006 | H | H | H | H | H | H | H | H | — | — | — | 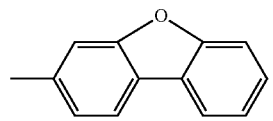 | 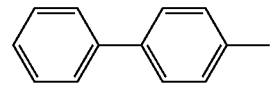 |
| D1007 | H | H | H | H | H | H | H | H | — | — | — | 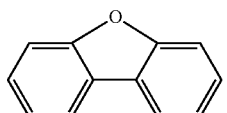 | 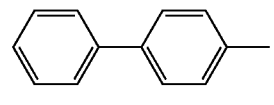 |
| D1008 | H | H | H | H | H | H | H | H | — | — | — | 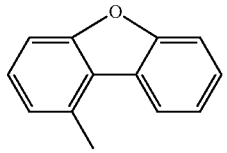 | 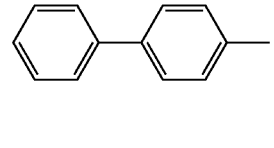 |
TABLE 42
| compound | R₂ | R₃ | R₄ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D1009 | H | H | H | H | H | H | H | H | — | — | — | 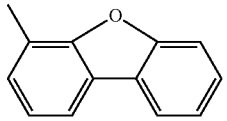 | 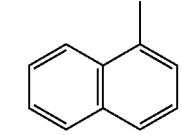 |
| D1010 | H | H | H | H | H | H | H | H | — | — | — | 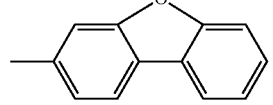 | 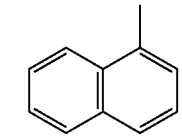 |
| D1011 | H | H | H | H | H | H | H | H | — | — | — | 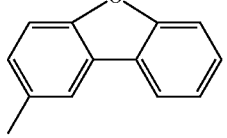 | 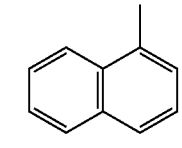 |
| D1012 | H | H | H | H | H | H | H | H | — | — | — | 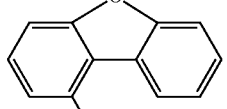 | 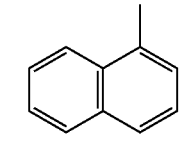 |
| D1013 | H | H | H | H | H | H | H | H | — | — | — | 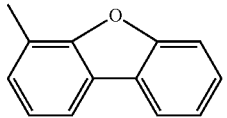 | 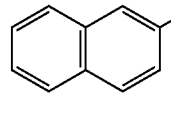 |

TABLE 42-continued
| compound | R₂ | R₃ | R₄ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D1014 | H | H | H | H | H | H | H | H | — | — | — | 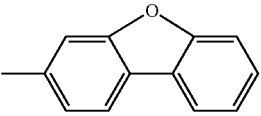 | 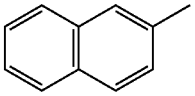 |
| D1015 | H | H | H | H | H | H | H | H | — | — | — | 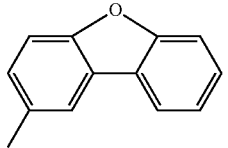 | 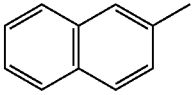 |
| D1016 | H | H | H | H | H | H | H | H | — | — | — | 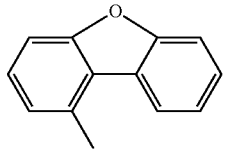 | 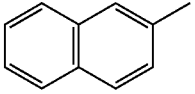 |
TABLE 43
| compound | R₂ | R₃ | R₄ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D1017 | H | H | H | H | H | H | H | H | — | — | — | 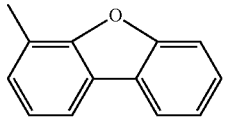 | 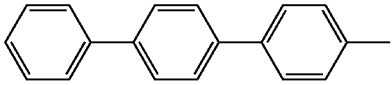 |
| D1018 | H | H | H | H | H | H | H | H | — | — | — | 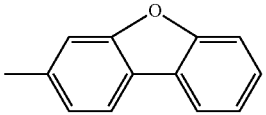 | 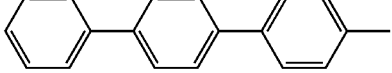 |
| D1019 | H | H | H | H | H | H | H | H | — | — | — | 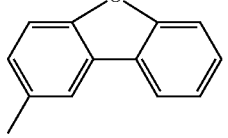 | 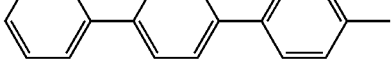 |
| D1020 | H | H | H | H | H | H | H | H | — | — | — | 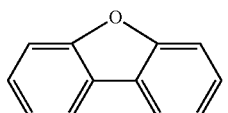 | 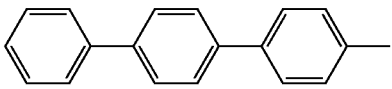 |
| D1021 | H | H | H | H | H | H | H | H | — | — | — | 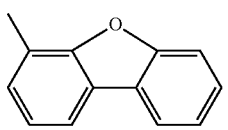 | 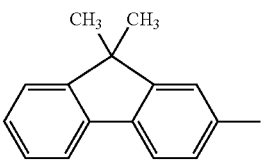 |
| D1022 | H | H | H | H | H | H | H | H | — | — | — | 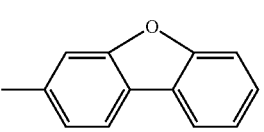 | 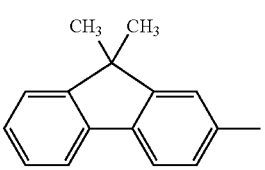 |

TABLE 43-continued
| compound | R₂ | R₃ | R₄ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D1023 | H | H | H | H | H | H | H | H | — | — | — | 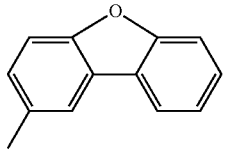 | 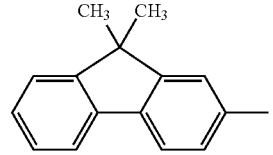 |
| D1024 | H | H | H | H | H | H | H | H | — | — | — | 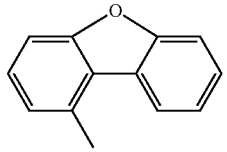 | 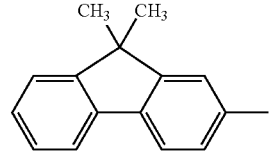 |
TABLE 44
| compound | R₂ | R₃ | R₄ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D1025 | H | H | H | H | H | H | H | H | — | — | — | 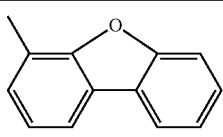 | 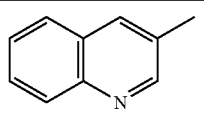 |
| D1026 | H | H | H | H | H | H | H | H | — | — | — | 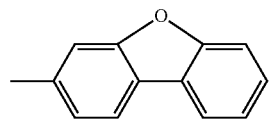 | 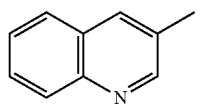 |
| D1027 | H | H | H | H | H | H | H | H | — | — | — | 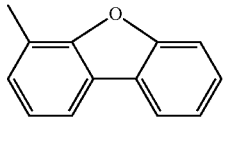 | 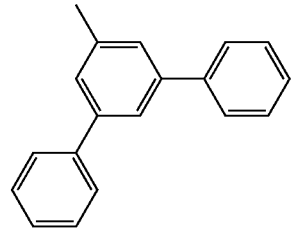 |
| D1028 | H | H | H | H | H | H | H | H | — | — | — | 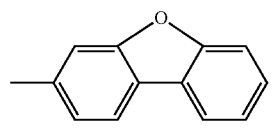 | 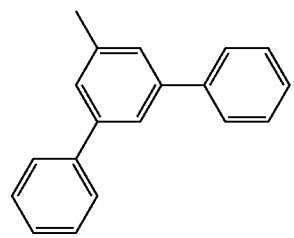 |
| D1029 | H | H | H | H | H | H | H | H | — | — | — | 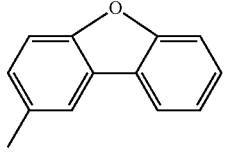 | 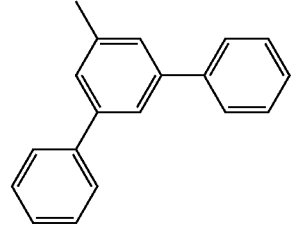 |

TABLE 44-continued
| compound | R₂ | R₃ | R₄ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D1030 | H | H | H | H | H | H | H | H | — | — | — |  |  |
TABLE 45
| compound | R₂ | R₃ | R₄ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D1031 | H | H | H | H | H | H | H | H | — | — | — | 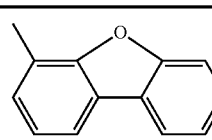 | 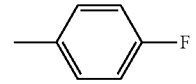 |
| D1032 | H | H | H | H | H | H | H | H | — | — | — | 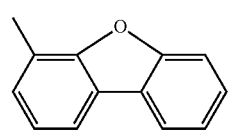 | 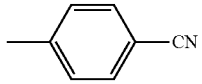 |
| D1033 | H | H | H | H | H | H | H | H | — | — | — | 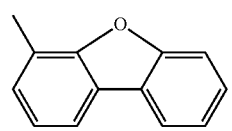 | 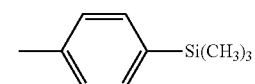 |
| D1034 | H | H | H | H | H | H | H | H | — | — | — | 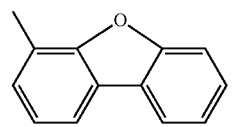 | 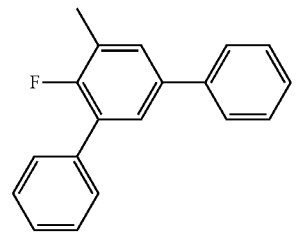 |
| D1035 | H | H | H | H | H | H | H | H | — | — | — | 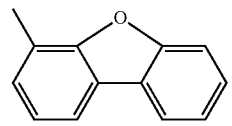 | 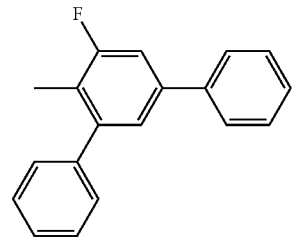 |
TABLE 46
| compound | R₂ | R₃ | R₄ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D1036 | H | H | H | H | H | H | H | H | — | — | — | 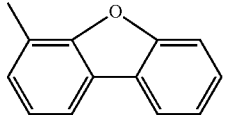 | 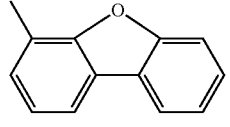 |

TABLE 46-continued
| compound | R₂ | R₃ | R₄ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D1037 | H | H | H | H | H | H | H | H | — | — | — | 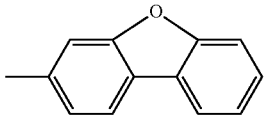 | 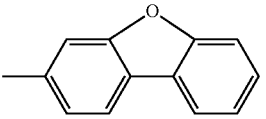 |
| D1038 | H | H | H | H | H | H | H | H | — | — | — | 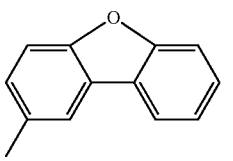 | 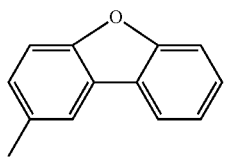 |
| D1039 | H | H | H | H | H | H | H | H | — | — | — | 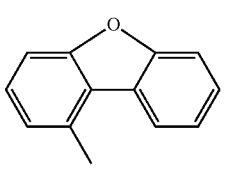 | 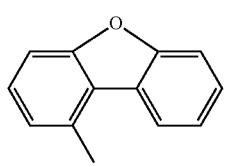 |
TABLE 47
| compound | R₂ | R₃ | R₄ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D1040 | H | H | H | H | H | H | H | H | — | — | — | 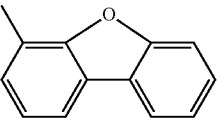 | 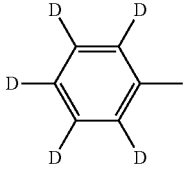 |
| D1041 | H | H | H | H | H | H | H | H | — | — | — | 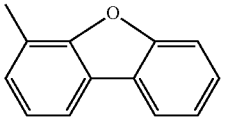 | 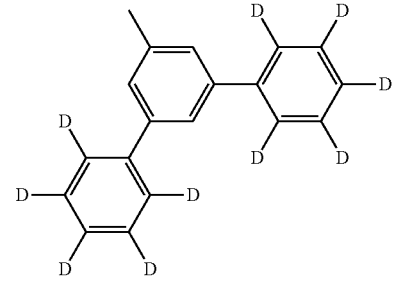 |
| D1042 | H | H | H | H | H | H | H | H | — | — | — | 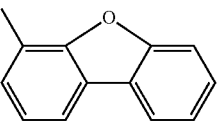 | 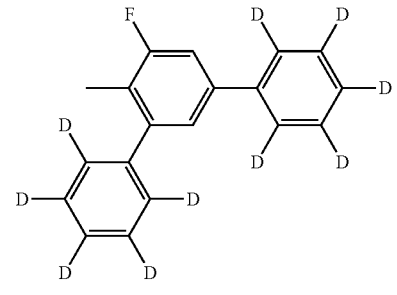 |

TABLE 47-continued
| compound | R₂ | R₃ | R₄ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D1043 | H | H | H | H | H | H | H | H | — | — | — | 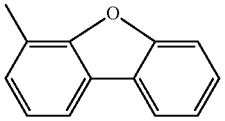 | 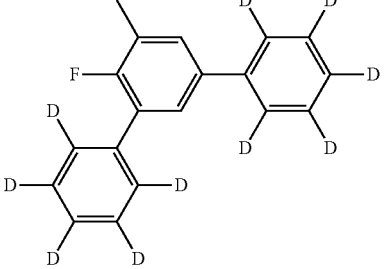 |
| D1044 | H | H | H | H | H | H | H | H | — | — | — | 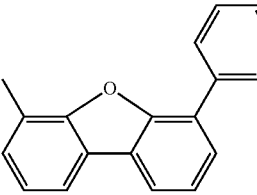 | 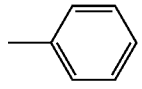 |
| D1045 | H | H | H | H | H | H | H | H | — | — | — | 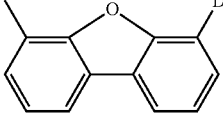 | 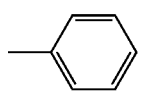 |
TABLE 48
| compound | R₂ | R₃ | R₄ | R₆ | R₇ | R₈ | R₉ | R₁₀ | L₁ | L₂ | L₃ |
|---|---|---|---|---|---|---|---|---|---|---|---|
| D1046 | H | H | H | H | H | H | H | H |  | — | — |
| D1047 | H | H | H | H | H | H | H | H | 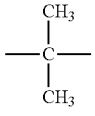 | — | — |
| D1048 | H | H | H | H | H | H | H | H | — | 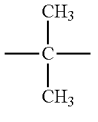 | — |
| D1049 | H | H | H | H | H | H | H | H | — | — | 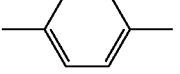 |
| D1050 | H | H | H | H | H | H | H | H |  | 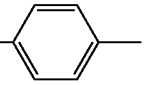 | — |
| D1051 | H | H | H | H | H | H | H | H | 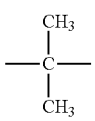 | 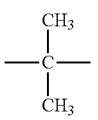 | — |

TABLE 48-continued

| compound | R2 | R3 | R4 | R6 | R7 | R8 | R9 | R10 | L1 | L2 | L3 | Ar1 | Ar2 |
|---|---|---|---|---|---|---|---|---|---|---|---|---|---|
| D1052 | H | H | H | H | H | H | H | H | — | — | | | 2,4-dimethylphenyl |

| compound | Ar1 | Ar2 |
|---|---|---|
| D1046 | methyl-dibenzofuran | phenyl |
| D1047 | methyl-dibenzofuran | phenyl |
| D1048 | methyl-dibenzofuran | phenyl |
| D1049 | methyl-dibenzofuran | phenyl |
| D1050 | methyl-dibenzofuran | methyl-dibenzofuran |
| D1051 | methyl-dibenzofuran | methyl-dibenzofuran |
| D1052 | methyl-dibenzofuran | methyl-dibenzofuran |

TABLE 49

| compound | R2 | R3 | R4 | R6 | R7 | R8 | R9 | R10 | L1 | L2 | L3 | Ar1 | Ar2 |
|---|---|---|---|---|---|---|---|---|---|---|---|---|---|
| D1053 | H | H | H | H | H | H | H | H | — | — | — | methyl-dibenzothiophene | phenyl |
| D1054 | H | H | H | H | H | H | H | H | — | — | — | methyl-dibenzothiophene | 9,9-dimethylfluorenyl |

TABLE 49-continued
| compound | R$_2$ | R$_3$ | R$_4$ | R$_6$ | R$_7$ | R$_8$ | R$_9$ | R$_{10}$ | L$_1$ | L$_2$ | L$_3$ | Ar$_1$ | Ar$_2$ |
|---|---|---|---|---|---|---|---|---|---|---|---|---|---|
| D1055 | H | H | H | H | H | H | H | H | — | — | — | 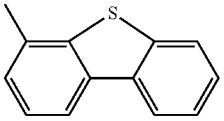 | 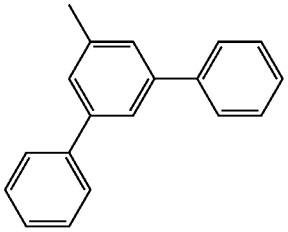 |
TABLE 50
| compound | R$_2$ | R$_3$ | R$_4$ | R$_6$ | R$_7$ | R$_8$ | R$_9$ | R$_{10}$ | L$_1$ | L$_2$ | L$_3$ | Ar$_1$ | Ar$_2$ |
|---|---|---|---|---|---|---|---|---|---|---|---|---|---|
| D1056 | H | H | H | H | H | H | H | H | — | — | — | 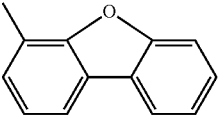 | 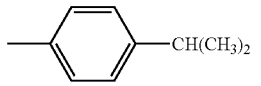 |
| D1057 | H | H | H | H | H | H | H | H | — | — | — | 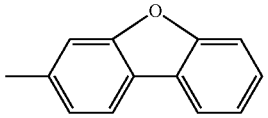 | 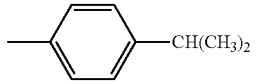 |
| D1058 | H | H | H | H | H | H | H | H | — | — | — | 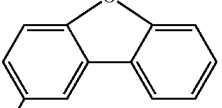 | 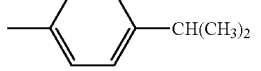 |
| D1059 | H | H | H | H | H | H | H | H | — | — | — | 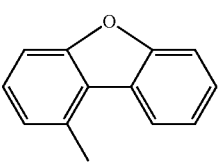 | 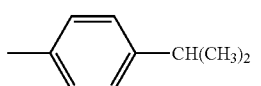 |
| D1060 | H | H | H | H | H | H | H | H | — | — | — | 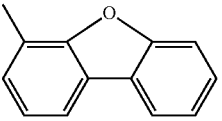 | 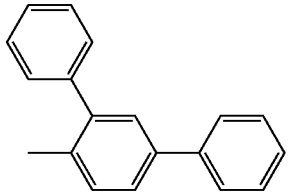 |
| D1061 | H | H | H | H | H | H | H | H | — | — | — | 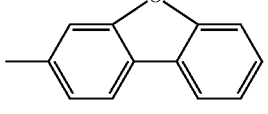 | 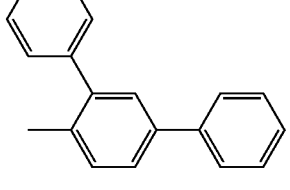 |
| D1062 | H | H | H | H | H | H | H | H | — | — | — | 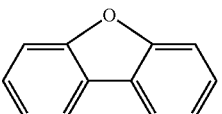 | 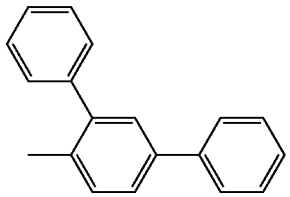 |

TABLE 50-continued

| compound | R₂ | R₃ | R₄ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D1063 | H | H | H | H | H | H | H | H | — | — | — | (1-methyldibenzofuran-4-yl) | (2-methyl-[1,1':4',1''-terphenyl]) |

The specific examples of the aromatic amine derivative are the compounds having $R_1$ and $R_5$ in the same structure represented by the formula (2), however, not limited thereto. The aromatic amine derivative may be a compound having $R_1$ and $R_5$ in different structures.

In the aromatic amine derivative according to the exemplary embodiment, $R_1$ and $R_8$ in the formula (1) are preferably represented by the formula (2). At this instance, the aromatic amine derivative has a structure represented by the following formula (1D).

[Formula 14]

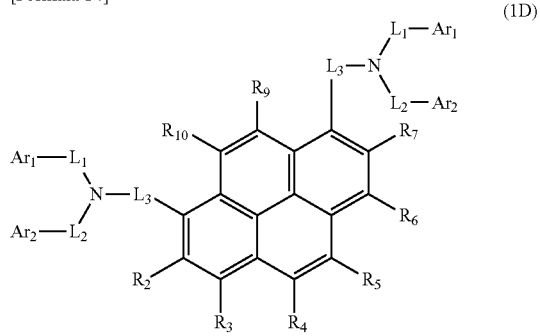

(1D)

Specific examples of the aromatic amine derivative according to the exemplary embodiment are aromatic amine derivatives described in Tables 51 to 81 for $R_2$ to $R_7$, $R_9$, $R_{10}$, $L_1$ to $L_3$, and $Ar_1$ to $Ar_2$ in the formula (1D). Note that "—" in $L_1$ to $L_3$ of the tables represents a single bond. Moreover, in $L_1$ to $L_3$ and $Ar_1$ to $Ar_2$ in the tables, a line extending outward from the cyclic structure and having no chemical formula (e.g., CH₃, Ph, CN, benzene ring) at an end of the line represents a single bond, not a methyl group. For instance, in the following compound D1501, $Ar_1$ has a single bond at a position 4 of a dibenzofuran ring. In short, $Ar_1$ represents a 4-dibenzofuranyl group. Likewise, $Ar_2$ represents a phenyl group.

TABLE 51

| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1501 | H | H | H | H | H | H | H | H | — | — | — | (4-dibenzofuranyl) | (phenyl) |
| D1502 | H | H | H | H | H | H | H | H | — | — | — | (dibenzofuranyl) | (phenyl) |
| D1503 | H | H | H | H | H | H | H | H | — | — | — | (dibenzofuranyl) | (phenyl) |

TABLE 51-continued
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1504 | H | H | H | H | H | H | H | H | — | — | — | 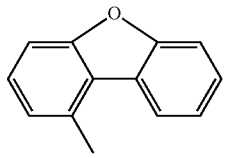 | 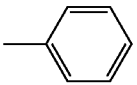 |
| D1505 | H | H | H | H | H | H | H | H | — | — | — | 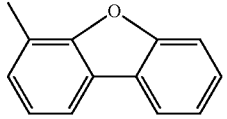 | 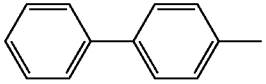 |
| D1506 | H | H | H | H | H | H | H | H | — | — | — | 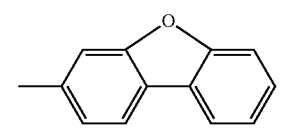 | 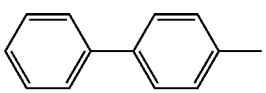 |
| D1507 | H | H | H | H | H | H | H | H | — | — | — | 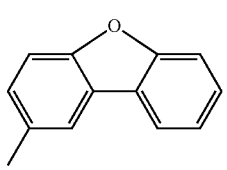 | 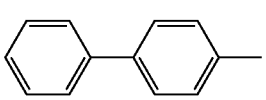 |
| D1508 | H | H | H | H | H | H | H | H | — | — | — | 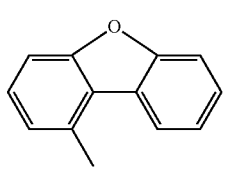 | 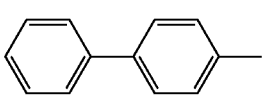 |
TABLE 52
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1509 | H | H | H | H | H | H | H | H | — | — | — | 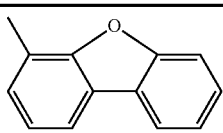 | 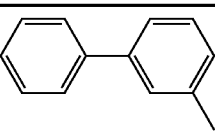 |
| D1510 | H | H | H | H | H | H | H | H | — | — | — | 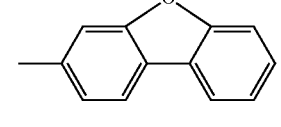 | 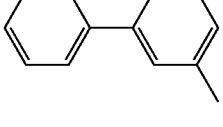 |
| D1511 | H | H | H | H | H | H | H | H | — | — | — | 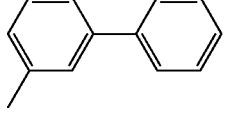 | 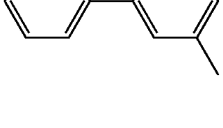 |
| D1512 | H | H | H | H | H | H | H | H | — | — | — | 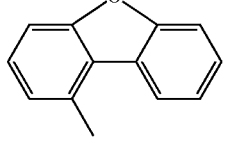 | 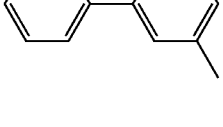 |

TABLE 52-continued
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1513 | H | H | H | H | H | H | H | H | — | — | — | 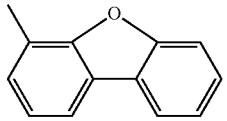 | 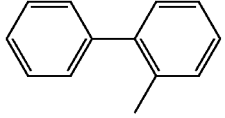 |
| D1514 | H | H | H | H | H | H | H | H | — | — | — | 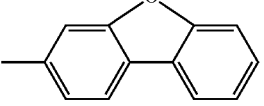 | 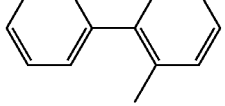 |
| D1515 | H | H | H | H | H | H | H | H | — | — | — | 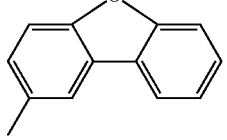 | 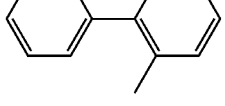 |
| D1516 | H | H | H | H | H | H | H | H | — | — | — | 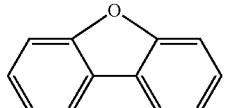 | 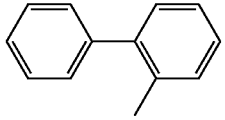 |
TABLE 53
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1517 | H | H | H | H | H | H | H | H | — | — | — | 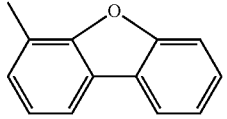 | 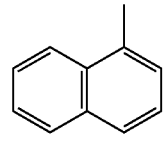 |
| D1518 | H | H | H | H | H | H | H | H | — | — | — | 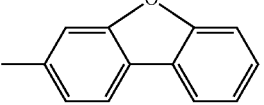 | 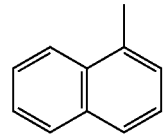 |
| D1519 | H | H | H | H | H | H | H | H | — | — | — | 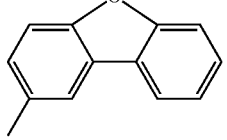 | 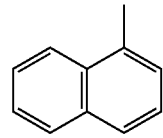 |
| D1520 | H | H | H | H | H | H | H | H | — | — | — | 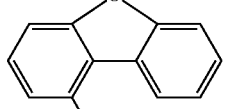 | 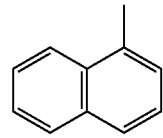 |
| D1521 | H | H | H | H | H | H | H | H | — | — | — | 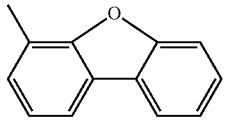 | 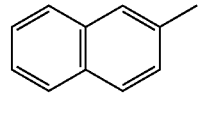 |

TABLE 53-continued
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1522 | H | H | H | H | H | H | H | H | — | — | — | 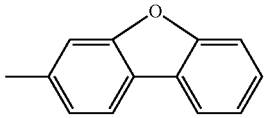 | 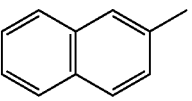 |
| D1523 | H | H | H | H | H | H | H | H | — | — | — | 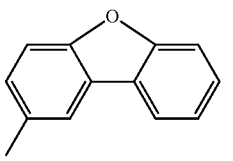 | 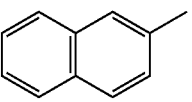 |
| D1524 | H | H | H | H | H | H | H | H | — | — | — | 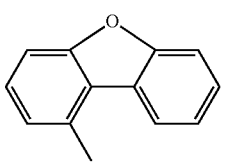 | 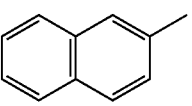 |
TABLE 54
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1525 | H | H | H | H | H | H | H | H | — | — | — | 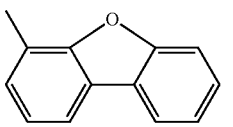 | 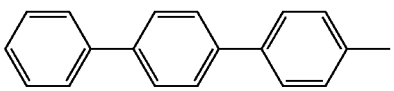 |
| D1526 | H | H | H | H | H | H | H | H | — | — | — | 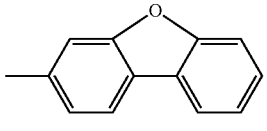 | 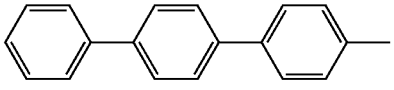 |
| D1527 | H | H | H | H | H | H | H | H | — | — | — | 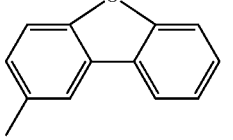 | 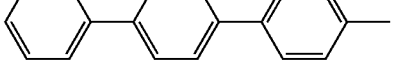 |
| D1528 | H | H | H | H | H | H | H | H | — | — | — | 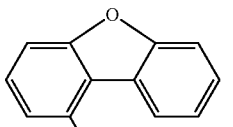 | 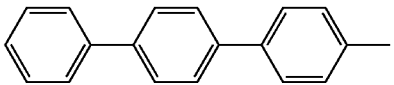 |
| D1529 | H | H | H | H | H | H | H | H | — | — | — | 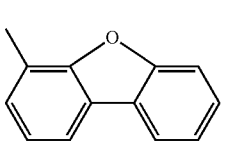 |  |
| D1530 | H | H | H | H | H | H | H | H | — | — | — | 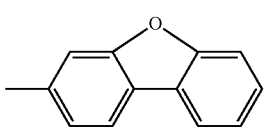 |  |

TABLE 54-continued
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1531 | H | H | H | H | H | H | H | H | — | — | — | 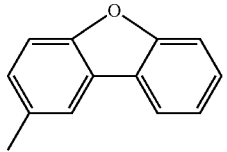 | 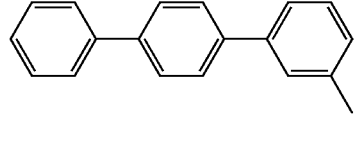 |
| D1532 | H | H | H | H | H | H | H | H | — | — | — | 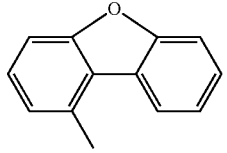 | 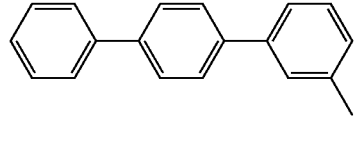 |
TABLE 55
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1533 | H | H | H | H | H | H | H | H | — | — | — | 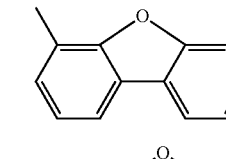 | 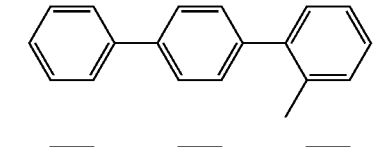 |
| D1534 | H | H | H | H | H | H | H | H | — | — | — | 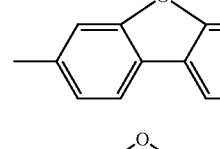 | 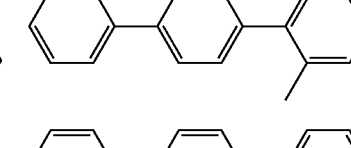 |
| D1535 | H | H | H | H | H | H | H | H | — | — | — | 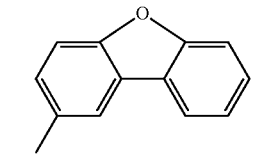 | 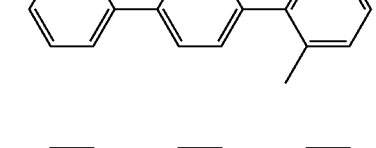 |
| D1536 | H | H | H | H | H | H | H | H | — | — | — | 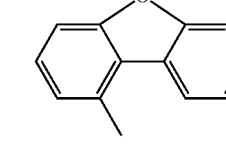 | 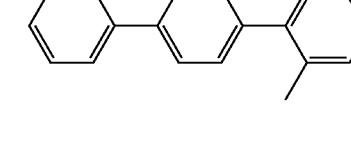 |
| D1537 | H | H | H | H | H | H | H | H | — | — | — | 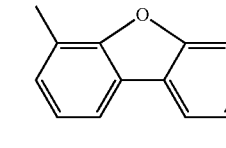 | 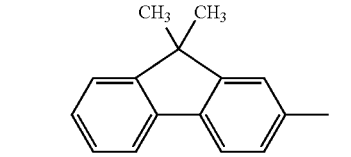 |
| D1538 | H | H | H | H | H | H | H | H | — | — | — | 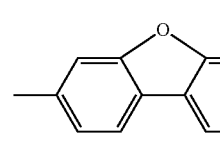 | 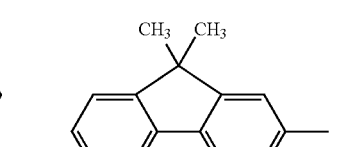 |
| D1539 | H | H | H | H | H | H | H | H | — | — | — | 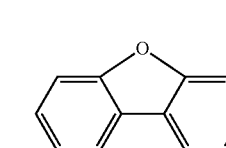 | 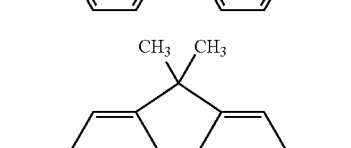 |

TABLE 55-continued
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1540 | H | H | H | H | H | H | H | H | — | — | — | 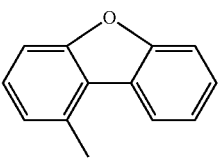 | 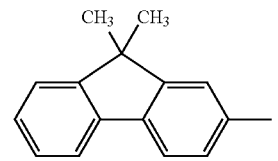 |
TABLE 56
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1541 | H | H | H | H | H | H | H | H | — | — | — | 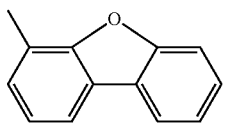 | 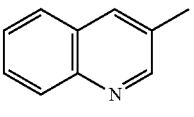 |
| D1542 | H | H | H | H | H | H | H | H | — | — | — | 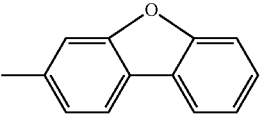 | 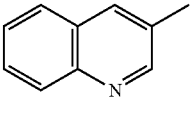 |
| D1543 | H | H | H | H | H | H | H | H | — | — | — | 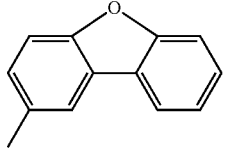 | 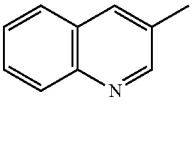 |
| D1544 | H | H | H | H | H | H | H | H | — | — | — | 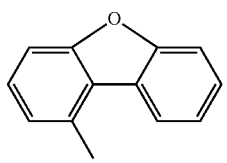 | 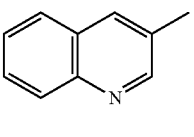 |
| D1545 | H | H | H | H | H | H | H | H | — | — | — | 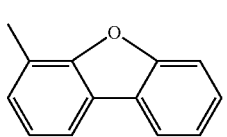 | 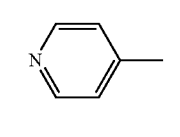 |
| D1546 | H | H | H | H | H | H | H | H | — | — | — | 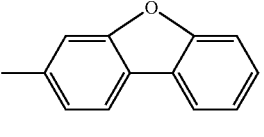 | 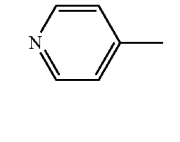 |
| D1547 | H | H | H | H | H | H | H | H | — | — | — | 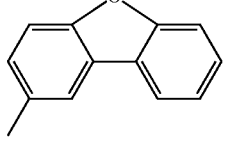 | 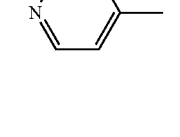 |
| D1548 | H | H | H | H | H | H | H | H | — | — | — | 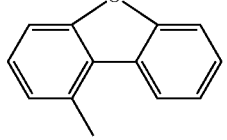 | 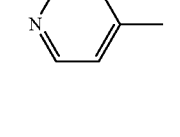 |

TABLE 57
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1549 | H | H | H | H | H | H | H | H | — | — | — | 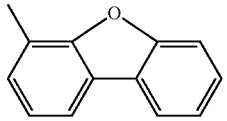 | 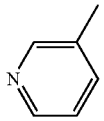 |
| D1550 | H | H | H | H | H | H | H | H | — | — | — | 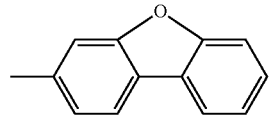 | 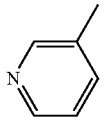 |
| D1551 | H | H | H | H | H | H | H | H | — | — | — | 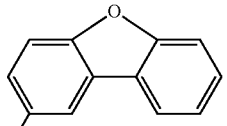 | 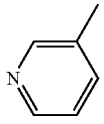 |
| D1552 | H | H | H | H | H | H | H | H | — | — | — | 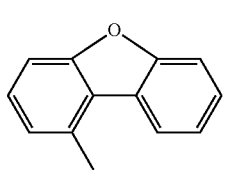 | 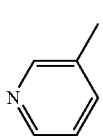 |
| D1553 | H | H | H | H | H | H | H | H | — | — | — | 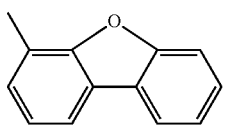 | 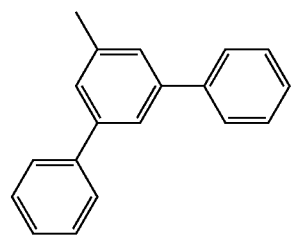 |
| D1554 | H | H | H | H | H | H | H | H | — | — | — | 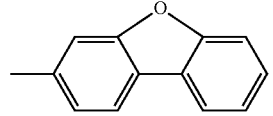 | 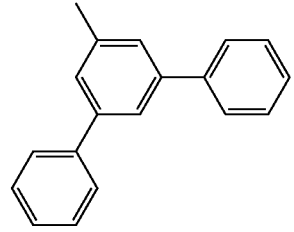 |
| D1555 | H | H | H | H | H | H | H | H | — | — | — | 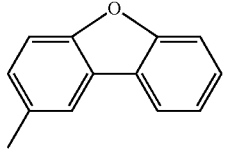 | 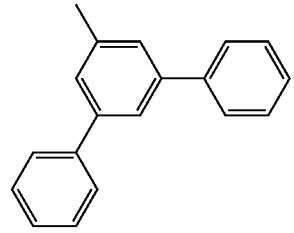 |
| D1556 | H | H | H | H | H | H | H | H | — | — | — | 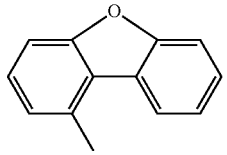 | 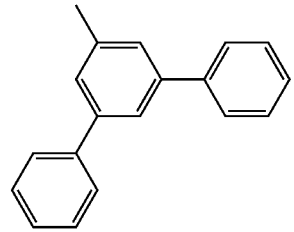 |

TABLE 58
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1557 | H | H | H | H | H | H | H | H | — | — | — | 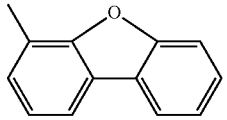 | 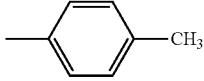 |
| D1558 | H | H | H | H | H | H | H | H | — | — | — | 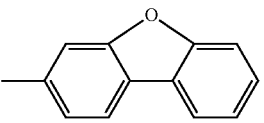 | 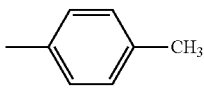 |
| D1559 | H | H | H | H | H | H | H | H | — | — | — |  |  |
| D1560 | H | H | H | H | H | H | H | H | — | — | — | 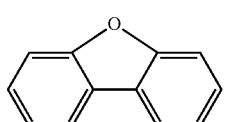 | 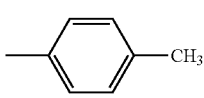 |
TABLE 59
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1561 | H | H | H | H | H | H | H | H | — | — | — | 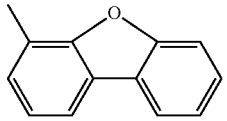 | 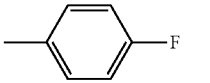 |
| D1562 | H | H | H | H | H | H | H | H | — | — | — | 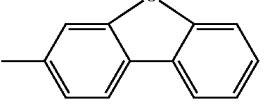 | 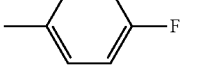 |
| D1563 | H | H | H | H | H | H | H | H | — | — | — | 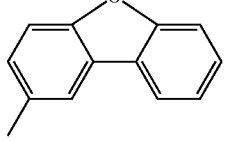 | 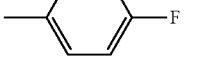 |
| D1564 | H | H | H | H | H | H | H | H | — | — | — | 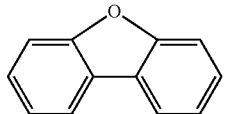 | 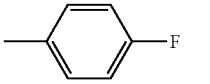 |
| D1565 | H | H | H | H | H | H | H | H | — | — | — | 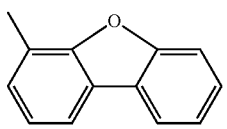 | 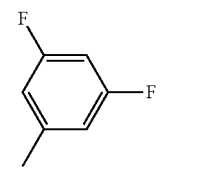 |

TABLE 59-continued

| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1566 | H | H | H | H | H | H | H | H | — | — | — | methyl-dibenzofuran | 3,5-difluorophenyl |
| D1567 | H | H | H | H | H | H | H | H | — | — | — | methyl-dibenzofuran | 3,5-difluorophenyl |
| D1568 | H | H | H | H | H | H | H | H | — | — | — | methyl-dibenzofuran | 3,5-difluorophenyl |

TABLE 60

| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1569 | H | H | H | H | H | H | H | H | — | — | — | methyl-dibenzofuran | 2,4-difluorophenyl |
| D1570 | H | H | H | H | H | H | H | H | — | — | — | methyl-dibenzofuran | 2,4-difluorophenyl |
| D1571 | H | H | H | H | H | H | H | H | — | — | — | methyl-dibenzofuran | 2,4-difluorophenyl |
| D1572 | H | H | H | H | H | H | H | H | — | — | — | methyl-dibenzofuran | 2,4-difluorophenyl |
| D1573 | H | H | H | H | H | H | H | H | — | — | — | methyl-dibenzofuran | 4-cyanophenyl |
| D1574 | H | H | H | H | H | H | H | H | — | — | — | methyl-dibenzofuran | 4-cyanophenyl |

TABLE 60-continued
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1575 | H | H | H | H | H | H | H | H | — | — | — | 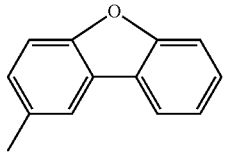 | 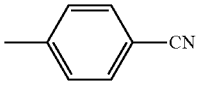 |
| D1576 | H | H | H | H | H | H | H | H | — | — | — | 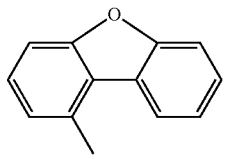 |  |
TABLE 61
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1577 | H | H | H | H | H | H | H | H | — | — | — | 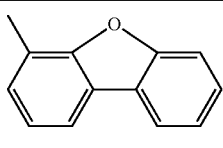 | 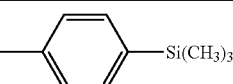 |
| D1578 | H | H | H | H | H | H | H | H | — | — | — | 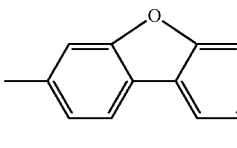 | 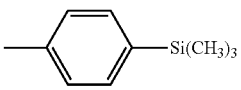 |
| D1579 | H | H | H | H | H | H | H | H | — | — | — | 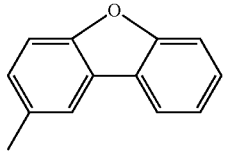 | 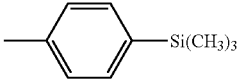 |
| D1580 | H | H | H | H | H | H | H | H | — | — | — | 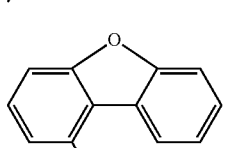 | 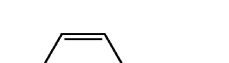 |
| D1581 | H | H | H | H | H | H | H | H | — | — | — | 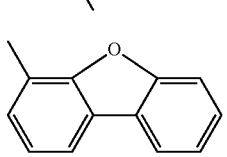 | 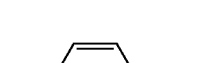 |
| D1582 | H | H | H | H | H | H | H | H | — | — | — | 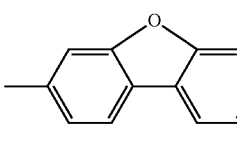 | 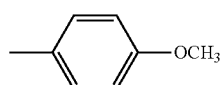 |
| D1583 | H | H | H | H | H | H | H | H | — | — | — | 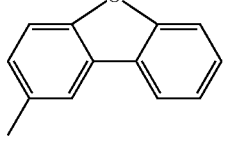 | 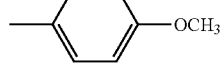 |

TABLE 61-continued
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1584 | H | H | H | H | H | H | H | H | — | — | — | 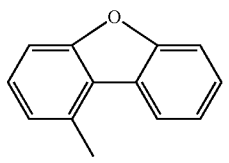 | 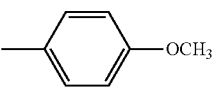 |
TABLE 62
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1585 | H | H | H | H | H | H | H | H | — | — | — | 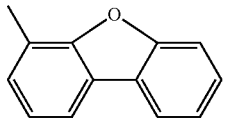 |  |
| D1586 | H | H | H | H | H | H | H | H | — | — | — | 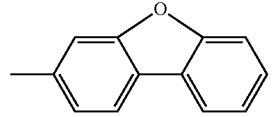 |  |
| D1587 | H | H | H | H | H | H | H | H | — | — | — | 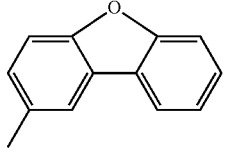 |  |
| D1588 | H | H | H | H | H | H | H | H | — | — | — | 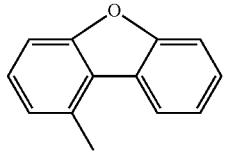 | 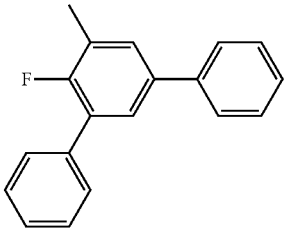 |

TABLE 63
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1589 | H | H | H | H | H | H | H | H | — | — | — | 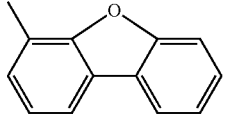 | 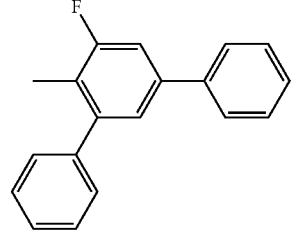 |
| D1590 | H | H | H | H | H | H | H | H | — | — | — | 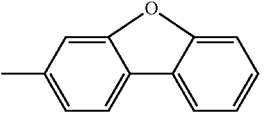 | 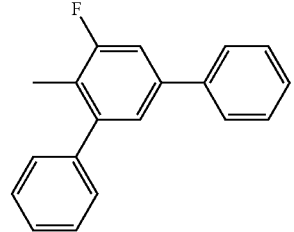 |
| D1591 | H | H | H | H | H | H | H | H | — | — | — | 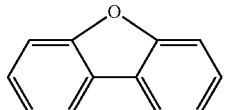 | 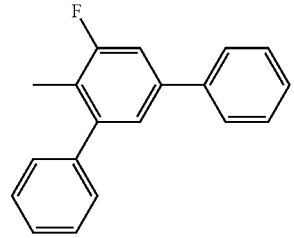 |
| D1592 | H | H | H | H | H | H | H | H | — | — | — | 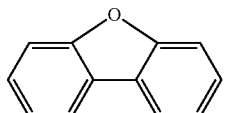 | 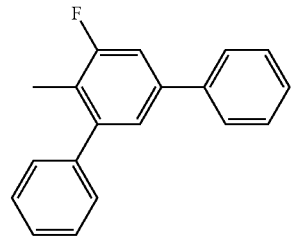 |
TABLE 64
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1593 | H | H | H | H | H | H | H | H | — | — | — | 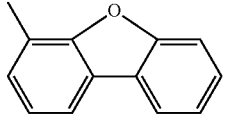 |  |
| D1594 | H | H | H | H | H | H | H | H | — | — | — | 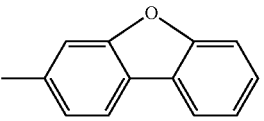 | 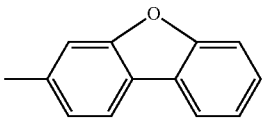 |
| D1595 | H | H | H | H | H | H | H | H | — | — | — | 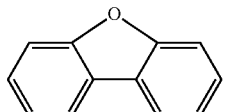 | 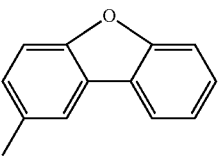 |

TABLE 64-continued
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1596 | H | H | H | H | H | H | H | H | — | — | — | 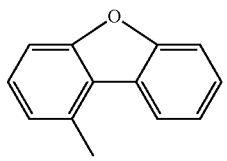 | 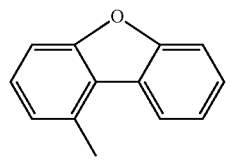 |
TABLE 65
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1597 | H | H | H | H | H | H | H | H | — | — | — | 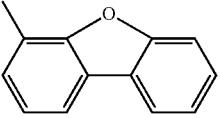 | 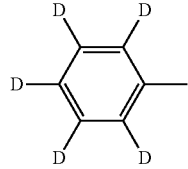 |
| D1598 | H | H | H | H | H | H | H | H | — | — | — | 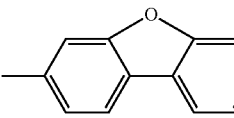 | 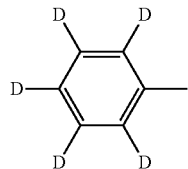 |
| D1599 | H | H | H | H | H | H | H | H | — | — | — | 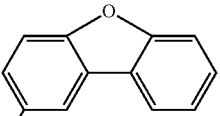 | 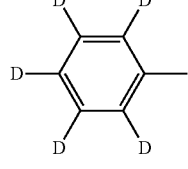 |
| D1600 | H | H | H | H | H | H | H | H | — | — | — | 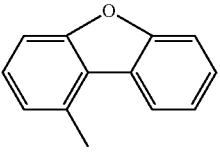 | 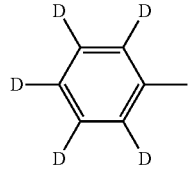 |
TABLE 66
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1601 | H | H | H | H | H | H | H | H | — | — | — | 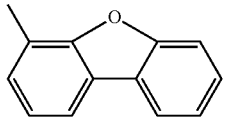 | 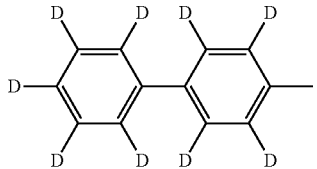 |
| D1602 | H | H | H | H | H | H | H | H | — | — | — | 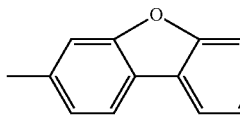 | 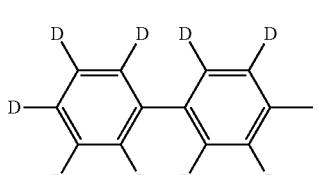 |

TABLE 66-continued
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1603 | H | H | H | H | H | H | H | H | — | — | — | 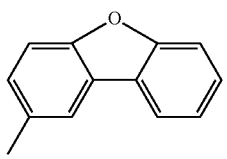 | 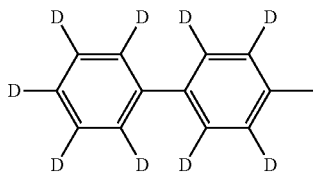 |
| D1604 | H | H | H | H | H | H | H | H | — | — | — | 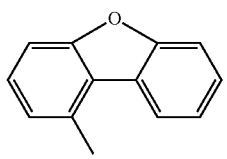 | 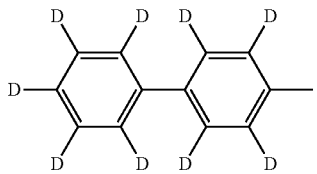 |
TABLE 67
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1605 | H | H | H | H | H | H | H | H | — | — | — | 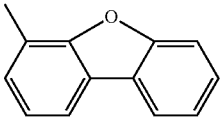 | 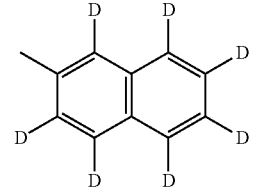 |
| D1606 | H | H | H | H | H | H | H | H | — | — | — | 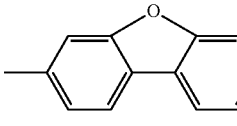 | 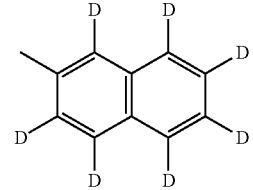 |
| D1607 | H | H | H | H | H | H | H | H | — | — | — | 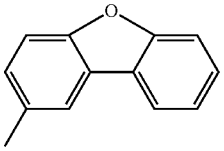 | 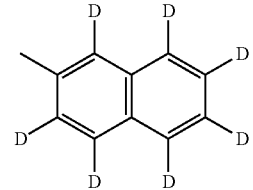 |
| D1608 | H | H | H | H | H | H | H | H | — | — | — | 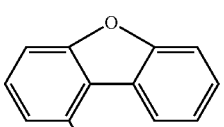 | 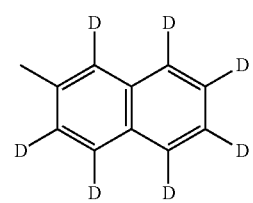 |

TABLE 68

| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1609 | H | H | H | H | H | H | H | H | — | — | — | (4-methyldibenzofuran) | (methyl-m-terphenyl-d9) |
| D1610 | H | H | H | H | H | H | H | H | — | — | — | (3-methyldibenzofuran) | (methyl-m-terphenyl-d9) |
| D1611 | H | H | H | H | H | H | H | H | — | — | — | (2-methyldibenzofuran) | (methyl-m-terphenyl-d9) |
| D1612 | H | H | H | H | H | H | H | H | — | — | — | (1-methyldibenzofuran) | (methyl-m-terphenyl-d9) |

TABLE 69

| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1613 | H | H | H | H | H | H | H | H | — | — | — | (4-methyldibenzofuran) | (fluoro-methyl-m-terphenyl-d8) |

TABLE 69-continued
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1614 | H | H | H | H | H | H | H | H | — | — | — | 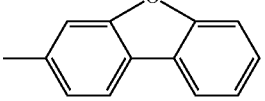 | 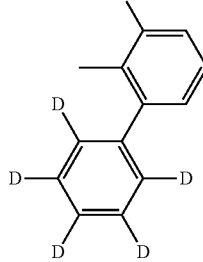 |
| D1615 | H | H | H | H | H | H | H | H | — | — | — | 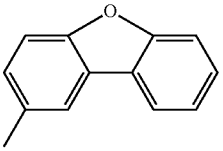 | 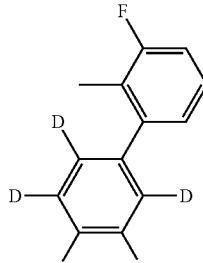 |
| D1616 | H | H | H | H | H | H | H | H | — | — | — | 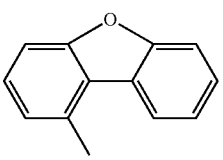 | 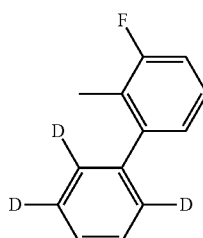 |
TABLE 70
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1617 | H | H | H | H | H | H | H | H | — | — | — | 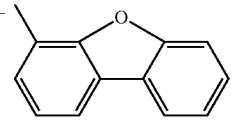 | 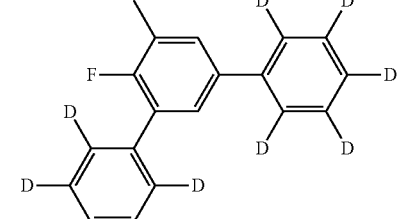 |
| D1618 | H | H | H | H | H | H | H | H | — | — | — | 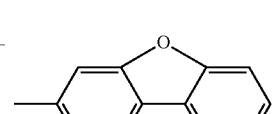 | 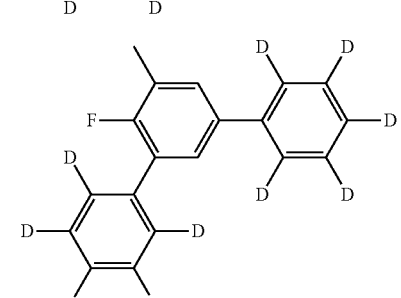 |

TABLE 70-continued
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1619 | H | H | H | H | H | H | H | H | — | — | — | 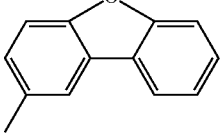 | 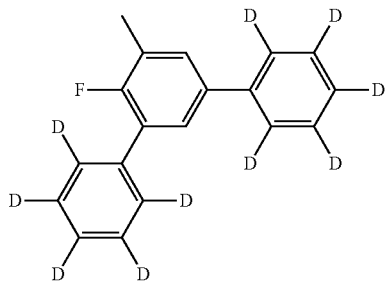 |
| D1620 | H | H | H | H | H | H | H | H | — | — | — | 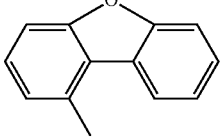 | 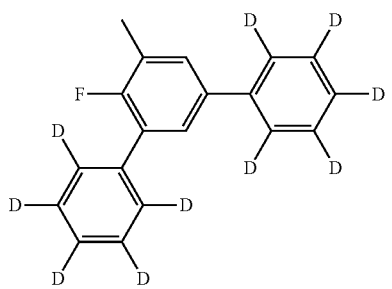 |
TABLE 71
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1621 | H | H | H | H | H | H | H | H | — | — | — | 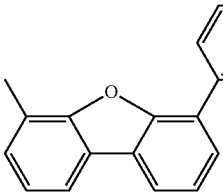 | 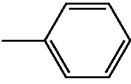 |
| D1622 | H | H | H | H | H | H | H | H | — | — | — | 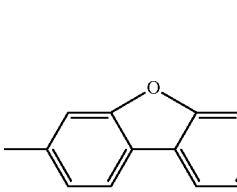 | 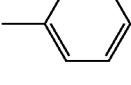 |
| D1623 | H | H | H | H | H | H | H | H | — | — | — | 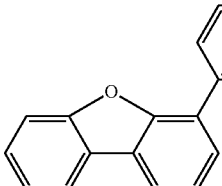 | 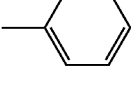 |
| D1624 | H | H | H | H | H | H | H | H | — | — | — | 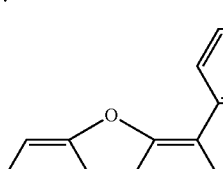 | 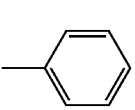 |

TABLE 72
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1625 | H | H | H | H | H | H | H | H | — | — | — | 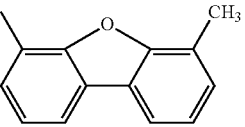 | 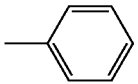 |
| D1626 | H | H | H | H | H | H | H | H | — | — | — | 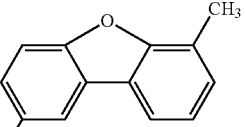 | 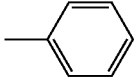 |
| D1627 | H | H | H | H | H | H | H | H | — | — | — | 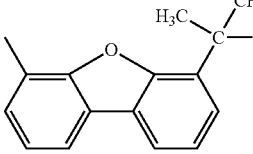 | 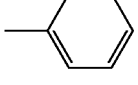 |
| D1628 | H | H | H | H | H | H | H | H | — | — | — | 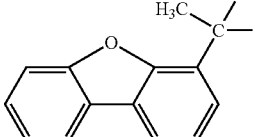 | 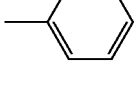 |
| D1629 | H | H | H | H | H | H | H | H | — | — | — | 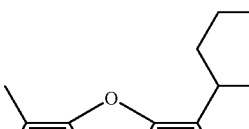 | 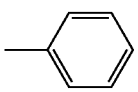 |
| D1630 | H | H | H | H | H | H | H | H | — | — | — |  | 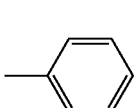 |
TABLE 73
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1631 | H | H | H | H | H | H | H | H | — | — | — | 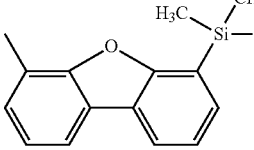 | 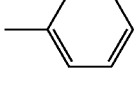 |

TABLE 73-continued
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1632 | H | H | H | H | H | H | H | H | — | — | — | 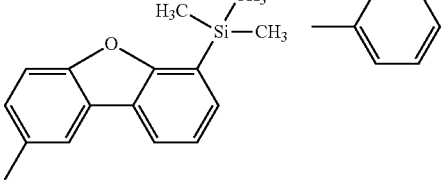 |  |
| D1633 | H | H | H | H | H | H | H | H | — | — | — | 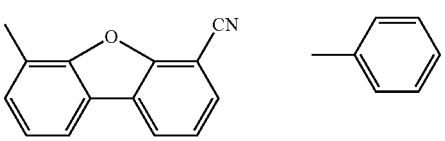 |  |
| D1634 | H | H | H | H | H | H | H | H | — | — | — | 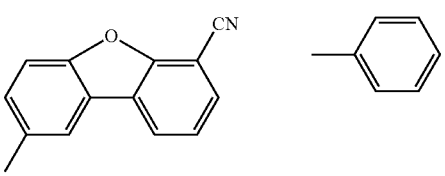 |  |
| D1635 | H | H | H | H | H | H | H | H | — | — | — | 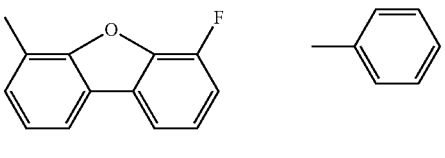 |  |
| D1636 | H | H | H | H | H | H | H | H | — | — | — | 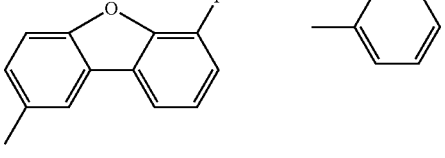 |  |
| D1637 | H | H | H | H | H | H | H | H | — | — | — | 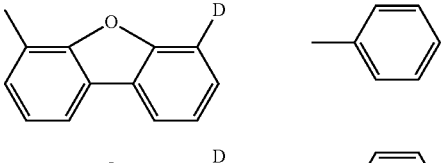 |  |
| D1638 | H | H | H | H | H | H | H | H | — | — | — | 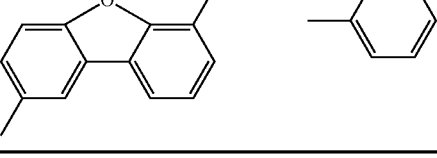 |  |
TABLE 74
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1639 | H | H | H | H | H | H | H | H | 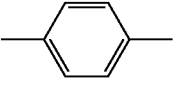 | — | — | 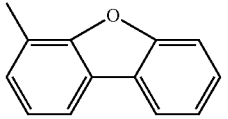 | 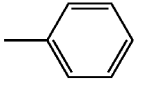 |
| D1640 | H | H | H | H | H | H | H | H | 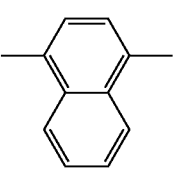 | — | — | 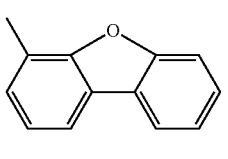 | 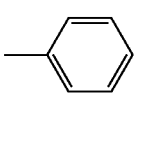 |

TABLE 74-continued
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1641 | H | H | H | H | H | H | H | H | 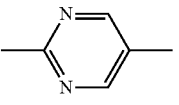 | — | — | 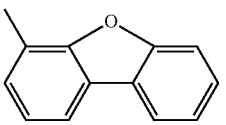 |  |
| D1642 | H | H | H | H | H | H | H | H | 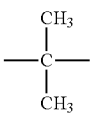 | — | — | 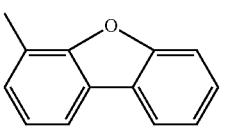 |  |
| D1643 | H | H | H | H | H | H | H | H | — | 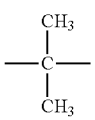 | — | 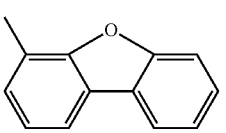 |  |
TABLE 75
| compound | R₂ | R₃ | R₄ | R₅ | R₆ | R₇ | R₉ | R₁₀ | L₁ | L₂ | L₃ |
|---|---|---|---|---|---|---|---|---|---|---|---|
| D1644 | H | H | H | H | H | H | H | H | — | — |  |
| D1645 | H | H | H | H | H | H | H | H | — | — |  |
| D1646 | H | H | H | H | H | H | H | H | — | — | 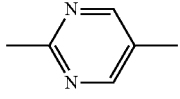 |
| D1647 | H | H | H | H | H | H | H | H |  | 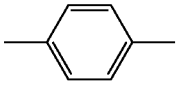 | — |
| D1648 | H | H | H | H | H | H | H | H | 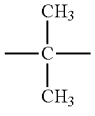 | 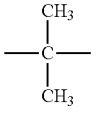 | — |
| D1649 | H | H | H | H | H | H | H | H | — | — |  |
| compound | Ar₁ | Ar₂ |
|---|---|---|
| D1644 | 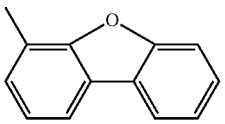 | 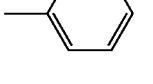 |
| D1645 | 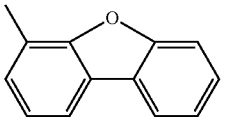 | 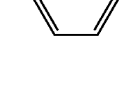 |

TABLE 75-continued
| | | |
|---|---|---|
| D1646 | 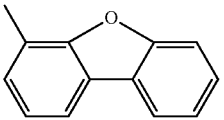 |  |
| D1647 | 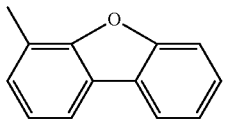 |  |
| D1648 | 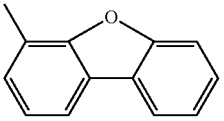 | 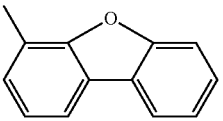 |
| D1649 | 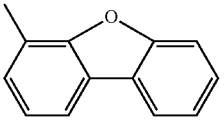 | 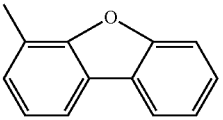 |
TABLE 76
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1650 | H | H | H | H | H | H | H | H | — | — | — | 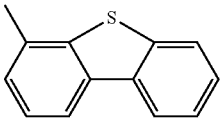 |  |
| D1651 | H | H | H | H | H | H | H | H | — | — | — | 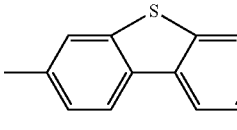 | 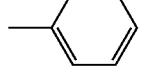 |
| D1652 | H | H | H | H | H | H | H | H | — | — | — | 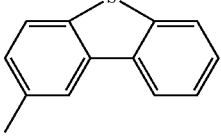 |  |
| D1653 | H | H | H | H | H | H | H | H | — | — | — | 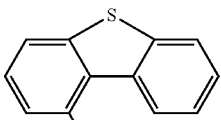 | 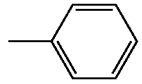 |
| D1654 | H | H | H | H | H | H | H | H | — | — | — | 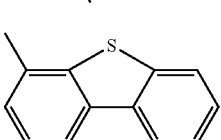 | 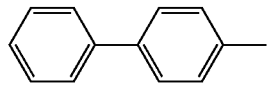 |
| D1655 | H | H | H | H | H | H | H | H | — | — | — | 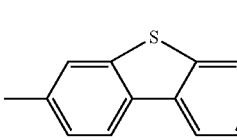 |  |

TABLE 76-continued
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1656 | H | H | H | H | H | H | H | H | — | — | — | 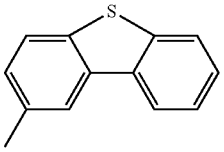 | 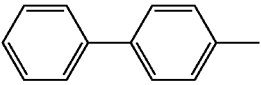 |
| D1657 | H | H | H | H | H | H | H | H | — | — | — | 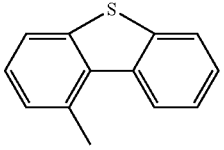 | 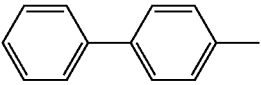 |
TABLE 77
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1658 | H | H | H | H | H | H | H | H | — | — | — | 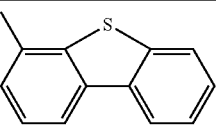 | 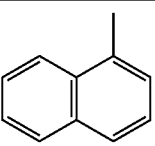 |
| D1659 | H | H | H | H | H | H | H | H | — | — | — | 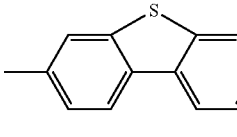 | 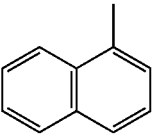 |
| D1660 | H | H | H | H | H | H | H | H | — | — | — | 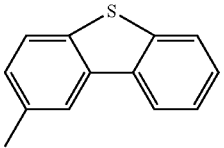 | 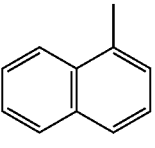 |
| D1661 | H | H | H | H | H | H | H | H | — | — | — | 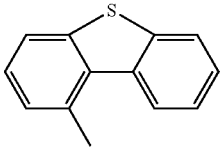 | 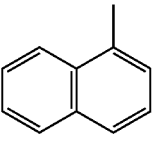 |
| D1662 | H | H | H | H | H | H | H | H | — | — | — | 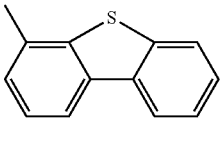 | 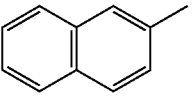 |
| D1663 | H | H | H | H | H | H | H | H | — | — | — | 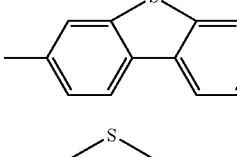 | 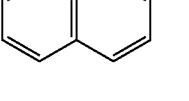 |
| D1664 | H | H | H | H | H | H | H | H | — | — | — | 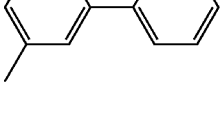 | 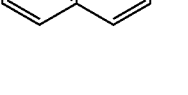 |

TABLE 77-continued
| compound | R$_2$ | R$_3$ | R$_4$ | R$_5$ | R$_6$ | R$_7$ | R$_9$ | R$_{10}$ | L$_1$ | L$_2$ | L$_3$ | Ar$_1$ | Ar$_2$ |
|---|---|---|---|---|---|---|---|---|---|---|---|---|---|
| D1665 | H | H | H | H | H | H | H | H | — | — | — | 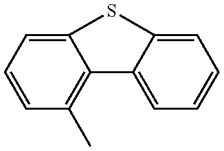 | 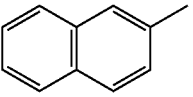 |
TABLE 78
| compound | R$_2$ | R$_3$ | R$_4$ | R$_5$ | R$_6$ | R$_7$ | R$_9$ | R$_{10}$ | L$_1$ | L$_2$ | L$_3$ | Ar$_1$ | Ar$_2$ |
|---|---|---|---|---|---|---|---|---|---|---|---|---|---|
| D1666 | H | H | H | H | H | H | H | H | — | — | — | 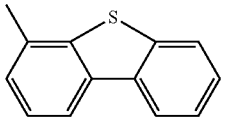 | 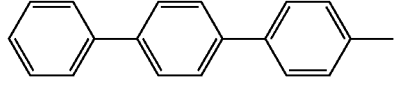 |
| D1667 | H | H | H | H | H | H | H | H | — | — | — | 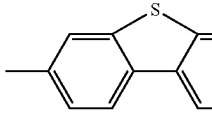 | 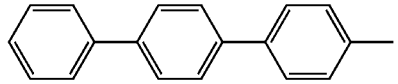 |
| D1668 | H | H | H | H | H | H | H | H | — | — | — | 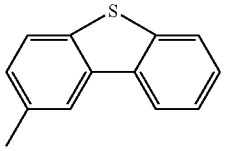 | 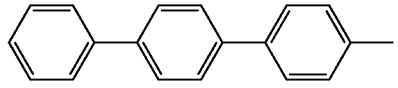 |
| D1669 | H | H | H | H | H | H | H | H | — | — | — | 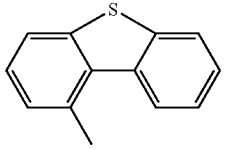 | 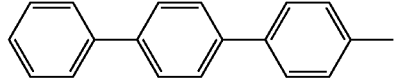 |
| D1670 | H | H | H | H | H | H | H | H | — | — | — | 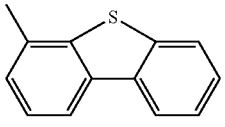 | 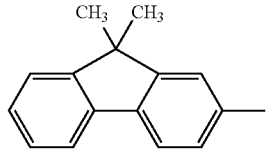 |
| D1671 | H | H | H | H | H | H | H | H | — | — | — | 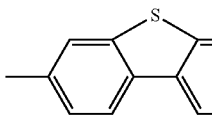 | 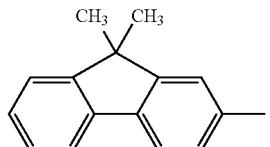 |
| D1672 | H | H | H | H | H | H | H | H | — | — | — | 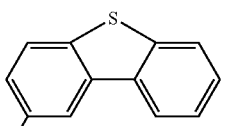 | 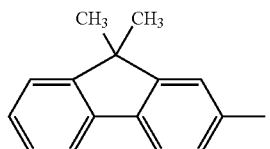 |
| D1673 | H | H | H | H | H | H | H | H | — | — | — | 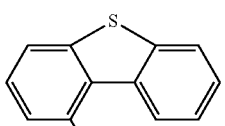 | 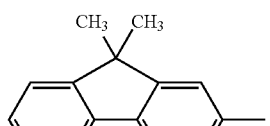 |

TABLE 79
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1674 | H | H | H | H | H | H | H | H | — | — | — | 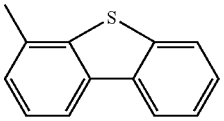 | 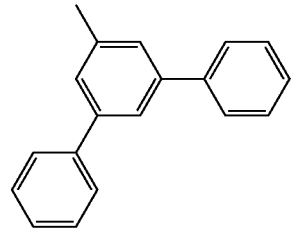 |
| D1675 | H | H | H | H | H | H | H | H | — | — | — | 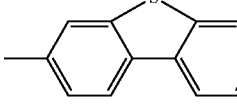 | 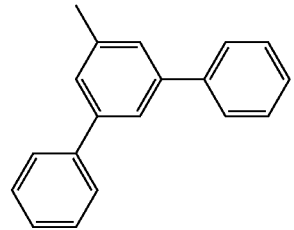 |
| D1676 | H | H | H | H | H | H | H | H | — | — | — | 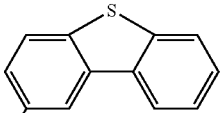 | 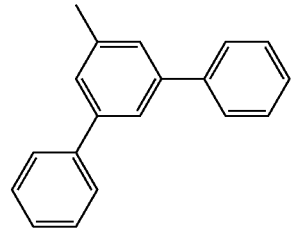 |
| D1677 | H | H | H | H | H | H | H | H | — | — | — | 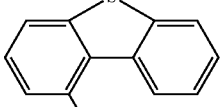 | 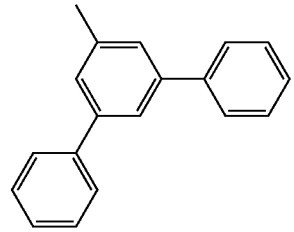 |
TABLE 80
| compound | R₂ | R₃ | R₄ | R₅ | R₆ | R₇ | R₉ | R₁₀ | L₁ | L₂ | L₃ | Ar₁ | Ar₂ |
|---|---|---|---|---|---|---|---|---|---|---|---|---|---|
| D1678 | H | H | H | H | H | H | H | H | — | — | — | 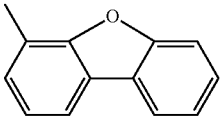 | 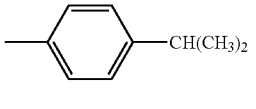 |
| D1679 | H | H | H | H | H | H | H | H | — | — | — | 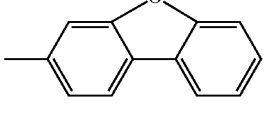 | 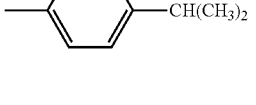 |
| D1680 | H | H | H | H | H | H | H | H | — | — | — | 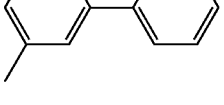 | 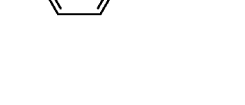 |

TABLE 80-continued
| compound | R2 | R3 | R4 | R5 | R6 | R7 | R9 | R10 | L1 | L2 | L3 | Ar1 | Ar2 |
|---|---|---|---|---|---|---|---|---|---|---|---|---|---|
| D1681 | H | H | H | H | H | H | H | H | — | — | — | 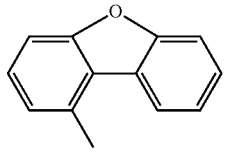 | 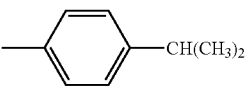 |
TABLE 81
| compound | R2 | R3 | R4 | R5 | R6 | R7 | R9 | R10 | L1 | L2 | L3 | Ar1 | Ar2 |
|---|---|---|---|---|---|---|---|---|---|---|---|---|---|
| D1682 | H | H | H | H | H | H | H | H | — | — | — | 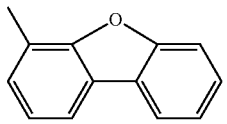 | 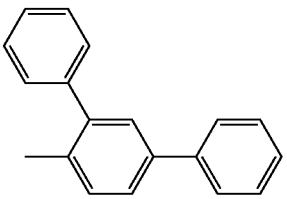 |
| D1683 | H | H | H | H | H | H | H | H | — | — | — | 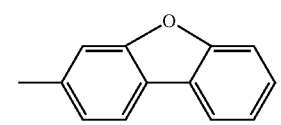 | 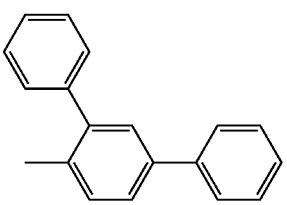 |
| D1684 | H | H | H | H | H | H | H | H | — | — | — | 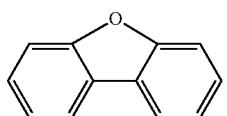 | 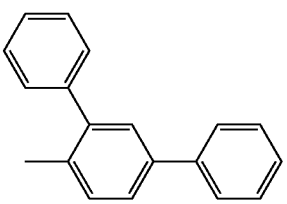 |
| D1685 | H | H | H | H | H | H | H | H | — | — | — | 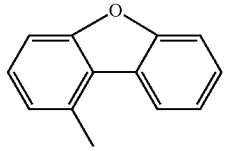 | 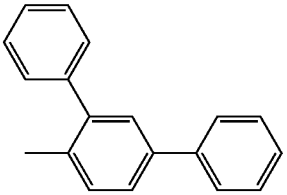 |

The specific examples of the aromatic amine derivative are the compounds having $R_1$ and $R_8$ in the same structure represented by the formula (2), however, not limited thereto. The aromatic amine derivative may be a compound having $R_1$ and $R_8$ in different structures.

In the aromatic amine derivative according to the exemplary embodiment, $R_1$ and $R_9$ in the formula (1) are preferably represented by the formula (2). At this instance, the aromatic amine derivative has a structure represented by the following formula (1E).

[Formula 15]

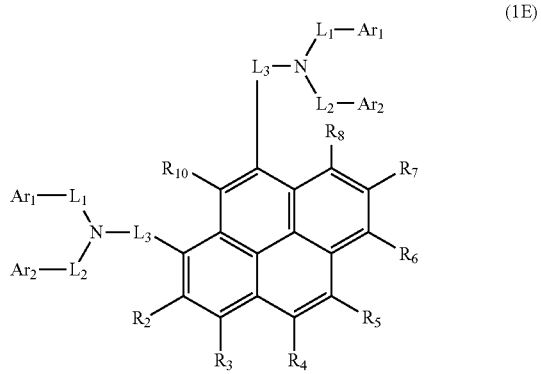

(1E)

Specific examples of the aromatic amine derivative according to the exemplary embodiment are aromatic amine derivatives described in Tables 82 to 91 for $R_2$ to $R_8$, $R_{10}$, $L_1$ to $L_3$, and $Ar_1$ to $Ar_2$ in the formula (1E). Note that "—" in $L_1$ to $L_3$ of the tables represents a single bond. Moreover, in $L_1$ to $L_3$ and $Ar_1$ to $Ar_2$ in the tables, a line extending outward from the cyclic structure and having no chemical formula (e.g., $CH_3$, Ph, CN, benzene ring) at an end of the line represents a single bond, not a methyl group. For instance, in the following compound D2001, $Ar_1$ has a single bond at a position 4 of a dibenzofuran ring. In short, $Ar_1$ represents a 4-dibenzofuranyl group. Likewise, $Ar_2$ represents a phenyl group.

TABLE 82

| compound | $R_2$ | $R_3$ | $R_4$ | $R_5$ | $R_6$ | $R_7$ | $R_8$ | $R_{10}$ | $L_1$ | $L_2$ | $L_3$ | $Ar_1$ | $Ar_2$ |
|---|---|---|---|---|---|---|---|---|---|---|---|---|---|
| D2001 | H | H | H | H | H | H | H | H | — | — | — | | |
| D2002 | H | H | H | H | H | H | H | H | — | — | — | | |
| D2003 | H | H | H | H | H | H | H | H | — | — | — | | |
| D2004 | H | H | H | H | H | H | H | H | — | — | — | | |
| D2005 | H | H | H | H | H | H | H | H | — | — | — | | |

TABLE 82-continued
| compound | R$_2$ | R$_3$ | R$_4$ | R$_5$ | R$_6$ | R$_7$ | R$_8$ | R$_{10}$ | L$_1$ | L$_2$ | L$_3$ | Ar$_1$ | Ar$_2$ |
|---|---|---|---|---|---|---|---|---|---|---|---|---|---|
| D2006 | H | H | H | H | H | H | H | H | — | — | — | 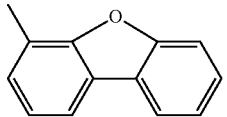 | 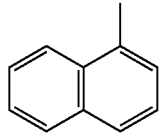 |
| D2007 | H | H | H | H | H | H | H | H | — | — | — | 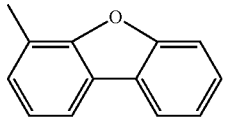 | 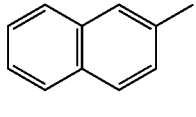 |
| D2008 | H | H | H | H | H | H | H | H | — | — | — | 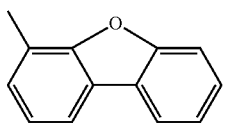 | 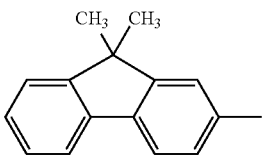 |
TABLE 83
| compound | R$_2$ | R$_3$ | R$_4$ | R$_5$ | R$_6$ | R$_7$ | R$_8$ | R$_{10}$ | L$_1$ | L$_2$ | L$_3$ | Ar$_1$ | Ar$_2$ |
|---|---|---|---|---|---|---|---|---|---|---|---|---|---|
| D2009 | H | H | H | H | H | H | H | H | — | — | — | 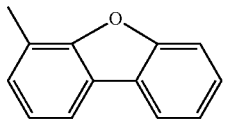 | 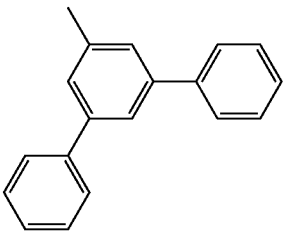 |
| D2010 | H | H | H | H | H | H | H | H | — | — | — | 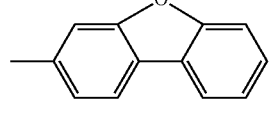 | 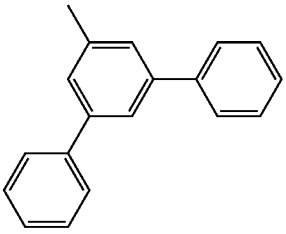 |
| D2011 | H | H | H | H | H | H | H | H | — | — | — | 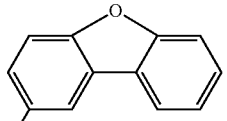 | 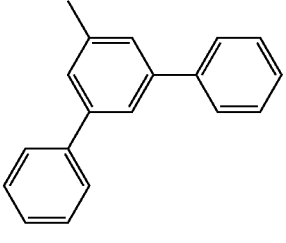 |
| D2012 | H | H | H | H | H | H | H | H | — | — | — | 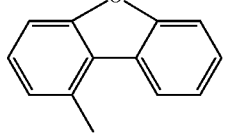 | 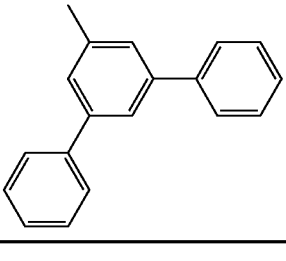 |

TABLE 84
| compound | R₂ | R₃ | R₄ | R₅ | R₆ | R₇ | R₈ | R₁₀ | L₁ | L₂ | L₃ | Ar₁ | Ar₂ |
|---|---|---|---|---|---|---|---|---|---|---|---|---|---|
| D2013 | H | H | H | H | H | H | H | H | — | — | — | 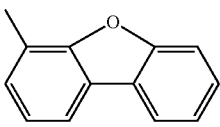 | 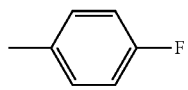 |
| D2014 | H | H | H | H | H | H | H | H | — | — | — | 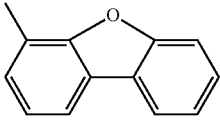 | 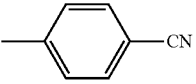 |
| D2015 | H | H | H | H | H | H | H | H | — | — | — | 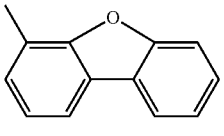 | 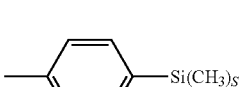 |
| D2016 | H | H | H | H | H | H | H | H | — | — | — | 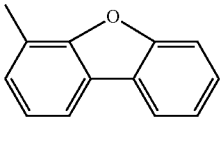 | 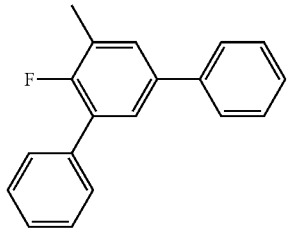 |
| D2017 | H | H | H | H | H | H | H | H | — | — | — | 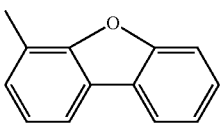 | 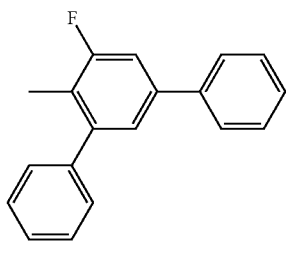 |
TABLE 85
| compound | R₂ | R₃ | R₄ | R₅ | R₆ | R₇ | R₈ | R₁₀ | L₁ | L₂ | L₃ | Ar₁ | Ar₂ |
|---|---|---|---|---|---|---|---|---|---|---|---|---|---|
| D2018 | H | H | H | H | H | H | H | H | — | — | — | 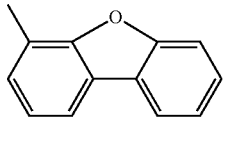 | 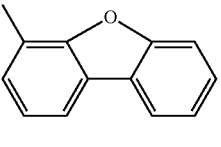 |
| D2019 | H | H | H | H | H | H | H | H | — | — | — | 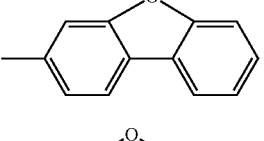 | 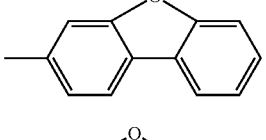 |
| D2020 | H | H | H | H | H | H | H | H | — | — | — | 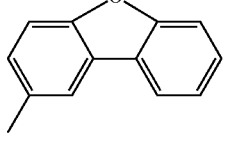 | 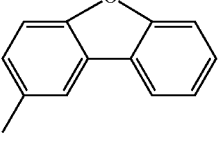 |

TABLE 85-continued
| compound | R2 | R3 | R4 | R5 | R6 | R7 | R8 | R10 | L1 | L2 | L3 | Ar1 | Ar2 |
|---|---|---|---|---|---|---|---|---|---|---|---|---|---|
| D2021 | H | H | H | H | H | H | H | H | — | — | — | 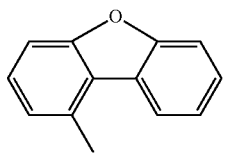 | 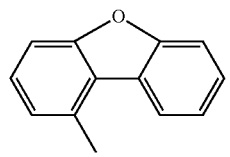 |
TABLE 86
| compound | R2 | R3 | R4 | R5 | R6 | R7 | R8 | R10 | L1 | L2 | L3 | Ar1 | Ar2 |
|---|---|---|---|---|---|---|---|---|---|---|---|---|---|
| D2022 | H | H | H | H | H | H | H | H | — | — | — | 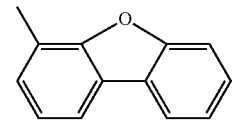 | 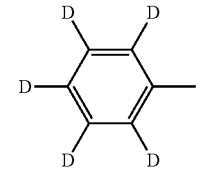 |
| D2023 | H | H | H | H | H | H | H | H | — | — | — | 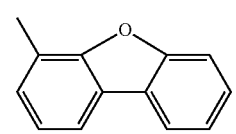 | 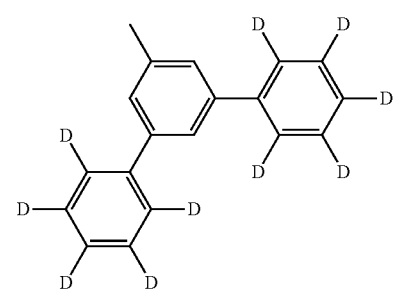 |
| D2024 | H | H | H | H | H | H | H | H | — | — | — | 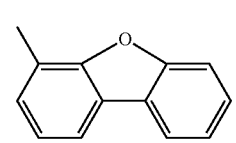 | 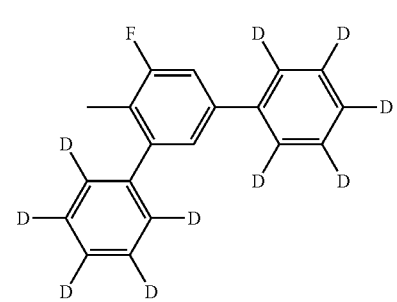 |
| D2025 | H | H | H | H | H | H | H | H | — | — | — | 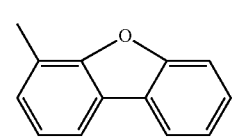 | 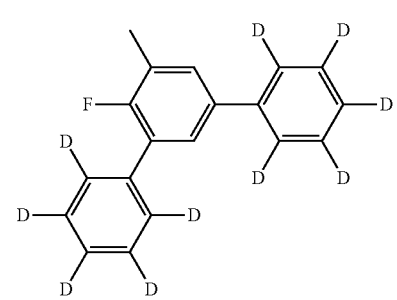 |

TABLE 87

| compound | R₂ | R₃ | R₄ | R₅ | R₆ | R₇ | R₈ | R₁₀ | L₁ | L₂ | L₃ | Ar₁ | Ar₂ |
|---|---|---|---|---|---|---|---|---|---|---|---|---|---|
| D2026 | H | H | H | H | H | H | H | H | — | — | — | 4-methyl-6-phenyldibenzofuran-yl | phenyl |
| D2027 | H | H | H | H | H | H | H | H | — | — | — | 4-methyl-6-D-dibenzofuran-yl | phenyl |

TABLE 88

| compound | R₂ | R₃ | R₄ | R₅ | R₆ | R₇ | R₈ | R₁₀ | L₁ | L₂ | L₃ |
|---|---|---|---|---|---|---|---|---|---|---|---|
| D2028 | H | H | H | H | H | H | H | H | 1,4-phenylene | — | — |
| D2029 | H | H | H | H | H | H | H | H | —C(CH₃)₂— | — | — |
| D2030 | H | H | H | H | H | H | H | H | — | —C(CH₃)₂— | — |
| D2031 | H | H | H | H | H | H | H | H | — | — | 1,4-phenylene |
| D2032 | H | H | H | H | H | H | H | H | 1,4-phenylene | 1,4-phenylene | — |
| D2033 | H | H | H | H | H | H | H | H | —C(CH₃)₂— | —C(CH₃)₂— | — |
| D2034 | H | H | H | H | H | H | H | H | — | — | 1,4-phenylene |

| compound | Ar₁ | Ar₂ |
|---|---|---|
| D2028 | 4-methyldibenzofuran-yl | phenyl |
| D2029 | 4-methyldibenzofuran-yl | phenyl |

TABLE 88-continued
| | | Ar₁ | Ar₂ |
|---|---|---|---|
| D2030 | | 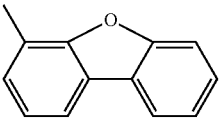 | 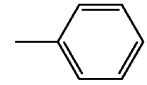 |
| D2031 | | 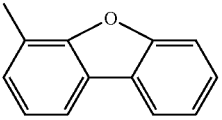 | 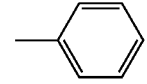 |
| D2032 | | 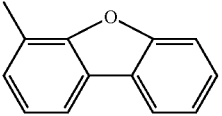 | 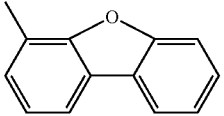 |
| D2033 | | 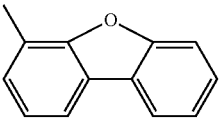 | 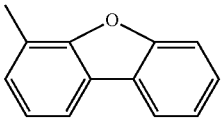 |
| D2034 | | 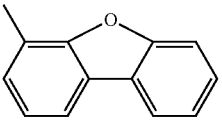 | 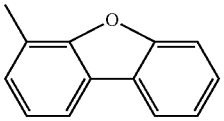 |
TABLE 89
| compound | R₂ | R₃ | R₄ | R₅ | R₆ | R₇ | R₈ | R₁₀ | L₁ | L₂ | L₃ | Ar₁ | Ar₂ |
|---|---|---|---|---|---|---|---|---|---|---|---|---|---|
| D2035 | H | H | H | H | H | H | H | H | — | — | — | 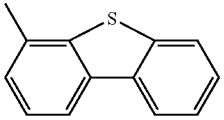 | 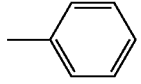 |
| D2036 | H | H | H | H | H | H | H | H | — | — | — | 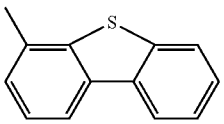 | 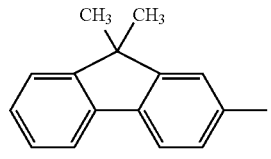 |
| D2037 | H | H | H | H | H | H | H | H | — | — | — | 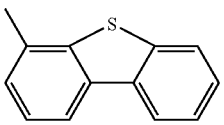 | 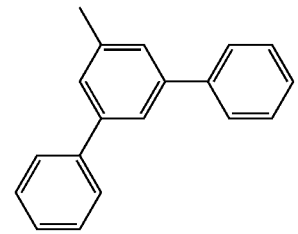 |
TABLE 90
| compound | R₂ | R₃ | R₄ | R₅ | R₆ | R₇ | R₈ | R₁₀ | L₁ | L₂ | L₃ | Ar₁ | Ar₂ |
|---|---|---|---|---|---|---|---|---|---|---|---|---|---|
| D2038 | H | H | H | H | H | H | H | H | — | — | — | 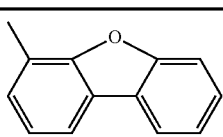 | 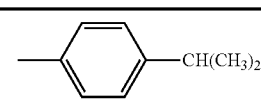 |

TABLE 90-continued
| compound | R2 | R3 | R4 | R5 | R6 | R7 | R8 | R10 | L1 | L2 | L3 | Ar1 | Ar2 |
|---|---|---|---|---|---|---|---|---|---|---|---|---|---|
| D2039 | H | H | H | H | H | H | H | H | — | — | — | 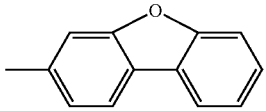 | 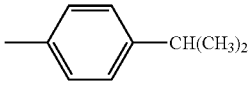 |
| D2040 | H | H | H | H | H | H | H | H | — | — | — | 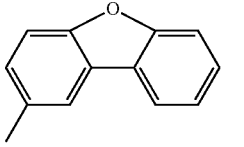 | 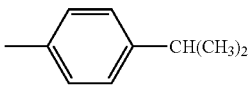 |
| D2041 | H | H | H | H | H | H | H | H | — | — | — | 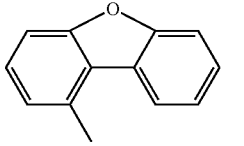 | 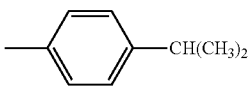 |
TABLE 91
| compound | R2 | R3 | R4 | R5 | R6 | R7 | R8 | R10 | L1 | L2 | L3 | Ar1 | Ar2 |
|---|---|---|---|---|---|---|---|---|---|---|---|---|---|
| D2042 | H | H | H | H | H | H | H | H | — | — | — | 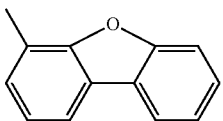 | 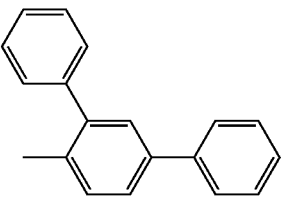 |
| D2043 | H | H | H | H | H | H | H | H | — | — | — | 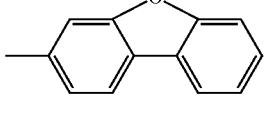 | 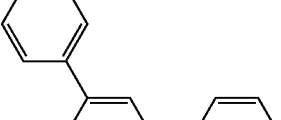 |
| D2044 | H | H | H | H | H | H | H | H | — | — | — | 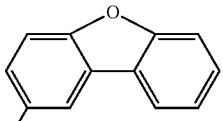 | 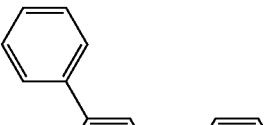 |
| D2045 | H | H | H | H | H | H | H | H | — | — | — | 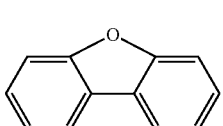 | 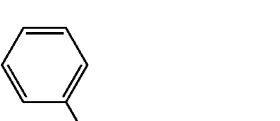 |

The specific examples of the aromatic amine derivative are the compounds having $R_1$ and $R_9$ in the same structure represented by the formula (2), however, not limited thereto. The aromatic amine derivative may be a compound having $R_1$ and $R_9$ in different structures.

In the aromatic amine derivative according to the exemplary embodiment, $R_1$ and $R_{10}$ in the formula (1) are preferably represented by the formula (2). At this instance, the aromatic amine derivative has a structure represented by the following formula (1F).

[Formula 16]

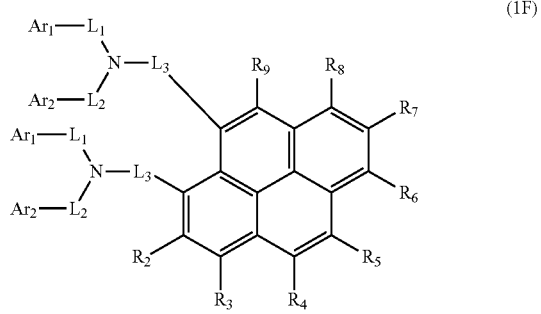

(1F)

Specific examples of the aromatic amine derivative according to the exemplary embodiment are aromatic amine derivatives described in Tables 92 to 101 for $R_2$ to $R_9$, $L_1$ to $L_3$, and $Ar_1$ to $Ar_2$ in the formula (1F). Note that "—" in $L_1$ to $L_3$ of the tables represents a single bond. Moreover, in $L_1$ to $L_3$ and $Ar_1$ to $Ar_2$ in the tables, a line extending outward from the cyclic structure and having no chemical formula (e.g., $CH_3$, Ph, CN, benzene ring) at an end of the line represents a single bond, not a methyl group. For instance, in the following compound D2101, $Ar_1$ has a single bond at a position 4 of a dibenzofuran ring. In short, $Ar_1$ represents a 4-dibenzofuranyl group. Likewise, $Ar_2$ represents a phenyl group.

TABLE 92

| compound | $R_2$ | $R_3$ | $R_4$ | $R_5$ | $R_6$ | $R_7$ | $R_8$ | $R_9$ | $L_1$ | $L_2$ | $L_3$ | $Ar_1$ | $Ar_2$ |
|---|---|---|---|---|---|---|---|---|---|---|---|---|---|
| D2101 | H | H | H | H | H | H | H | H | — | — | — | 4-dibenzofuranyl | phenyl |
| D2102 | H | H | H | H | H | H | H | H | — | — | — | dibenzofuranyl | phenyl |
| D2103 | H | H | H | H | H | H | H | H | — | — | — | dibenzofuranyl | phenyl |
| D2104 | H | H | H | H | H | H | H | H | — | — | — | dibenzofuranyl | phenyl |
| D2105 | H | H | H | H | H | H | H | H | — | — | — | dibenzofuranyl | biphenyl |
| D2106 | H | H | H | H | H | H | H | H | — | — | — | dibenzofuranyl | naphthyl |

TABLE 92-continued
| compound | R₂ | R₃ | R₄ | R₅ | R₆ | R₇ | R₈ | R₉ | L₁ | L₂ | L₃ | Ar₁ | Ar₂ |
|---|---|---|---|---|---|---|---|---|---|---|---|---|---|
| D2107 | H | H | H | H | H | H | H | H | — | — | — | 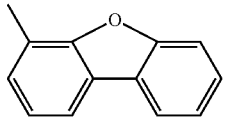 | 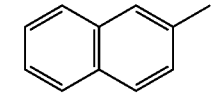 |
| D2108 | H | H | H | H | H | H | H | H | — | — | — | 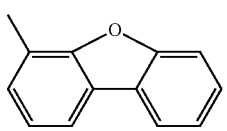 | 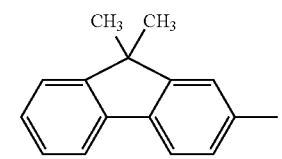 |
TABLE 93
| compound | R₂ | R₃ | R₄ | R₅ | R₆ | R₇ | R₈ | R₉ | L₁ | L₂ | L₃ | Ar₁ | Ar₂ |
|---|---|---|---|---|---|---|---|---|---|---|---|---|---|
| D2109 | H | H | H | H | H | H | H | H | — | — | — | 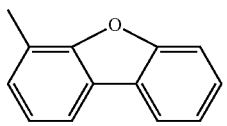 | 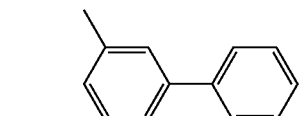 |
| D2110 | H | H | H | H | H | H | H | H | — | — | — | 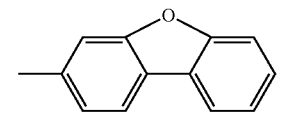 | 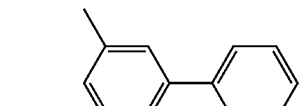 |
| D2111 | H | H | H | H | H | H | H | H | — | — | — | 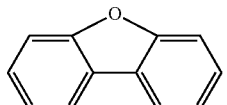 | 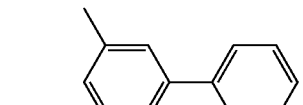 |
| D2112 | H | H | H | H | H | H | H | H | — | — | — | 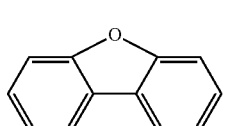 | 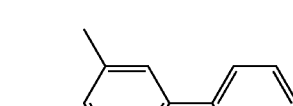 |

TABLE 94
| compound | R₂ | R₃ | R₄ | R₅ | R₆ | R₇ | R₈ | R₉ | L₁ | L₂ | L₃ | Ar₁ | Ar₂ |
|---|---|---|---|---|---|---|---|---|---|---|---|---|---|
| D2113 | H | H | H | H | H | H | H | H | — | — | — | 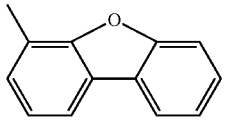 |  |
| D2114 | H | H | H | H | H | H | H | H | — | — | — | 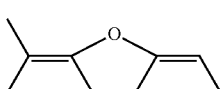 |  |
| D2115 | H | H | H | H | H | H | H | H | — | — | — | 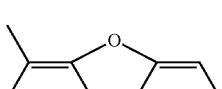 | 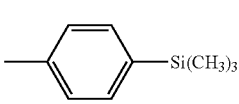 |
| D2116 | H | H | H | H | H | H | H | H | — | — | — | 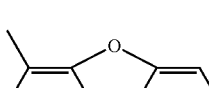 | 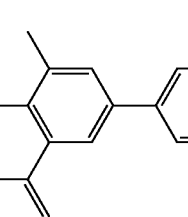 |
| D2117 | H | H | H | H | H | H | H | H | — | — | — | 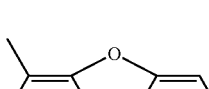 | 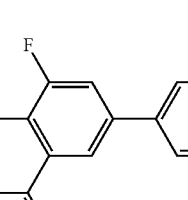 |
TABLE 95
| compound | R₂ | R₃ | R₄ | R₅ | R₆ | R₇ | R₈ | R₉ | L₁ | L₂ | L₃ | Ar₁ | Ar₂ |
|---|---|---|---|---|---|---|---|---|---|---|---|---|---|
| D2118 | H | H | H | H | H | H | H | H | — | — | — | 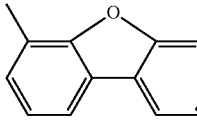 | 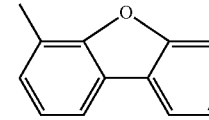 |
| D2119 | H | H | H | H | H | H | H | H | — | — | — | 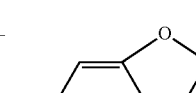 | 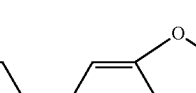 |
| D2120 | H | H | H | H | H | H | H | H | — | — | — | 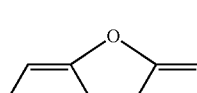 | 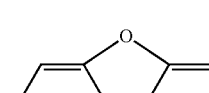 |

TABLE 95-continued
| compound | R2 | R3 | R4 | R5 | R6 | R7 | R8 | R9 | L1 | L2 | L3 | Ar1 | Ar2 |
|---|---|---|---|---|---|---|---|---|---|---|---|---|---|
| D2121 | H | H | H | H | H | H | H | H | — | — | — | 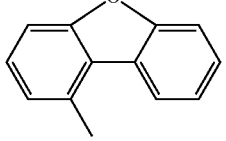 | 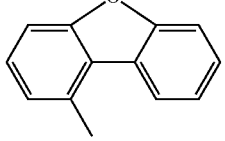 |
TABLE 96
| compound | R2 | R3 | R4 | R5 | R6 | R7 | R8 | R9 | L1 | L2 | L3 | Ar1 | Ar2 |
|---|---|---|---|---|---|---|---|---|---|---|---|---|---|
| D2122 | H | H | H | H | H | H | H | H | — | — | — | 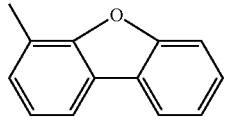 | 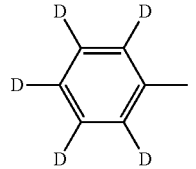 |
| D2123 | H | H | H | H | H | H | H | H | — | — | — | 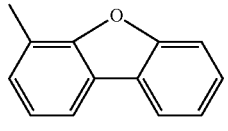 | 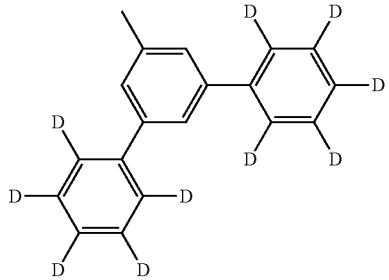 |
| D2124 | H | H | H | H | H | H | H | H | — | — | — | 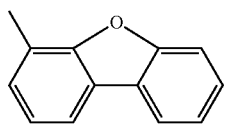 | 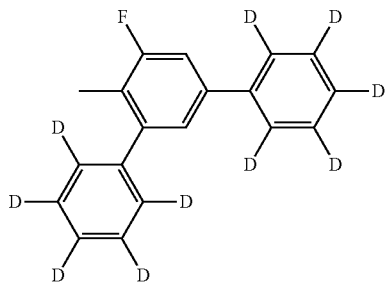 |
| D2125 | H | H | H | H | H | H | H | H | — | — | — | 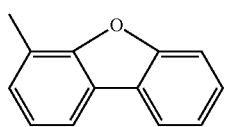 | 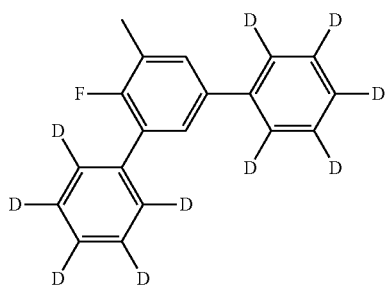 |

TABLE 97
| compound | R2 | R3 | R4 | R5 | R6 | R7 | R8 | R9 | L1 | L2 | L3 | Ar1 | Ar2 |
|---|---|---|---|---|---|---|---|---|---|---|---|---|---|
| D2126 | H | H | H | H | H | H | H | H | — | — | — | 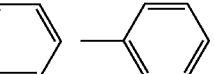 | 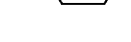 |
| D2127 | H | H | H | H | H | H | H | H | — | — | — | 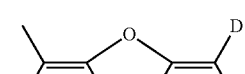 | 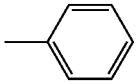 |
TABLE 98
| compound | R2 | R3 | R4 | R5 | R6 | R7 | R8 | R9 | L1 |
|---|---|---|---|---|---|---|---|---|---|
| D2128 | H | H | H | H | H | H | H | H |  |
| D2129 | H | H | H | H | H | H | H | H | 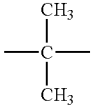 |
| D2130 | H | H | H | H | H | H | H | H | — |
| D2131 | H | H | H | H | H | H | H | H | — |
| D2132 | H | H | H | H | H | H | H | H |  |
| D2133 | H | H | H | H | H | H | H | H | 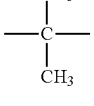 |
| D2134 | H | H | H | H | H | H | H | H | — |
| compound | L2 | L3 | Ar1 | Ar2 |
|---|---|---|---|---|
| D2128 | — | — |  | 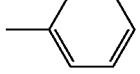 |
| D2129 | — | — | 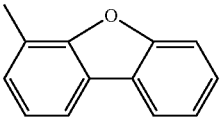 | 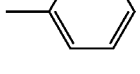 |
| D2130 | 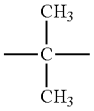 | — | 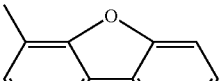 | 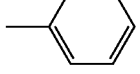 |
| D2131 | — | 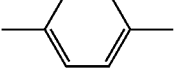 | 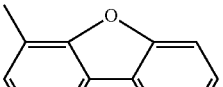 | 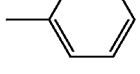 |

TABLE 98-continued

| | | | | |
|---|---|---|---|---|
| D2132 | [p-phenylene] | — | [4-methyldibenzofuran] | [4-methyldibenzofuran] |
| D2133 | [C(CH₃)₂] | — | [4-methyldibenzofuran] | [4-methyldibenzofuran] |
| D2134 | — | [p-phenylene] | [4-methyldibenzofuran] | [4-methyldibenzofuran] |

TABLE 99

| compound | R₂ | R₃ | R₄ | R₅ | R₆ | R₇ | R₈ | R₉ | L₁ | L₂ | L₃ | Ar₁ | Ar₂ |
|---|---|---|---|---|---|---|---|---|---|---|---|---|---|
| D2135 | H | H | H | H | H | H | H | H | — | — | — | [4-methyldibenzothiophene] | [phenyl] |
| D2136 | H | H | H | H | H | H | H | H | — | — | — | [4-methyldibenzothiophene] | [9,9-dimethyl-2-methylfluorene] |
| D2137 | H | H | H | H | H | H | H | H | — | — | — | [4-methyldibenzothiophene] | [3-methyl-5-phenyl-biphenyl] |

TABLE 100

| compound | R₂ | R₃ | R₄ | R₅ | R₆ | R₇ | R₈ | R₉ | L₁ | L₂ | L₃ | Ar₁ | Ar₂ |
|---|---|---|---|---|---|---|---|---|---|---|---|---|---|
| D2138 | H | H | H | H | H | H | H | H | — | — | — | [4-methyldibenzofuran] | [4-isopropylphenyl]—CH(CH₃)₂ |
| D2139 | H | H | H | H | H | H | H | H | — | — | — | [methyldibenzofuran] | [4-isopropylphenyl]—CH(CH₃)₂ |
| D2140 | H | H | H | H | H | H | H | H | — | — | — | [methyldibenzofuran] | [4-isopropylphenyl]—CH(CH₃)₂ |

TABLE 100-continued

| compound | R₂ | R₃ | R₄ | R₅ | R₆ | R₇ | R₈ | R₉ | L₁ | L₂ | L₃ | Ar₁ | Ar₂ |
|---|---|---|---|---|---|---|---|---|---|---|---|---|---|
| D2141 | H | H | H | H | H | H | H | H | — | — | — | 1-methyldibenzofuran-yl | 4-isopropylphenyl |

TABLE 101

| compound | R₂ | R₃ | R₄ | R₅ | R₆ | R₇ | R₈ | R₉ | L₁ | L₂ | L₃ | Ar₁ | Ar₂ |
|---|---|---|---|---|---|---|---|---|---|---|---|---|---|
| D2142 | H | H | H | H | H | H | H | H | — | — | — | methyldibenzofuranyl | methyl-biphenylyl |
| D2143 | H | H | H | H | H | H | H | H | — | — | — | methyldibenzofuranyl | methyl-biphenylyl |
| D2144 | H | H | H | H | H | H | H | H | — | — | — | methyldibenzofuranyl | methyl-biphenylyl |
| D2145 | H | H | H | H | H | H | H | H | — | — | — | methyldibenzofuranyl | methyl-biphenylyl |

The specific examples of the aromatic amine derivative are the compounds having $R_1$ and $R_{10}$ in the same structure represented by the formula (2), however, not limited thereto. The aromatic amine derivative may be a compound having $R_1$ and $R_{10}$ in different structures.

Organic-EL-Device Material

The aromatic amine derivative according to the exemplary embodiment is usable as an organic-EL-device material. The organic-EL-device material according to the exemplary embodiment may be composed solely of the aromatic amine derivative according to the above exemplary embodiment, or alternatively, may contain another compound(s) in addition to the aromatic amine derivative according to the above exemplary embodiment. The organic-EL-device material containing the aromatic amine derivative according to the exemplary embodiment is exemplarily usable as a dopant material.

The organic-EL-device material containing the aromatic amine derivative according to the exemplary embodiment and another compound is exemplified by an organic-EL-device material containing the aromatic amine derivative according to the exemplary embodiment and an anthracene derivative represented by the formula (20).

Moreover, an organic-EL-device material containing the aromatic amine derivative according to the exemplary embodiment and a pyrene derivative represented by the following formula (30) in place of the anthracene derivative is usable as the organic-EL-device material according to the exemplary embodiment.

Furthermore, an organic-EL-device material containing the aromatic amine derivative according to the exemplary embodiment, the anthracene derivative represented by the formula (20) and the pyrene derivative represented by the following formula (30) is usable as the organic-EL-device material according to the exemplary embodiment.

Organic EL Device

The organic EL device according to this exemplary embodiment includes an organic compound layer between a cathode and an anode.

The aromatic amine derivative according to the exemplary embodiment is contained in the organic compound layer. The organic compound layer is formed using the organic-EL-device material containing the aromatic amine derivative according to the exemplary embodiment.

The organic compound layer has at least one layer of an organic thin-film layer formed of an organic compound. At least one layer of the organic thin-film layer contains the aromatic amine derivative according to the exemplary embodiment singularly or as a component of a mixture. The organic thin-film layer may contain an inorganic compound.

At least one layer of the organic thin-film layer is an emitting layer. Accordingly, the organic compound layer may be provided by a single emitting layer. Alternatively, the organic compound layer may be provided by layers applied in a known organic EL device such as a hole injecting layer, a hole transporting layer, an electron injecting layer, an electron transporting layer, a hole blocking layer and an electron blocking layer. When the organic thin-film layer is provided by plural layers, the aromatic amine derivative according to the exemplary embodiment is contained singularly or as a component of a mixture in at least one of the layers.

The emitting layer preferably contains the aromatic amine derivative according to the exemplary embodiment. In this arrangement, the emitting layer may be formed of the aromatic amine derivative alone. Alternatively, the emitting layer may contain the aromatic amine derivative as a host material or a dopant material.

Representative arrangement examples of the organic EL device are as follows:
(a) anode/emitting layer/cathode;
(b) anode/hole injecting•transporting layer/emitting layer/cathode;
(c) anode/emitting layer/electron injecting•transporting layer/cathode;
(d) anode/hole injecting•transporting layer/emitting layer/electron injecting•transporting layer/cathode; and
(e) anode/hole injecting•transporting layer/emitting layer/blocking layer/electron injecting•transporting layer/cathode.
While the arrangement (d) is preferably used among the above arrangements, the arrangement of the invention is not limited to the above arrangements.

It should be noted that the aforementioned "emitting layer" is an organic layer having an emission function, the organic layer including a host material and a dopant material when employing a doping system. Herein, the host material mainly has a function to promote recombination of electrons and holes and to confine excitons in the emitting layer while the dopant material has a function to efficiently emit the excitons obtained by the recombination.

The "hole injecting/transporting layer" means "at least one of a hole injecting layer and a hole transporting layer" while the "electron injecting/transporting layer" means "at least one of an electron injecting layer and an electron transporting layer." Herein, when the hole injecting layer and the hole transporting layer are provided, the hole injecting layer is preferably close to the anode. When the electron injecting layer and the electron transporting layer are provided, the electron injecting layer is preferably close to the cathode. The hole injecting layer, the emitting layer and the electron injecting layer may respectively be formed in a layered structure having two or more layers. As for the hole injecting layer in such an arrangement, a layer that injects holes from the electrode is referred to as a hole injecting layer while a layer that receives the holes from the hole injecting layer and transports the holes to the emitting layer is referred to as a hole transporting layer. Likewise, as for the electron injecting layer, a layer that injects electrons from the electrode is referred to as an electron injecting layer while a layer that receives the electrons from the hole injecting layer and transports the electrons to the emitting layer is referred to as an electron transporting layer.

When the organic EL device is in a multi-layered structure of the organic thin-film layers, decrease in luminance intensity and lifetime caused by quenching effects can be prevented. If necessary, the luminescent material, doping material, hole injecting material and electron injecting material may be combined in use. The luminescence intensity and luminous efficiency are occasionally improved by the doping material.

Each of the organic thin-film layers is selected in use according to factors such as an energy level, heat resistance, and adhesiveness to the organic layer or metal electrode of the material.

FIG. 1 schematically shows an exemplary arrangement of the organic EL device according to the exemplary embodiment.

An organic EL device 1 includes a transparent substrate 2, an anode 3, a cathode 4 and an organic compound layer 10 interposed between the anode 3 and the cathode 4.

The organic compound layer 10 sequentially includes a hole injecting layer 5, a hole transporting layer 6, an emitting layer 7, an electron transporting layer 8 and an electron injection layer 9 on the anode 3.

Emitting Layer

The emitting layer of the organic EL device has a function for providing conditions for recombination of electrons and holes to emit light.

In the organic EL device according to the exemplary embodiment, at least one layer of the organic thin-film layers preferably includes the aromatic amine derivative according to the exemplary embodiment, and at least one of the anthracene derivative represented by the formula (20) and the pyrene derivative represented by the formula (30). In particular, the emitting layer preferably includes the aromatic amine derivative according to the exemplary embodiment as the dopant material and the anthracene derivative represented by the formula (20) as the host material.

Anthracene Derivative

The anthracene derivative that may be included in the emitting layer as the host material is represented by the formula (20).

In the formula (20), $Ar^{11}$ and $Ar^{12}$ each independently represent a substituted or unsubstituted monocyclic group having 5 to 30 ring carbon atoms, a substituted or unsubstituted fused ring group having 10 to 30 ring atoms, or a group formed by combining the monocyclic group and the fused ring group.

The monocyclic group in the formula (20) is a group that is composed only of cyclic structures having no fused structure.

The monocyclic group has 5 to 30 ring atoms, preferably 5 to 20 ring atoms. Examples of the monocyclic group include: an aromatic group such as a phenyl group, biphenyl group, terphenyl group and quarter phenyl group; and a heterocyclic group such as a pyridyl group, pyrazyl group, pyrimidyl group, triazinyl group, furyl group and thienyl group. Among the above groups, a phenyl group, biphenyl group and terphenyl group are preferable.

The fused ring group in the formula (20) is a group that is formed by fusing two or more cyclic structures.

The fused ring group has 10 to 30 ring atoms, preferably 8 to 20 ring atoms. Examples of the fused ring group include: a fused aromatic cyclic group such as a naphthyl group, phenanthryl group, anthryl group, chrysenyl group, benzoanthryl group, benzophenanthryl group, triphenylenyl group, benzochrysenyl group, indenyl group, fluorenyl group, 9,9-dimethylfluorenyl group, benzofluorenyl group, dibenzofluorenyl group fluoranthenyl group, and benzofluoranthenyl group; and a fused heterocyclic group such as a benzofuranyl group, benzothiophenyl group, indolyl group, dibenzofuranyl group, dibenzothiophenyl group, carbazolyl group, quinolyl group and phenanthrolinyl group. Among these groups, a naphthyl group, phenanthryl group, anthryl group, 9,9-dimethylfluorenyl group, fluoranthenyl group, benzoanthryl group, dibenzothiophenyl group, dibenzofuranyl group and carbazolyl group are preferable.

The group formed by combining the monocyclic group and the fused ring group in the formula (20) is exemplified by a group formed by sequentially combining a phenyl group, naphthyl group and phenyl group to the anthracene ring (see the following compound EM50, etc.).

Examples of the alkyl group, silyl group, alkoxy group, aryloxy group, aralkyl group and halogen atom for $R^{101}$ to $R^{108}$ in the formula (20) are the same as $R_2$ to $R_{10}$ in the formula (1). Examples of the cycloalkyl group are the same as the above examples. Moreover, examples of "substituted or unsubstituted" ones of the above substituents are the same as those in the above description.

Preferable specific examples in the formula (20) will be shown below.

Preferable examples of the "substituted or unsubstituted" substituents for $Ar^{11}$, $Ar^{12}$ and $R^{101}$ to $R^{108}$ in the formula (20) are a monocyclic group, fused ring group, alkyl group, cycloalkyl group, silyl group, alkoxy group, cyano group and halogen atom (particularly, fluorine). The monocyclic ring and the fused ring group are particularly preferable. Preferable specific examples of the substituents are the same as those of the groups in the formula (20) and those of the groups in the formula (1).

The anthracene derivative represented by the formula (20) is preferably one of the following anthracene derivatives (A), (B) and (C) and is selected according to an arrangement and a desired property of an organic EL device to which the anthracene derivative is applied.

Anthracene Derivative (A)

An anthracene derivative (A) is an anthracene derivative of the formula (20) in which $Ar^{11}$ and $Ar^{12}$ are a substituted or unsubstituted fused ring group having 10 to 30 ring atoms. The anthracene derivative (A) is classified into an anthracene derivative in which $Ar^{11}$ and $Ar^{12}$ are substituted or unsubstituted fused ring groups the same as each other, and an anthracene derivative in which $Ar^{11}$ and $Ar^{12}$ are substituted or unsubstituted fused ring groups different from each other. The instance where $Ar^{11}$ and $Ar^{12}$ are different from each other also includes an instance where substitution positions of $Ar^{11}$ and $Ar^{12}$ are different from each other.

The anthracene derivative (A) is particularly preferably the anthracene derivative of the formula (20) in which $Ar^{11}$ and $Ar^{12}$ are substituted or unsubstituted fused ring groups different from each other.

In the anthracene derivative (A), preferable specific examples of the fused ring group for $Ar^{11}$ and $Ar^{12}$ in the formula (20) are the same as described above. Among the fused ring groups, a naphthyl group, phenanthryl group, benzoanthryl group, 9,9-dimethylfluorenyl group and dibenzofuranyl group are preferable.

Anthracene Derivative (B)

The anthracene derivatives (B) is an anthracene derivative of the formula (20) in which one of $Ar^{11}$ and $Ar^{12}$ is a substituted or unsubstituted monocyclic group having 5 to 30 ring atoms and the other of $Ar^{11}$ and $Ar^{12}$ is a substituted or unsubstituted fused ring group having 10 to 30 ring atoms.

The anthracene derivative (B) is preferably an anthracene derivative in which $Ar^{12}$ is selected from a naphthyl group, phenanthryl group, benzoanthryl group, 9,9-dimethylfluorenyl group and dibenzofuranyl group, and $Ar^{11}$ is an unsubstituted phenyl group or a phenyl group substituted by at least one of the monocyclic group and the fused ring group.

In the anthracene derivative (B), preferable specific examples of the monocyclic group and the fused ring group are the same as described above.

In addition, the anthracene derivative (B) is preferably an anthracene derivative in which $Ar^{12}$ is a substituted or unsubstituted fused ring group having 10 to 30 ring atoms, and $Ar^{11}$ is an unsubstituted phenyl group. In this arrangement, a phenanthryl group, 9,9-dimethylfluorenyl group, dibenzofuranyl group and benzoanthryl group are particularly preferable as the fused ring groups.

Anthracene Derivative (C)

An anthracene derivative (C) is an anthracene derivative of the formula (20) in which $Ar^{11}$ and $Ar^{12}$ are each independently a substituted or unsubstituted monocylic ring group having 5 to 30 ring atoms.

The anthracene derivative (C) is preferably an anthracene derivative in which $Ar^{11}$ and $Ar^{12}$ are each independently a substituted or unsubstituted phenyl group.

The anthracene derivative (C) is more preferably an anthracene derivative in which $Ar^{11}$ is an unsubstituted phenyl group and $Ar^{12}$ is a phenyl group having at least one of the monocyclic group and the fused ring group as a substituent, and anthracene derivative in which $Ar^{11}$ and $Ar^{12}$ are each independently a phenyl group having at least one of the monocyclic group and the fused ring group as a substituent.

Preferable specific examples of the monocyclic group and the fused ring group as a substituent for $Ar^{11}$ and $Ar^{12}$ in the formula (20) are the same as described above. The monocyclic group as the substituent is more preferably a phenyl group and a biphenyl group. The fused ring group as the substituent is more preferably a naphthyl group, phenanthryl group, 9,9-dimethylfluorenyl group, dibenzofuranyl group and benzoanthryl group.

Examples of the anthracene derivative represented by the formula (20) are as follows. However, the invention is not limited to the anthracene derivatives having these structures.

[Formula 17]

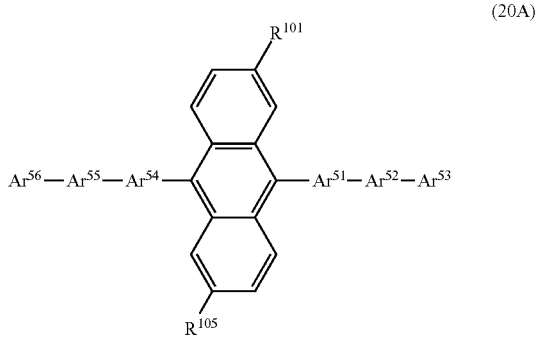

(20A)

In the formula (20A), $R^{101}$ and $R^{105}$ are each independently a hydrogen atom, halogen atom, cyano group, substituted or unsubstituted monocyclic group having 5 to 30 ring atoms, substituted or unsubstituted fused ring group having 10 to 30 ring atoms, a group provided by combining the monocyclic group and the fused ring group, substituted or unsubstituted alkyl group having 1 to 30 carbon atoms, substituted or unsubstituted cycloalkyl group having 3 to 30 ring carbon atoms, substituted or unsubstituted alkoxy group having 1 to 30 carbon atoms, substituted or unsubstituted aralkyl group having 7 to 30 carbon atoms, substituted or unsubstituted aryloxy having 6 to 30 ring carbon atoms, or substituted or unsubstituted silyl group.

In the formula (20A), $Ar^{51}$ and $Ar^{54}$ are each independently a substituted or unsubstituted divalent monocyclic residue having 5 to 30 ring atoms, or a substituted or unsubstituted divalent fused ring residue having 10 to 30 ring atoms.

In the formula (20A), $Ar^{52}$ and $Ar^{55}$ are each independently a single bond, a substituted or unsubstituted divalent monocyclic residue having 5 to 30 ring atoms, or a substituted or unsubstituted divalent fused ring residue having 10 to 30 ring atoms.

In the formula (20A), $Ar^{53}$ and $Ar^{56}$ are each independently a hydrogen atom, a substituted or unsubstituted monocyclic group having 5 to 30 ring atoms, or a substituted or unsubstituted fused ring having 10 to 30 ring atoms.

[Formula 18]

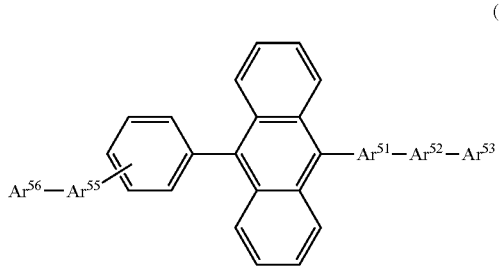

(20B)

In the formula (20B), $Ar^{51}$ is a substituted or unsubstituted divalent monocyclic residue having 5 to 30 ring atoms, or a substituted or unsubstituted divalent fused ring residue having 10 to 30 ring atoms.

In the formula (20B), $Ar^{52}$ and $Ar^{55}$ are each independently a single bond, a substituted or unsubstituted divalent monocyclic residue having 5 to 30 ring atoms, or a substituted or unsubstituted divalent fused ring residue having 10 to 30 ring atoms.

In the formula (20B), $Ar^{53}$ and $Ar^{56}$ are each independently a hydrogen atom, a substituted or unsubstituted monocyclic group having 5 to 30 ring atoms, or a substituted or unsubstituted fused ring having 10 to 30 ring atoms.

[Formula 19]

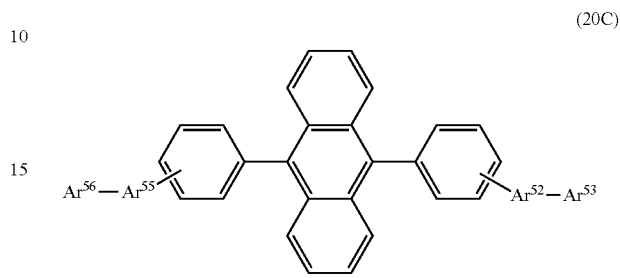

(20C)

In the formula (20C), $Ar^{52}$ is a substituted or unsubstituted divalent monocyclic residue having 5 to 30 ring atoms, or a substituted or unsubstituted divalent fused ring residue having 10 to 30 ring atoms.

In the formula (20C), $Ar^{55}$ is a single bond, a substituted or unsubstituted divalent monocyclic residue having 5 to 30 ring atoms, or a substituted or unsubstituted divalent fused ring residue having 10 to 30 ring atoms.

In the formula (20C), $Ar^{53}$ and $Ar^{56}$ are each independently a hydrogen atom, a substituted or unsubstituted monocyclic group having 5 to 30 ring atoms, or a substituted or unsubstituted fused ring having 10 to 30 ring atoms.

[Formula 20]

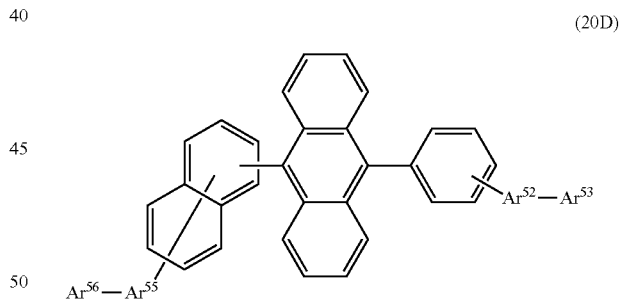

(20D)

In the formula (20D), $Ar^{52}$ is a substituted or unsubstituted divalent monocyclic residue having 5 to 30 ring atoms, or a substituted or unsubstituted divalent fused ring residue having 10 to 30 ring atoms.

In the formula (20D), $Ar^{55}$ is a single bond, a substituted or unsubstituted divalent monocyclic residue having 5 to 30 ring atoms, or a substituted or unsubstituted divalent fused ring residue having 10 to 30 ring atoms.

In the formula (20D), $Ar^{53}$ and $Ar^{56}$ are each independently a hydrogen atom, a substituted or unsubstituted monocyclic group having 5 to 30 ring atoms, or a substituted or unsubstituted fused ring having 10 to 30 ring atoms.

[Formula 21]

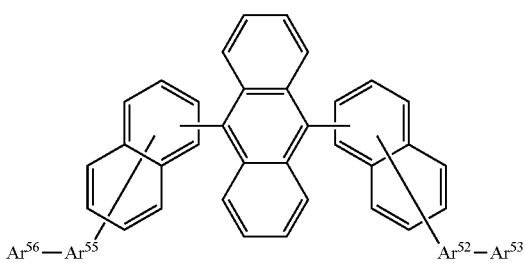

In the formula (20E), $Ar^{52}$ and $Ar^{55}$ are each independently a single bond, a substituted or unsubstituted divalent monocyclic residue having 5 to 30 ring atoms, or a substituted or unsubstituted divalent fused ring residue having 10 to 30 ring atoms.

In the formula (20E), $Ar^{53}$ and $Ar^{56}$ are each independently a hydrogen atom, a substituted or unsubstituted monocyclic group having 5 to 30 ring atoms, or a substituted or unsubstituted fused ring having 10 to 30 ring atoms.

More specific examples of the anthracene derivative are as follows. However, the invention is not limited to the anthracene derivatives having these structures.

In compounds EM36, EM44, EM77, EM85, EM86 and the like among the following specific structures of the anthracene derivatives, a line extending from a position 9 of a fluorene ring represents a methyl group. In other words, the fluorene ring is a 9,9-dimethylfluorene ring.

In compounds EM151, EM154, EM157, EM161, EM163, EM166, EM169, EM173 and the like among the following specific structures of the anthracene derivatives, a crossline extending outward from a cyclic structure represents a tertiary butyl group.

In compounds EM152, EM155, EM158, EM164, EM167, EM170, EM171, EM180, EM181, EM182, EM183, EM184, EM185 and the like among the following specific structures of the anthracene derivatives, a line extending from a silicon atom (Si) represents a methyl group. In other words, a substituent having the silicon atom is trimethylsilyl group.

[Formula 22]

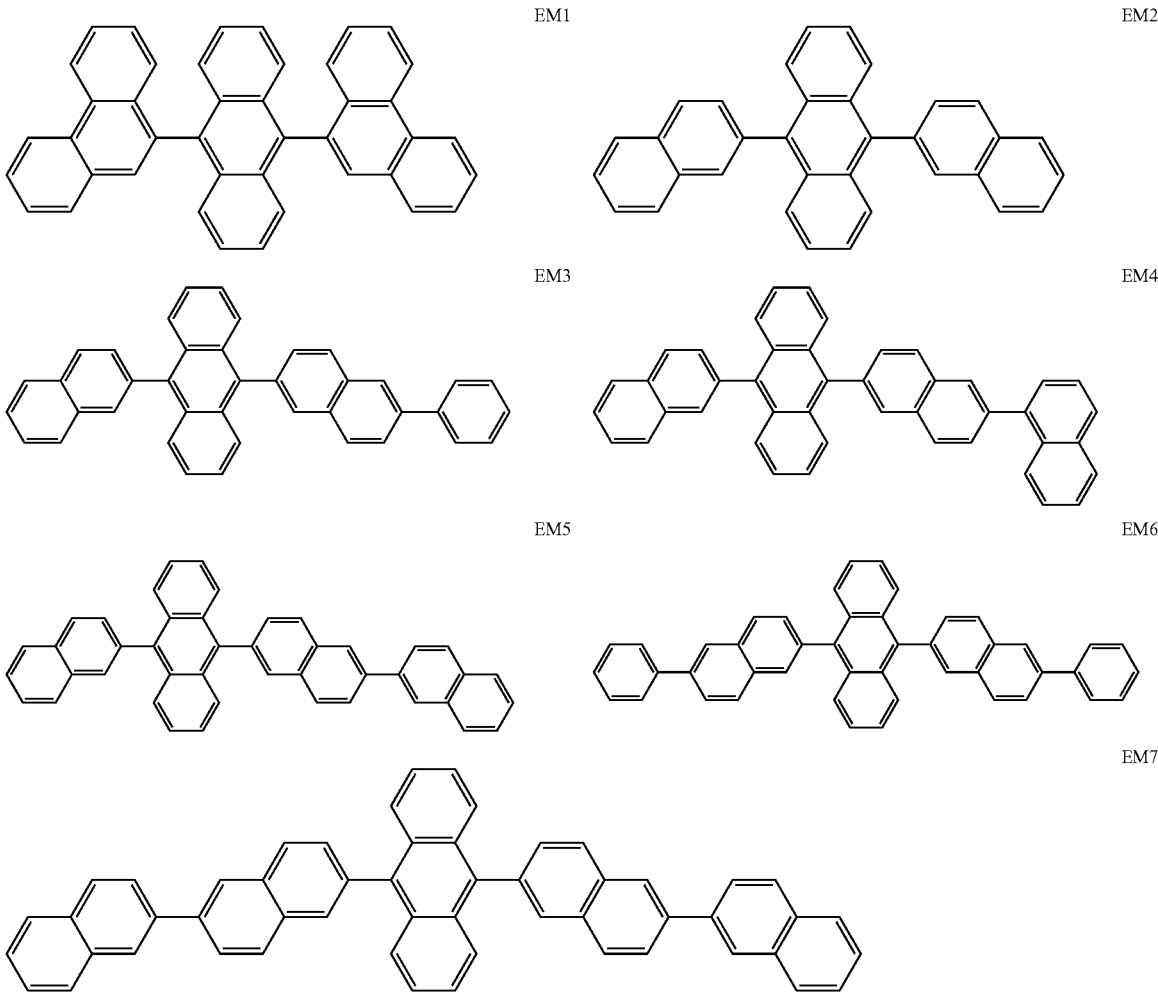

EM8
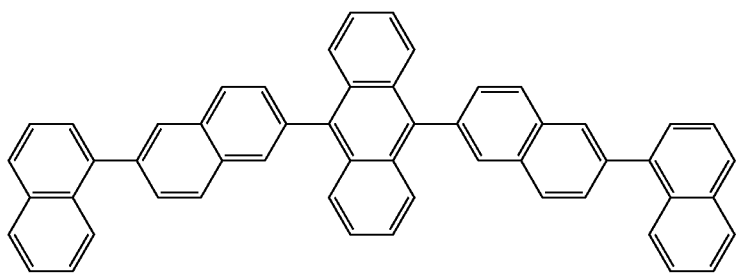
EM9
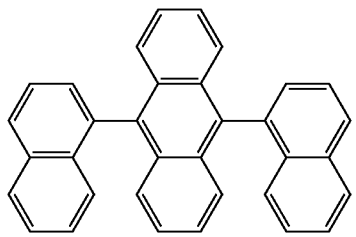
EM10
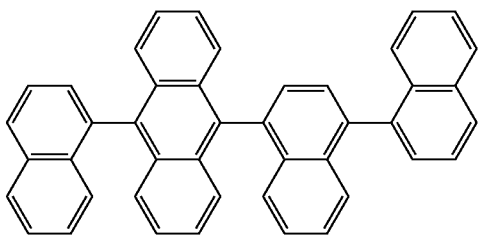
EM11
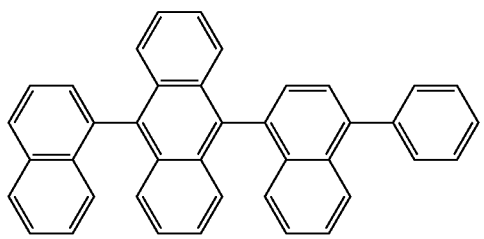
EM12
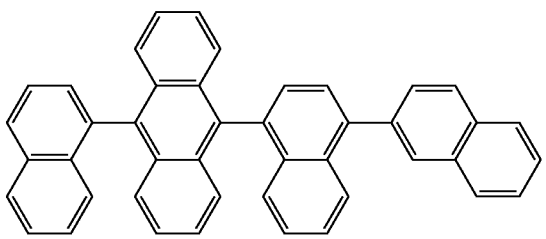
[Formula 23]
EM13
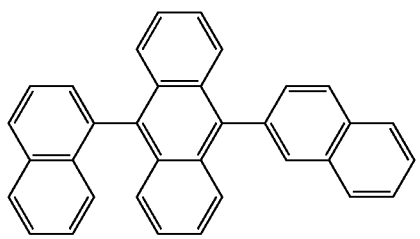
EM14
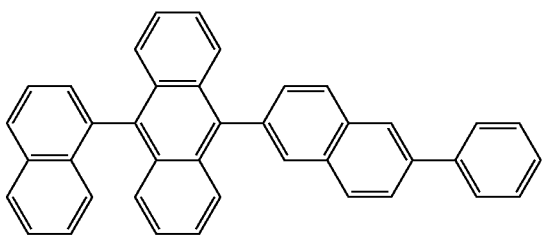
EM15
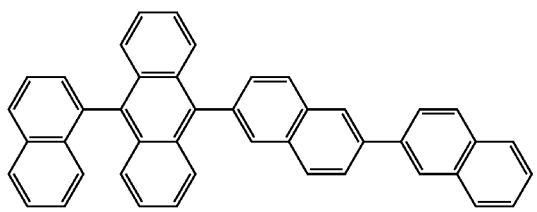
EM16
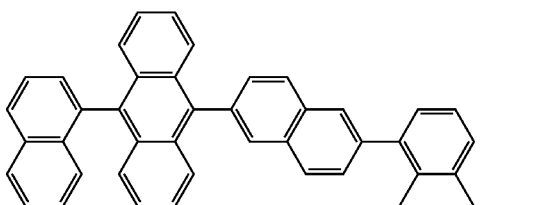
EM17
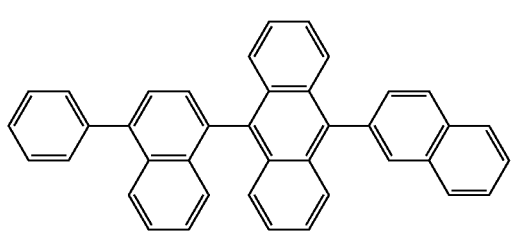
EM18
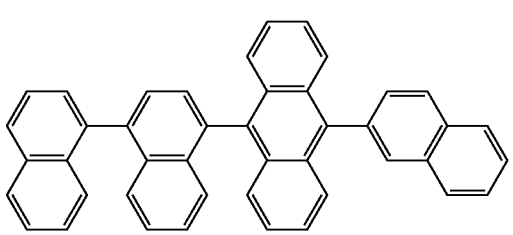

EM19
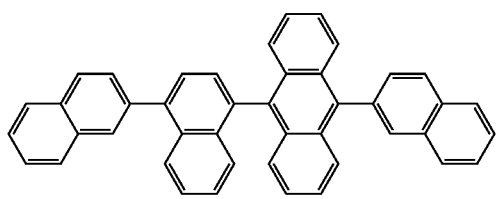
EM20
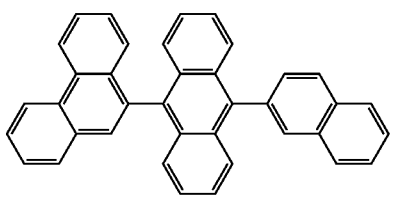
EM21
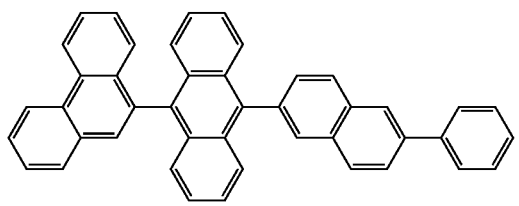
EM22
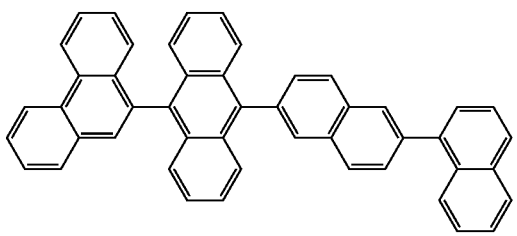
EM23
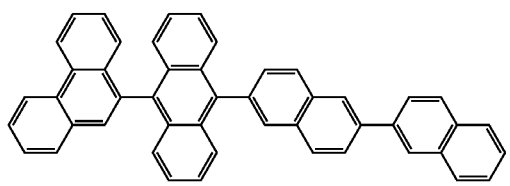
EM24
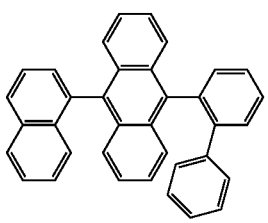
EM25
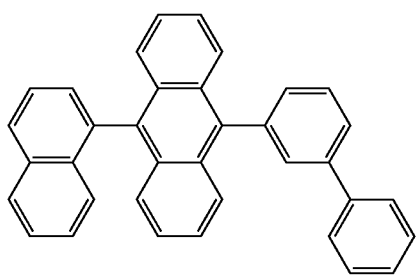
EM26
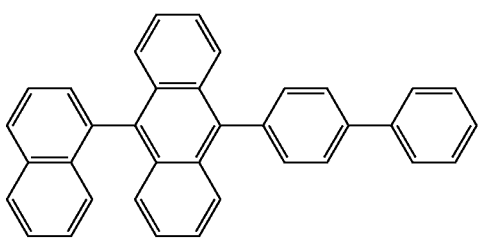
EM27
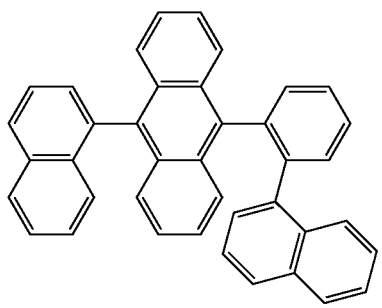
EM28
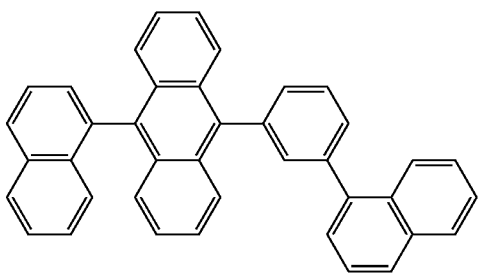
EM29
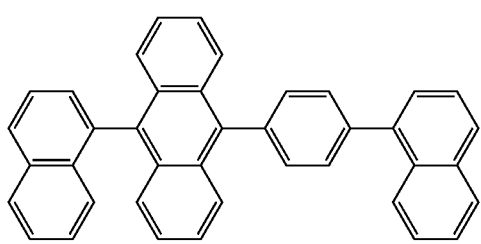

[Formula 24]
EM30 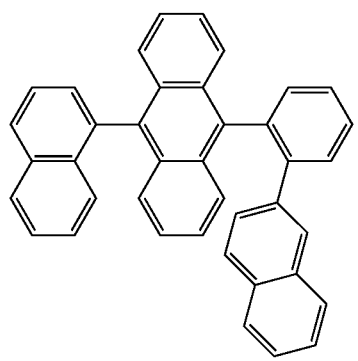
EM31 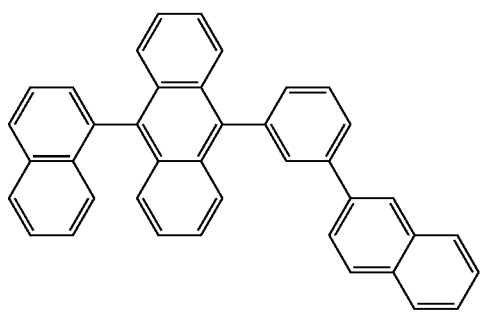
EM32 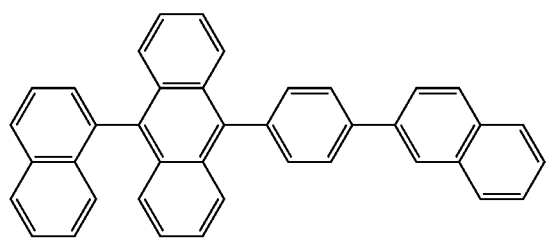
EM33 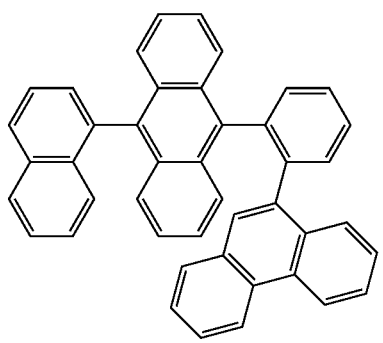
EM34 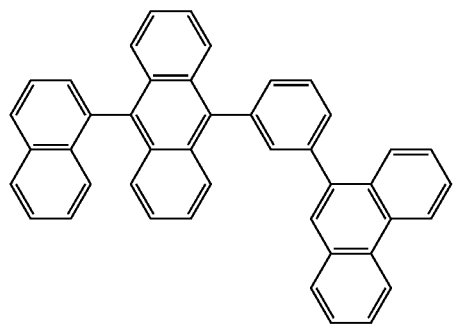
EM35 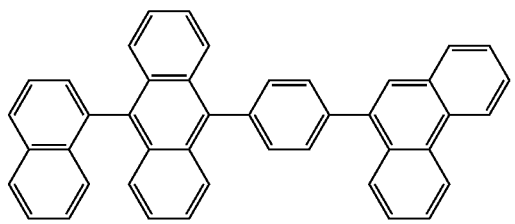
EM36 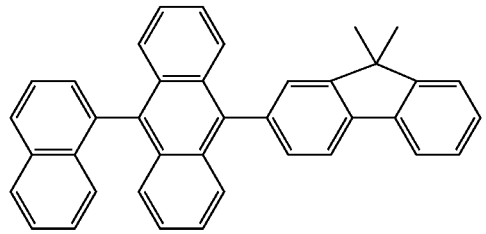
EM37 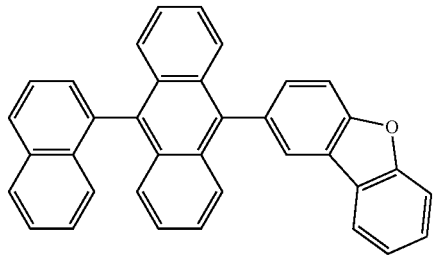
EM38 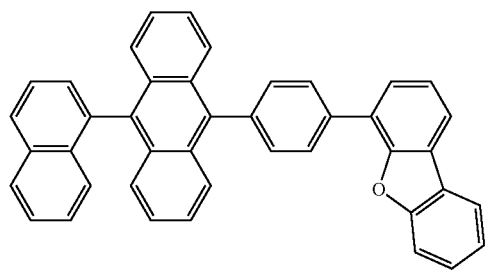
EM39 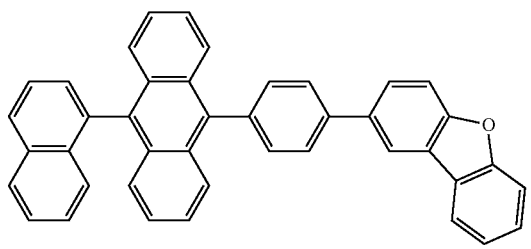

-continued
EM40
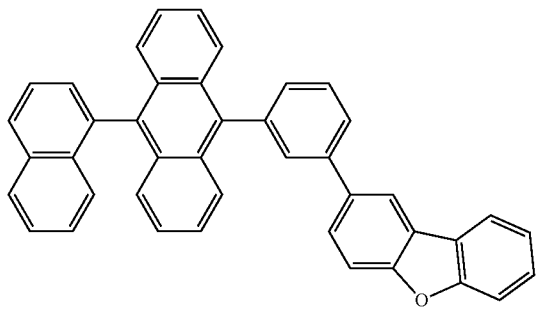
EM41
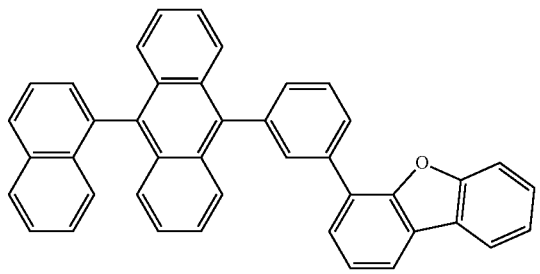
EM42
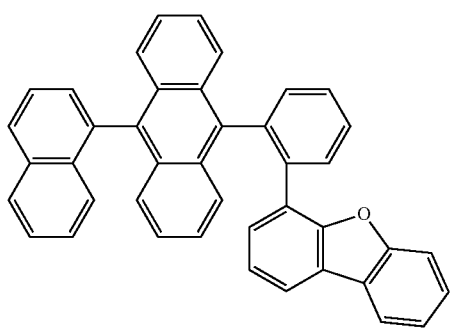
EM43
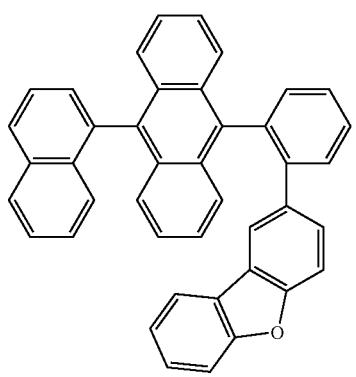
EM44
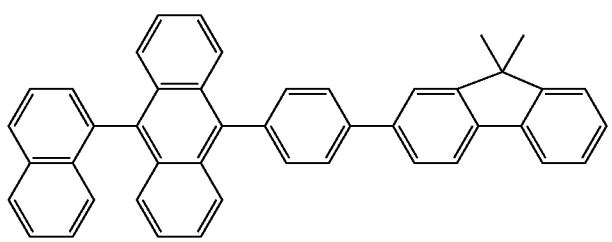
[Formula 25]
EM45
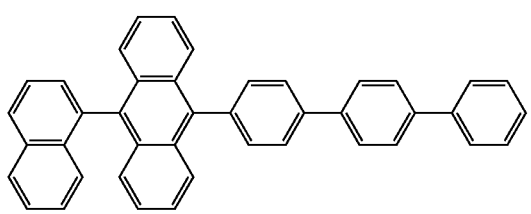
EM46
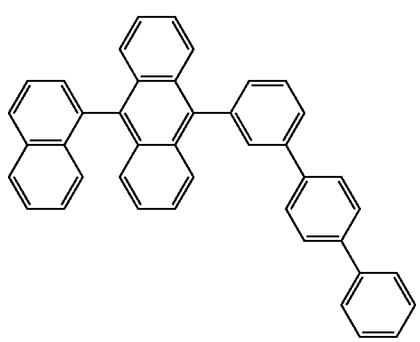

-continued
EM47
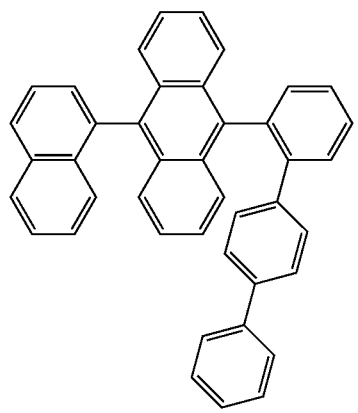
EM48
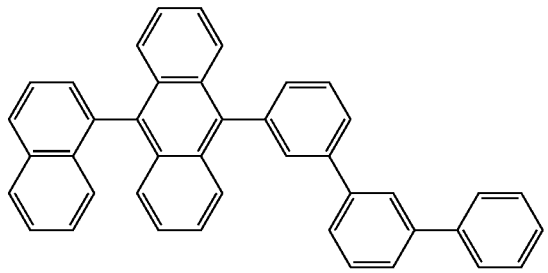
EM49
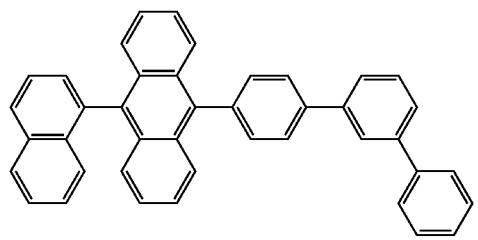
EM50
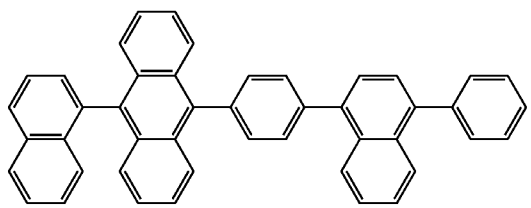
EM51
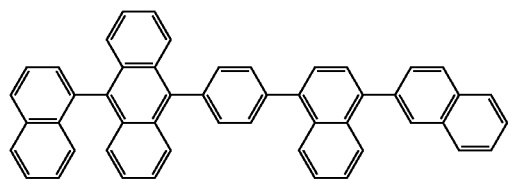
EM52
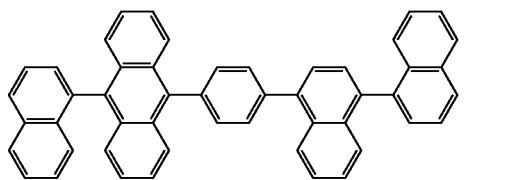
EM53
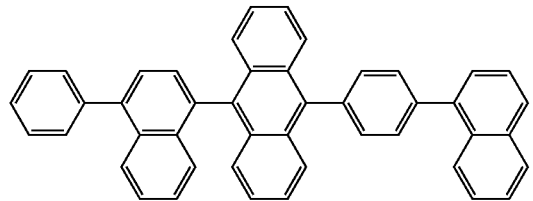
EM54
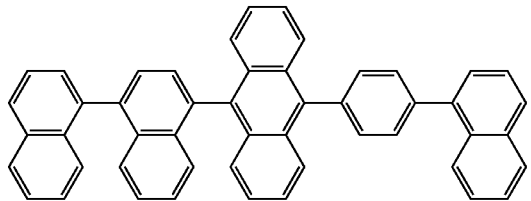
EM55
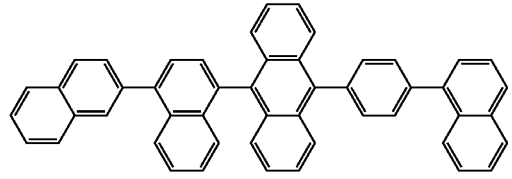
EM56
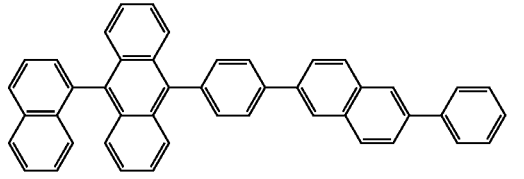
EM57
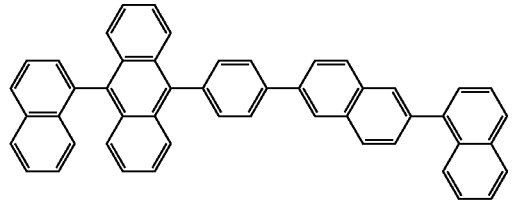
EM58
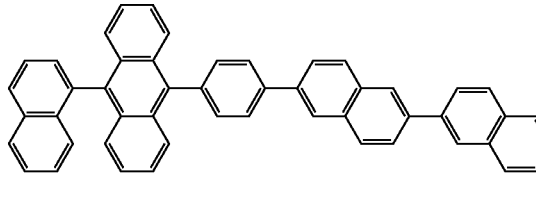

-continued
EM59
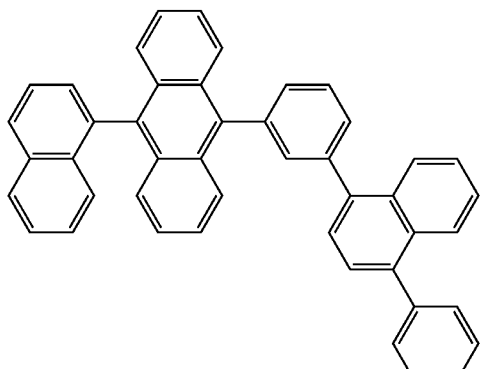
EM60
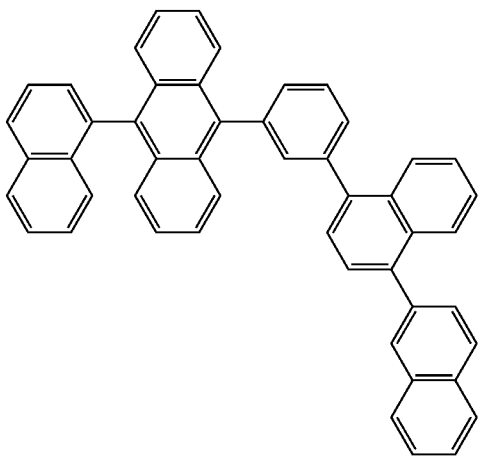
EM61
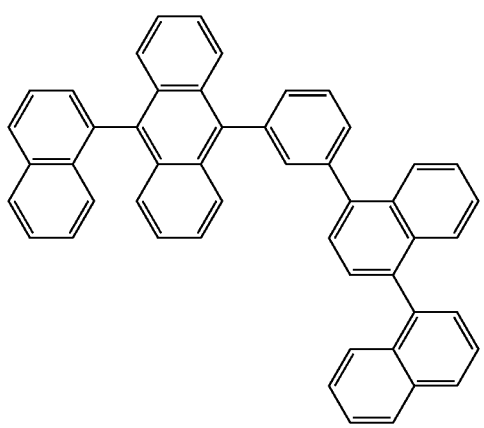
[Formula 26]
EM62
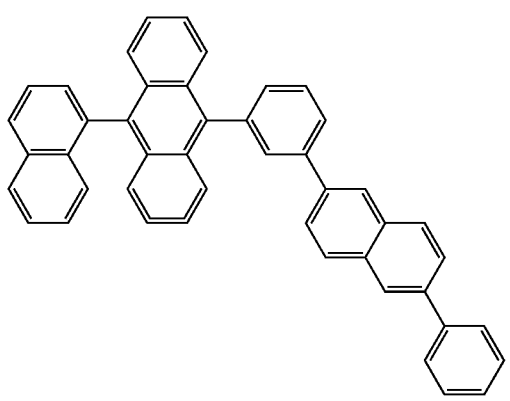
EM63
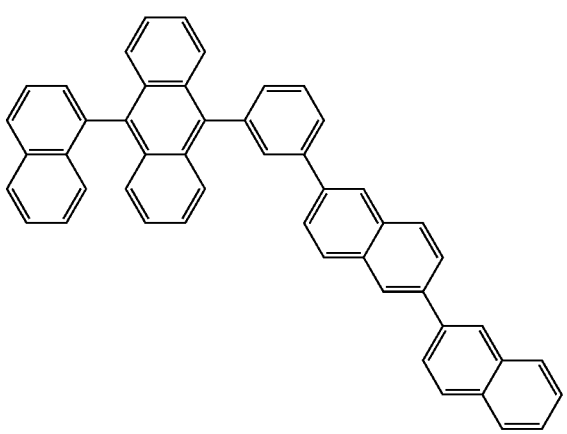

-continued

EM64

EM65

EM66

EM67

EM68

EM69

EM70

EM71

-continued
EM72
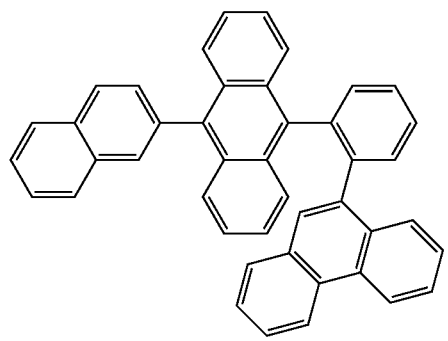
EM73
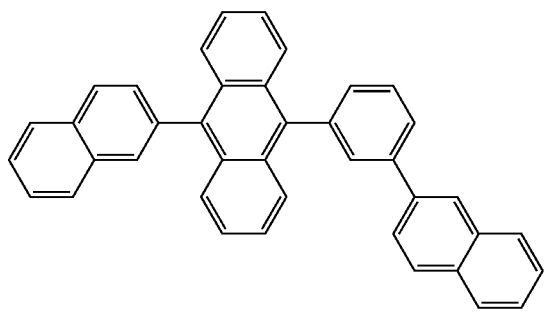
EM74
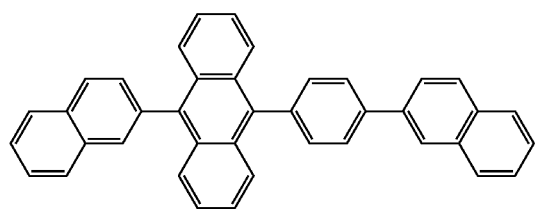
EM75
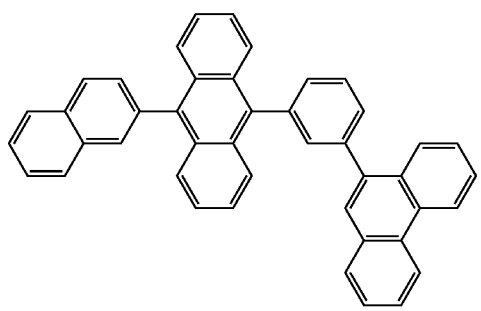
EM76
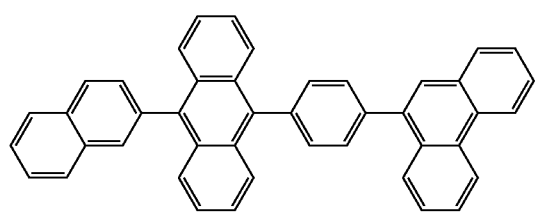
EM77
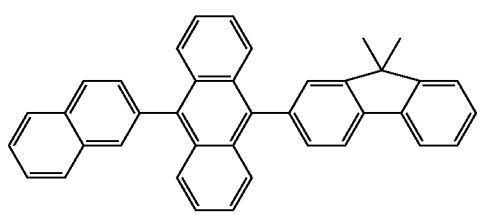
EM78
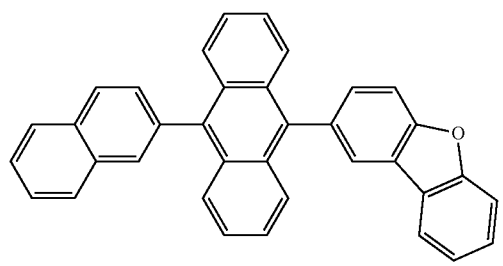
[Formula 27]
EM79
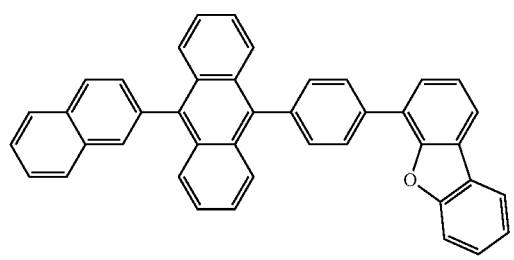
EM80
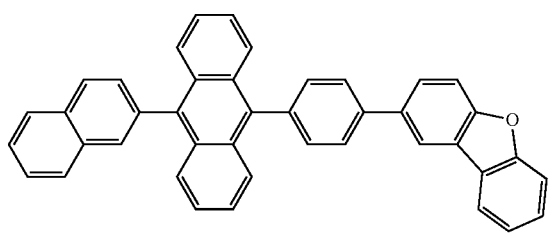

-continued
EM81
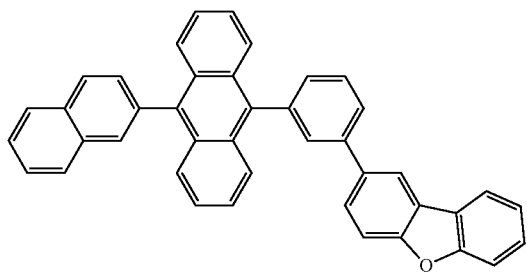
EM82
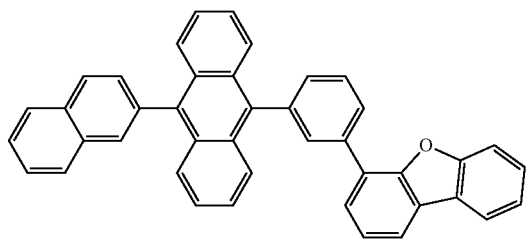
EM83
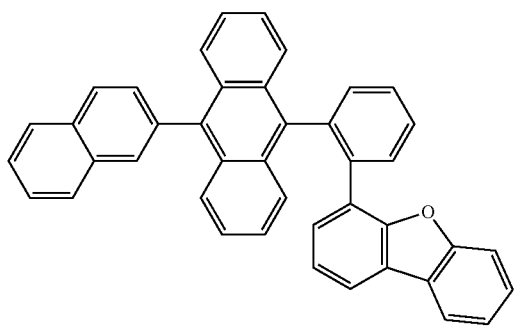
EM84
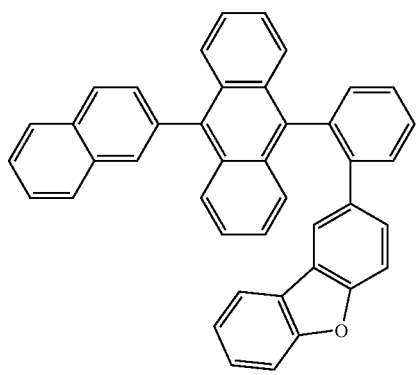
EM85
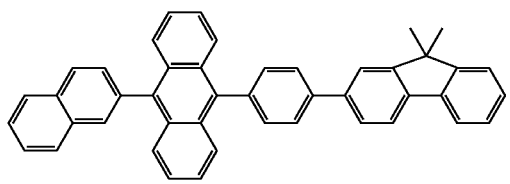
EM86
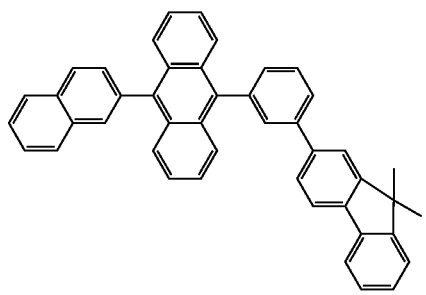
EM87
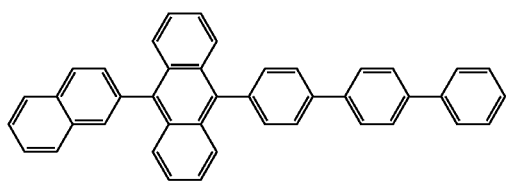
EM88
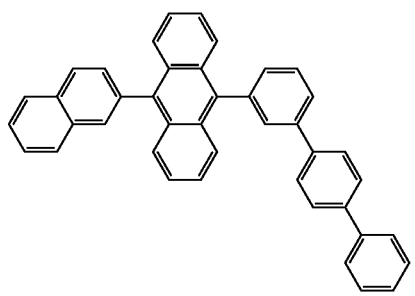

-continued
EM89
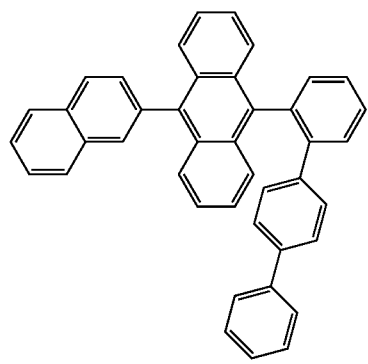
EM90
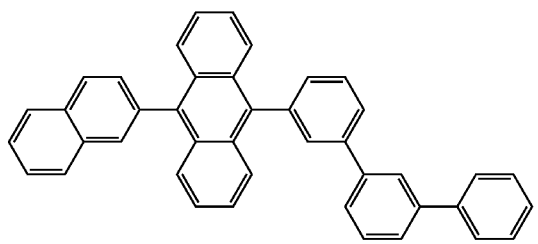
EM91
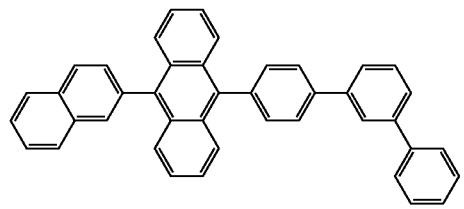
EM92
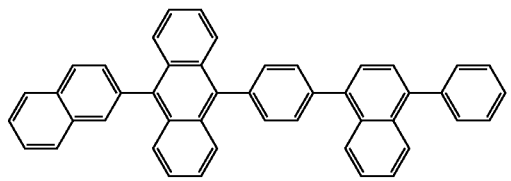
EM93
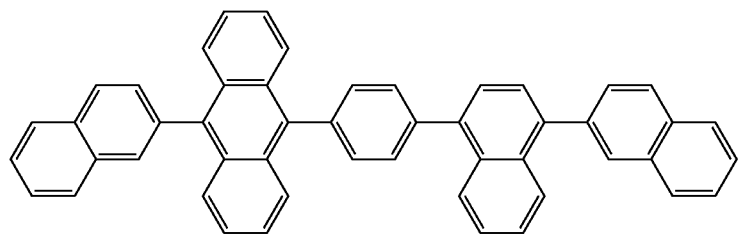
EM94
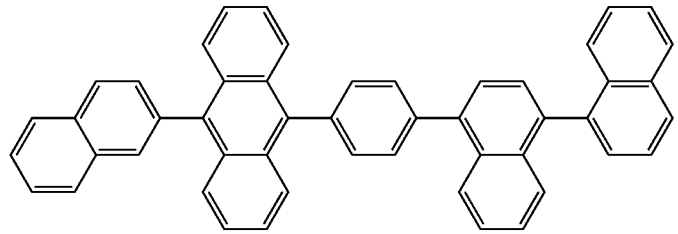
EM95
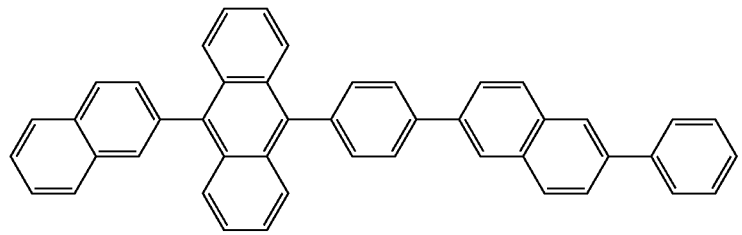
[Formula 28]
EM96
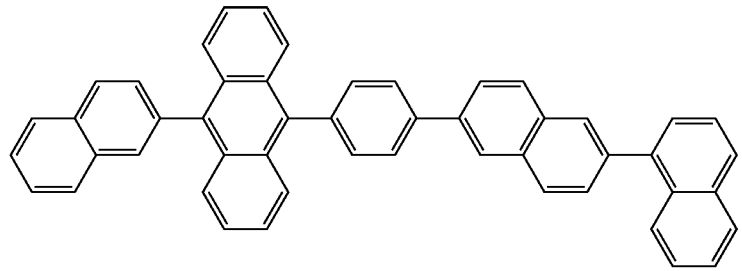

-continued
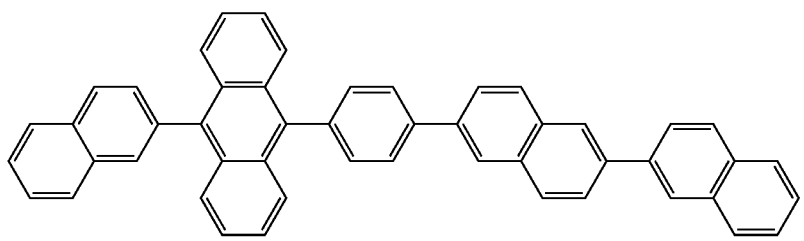
EM97
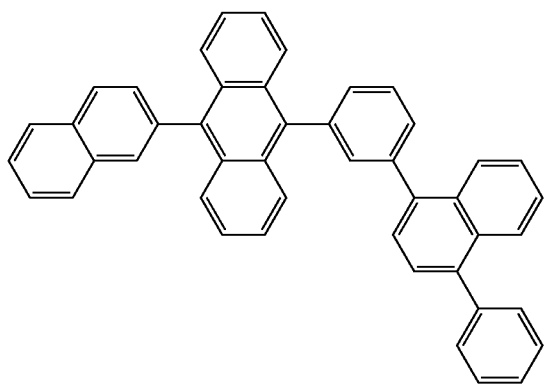
EM98
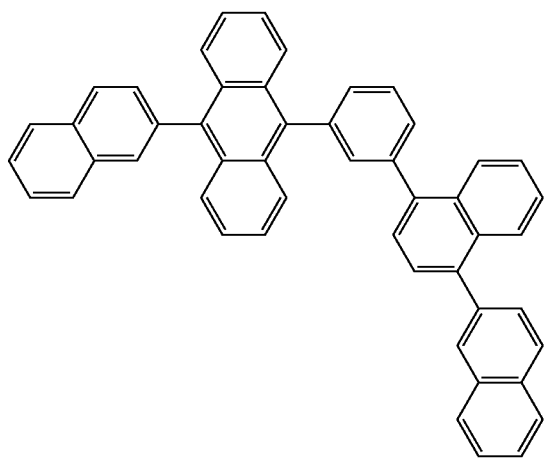
EM99
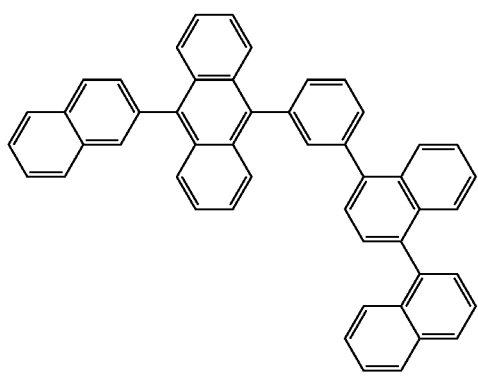
EM100
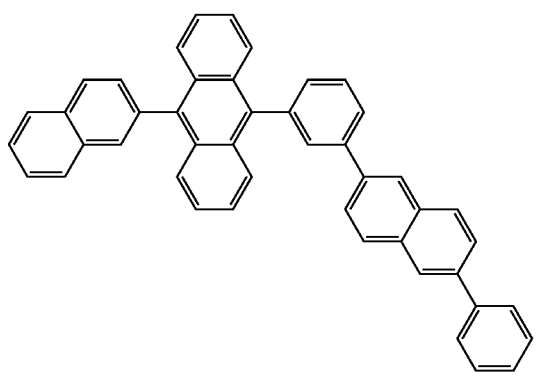
EM101
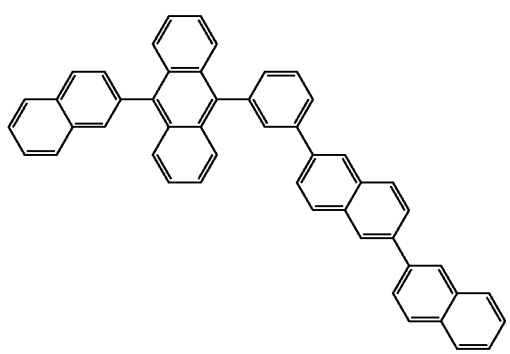
EM102
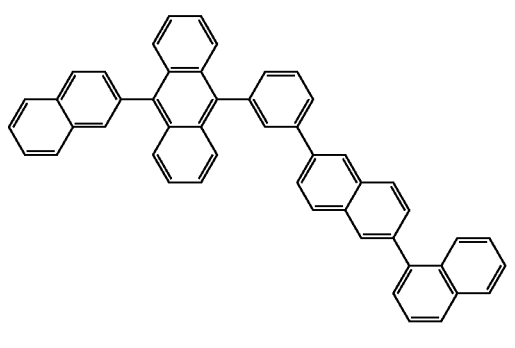
EM103

-continued
EM104
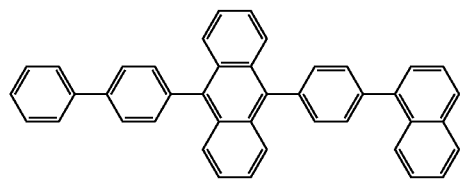
EM105
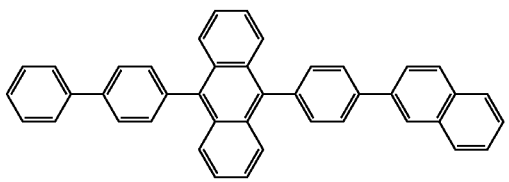
EM106
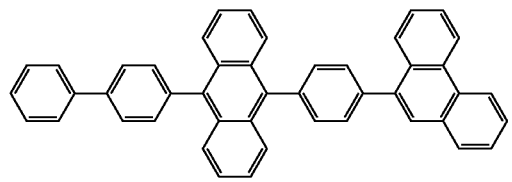
EM107
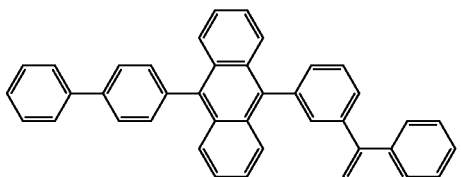
EM108
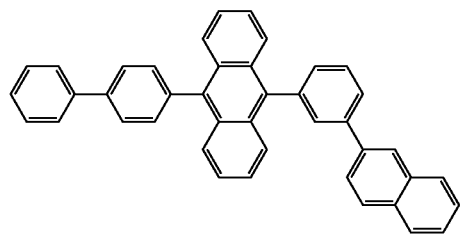
EM109
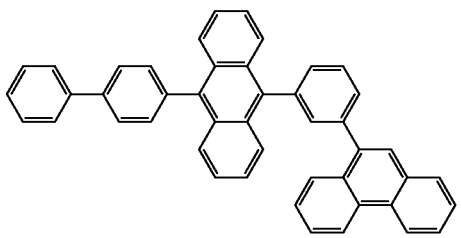
[Formula 29]
EM110
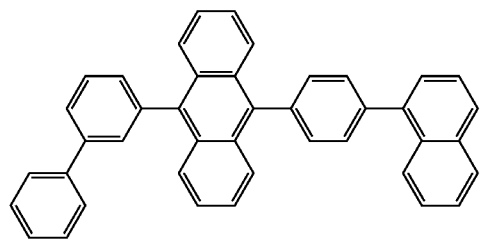
EM111
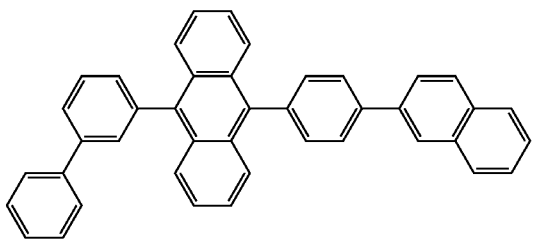
EM112
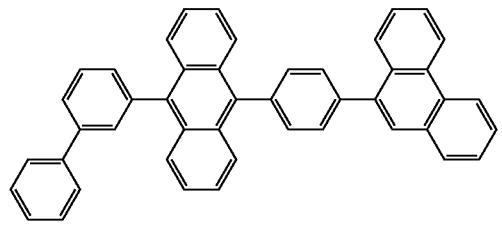
EM113
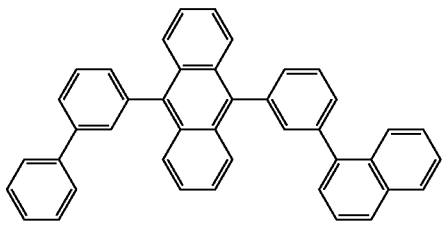
EM114
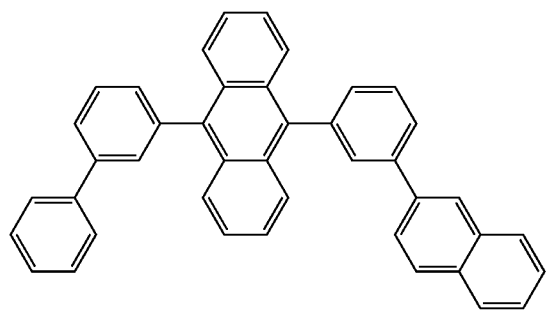
EM115
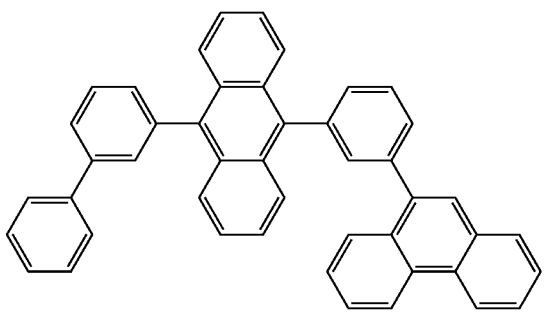

-continued
EM116
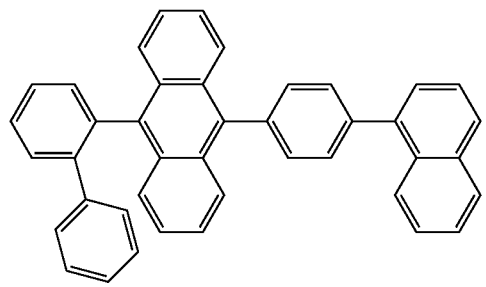
EM117
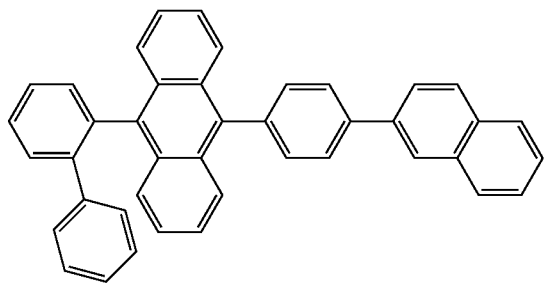
EM118
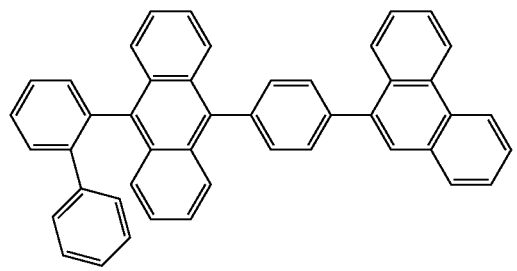
EM119
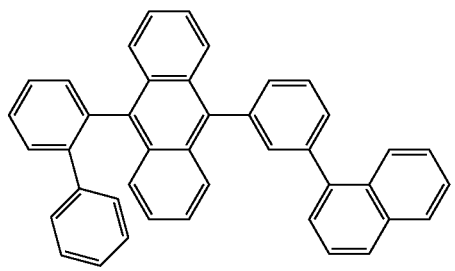
EM120
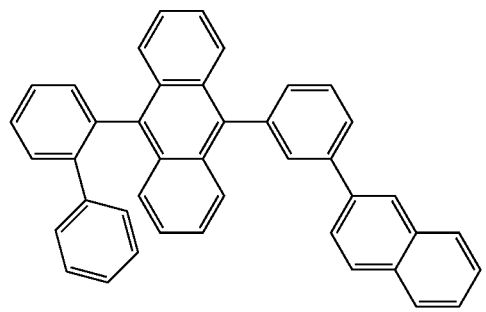
EM121
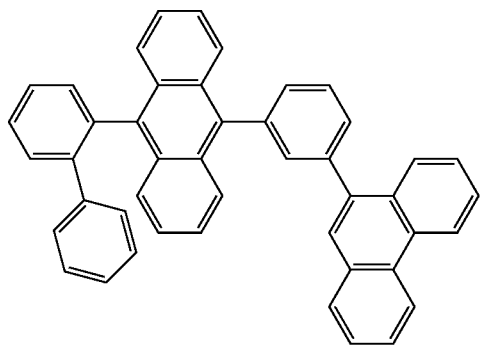
EM122
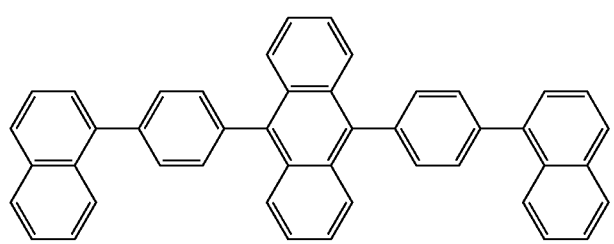
EM123
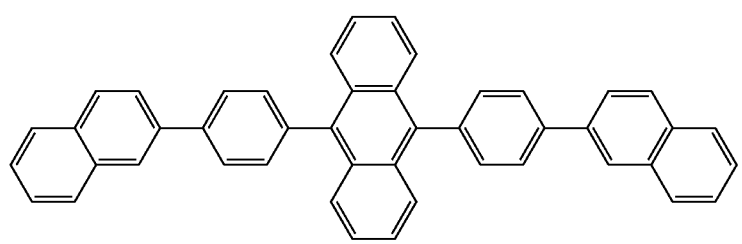

EM124
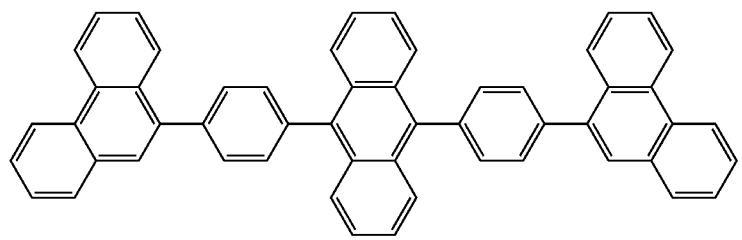
EM125
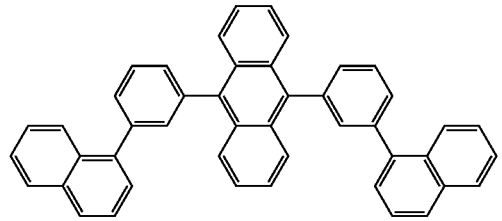
EM126
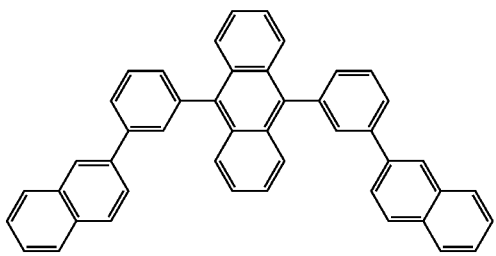
[Formula 30]
EM127
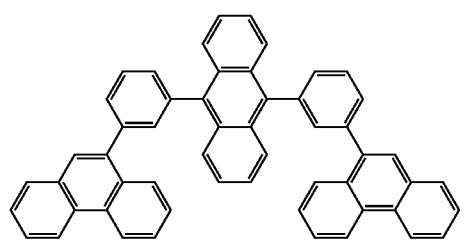
EM128
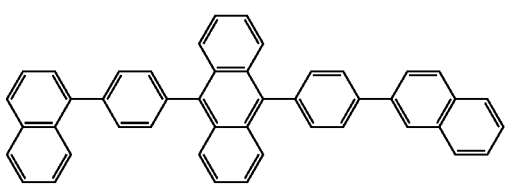
EM129
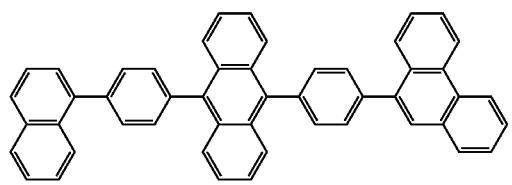
EM130
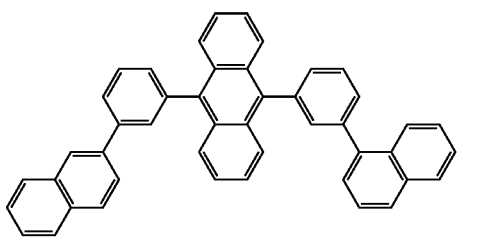
EM131
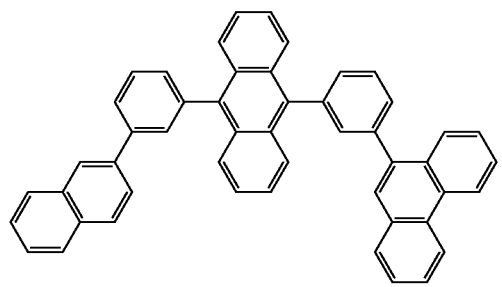
EM132
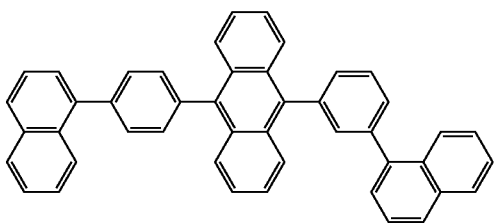
EM133
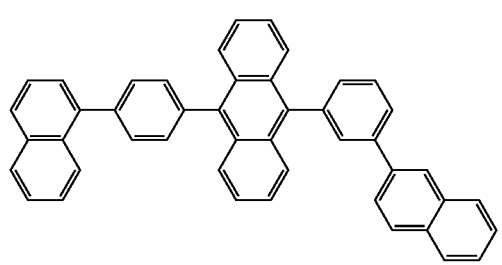
EM134
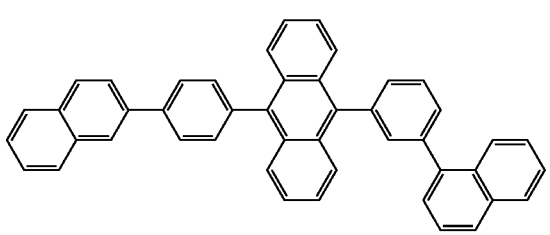

-continued
EM135
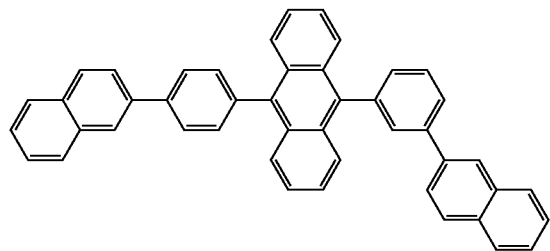
EM136
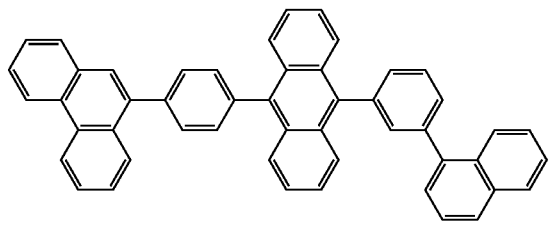
EM137
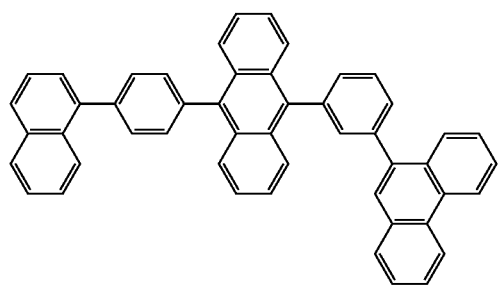
EM138
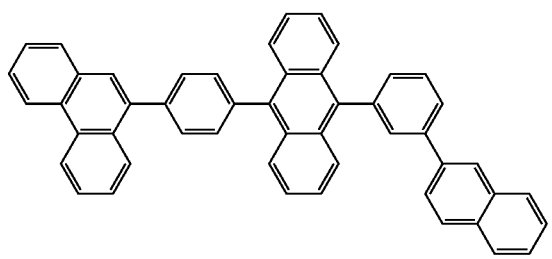
EM139
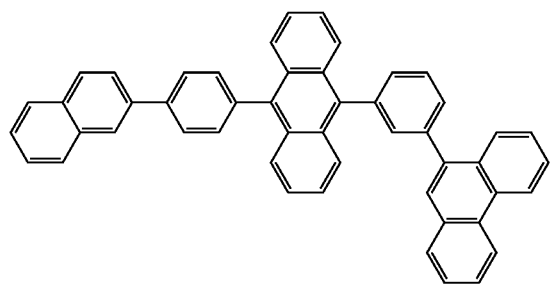
EM140
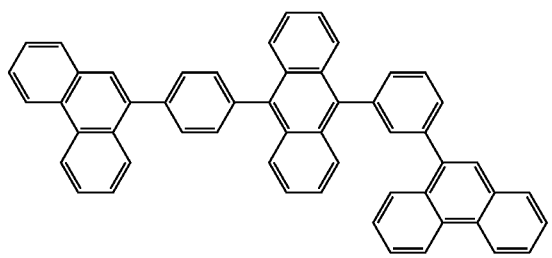
EM141
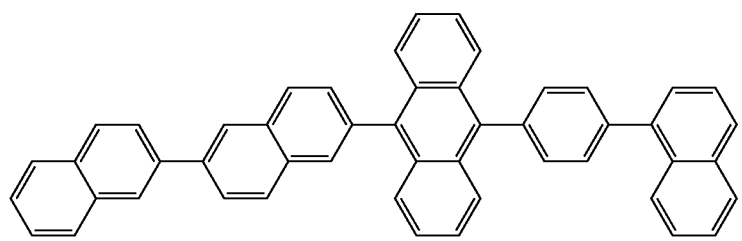
EM142
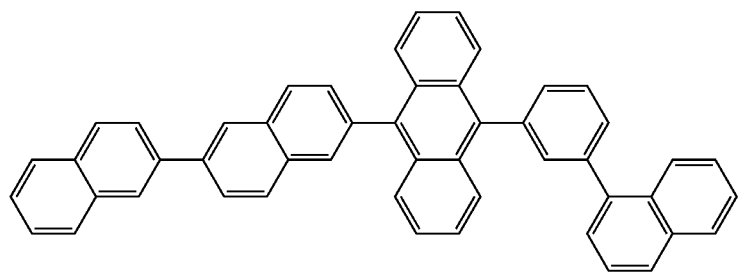

[Formula 31]
EM143
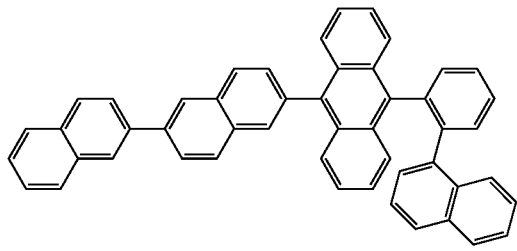
EM144
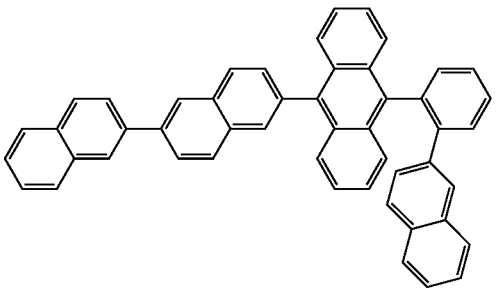
EM145
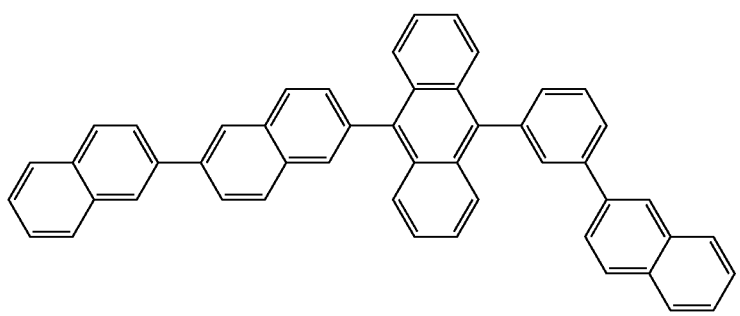
EM146
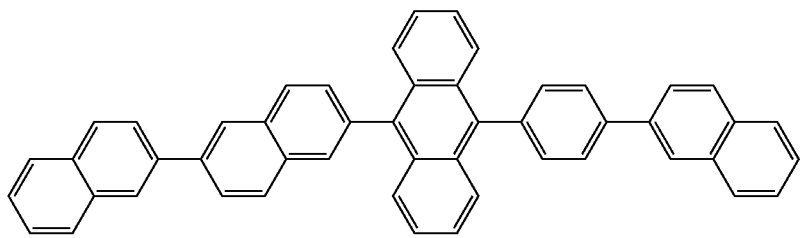
EM147
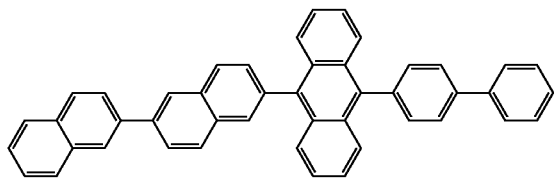
EM148
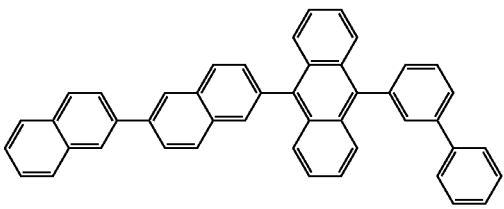
EM149
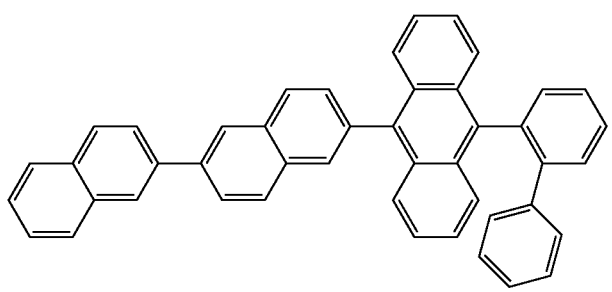

[Formula 32]
EM150 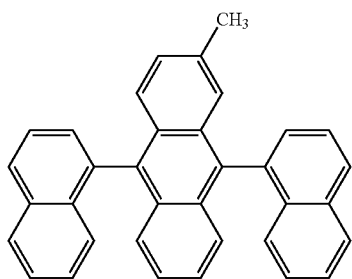
EM151 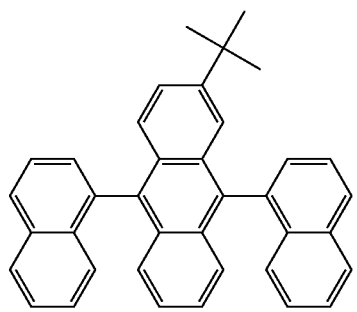
EM152 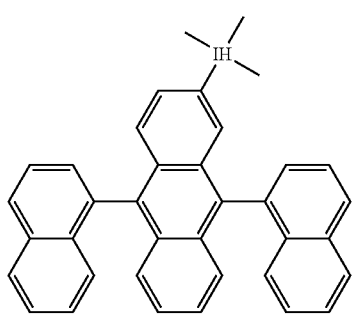
EM153 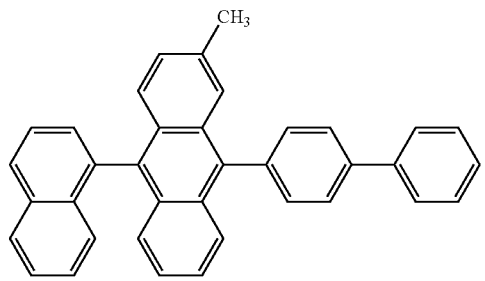
EM154 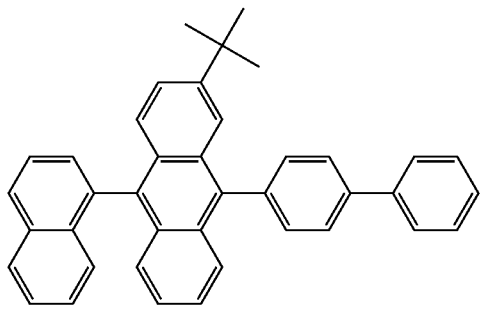
EM155 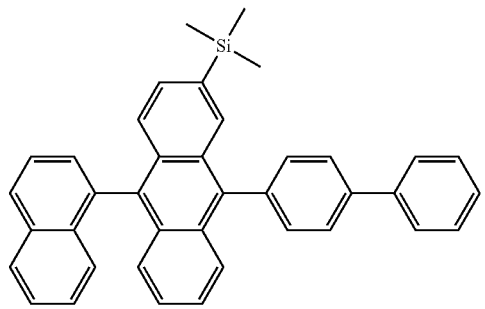
EM156 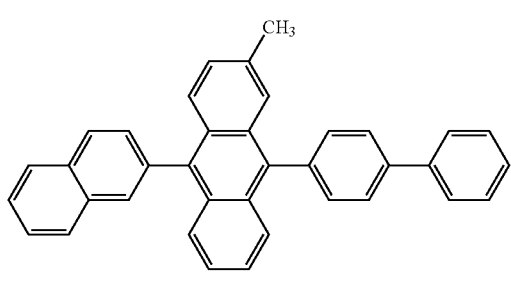
EM157 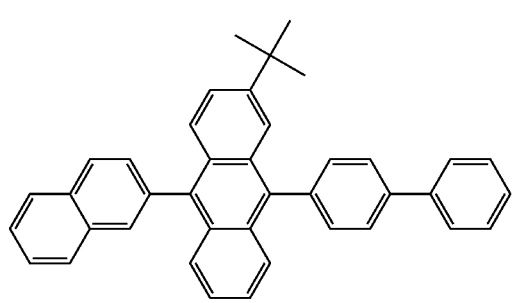
EM158 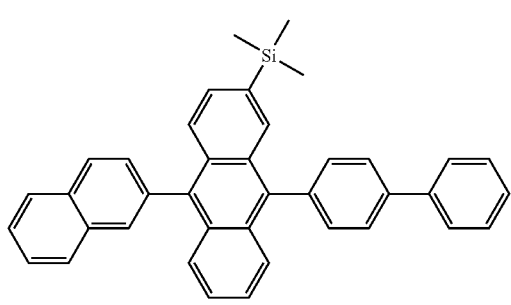
EM159 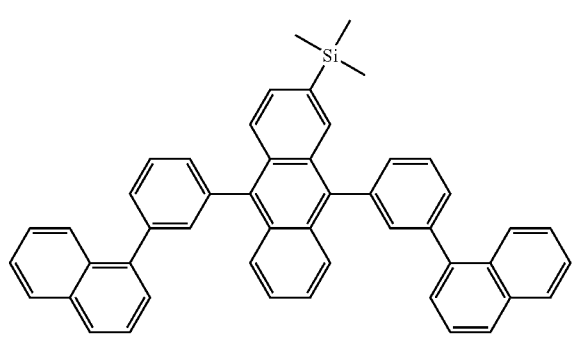

EM160
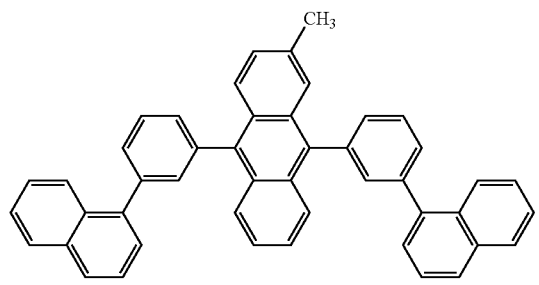
EM161
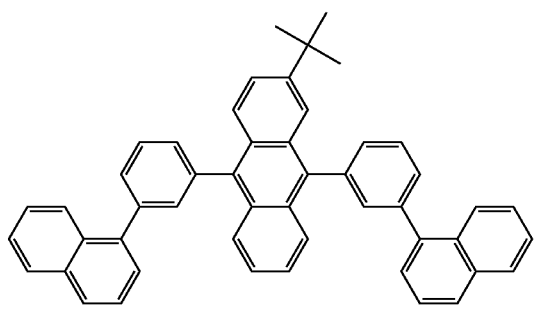
EM162
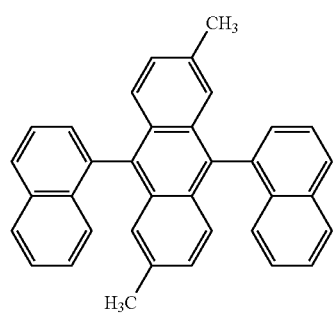
EM163
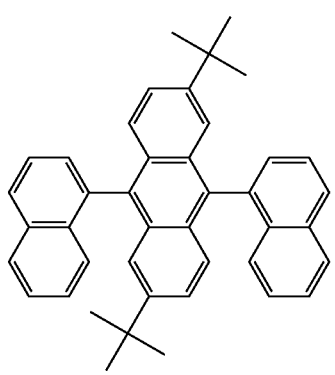
EM164
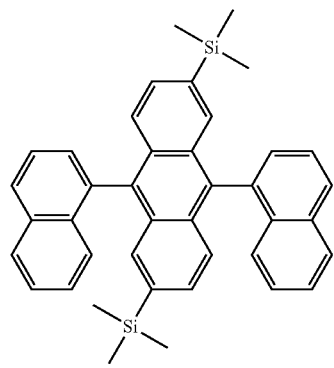
[Formula 33]
EM165
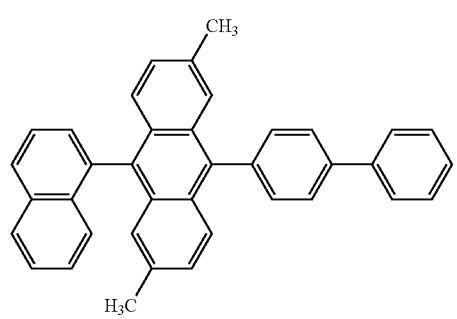
EM166
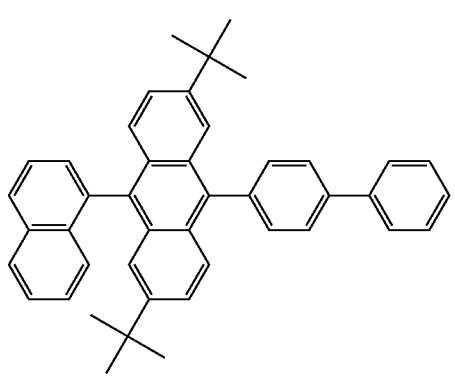

-continued
EM167
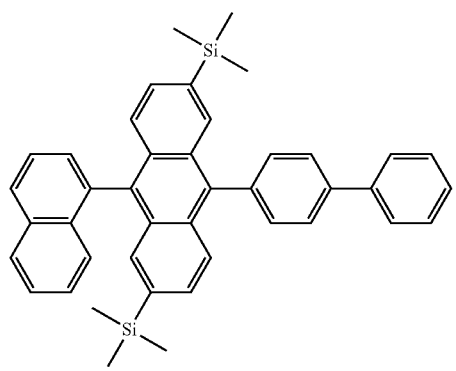
EM168
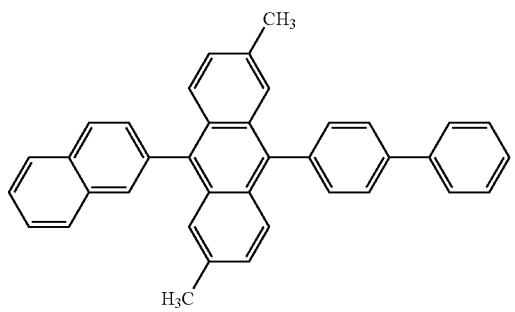
EM169
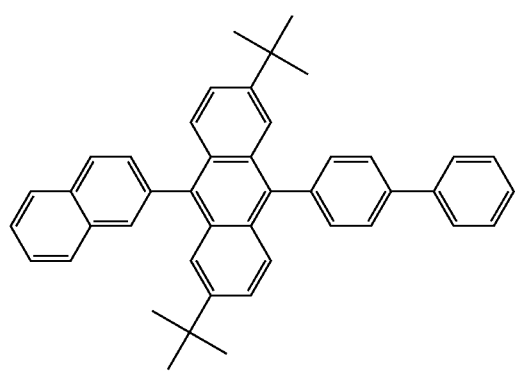
EM170
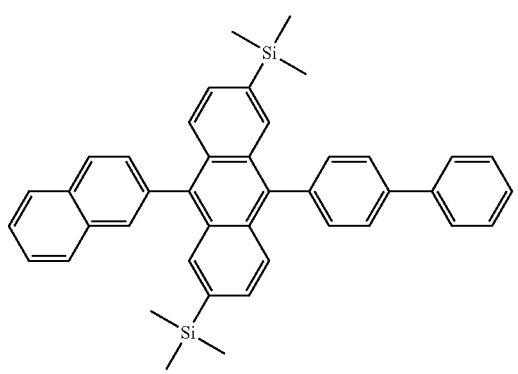
EM171
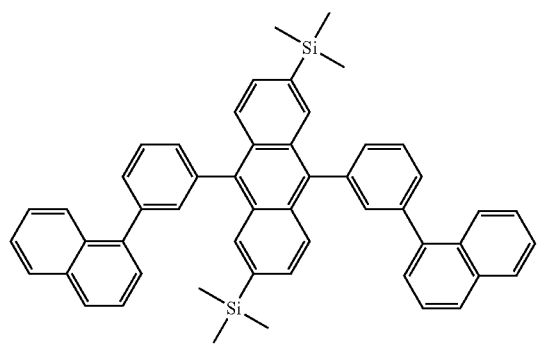
EM172
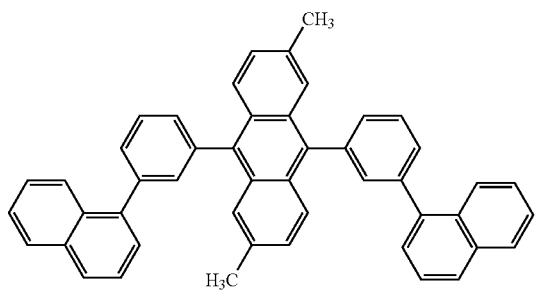
EM173
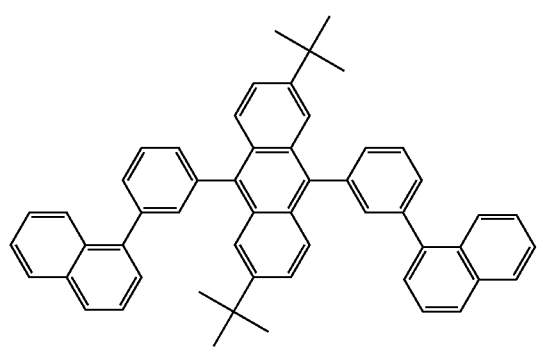
EM174
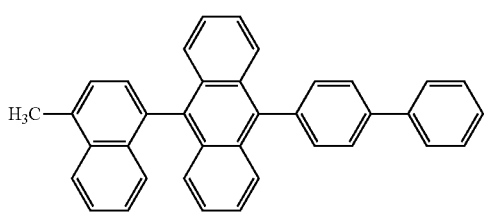

-continued
EM175
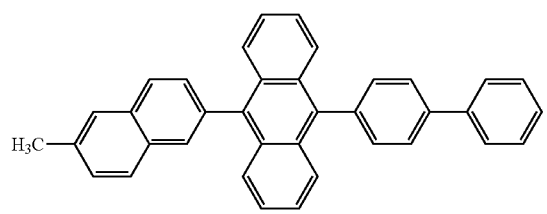
EM176
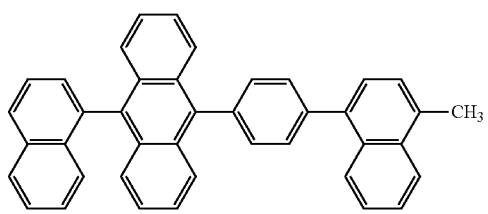
EM177
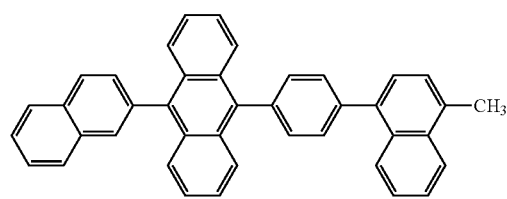
EM178
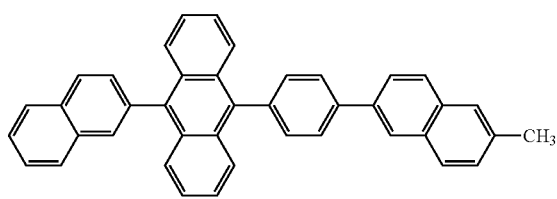
EM179
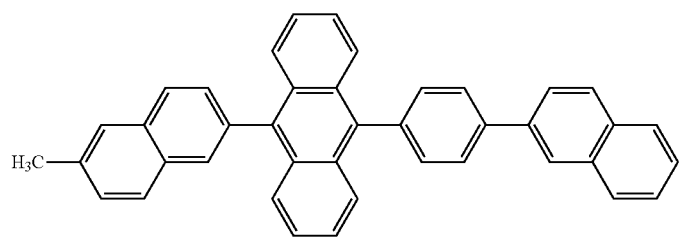
[Formula 34]
EM180
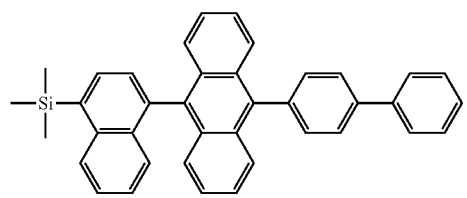
EM181
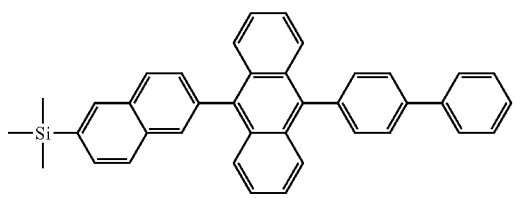
EM182
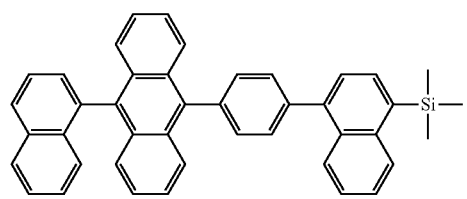
EM183
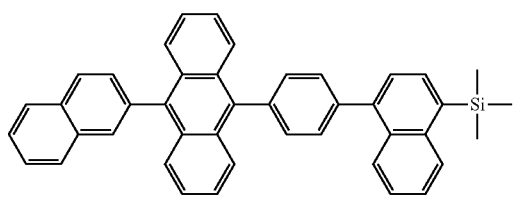
EM184
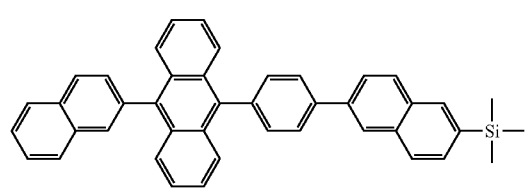
EM185
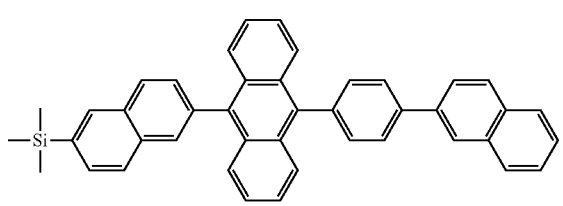

-continued
EM186
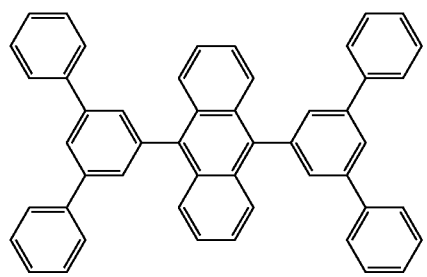
EM187
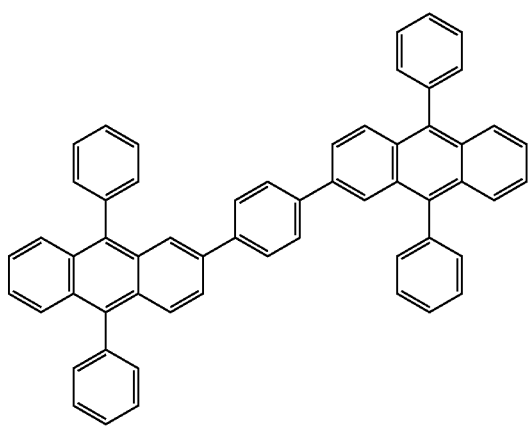
EM188
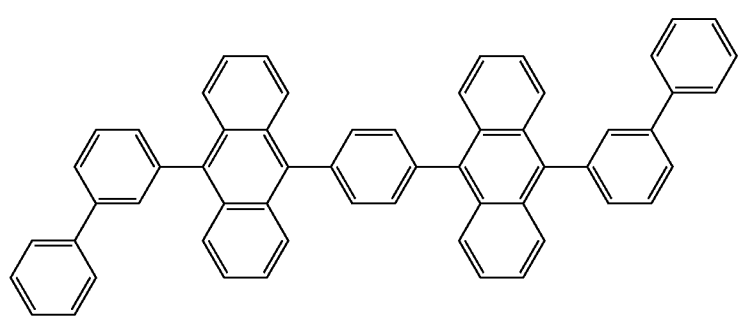
EM189
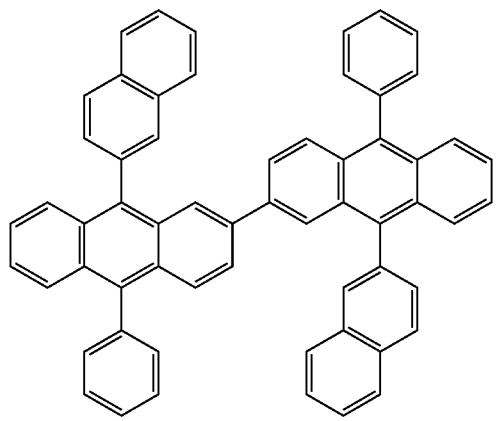
EM190
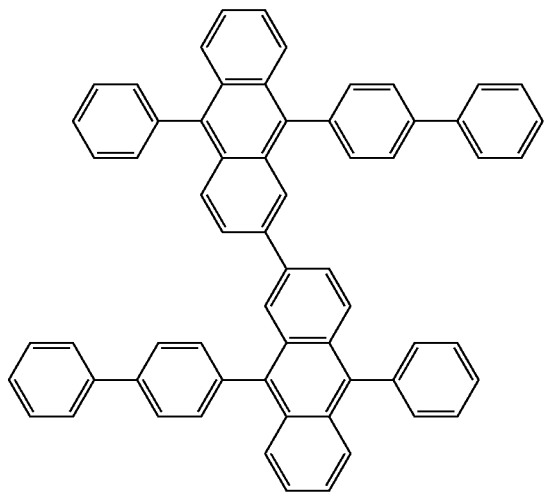
EM191
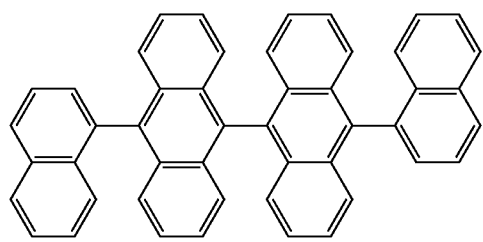

[Formula 35]
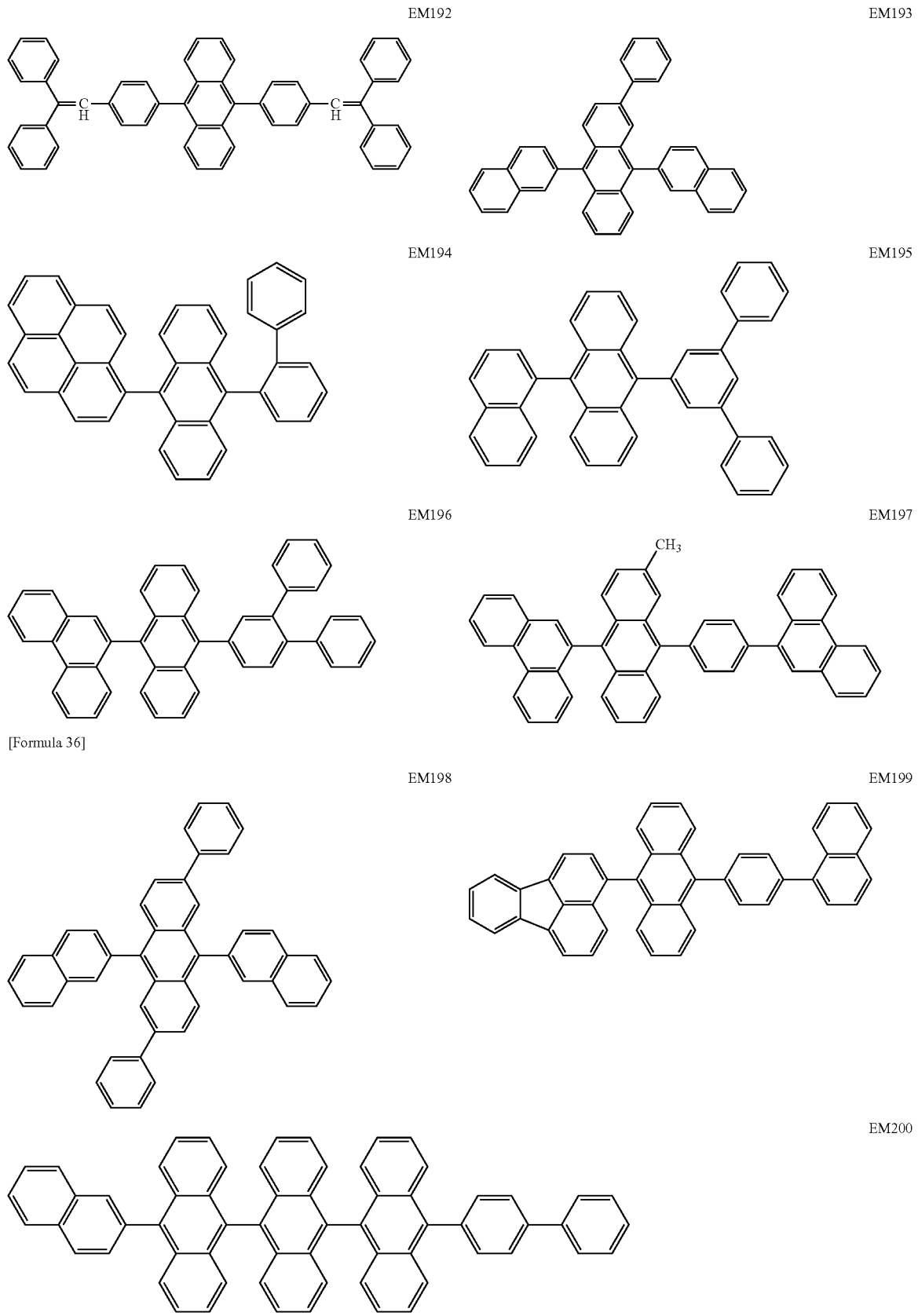
[Formula 36]

-continued
EM201
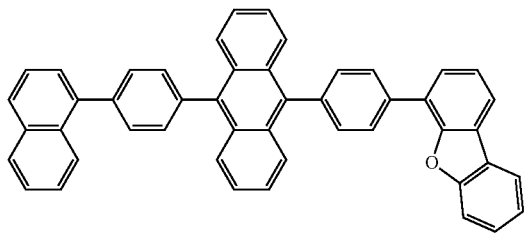
EM202
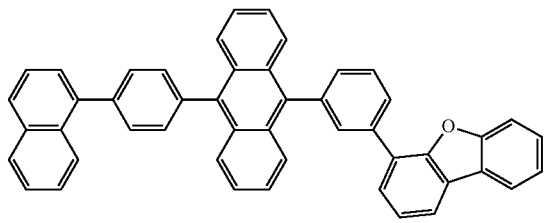
EM203
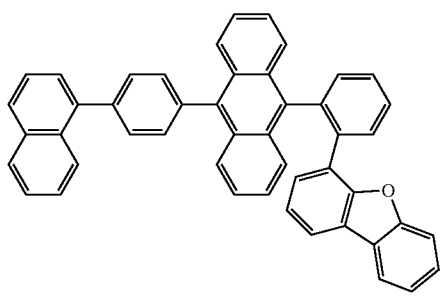
EM204
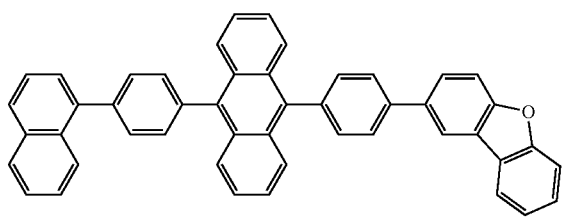
EM205
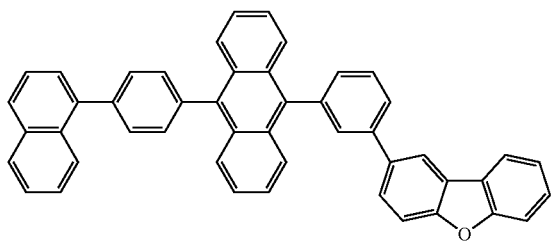
EM206
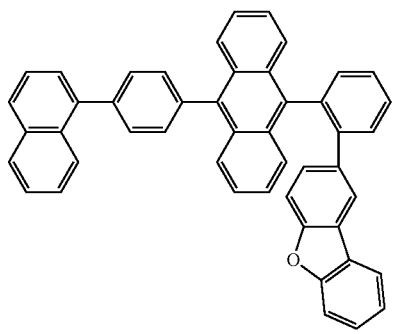
EM207
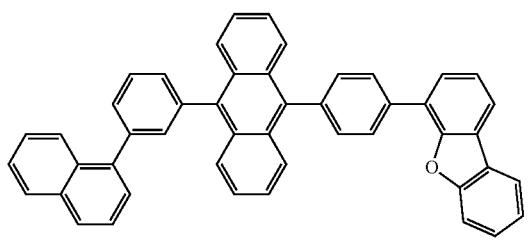
EM208
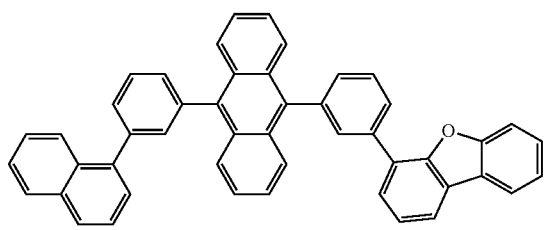
[Formula 37]
EM209
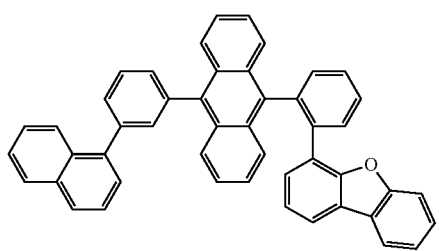
EM210
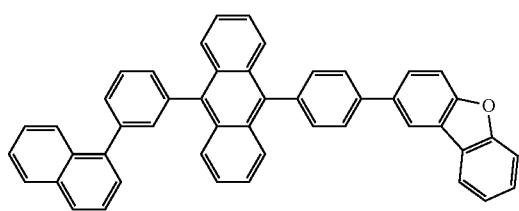

-continued
EM211
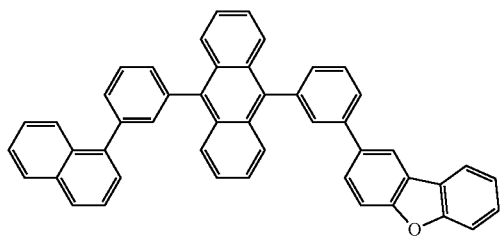
EN112
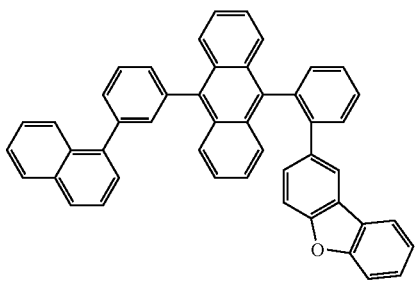
EM213
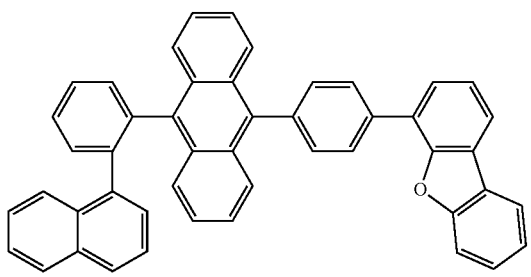
EM214
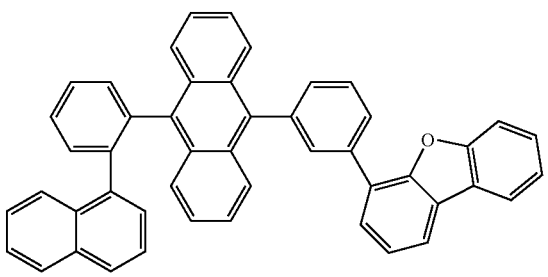
[Formula 38]
EM215
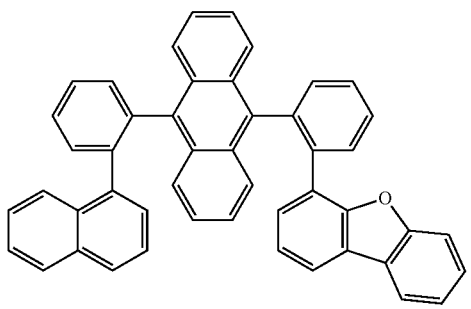
EM216
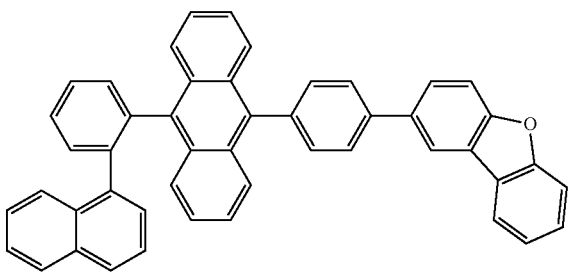
EM217
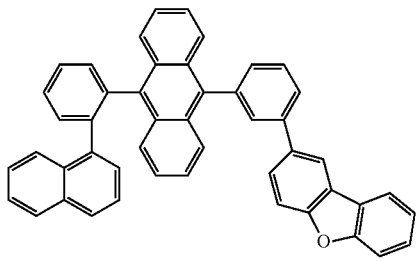
EM218
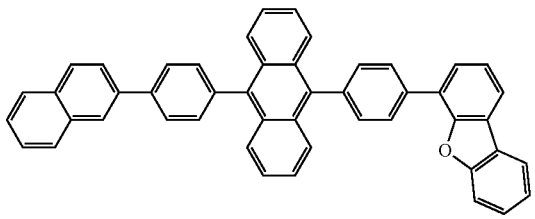
EM219
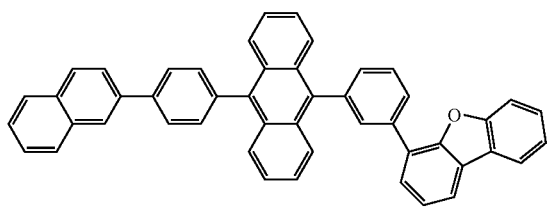
EM220
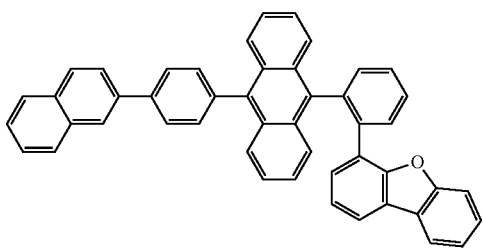

-continued
EM221
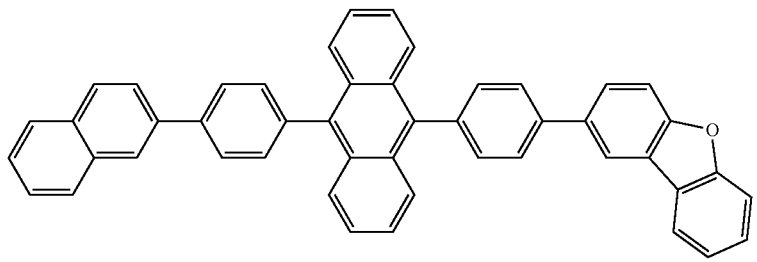
EM222
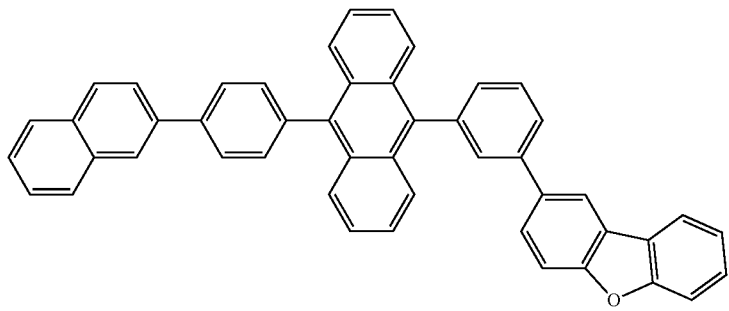
EM223
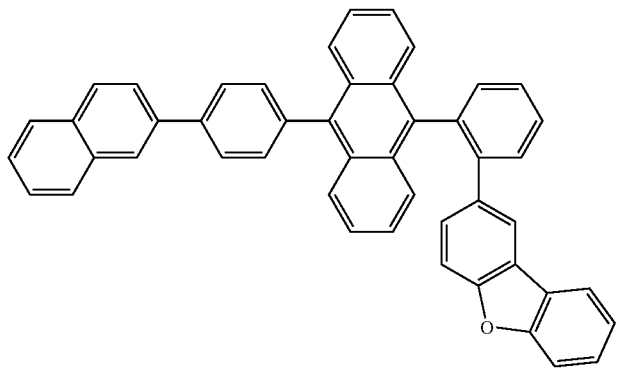
[Formula 39]
EM224
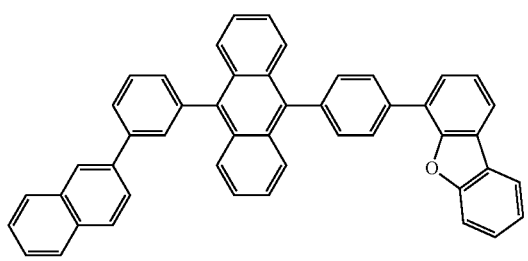
EM225
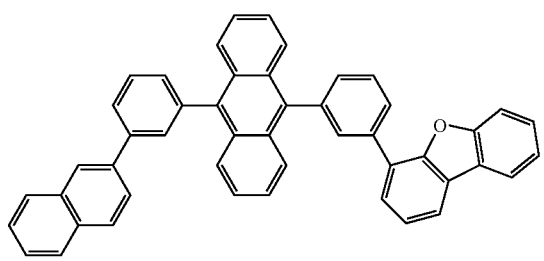
EM226
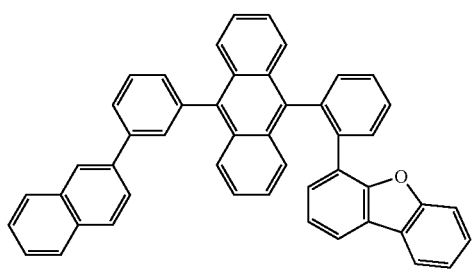
EM227
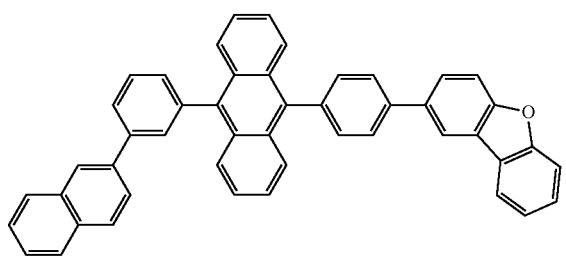

-continued
EM228
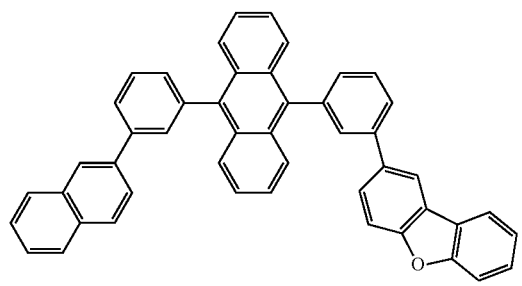
EM229
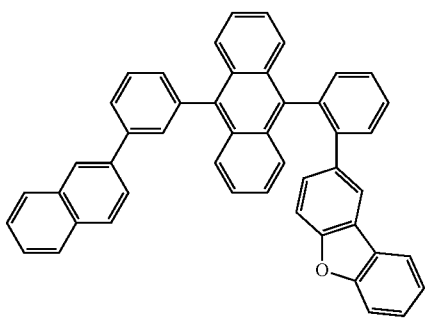
EM230
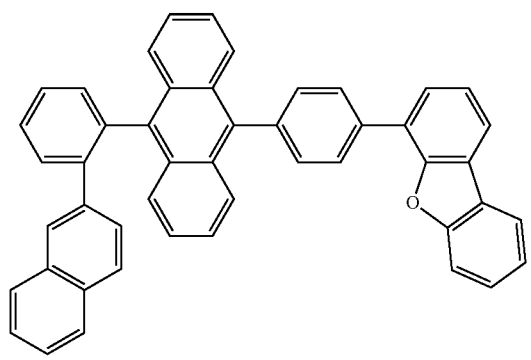
EM231
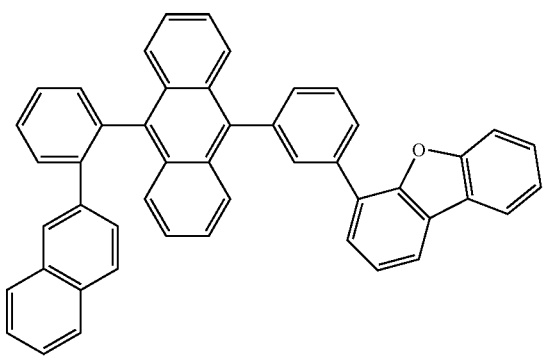
EM232
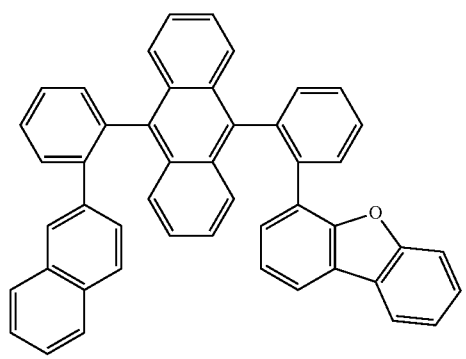
[Formula 40]
EM233
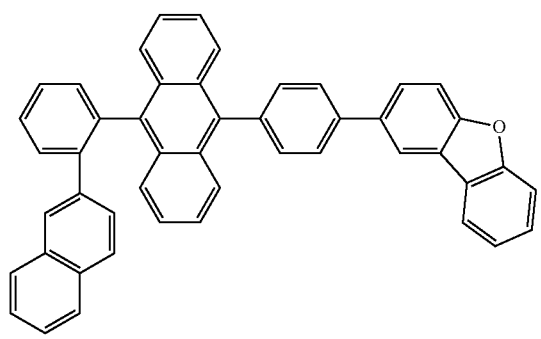
EM234
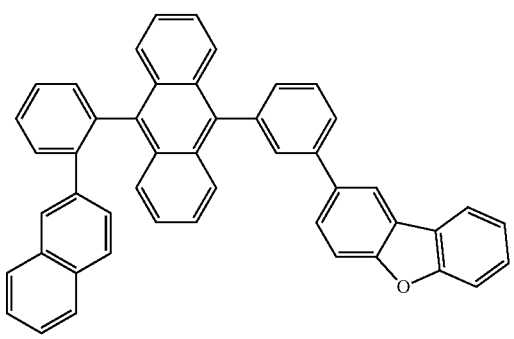

-continued
EM225
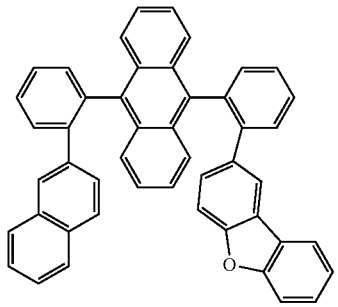
EM236
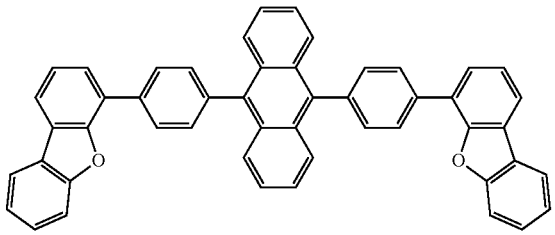
EM237
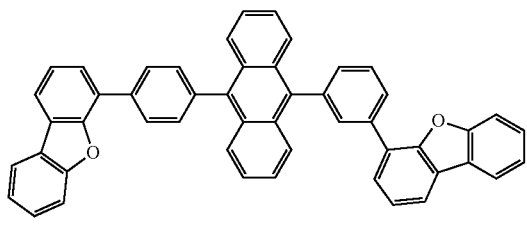
EM238
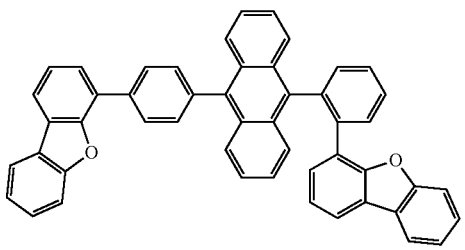
EM239
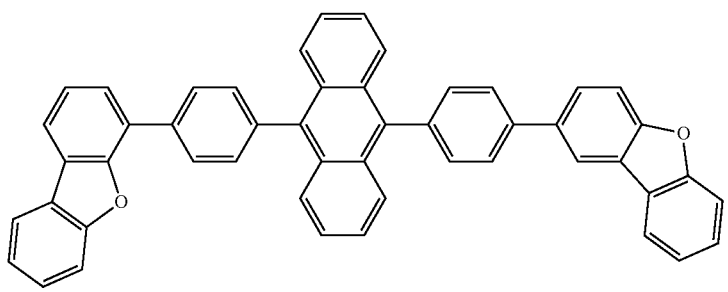
EM240
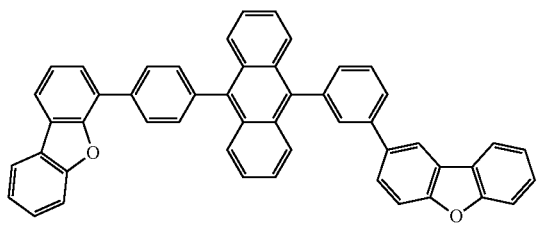
EM241
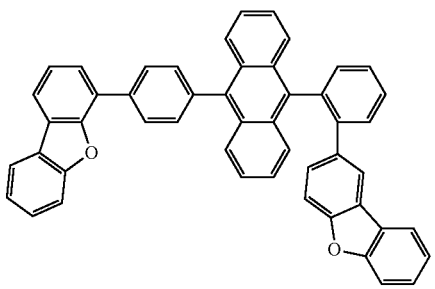
EM242
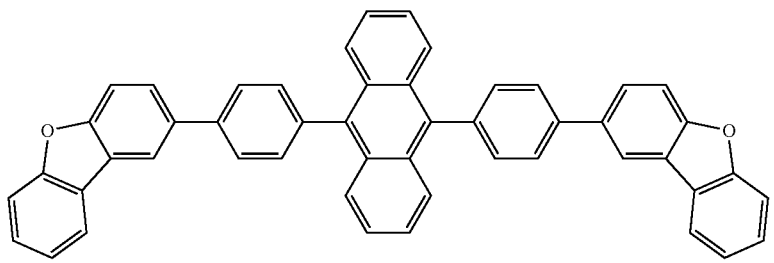

-continued
EM243
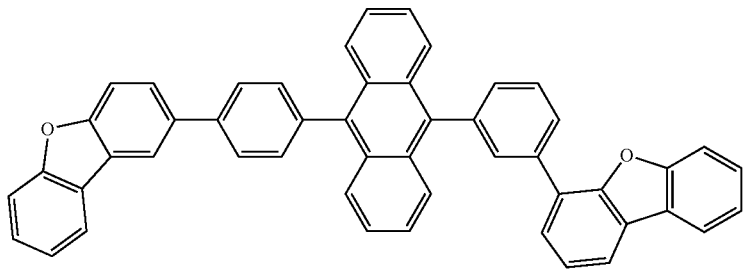
EM244
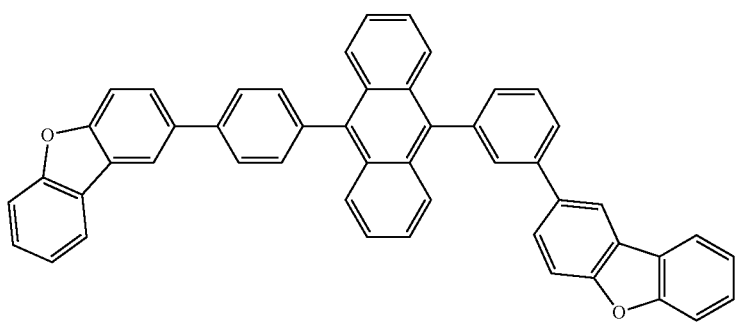
EM245
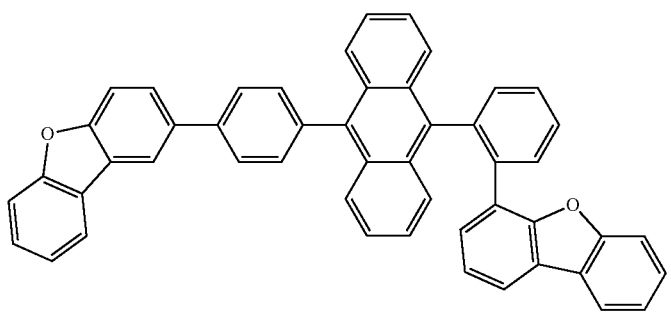
[Formula 41]
EM246
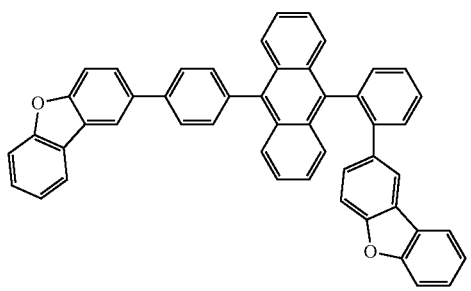
EM247
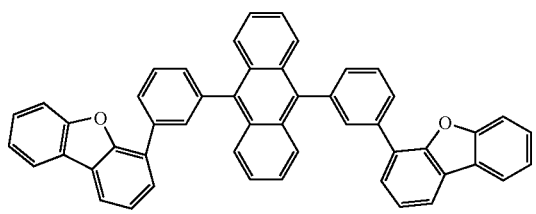
EM248
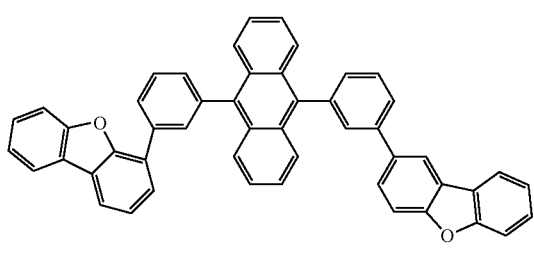
EM249
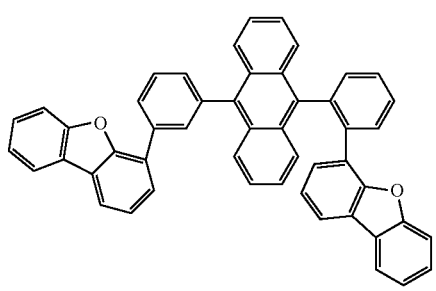

EM250
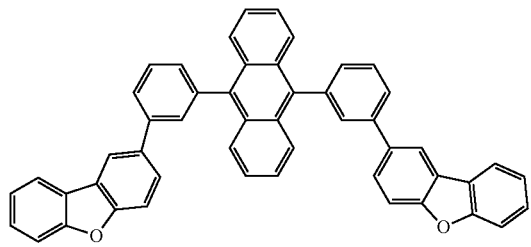
EM251
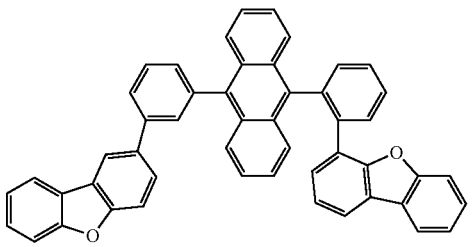
EM252
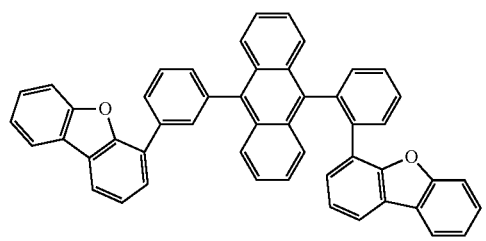
EM253
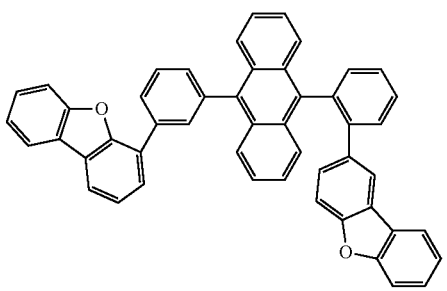
EM254
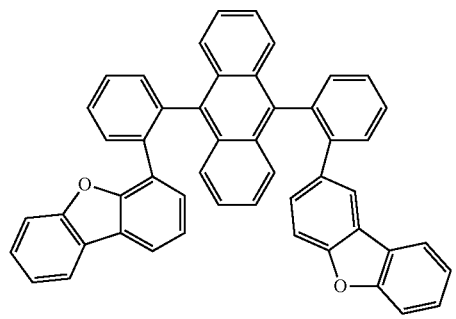
EM255
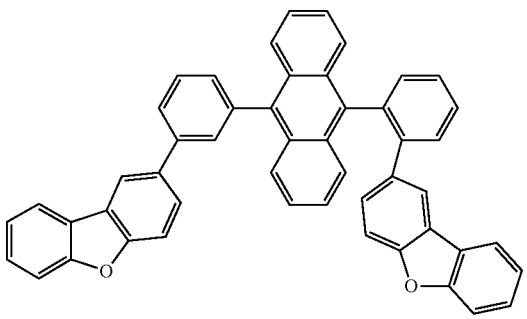
EM256
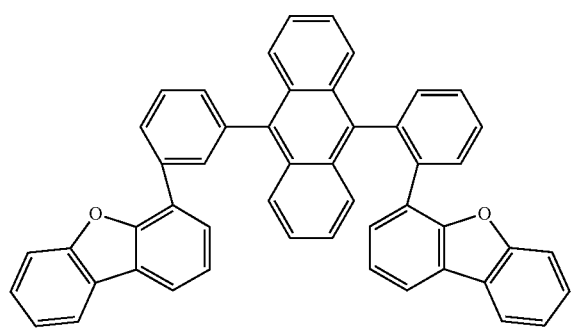
[Formula 42]
EM257
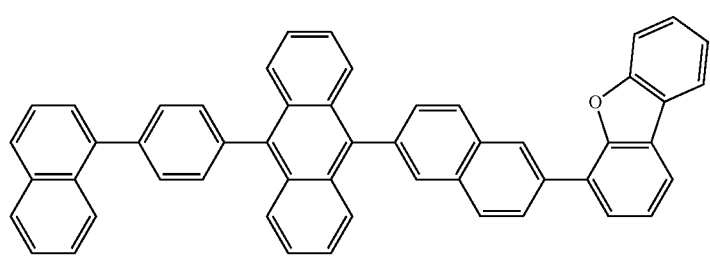

-continued
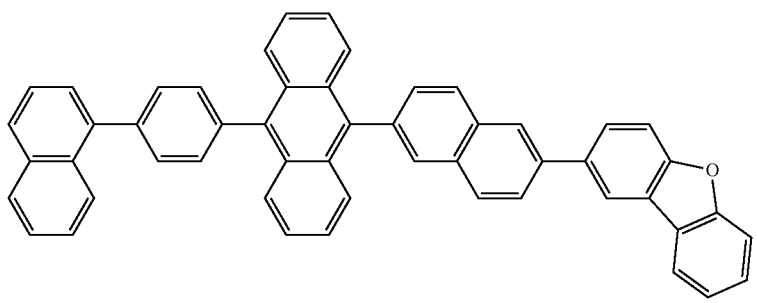
EM258
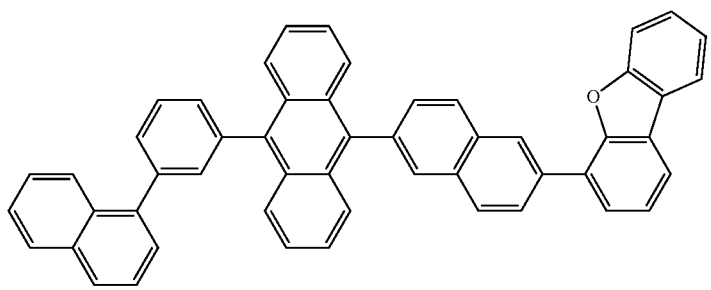
EM259
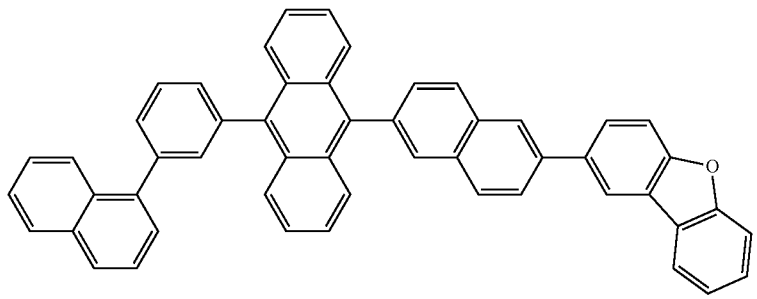
EM260
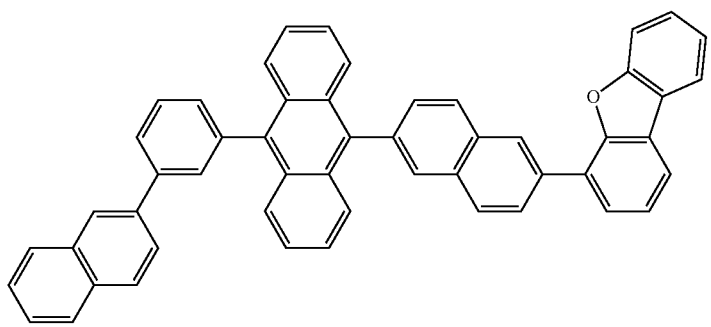
EM261
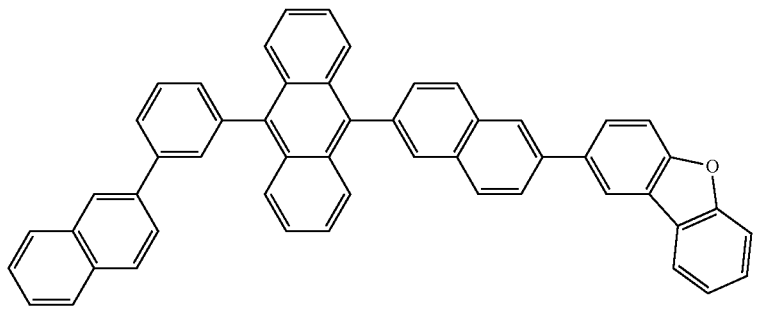
EM262

[Formula 43]
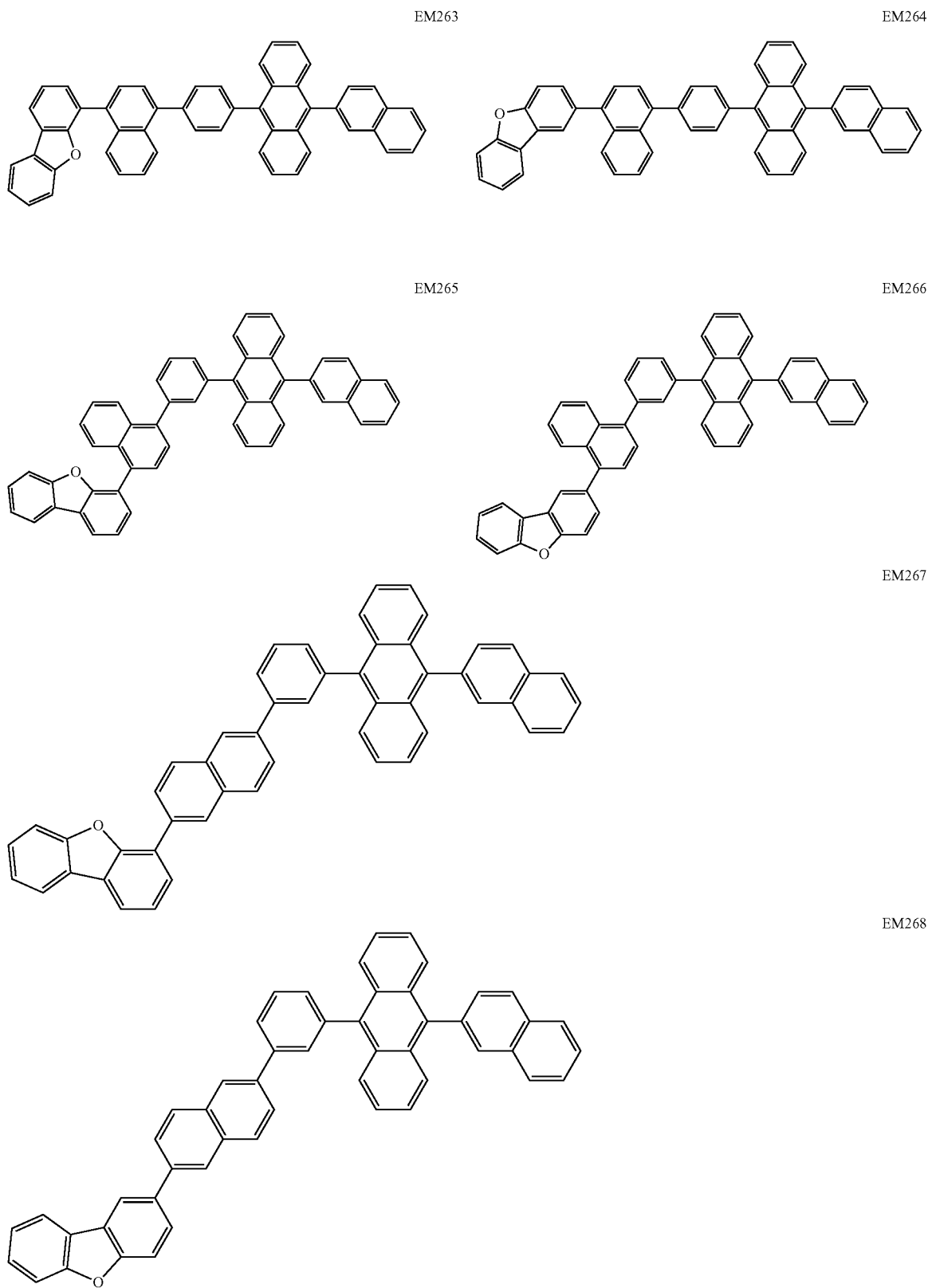

[Formula 44]
EM269
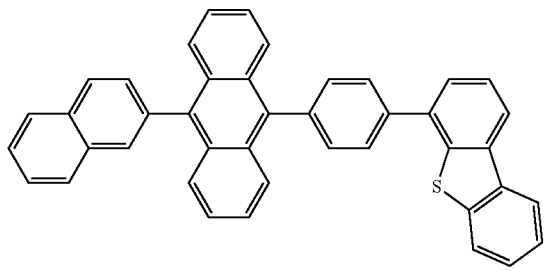
EM270
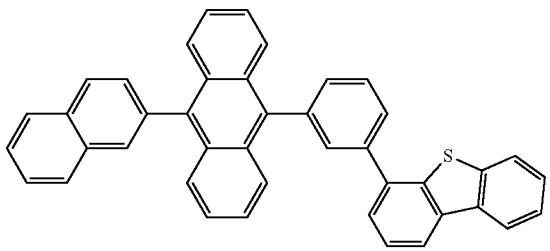
EM271
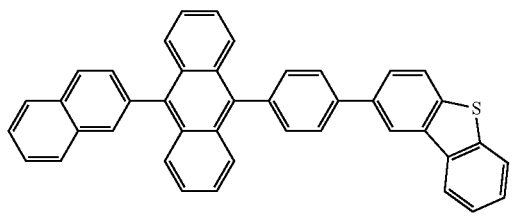
EM272
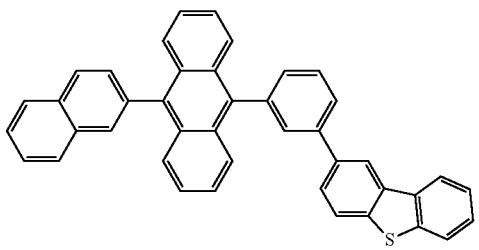
EM273
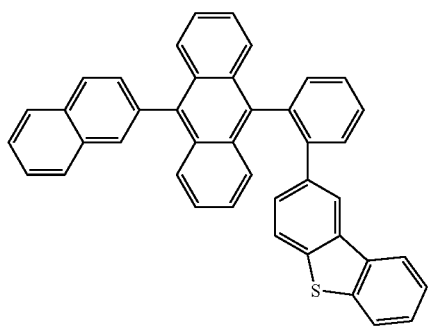
EM274
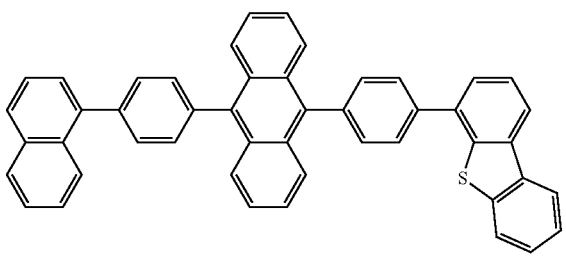
EM275
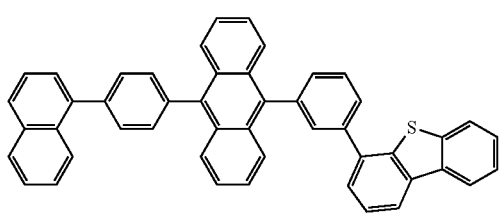
EM276
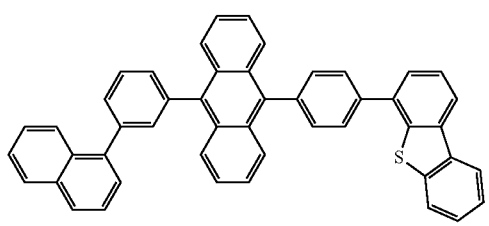
EM277
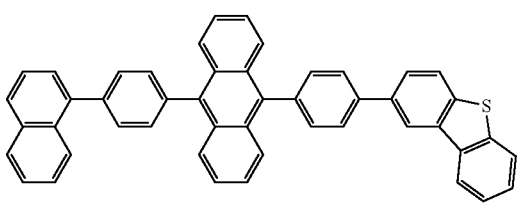

-continued
EM278
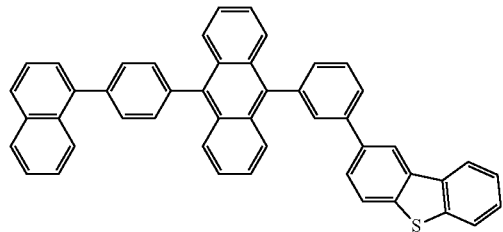
EM279
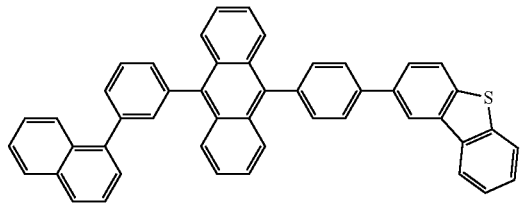
[Formula 45]
EM280
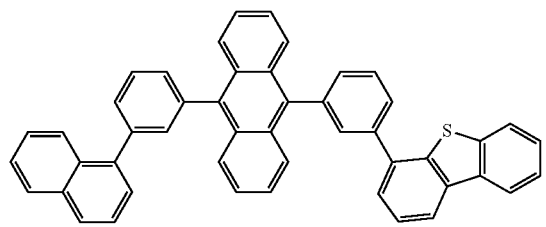
EM281
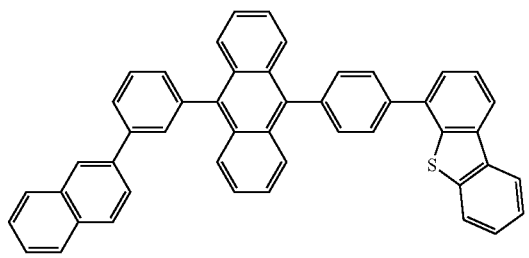
EM282
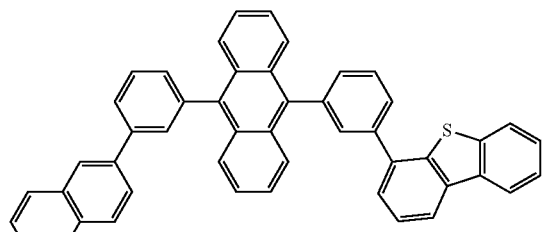
EM283
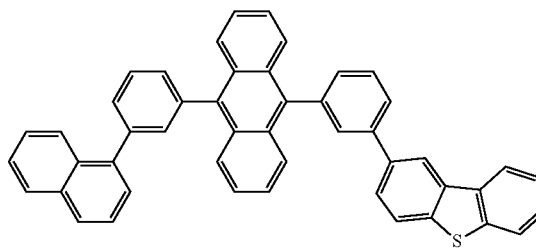
EM284
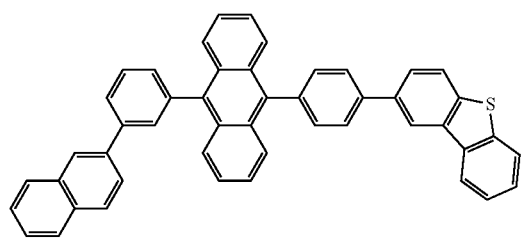
EM285
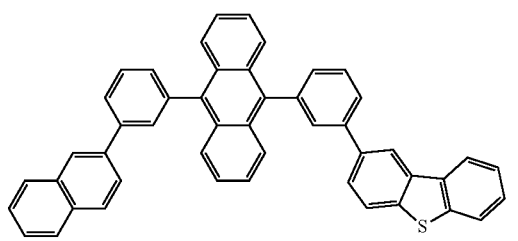
EM286
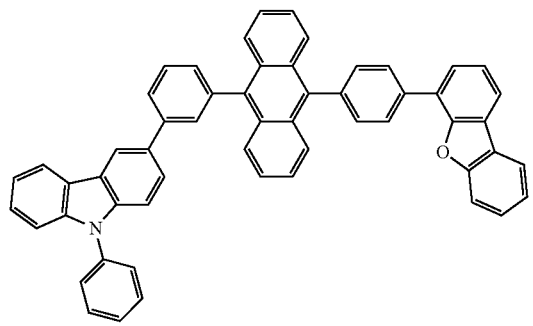
EM287
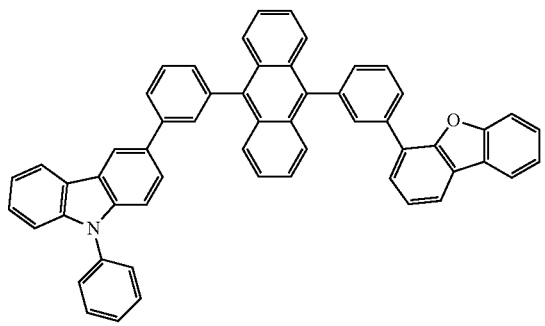

-continued
EM288  EM289
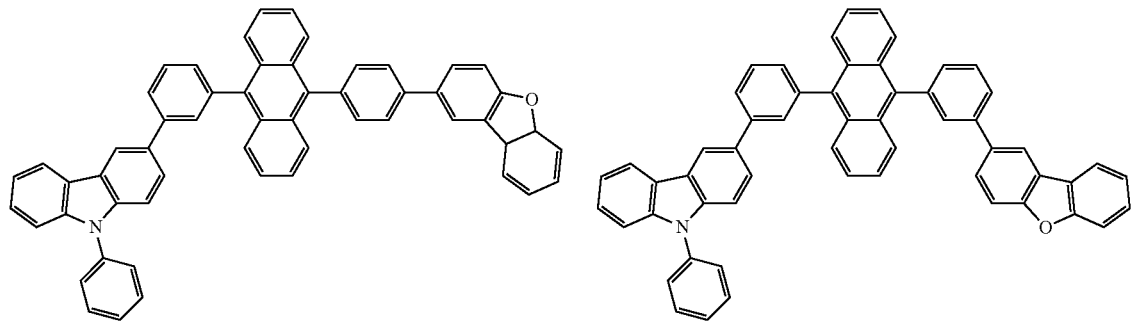
EM290  EM291
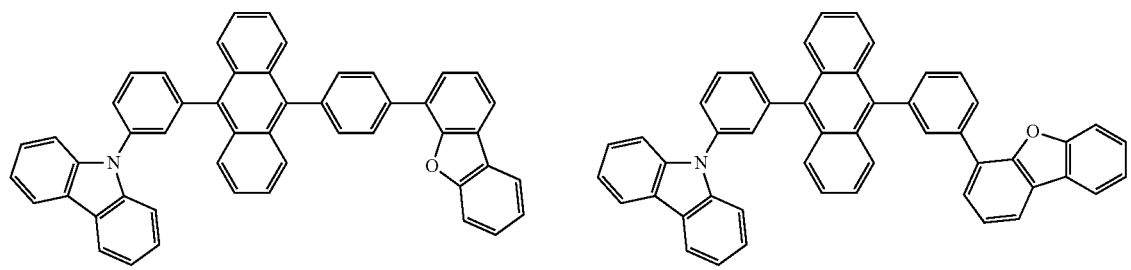
[Formula 46]
EM292  EM293
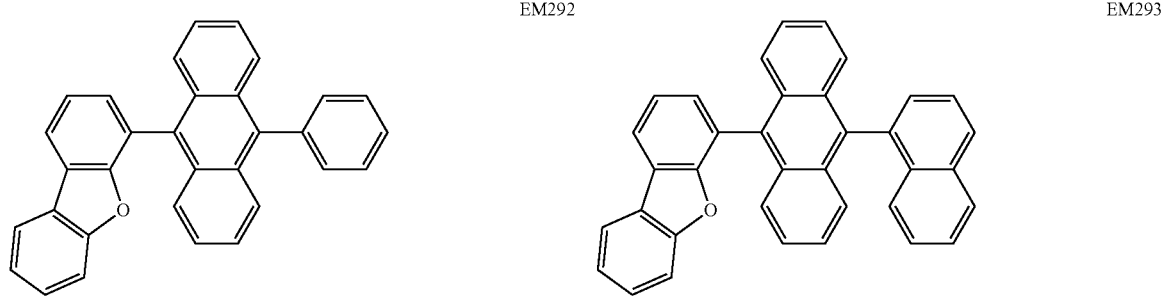
EM294  EM295
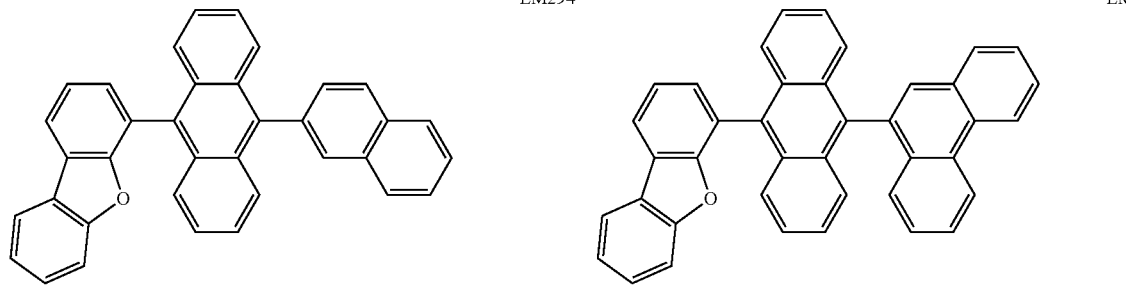
EM296  EM297
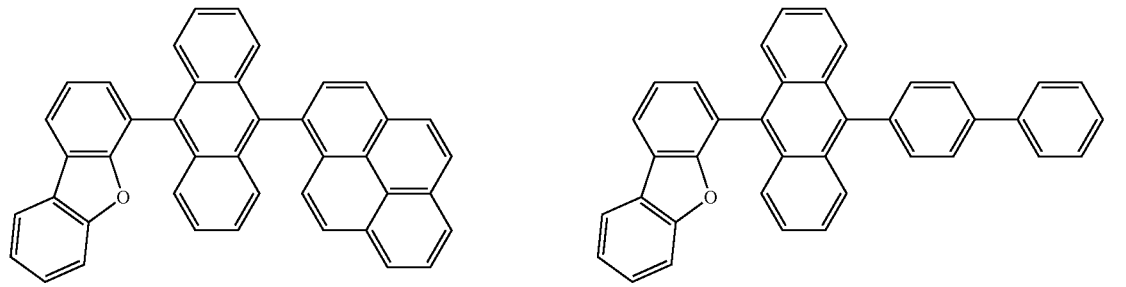

-continued
[Formula 47]
EM298
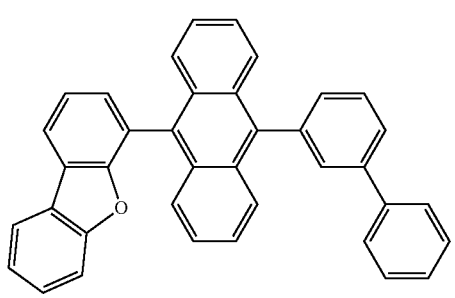
EM299
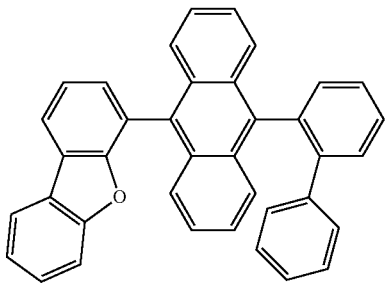
EM300
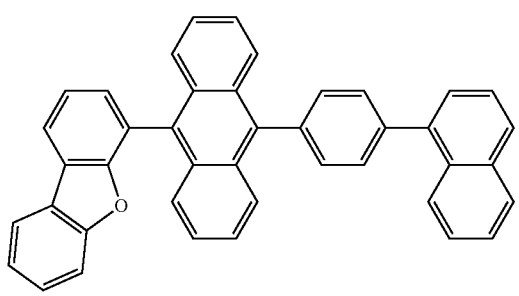
EM301
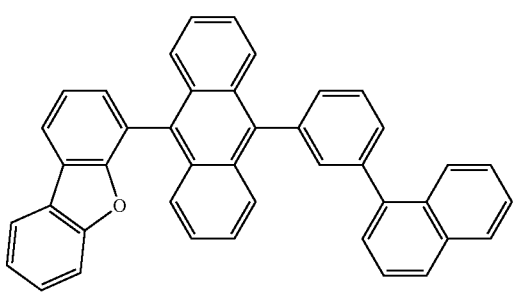
EM302
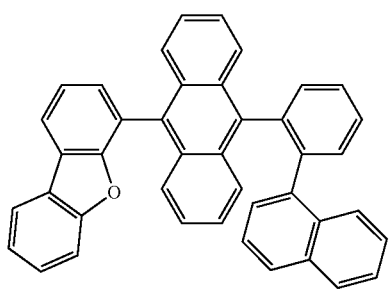
EM303
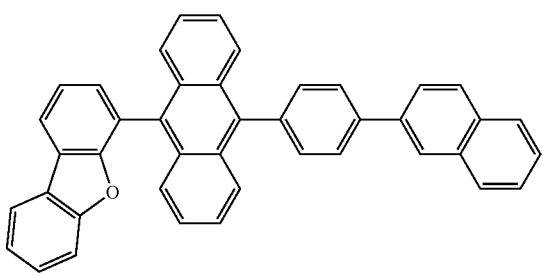
EM304
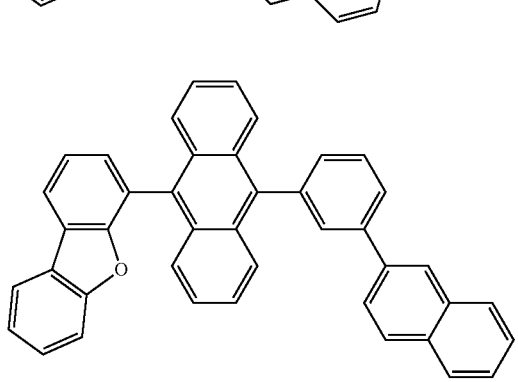
EM305
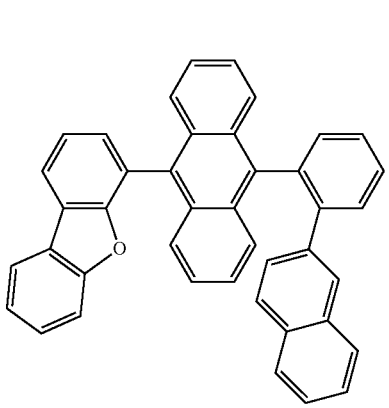
EM306
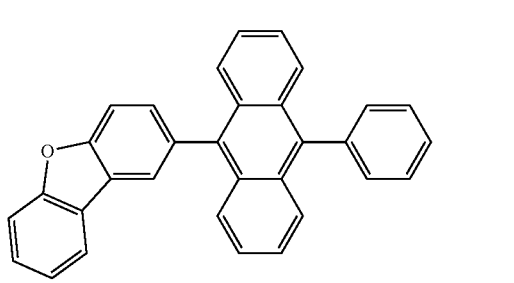
EM307
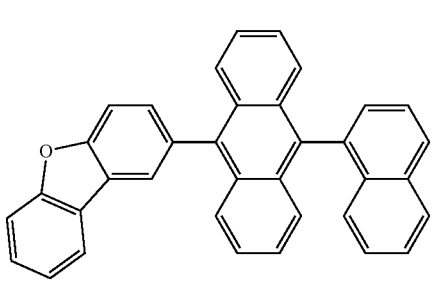

EM308
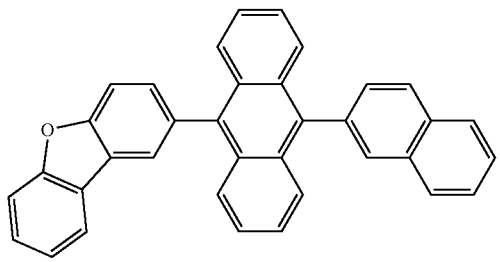
[Formula 48]
EM309
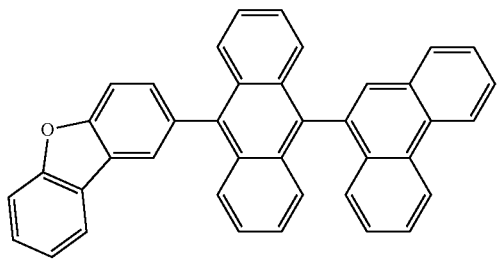
EM310
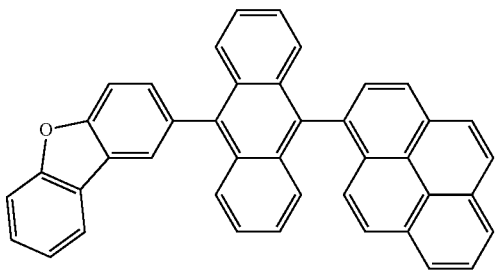
EM311
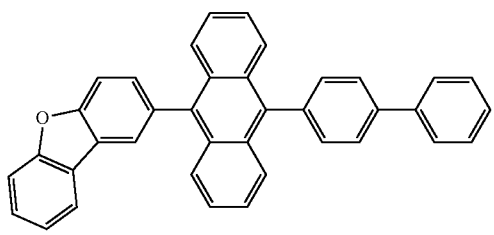
EM312
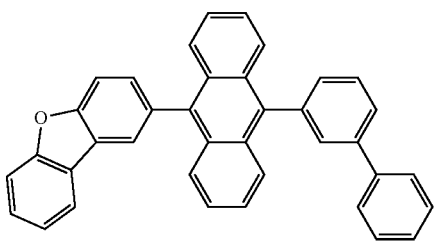
EM313
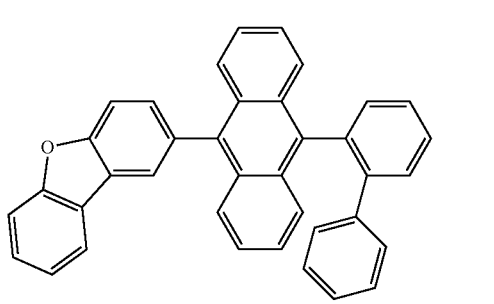
EM314
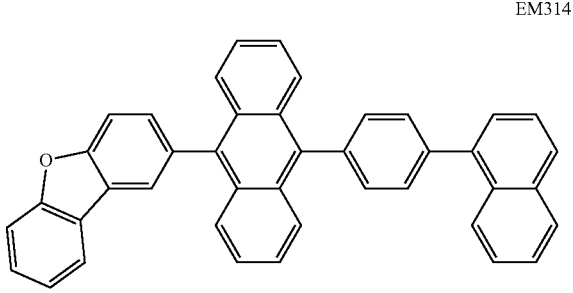
EM315
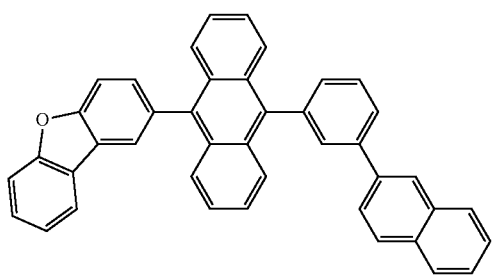
EM316
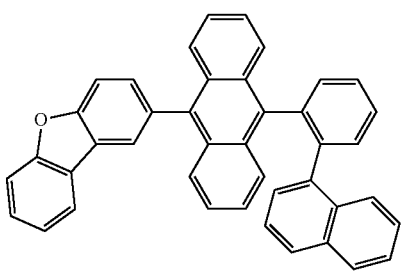

EM317
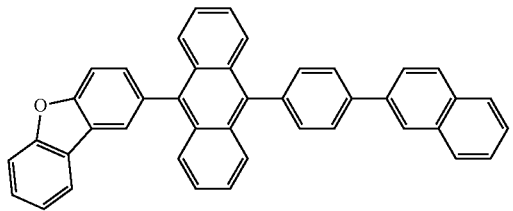
EM318
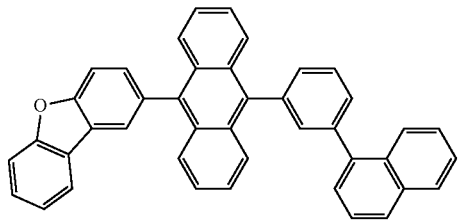
EM319
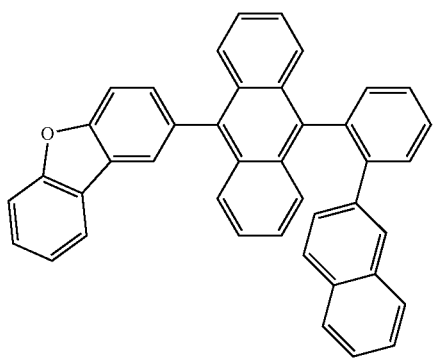
EM320
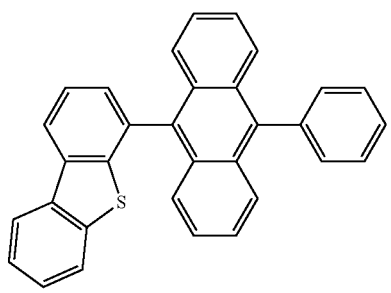
EM321
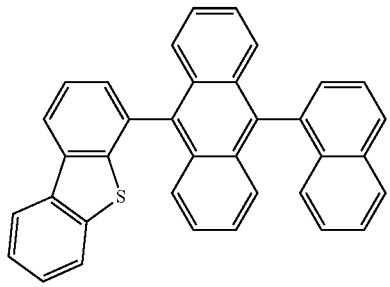
EM322
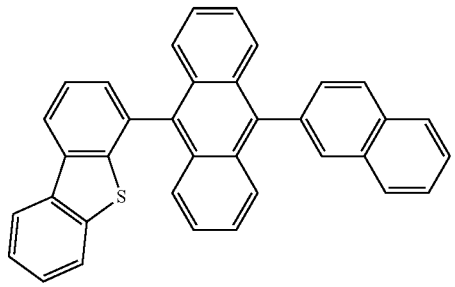
EM323
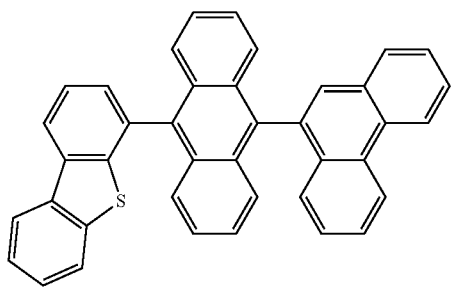
[Formula 49]
EM324
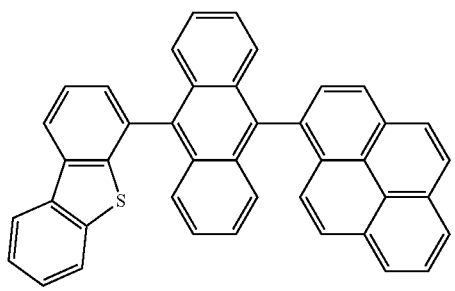
EM325
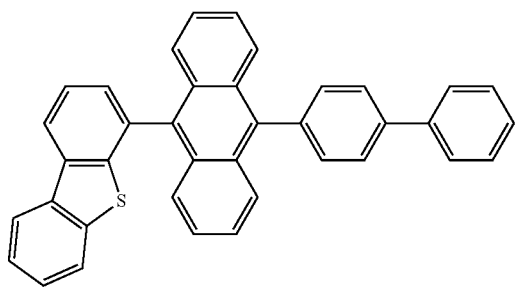

-continued
EM326
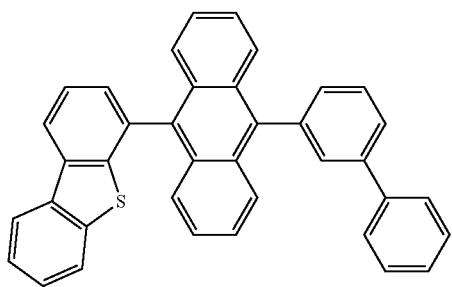
EM327
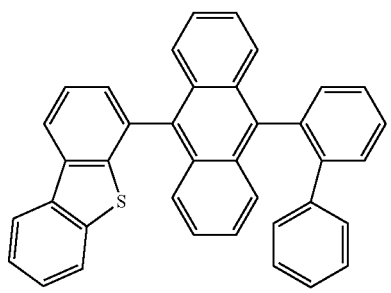
EM328
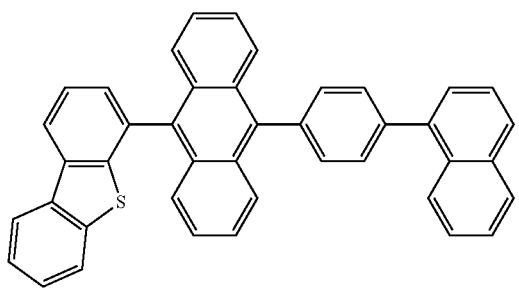
EM329
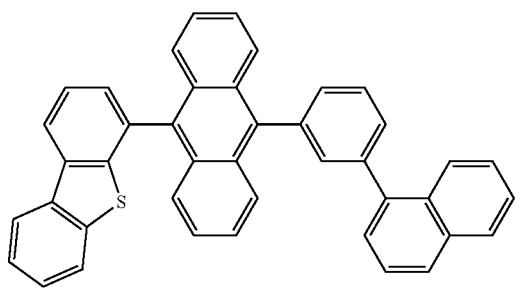
EM330
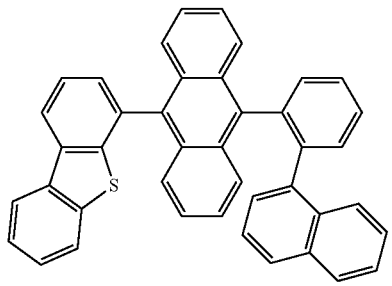
EM331
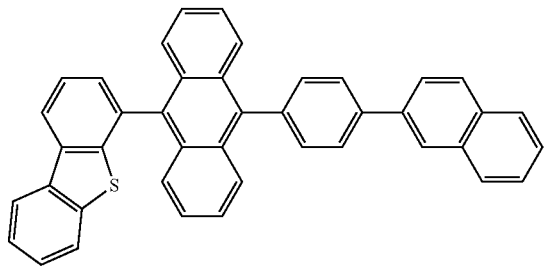
EM332
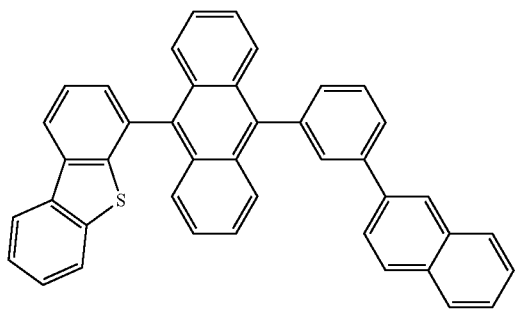
EM333
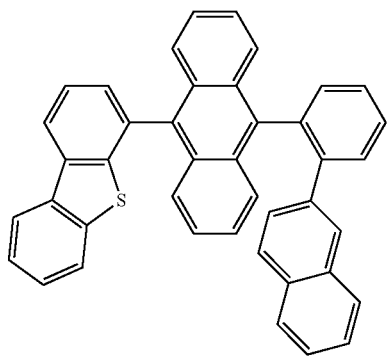
EM334
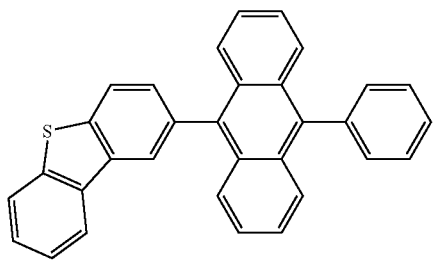
EM335
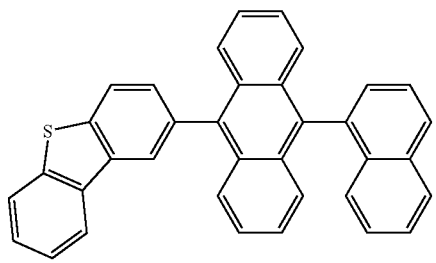

-continued
EM336
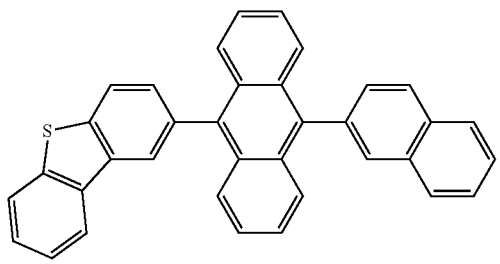
EM337
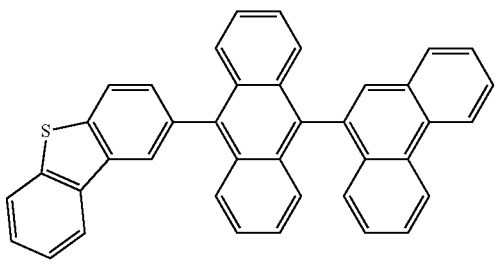
EM338
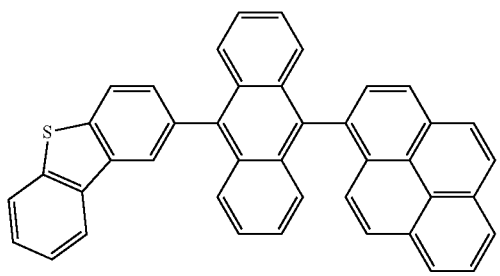
EM339
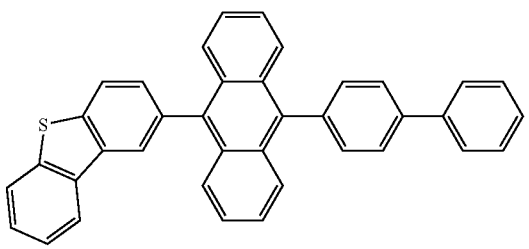
EM340
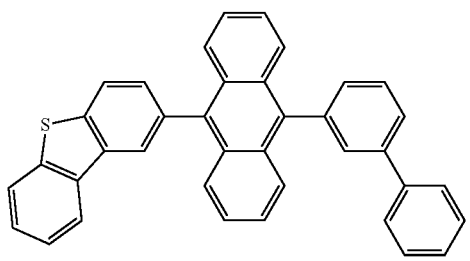
EM341
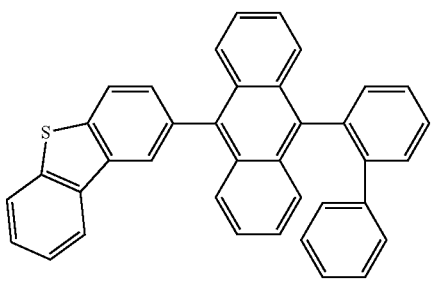
EM342
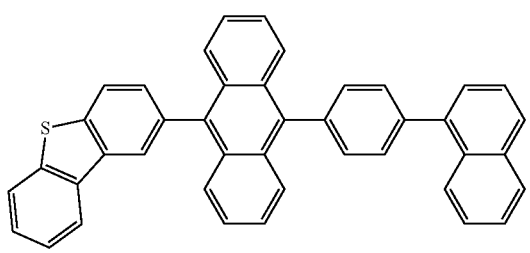
EM343
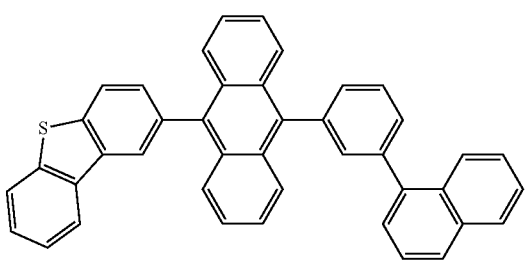
EM344
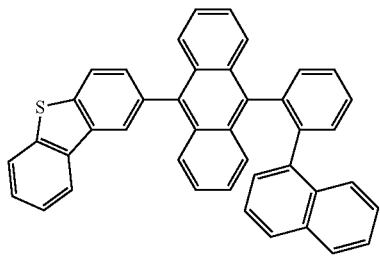
EM345
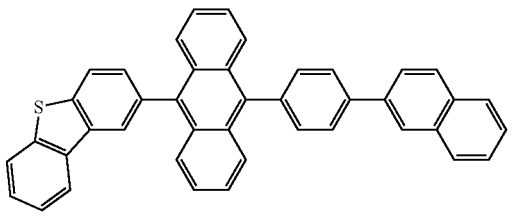

-continued
EM346
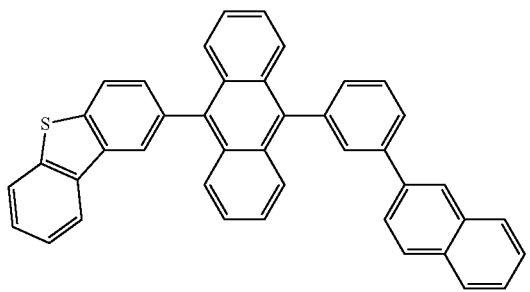
EM347
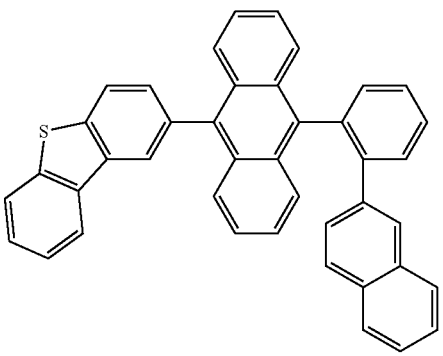
[Formula 50]
EM348
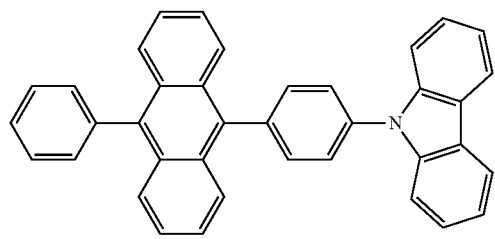
EM349
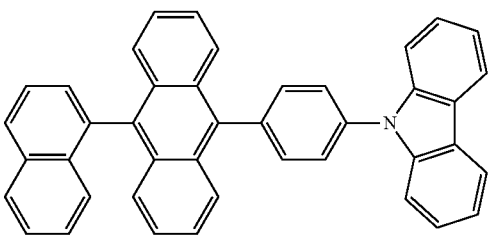
EM350
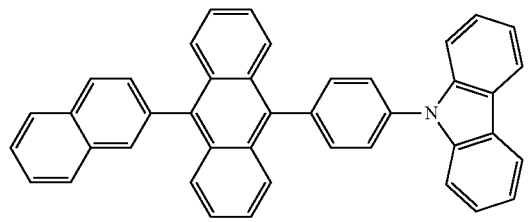
EM51
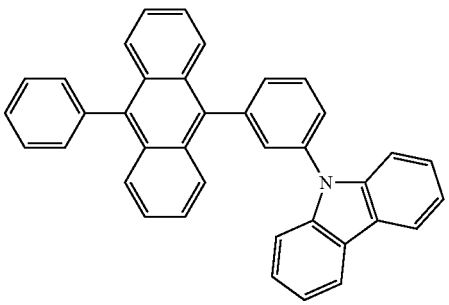
EM352
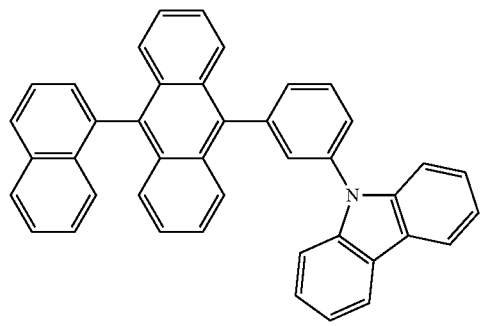
EM353
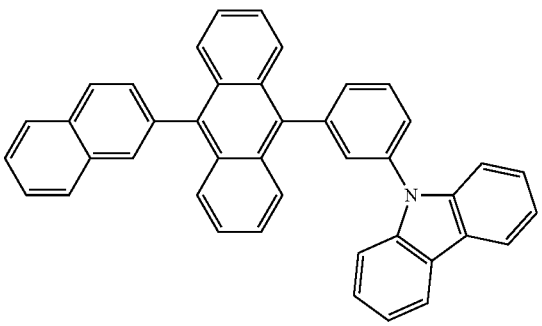
EM354
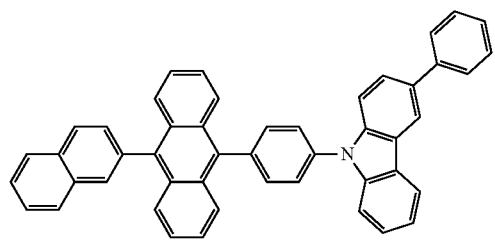
EM355
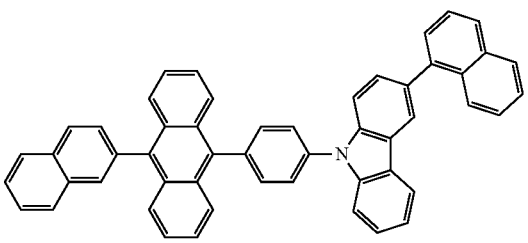

-continued
EM356
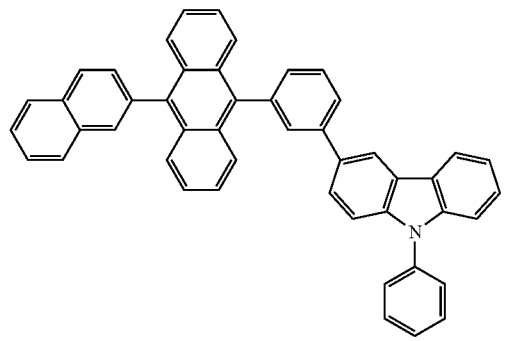
EM357
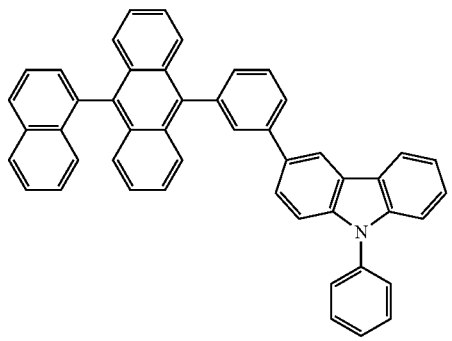
[Formula 51]
EM358
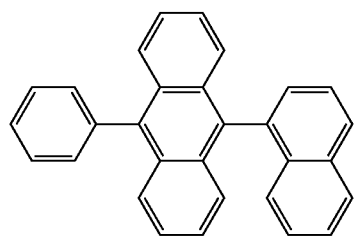
EM359
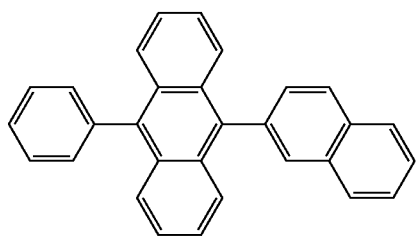
EM360
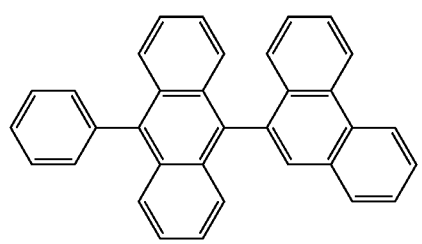
EM361
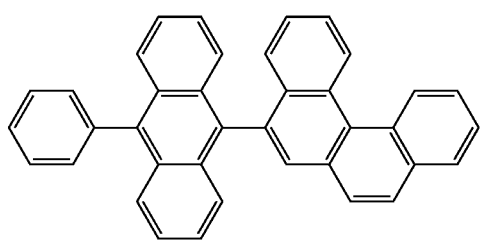
EM362
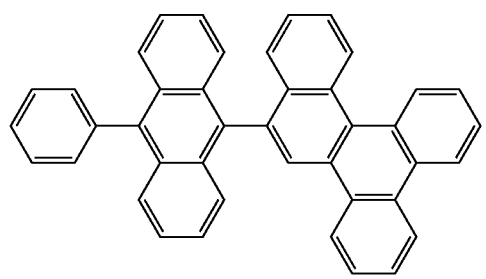
EM363
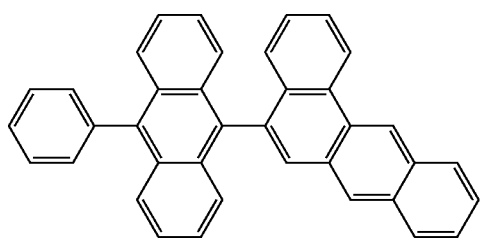
EM364
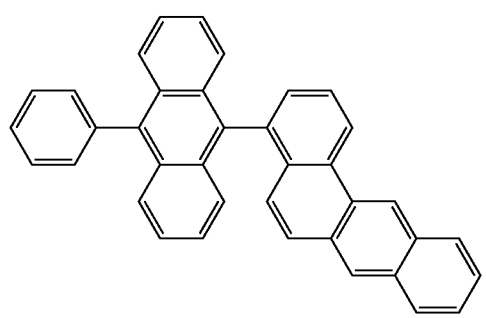
EM365
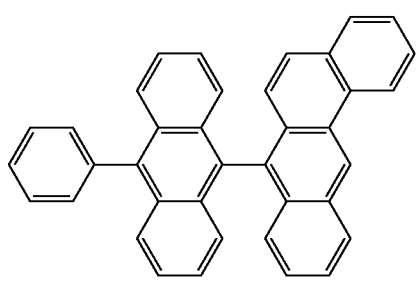

-continued
EM366
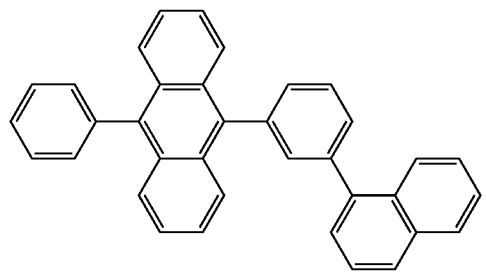
EM367
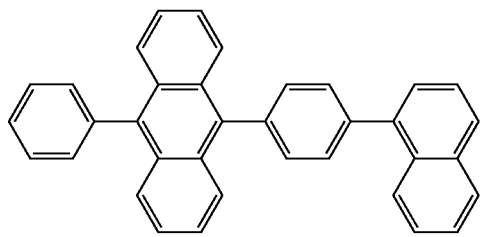
EM368
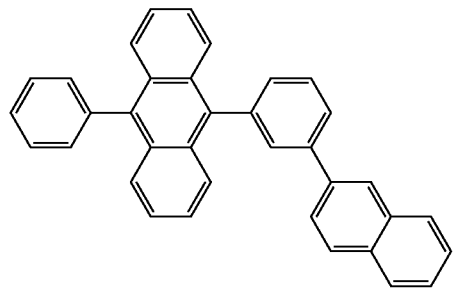
EM369
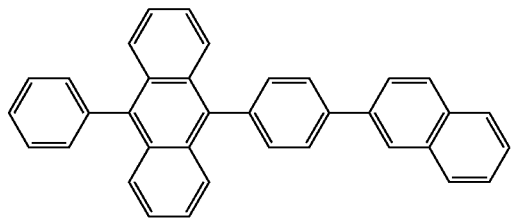
EM370
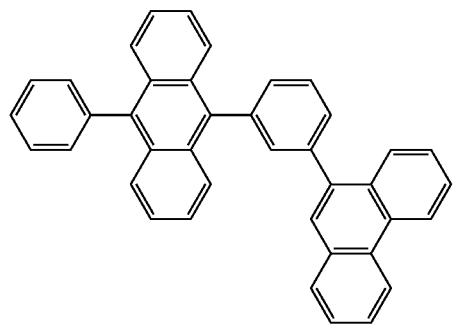
EM371
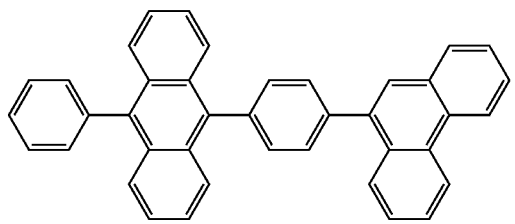
EM372
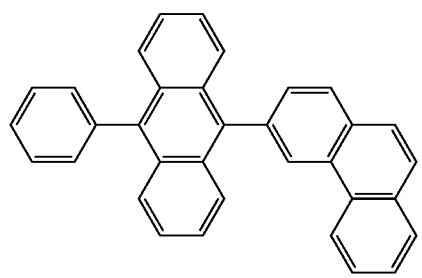
[Formula 52]
EM373
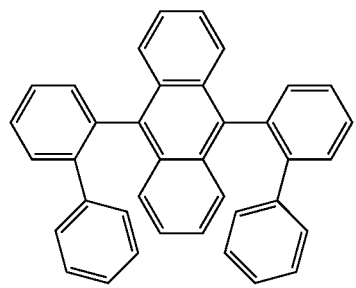
EM374
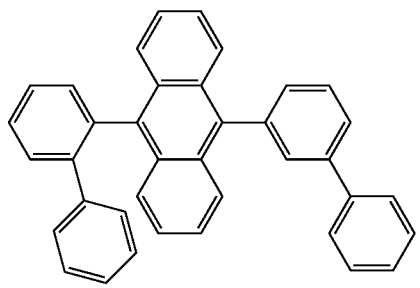

-continued
EM375
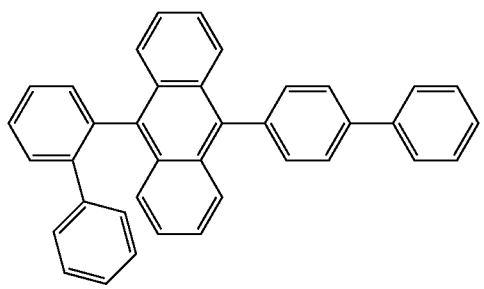
EM376
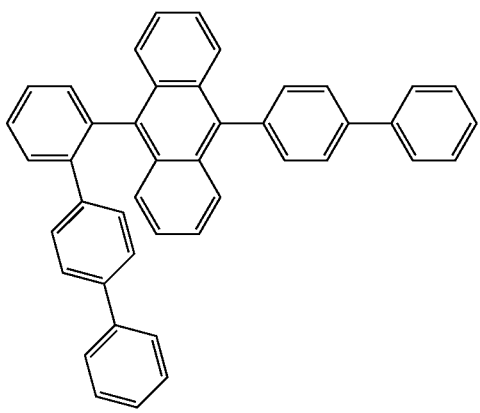
EM377
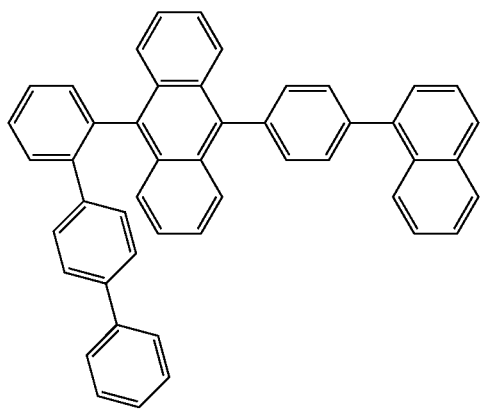
EM378
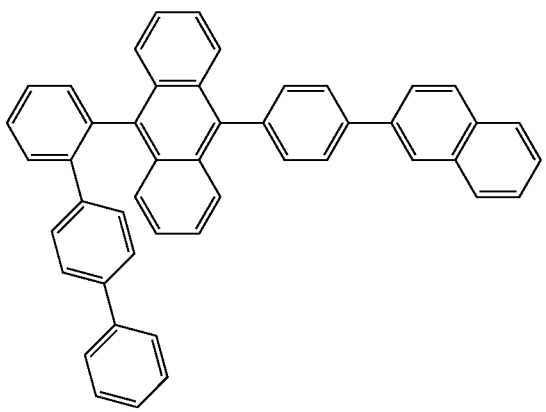
EM379
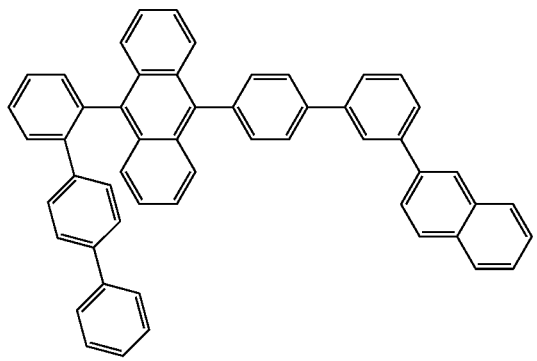
EM380
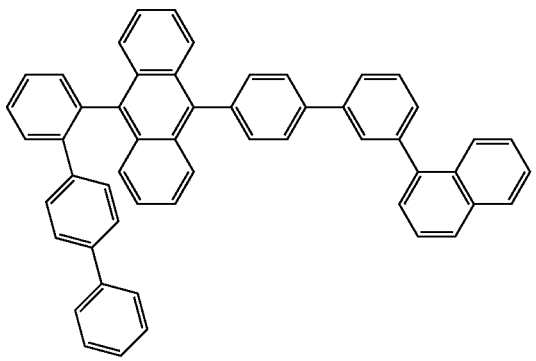
[Formula 53]
EM381
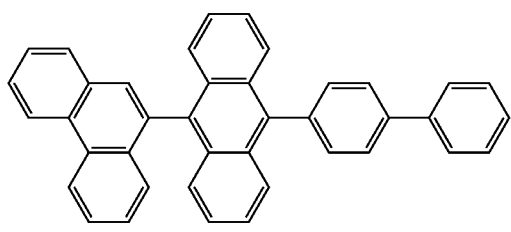
EM382
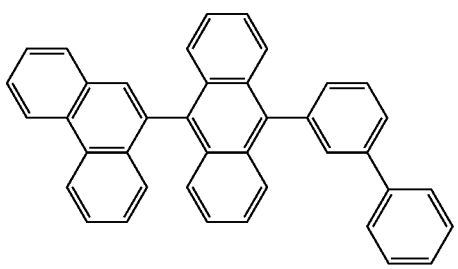

-continued
EM383
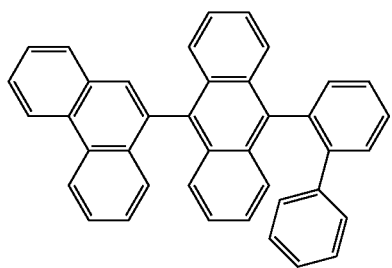
EM384
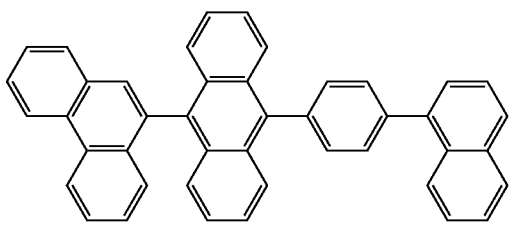
EM385
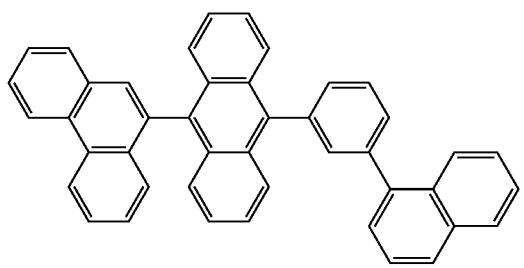
EM386
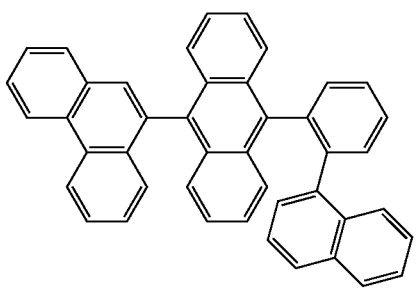
EM387
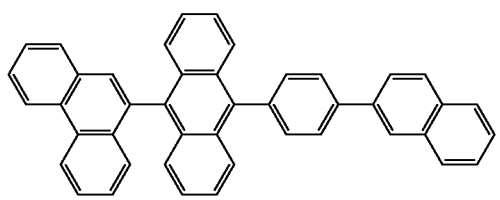
EM388
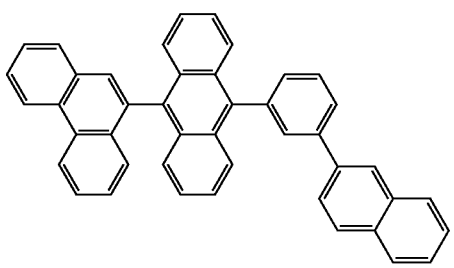
EM389
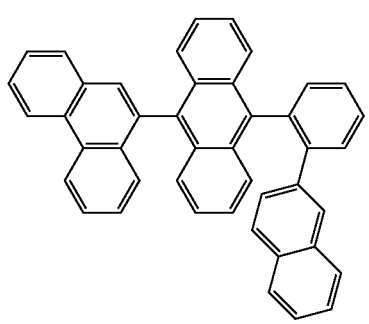
EM390
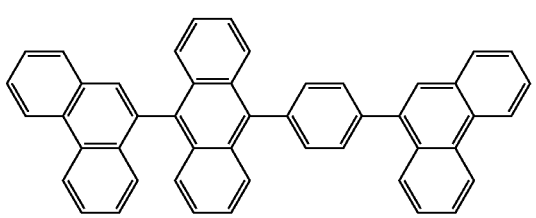
EM391
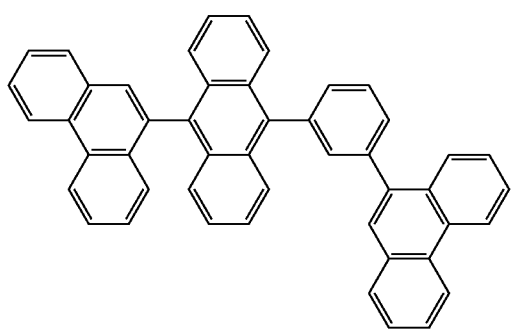
EM392
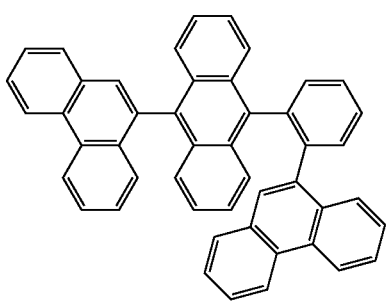

Pyrene Derivative

In the organic EL device according to another aspect of the invention, at least one layer of the organic thin-film layers includes the aromatic amine derivative represented by the formula (1) and a pyrene derivative represented by the following formula (30). The emitting layer preferably includes the aromatic amine derivative as the dopant material and the pyrene derivative as the host material.

[Formula 54]

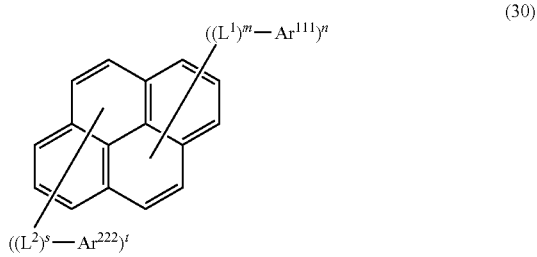

(30)

In the formula (30), $Ar^{111}$ and $Ar^{222}$ are each independently a substituted or unsubstituted aryl group having 6 to 30 ring carbon atoms.

In the formula (30), $L^1$ and $L^2$ are each independently a substituted or unsubstituted divalent aryl group having 6 to 30 ring carbon atoms or a heterocyclic group.

In the formula (30), m is an integer of 0 to 1, n is an integer of 1 to 4, s is an integer of 0 to 1 and t is an integer of 0 to 3.

In the formula (30), $L^1$ or $Ar^{111}$ is bonded to pyrene at any one of positions 1 to 5, and $L^2$ or $Ar^{222}$ is bonded to pyrene at any one of positions 6 to 10.

Moreover, examples of "substituted or unsubstituted" substituents for $Ar^{111}$, $Ar^{112}$, $L^1$ and $L^2$ in the formula (30) are the same as those in the above description.

$L^1$ and $L^2$ in the formula (30) are preferably selected from a substituted or unsubstituted phenylene group, a substituted or unsubstituted biphenyldiyl group, a substituted or unsubstituted naphthylene group, a substituted or unsubstituted terphenylene group, a substituted or unsubstituted fluorenylene group, and a divalent aryl group provided by combinations of the above groups.

m in the formula (30) is preferably an integer of 0 to 1.
n in the formula (30) is preferably an integer of 1 to 2.
s in the formula (30) is preferably an integer of 0 to 1.
t in the formula (30) is preferably an integer of 0 to 2.

The aryl group for $Ar^{111}$ and $Ar^{222}$ in the formula (30) represents the same as $R_2$ to $R_{10}$ in the formula (1). A substituted or unsubstituted aryl group having 6 to 20 ring carbon atoms is preferable. A substituted or unsubstituted aryl group having 6 to 16 ring carbon atoms is more preferable. Specific examples of the aryl group are a phenyl group, naphthyl group, phenanthryl group, fluorenyl group, biphenyl group, anthryl group and pyrenyl group.

Other Application of Compounds

The aromatic amine derivative according to the exemplary embodiment, the anthracene derivative represented by the above formula (20), and the pyrene derivative represented by the above formula (30) are applicable to the hole injecting layer, hole transporting layer, electron injecting layer and electron transporting layer in addition to the emitting layer.

Other Materials Usable in Emitting Layer

Examples of materials other than the derivatives represented by the formulae (20) and (30) usable in the emitting layer together with the aromatic amine derivative according to the exemplary embodiment include: a fused polycyclic aromatic compound such as naphthalene, phenanthrene, rubrene, anthracene, tetracene, pyrene, perylene, chrysene, decacyclene, coronene, tetraphenylcyclopentadiene, pentaphenylcyclopentadiene, fluorene, and spirofluorene, and derivatives thereof; an organic metal complex such as tris (8-quinolinolate)aluminium; triaryl amine derivative; styryl amine derivative; stilbene derivative; coumaline derivative; pyrane derivative; oxazone derivative; benzothiazole derivative; benzooxazole derivative; benzimidazole derivative; pyrazine derivative; cinnamic acid ester derivative; diketopyrrolopyrrole derivative; acridone derivative and quinacridone derivative. However, the materials are not limited thereto.

Content

When the organic thin-film layer includes the aromatic amine derivate according to the exemplary embodiment as the dopant material, a content of the aromatic amine derivate is preferably in a range of 0.1 mass % to 20 mass %, more preferably of 1 mass % to 10 mass %.

Substrate

The organic EL device according to the exemplary embodiment is formed on a light-transmissive substrate. The light-transmissive substrate, which supports the organic EL device, is preferably a smoothly-shaped substrate that transmits 50% or more of light in a visible region of 400 nm to 700 nm. Preferably, the substrate further has mechanical and thermal strength.

Specifically, a glass plate, a polymer plate and the like are preferable.

For the glass plate, materials such as soda-lime glass, barium/strontium-containing glass, lead glass, aluminosilicate glass, borosilicate glass, barium borosilicate glass and quartz can be used.

For the polymer plate, materials such as polycarbonate, acryl, polyethylene terephthalate, polyether sulfide and polysulfone can be used. A polymer film can also be used as the substrate.

Anode and Cathode

As a conductive material used in the anode of the organic EL device according to the exemplary embodiment, a conductive material having a work function of more than 4 eV is suitable. Examples of such a conductive material include: carbon, aluminium, vanadium, iron, cobalt, nickel, tungsten, silver, gold, platinum, palladium and alloys thereof; metal oxide such as tin oxide and indium oxide used in an ITO substrate and an NESA substrate; and an organic conductive resin such as polythiophene and polypyrrole. The anode can be prepared by forming a thin film of these conductive materials by vapor deposition, sputtering or the like.

When emission from the emitting layer is extracted through the anode, the anode preferably transmits more than 10% of the light in the visible region. Sheet resistance of the anode is preferably several hundreds Ω/square or less. Although depending on the material of the anode, a film thickness of the anode is typically in a range of 10 nm to 1 μm, preferably in a range of 10 nm to 200 nm.

As a conductive substance used in the cathode of the organic EL device according to the exemplary embodiment, a conductive substance having a work function of less than 4 eV is suitable. Examples of such a conductive substance include magnesium, calcium, tin, lead, titanium, yttrium, lithium, ruthenium, manganese, aluminium, lithium fluoride and alloys thereof. However, the conductive substance is not limited thereto. Representative examples of the alloys are magnesium/silver, magnesium/indium and lithium/aluminium, but the alloys are not limited thereto. A ratio in each of the alloys is controlled by a temperature of a deposition source, atmosphere, vacuum and the like to be selected in an appropriate ratio. Like the anode, the cathode can be made by forming a thin film of the above materials by a method such as vapor deposition or sputtering. In addition, an arrangement to extract emission through the cathode is applicable.

When emission from the emitting layer is extracted through the cathode, the cathode preferably transmits more than 10% of the light in the visible region. Sheet resistance of the cathode is preferably several hundreds Ω/square or less. The thickness of the cathode is typically in a range of 10 nm to 1 µm, and preferably in a range of 50 nm to 200 nm, though it depends on the material of the cathode.

The anode and the cathode may be formed in a layered structure having two or more layers, if necessary.

In the organic EL device according to the exemplary embodiment, it is desirable that at least one surface of the organic EL device is sufficiently transparent in an emission wavelength region in order to efficiently emit light. It is also desirable that the substrate is transparent. A transparent electrode is set using the above conductive material by a method such as vapor deposition or sputtering so that a predetermined transparency of the electrode is ensured.

Hole Injecting/Transporting Layer

The hole injecting/transporting layer is manufactured using the following hole injecting material and hole transporting material.

The hole injecting material is preferably a compound having hole transporting capability, exhibiting an excellent hole injecting effect from the anode and an excellent hole injecting effect to the emitting layer or the luminescent material, and exhibiting an excellent thin-film forming capability. Specific examples of the hole injecting material include: a phthalocyanine derivative; a naphthalocyanine derivative; a porphyrin derivative; benzidine-type triphenyl amine, diamine-type triphenyl amine, hexacyanohexaazatriphenylene and derivatives thereof; and a polymer material such as polyvinyl carbazole, polysilane and a conductive polymer. However, the hole injecting material is not limited thereto.

Among the hole injecting materials usable in the organic EL device according to the exemplary embodiment, a further effective hole injecting material is a phthalocyanine derivative.

Examples of the phthalocyanine (Pc) derivative include a phthalocyanine derivative such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, and GaPc-O-GaPc; and a naphthalocyanine derivative. However, the phthalocyanine (Pc) derivative is not limited thereto.

Moreover, carriers can be promoted by adding an electron accepting substance (eg., a TCNQ derivative) to the hole injecting material.

In the organic EL device according to this exemplary embodiment, the hole transporting material is preferably an aromatic tertiary amine derivative.

Examples of the aromatic tertiary amine derivative include N,N'-diphenyl-N,N'-dinaphthyl-1,1'-biphenyl-4,4'-diamine, N,N,N',N'-tetrabiphenyl-1,1'-biphenyl-4,4'-diamine, or an oligomer or a polymer thereof having such an aromatic tertiary amine skeleton. However, the aromatic tertiary amine derivative is not limited thereto.

Electron Injecting/Transporting Layer

The electron injecting/transporting layer is manufactured using the following electron injecting material and the like.

The electron injecting material is preferably a compound having electron transporting capability, exhibiting an excellent electron injecting effect from the chathode and an excellent electron injecting effect to the emitting layer or the luminescent material, and exhibiting an excellent thin-film forming capability.

In the organic EL device according to the exemplary embodiment, more effective electron injecting materials are a metal complex compound and a nitrogen-containing heterocyclic derivative.

Examples of the metal complex compound include 8-hydroxyquinolinolato-lithium, bis(8-hydroxyquinolinolato) zinc, tris(8-hydroxyquinolinolato)aluminium, tris(8-hydroxyquinolinolato)gallium, bis(10-hydroxybenzo[h] quinolinolato)beryllium, and bis(10-hydroxybenzo[h] quinolinolato)zinc. However, the metal complex compound is not limited thereto.

Preferable examples of the nitrogen-containing heterocyclic derivative group are oxazole, thiazole, oxadiazole, thiadiazole, triazole, pyridine, pyrimidine, triazine, phenanthroline, benzimidazole, and imidazopyridine, among which a benzimidazole derivative, phenanthroline derivative and imidazopyridine derivative are preferable.

The organic EL device according to the exemplary embodiment is preferably an organic EL device including at least one of an electron-donating dopant and an organic metal complex in addition to the electron injecting material. More preferably, in order to easily accept electrons from the cathode, at least one of the electron-donating dopant and the organic metal complex is doped in the vicinity of an interface between the organic thin-film layer and the cathode.

With this arrangement, a luminance intensity of the organic EL device is improved and a lifetime thereof is prolonged.

The electron-donating dopant may be at least one selected from an alkali metal, an alkali metal compound, an alkaline-earth metal, an alkaline-earth metal compound, a rare-earth metal, a rare-earth metal compound and the like.

The organic metal complex may be at least one selected from an organic metal complex including an alkali metal, an organic metal complex including an alkaline-earth metal, an organic metal complex including a rare-earth metal and the like.

Examples of the alkali metal are lithium (Li) (work function: 2.93 eV), sodium (Na) (work function: 2.36 eV), potassium (K) (work function: 2.28 eV), rubidium (Rb) (work function: 2.16 eV) and cesium (Cs) (work function: 1.95 eV), which particularly preferably has a work function of 2.9 eV or less. Among the above, the reductive dopant is preferably K, Rb or Cs, more preferably Rb or Cs, the most preferably Cs.

Examples of the alkaline-earth metal are calcium (Ca) (work function: 2.9 eV), strontium (Sr) (work function: 2.0 to 2.5 eV), and barium (Ba) (work function: 2.52 eV), among which a substance having a work function of 2.9 eV or less is particularly preferable.

Examples of the rare-earth metal are scandium (Sc), yttrium (Y), cerium (Ce), terbium (Tb), and ytterbium (Yb), among which a substance having a work function of 2.9 eV or less is particularly preferable.

Since the above preferred metals have particularly high reducibility, addition of a relatively small amount of the metals to an electron injecting zone can enhance luminance intensity and lifetime of the organic EL device.

Examples of the alkali metal compound are an alkali oxide such as lithium oxide ($Li_2O$), cesium oxide ($Cs_2O$) and potassium oxide ($K_2O$), and an alkali halogenide such as sodium fluoride (NaF), cesium fluoride (CsF) and potassium fluoride (KF), among which lithium fluoride (LiF), lithium oxide ($Li_2O$) and sodium fluoride (NaF) are preferable.

Examples of the alkaline-earth metal compound are barium oxide (BaO), strontium oxide (SrO), calcium oxide (CaO) and a mixture thereof, i.e., barium strontium oxide ($Ba_xSr_{1-x}O$) (0<x<1), barium calcium oxide ($Ba_xCa_{1-x}O$) (0<x<1), among which BaO, SrO and CaO are preferable.

Examples of the rare earth metal compound are ytterbium fluoride ($YbF_3$), scandium fluoride ($ScF_3$), scandium oxide ($ScO_3$), yttrium oxide ($Y_2O_3$), cerium oxide ($Ce_2O_3$), gadolinium fluoride ($GdF_3$) and terbium fluoride ($TbF_3$), among which $YbF_3$, $ScF_3$, and $TbF_3$ are preferable.

The organic metal complex is not specifically limited as long as containing at least one metal ion of an alkali metal ion, an alkaline-earth metal ion and a rare earth metal ion. A ligand for each of the complexes is preferably quinolinol, benzoquinolinol, acridinol, phenanthridinol, hydroxyphenyl oxazole, hydroxyphenyl thiazole, hydroxydiaryl oxadiazole, hydroxydiaryl thiadiazole, hydroxyphenyl pyridine, hydroxyphenyl benzimidazole, hydroxybenzo triazole, hydroxy fluborane, bipyridyl, phenanthroline, phthalocyanine, porphyrin, cyclopentadiene, β-diketones, azomethines, or a derivative thereof, but the ligand is not limited thereto.

One of the electron-donating dopant and the organic metal complex may be singularly used, or two or more of the above may be used together.

Formation Method of Each Layer of Organic EL Device

Each layer of the organic EL device according to the exemplary embodiment can be formed by any method of dry film-forming such as vacuum deposition, sputtering, plasma or ion plating and of wet film-forming such as spin coating, dipping, flow coating or ink-jet.

In wet film-forming, a material for forming each layer is dissolved or dispersed in an appropriate solvent such as ethanol, chloroform, tetrahydrofuran or dioxane to form a thin film, in which any one of the solvent is usable.

An organic-EL-device-material-containing solution that contains the aromatic amine derivative according to the exemplary embodiment (organic-EL-device material) and the solvent is usable as a solution appropriate for such wet film-forming.

An appropriate resin and an additive may be used in any organic thin-film layer for improvement in film formation, prevention of pin holes on a film, and the like.

Film Thickness of Each Layer of Organic EL Device

A film thickness is not particularly limited, but needs to be set to be appropriate. When the film thickness is too large, a large voltage needs to be applied for outputting light at a certain level, thereby deteriorating efficiency. When the film thickness is too small, pin holes and the like are generated, whereby a sufficient luminescence intensity cannot be obtained even by applying an electric field. The film thickness is typically appropriately in a range of 5 nm to 10 μm, preferably in a range of 10 nm to 0.2 μm.

Use of Organic EL Device

The organic EL device according to the exemplary embodiment is applicable to a flat light-emitting body such as a flat panel display, a light source of instruments or a backlight of a copy machine, a printer and a liquid crystal display, an illuminator, a display plate, a sign lamp and the like. Moreover, the compound according to the exemplary embodiment is usable not only in the organic EL device but also in fields such as an electrophotographic photoreceptor, photoelectric conversion element, solar battery and image sensor.

Second Exemplary Embodiment

An aromatic amine derivative according to a second exemplary embodiment of the invention is represented by the formula (1a).

$R_1$ and $R_3$ to $R_{10}$ in the formula (1a) will be described as follows.

The aryl group having 6 to 30 ring carbon atoms in the formula (1a) represents the same as the aryl group having 6 to 30 ring carbon atoms in the formula (1).

The heterocyclic group having 5 to 30 ring atoms in the formula (1a) represents the same as the heterocyclic group having 5 to 30 ring atoms in the formula (1).

The alkyl group having 1 to 30 carbon atoms in the formula (1a) represents the same as the alkyl group having 1 to 30 carbon atoms in the formula (1).

The alkenyl group having 2 to 30 carbon atoms in the formula (1a) represents the same as the alkenyl group having 2 to 30 carbon atoms in the formula (1).

The alkynyl group having 2 to 30 carbon atoms in the formula (1a) represents the same as the alkynyl group having 2 to 30 carbon atoms in the formula (1).

The alkylsilyl group having 3 to 30 carbon atoms in the formula (1a) represents the same as the alkylsilyl group having 3 to 30 carbon atoms in the formula (1).

The arylsilyl group having 6 to 30 ring carbon atoms in the formula (1a) represents the same as the arylsilyl group having 6 to 30 ring carbon atoms in the formula (1).

The alkoxy group having 1 to 30 carbon atoms in the formula (1a) represents the same as the alkoxy group having 1 to 30 carbon atoms in the formula (1). The same applies to a haloalkoxy group.

The aralkyl group having 6 to 30 ring carbon atoms in the formula (1a) represents the same as the aralkyl group having 6 to 30 ring carbon atoms in the formula (1).

The aryloxy group having 6 to 30 ring carbon atoms in the formula (1a) represents the same as the aryloxy group having 6 to 30 ring carbon atoms in the formula (1).

The halogen atom in the formula (1a) represents the same as the halogen atom in the formula (1).

Preferable examples of each of the above groups in the formula (1a) represent the same as those in the formula (1).

In the formula (1a), $R_2$ is represented by the formula (2a). In the formula (1a), any one of $R_3$ to $R_{10}$ is represented by the formula (2a).

In the formula (2a), $L_1$, $L_2$ and $L_3$ each independently represent a single bond, a divalent residue of a substituted or unsubstituted aryl group having 6 to 30 ring carbon atoms, or a divalent residue of a substituted or unsubstituted heterocyclic group having 5 to 30 ring atoms.

The divalent residue of the aryl group having 6 to 30 ring carbon atoms is exemplified by a divalent residue derived from an aryl group having 6 to 30 ring carbon atoms for $R_1$ and $R_3$ to $R_{10}$ in the formula (1a).

The divalent residue of the heterocyclic group having 5 to 30 ring atoms is exemplified by a divalent residue derived from a heterocyclic group having 5 to 30 ring atoms for $R_1$ and $R_3$ to $R_{10}$ in the formula (1a).

In the formula (2a), $Ar_1$ is a monovalent substituent having a partial structure represented by the formula (3a).

In the formula (3a), X represents an oxygen atom or a sulfur atom. In the formula (3a), A and B represent a six-membered ring. The six-membered ring represented by A and B may be fused with another ring.

In the formula (2a), $Ar_2$ is a substituted or unsubstituted aryl group having 6 to 30 ring carbon atoms, a substituted or unsubstituted heterocyclic group having 5 to 30 ring atoms, or a monovalent substituent having a partial structure represented by the formula (3a). The aryl group and heterocyclic group for $Ar_2$ are the same as $R_1$ and $R_3$ to $R_{10}$ in the formula (1a).

In the aromatic amine derivative according to the second exemplary embodiment of the invention, the monovalent substituent having the partial structure represented by the formula (3a) is preferably a monovalent residue represented by the formula (4).

In the formula (4), X represents an oxygen atom or a sulfur atom.

$R_{11}$ to $R_{18}$ in the formula (4) each independently represent the same as $R_1$ and $R_3$ to $R_{10}$ in the formula (1). However, in the formula (2); when $Ar_1$ is a monovalent residue of the formula (4), one of $R_{11}$ to $R_{18}$ is a single bond to be bonded to $L_1$; and when $Ar_2$ is a monovalent residue of the formula (4), one of $R_{11}$ to $R_{18}$ is a single bond to be bonded to $L_2$. Thus, the structure of the formula (4) in which one of $R_{11}$ to $R_{18}$ is a single bond is exemplarily represented by the formulae (4A) to (4D). In the formula (4), at least one combination of $R_{11}$ and $R_{12}$, $R_{12}$ and $R_{13}$, $R_{13}$ and $R_{14}$, $R_{15}$ and $R_{16}$, $R_{16}$ and $R_{17}$, and $R_{17}$ and $R_{18}$ may form a saturated or unsaturated ring. An instance where such a ring may be formed in the formula (4) is exemplarily represented by the formulae (4E), (4F) and (4G).

A specific structure of the aromatic amine derivative according to the second exemplary embodiment is exemplified by those of the following compounds. However, the invention is not limited to the aromatic amine derivatives having the structures.

In the aromatic amine derivative according to the exemplary embodiment, $R_2$ and $R_4$ in the formula (1a) are preferably represented by the formula (2a). At this instance, the aromatic amine derivative has a structure represented by the following formula (1 G).

[Formula 55]

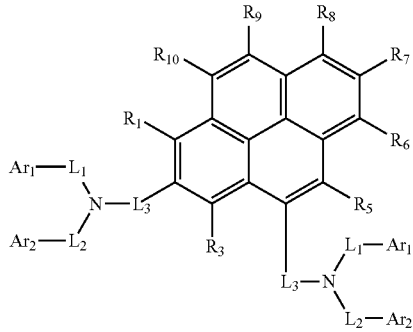

(1G)

Specific examples of the aromatic amine derivative according to the exemplary embodiment are aromatic amine derivatives described in Tables 102 to 106 for $R_1$, $R_3$, $R_5$ to $R_{10}$, $L_1$ to $L_3$, and $Ar_1$ to $Ar_2$ in the formula (1G). Note that "—" in $L_1$ to $L_3$ of the tables represents a single bond. Moreover, in $L_1$ to $L_3$ and $Ar_1$ to $Ar_2$ in the tables, a line extending outward from the cyclic structure and having no chemical formula (e.g., $CH_3$, Ph, CN, benzene ring) at an end of the line represents a single bond, not a methyl group. For instance, in the following compound D2501, $Ar_1$ has a single bond at a position 4 of a dibenzofuran ring. In short, $Ar_1$ represents a 4-dibenzofuranyl group. Likewise, $Ar_2$ represents a phenyl group.

TABLE 102

| compound | $R_1$ | $R_3$ | $R_5$ | $R_6$ | $R_7$ | $R_8$ | $R_9$ | $R_{10}$ | $L_1$ | $L_2$ | $L_3$ | $Ar_1$ | $Ar_2$ |
|---|---|---|---|---|---|---|---|---|---|---|---|---|---|
| D2501 | H | H | H | H | H | H | H | H | — | — | — | (4-dibenzofuranyl) | (phenyl) |
| D2502 | H | H | H | H | H | H | H | H | — | — | — | (dibenzofuranyl) | (phenyl) |
| D2503 | H | H | H | H | H | H | H | H | — | — | — | (dibenzofuranyl) | (phenyl) |
| D2504 | H | H | H | H | H | H | H | H | — | — | — | (dibenzofuranyl) | (phenyl) |

TABLE 102-continued
| compound | R₁ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D2505 | H | H | H | H | H | H | H | H | — | — | — | 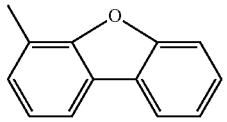 | 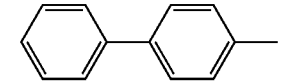 |
| D2506 | H | H | H | H | H | H | H | H | — | — | — | 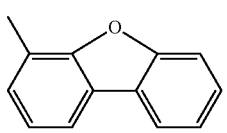 | 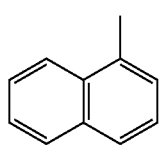 |
| D2507 | H | H | H | H | H | H | H | H | — | — | — | 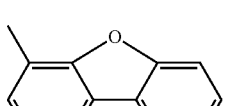 | 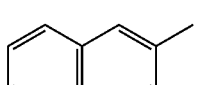 |
TABLE 103
| compound | R₁ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D2508 | H | H | H | H | H | H | H | H | — | — | — | 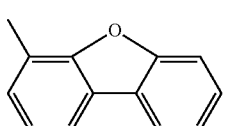 | 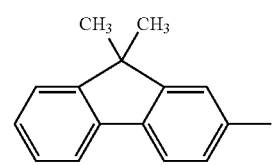 |
| D2509 | H | H | H | H | H | H | H | H | — | — | — | 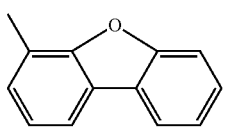 | 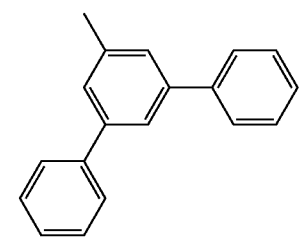 |
| D2510 | H | H | H | H | H | H | H | H | — | — | — | 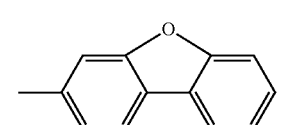 | 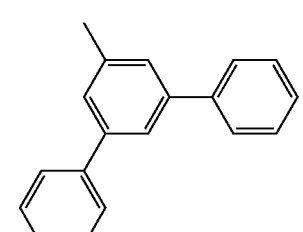 |
| D2511 | H | H | H | H | H | H | H | H | — | — | — | 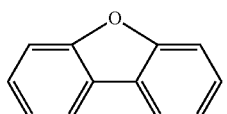 | 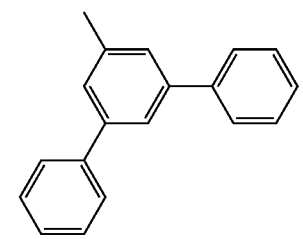 |

TABLE 103-continued
| compound | R₁ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D2512 | H | H | H | H | H | H | H | H | — | — | — | 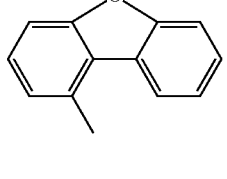 | 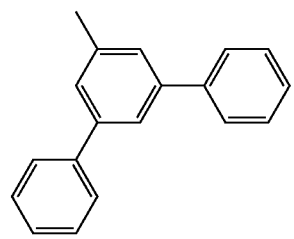 |
| D2513 | H | H | H | H | H | H | H | H | — | — | — | 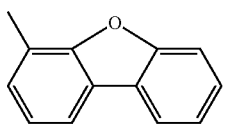 |  |
| D2514 | H | H | H | H | H | H | H | H | — | — | — | 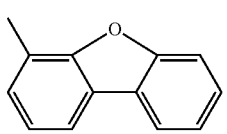 | 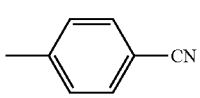 |
| D2515 | H | H | H | H | H | H | H | H | — | — | — | 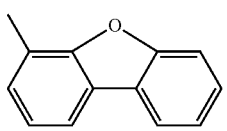 | 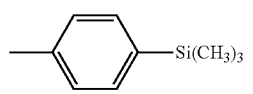 |
TABLE 104
| compound | R₁ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D2516 | H | H | H | H | H | H | H | H | — | — | — | 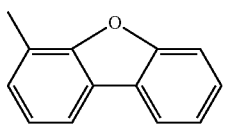 | 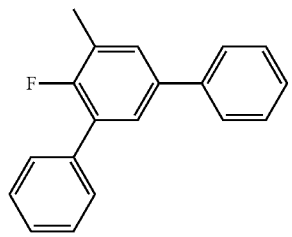 |
| D2517 | H | H | H | H | H | H | H | H | — | — | — | 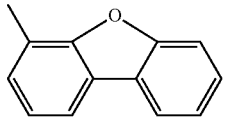 | 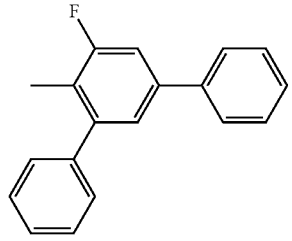 |
| D2618 | H | H | H | H | H | H | H | H | — | — | — | 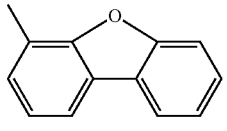 | 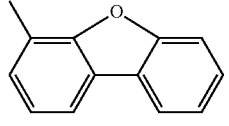 |
| D2619 | H | H | H | H | H | H | H | H | — | — | — | 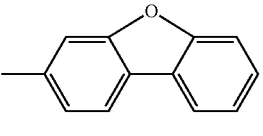 | 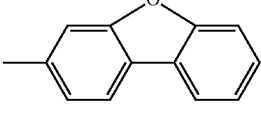 |

TABLE 104-continued
| compound | R₁ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D2520 | H | H | H | H | H | H | H | H | — | — | — |  |  |
| D2621 | H | H | H | H | H | H | H | H | — | — | — | 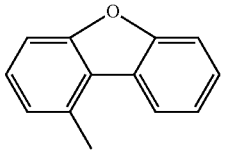 | 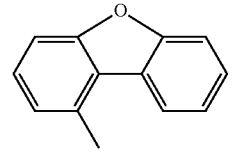 |
| D2522 | H | H | H | H | H | H | H | H | — | — | — | 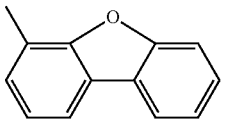 | 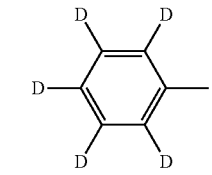 |
| D2523 | H | H | H | H | H | H | H | H | — | — | — | 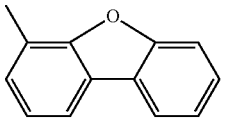 | 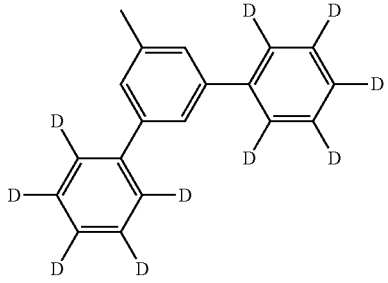 |
| D2524 | H | H | H | H | H | H | H | H | — | — | — | 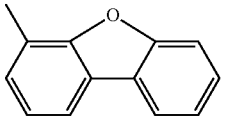 | 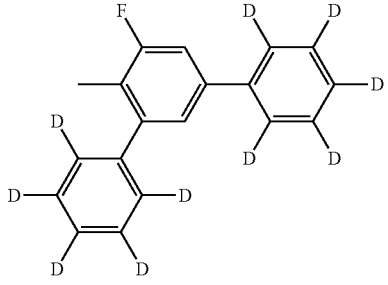 |
| D2525 | H | H | H | H | H | H | H | H | — | — | — | 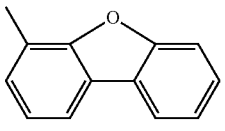 | 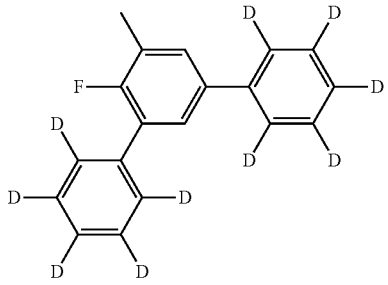 |
TABLE 105
| compound | R₁ | R₃ | R₅ | R₆ | R₇ | R₈ | R₉ | R₁₀ | L₁ |
|---|---|---|---|---|---|---|---|---|---|
| D2526 | H | H | H | H | H | H | H | H | — |
| D2527 | H | H | H | H | H | H | H | H | |

TABLE 105-continued

| compound | | | | | | | | | |
|---|---|---|---|---|---|---|---|---|---|
| D2528 | H | H | H | H | H | H | H | H | (p-phenylene) |
| D2529 | H | H | H | H | H | H | H | H | -C(CH₃)₂- |
| D2530 | H | H | H | H | H | H | H | H | — |
| D2531 | H | H | H | H | H | H | H | H | — |
| D2532 | H | H | H | H | H | H | H | H | (p-phenylene) |
| D2533 | H | H | H | H | H | H | H | H | -C(CH₃)₂- |
| D2534 | H | H | H | H | H | H | H | H | — |
| D2535 | H | H | H | H | H | H | H | H | — |
| D2536 | H | H | H | H | H | H | H | H | — |
| D2537 | H | H | H | H | H | H | H | H | — |

| compound | L₂ | L₃ | Ar₁ | Ar₂ |
|---|---|---|---|---|
| D2526 | — | — | 4-phenyldibenzofuran-6-yl | phenyl |
| D2527 | — | — | 6-deutero-dibenzofuran-4-yl | phenyl |
| D2528 | — | — | dibenzofuran-4-yl | phenyl |
| D2529 | — | — | dibenzofuran-4-yl | phenyl |
| D2530 | -C(CH₃)₂- | — | dibenzofuran-4-yl | phenyl |
| D2531 | — | p-phenylene | dibenzofuran-4-yl | phenyl |
| D2532 | p-phenylene | — | dibenzofuran-4-yl | dibenzofuran-4-yl |
| D2533 | -C(CH₃)₂- | — | dibenzofuran-4-yl | dibenzofuran-4-yl |

TABLE 105-continued
| D2534 | — | 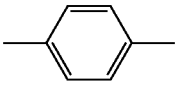 | 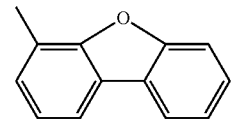 | 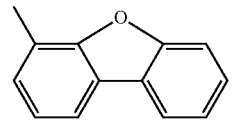 |
| D2535 | — | — | 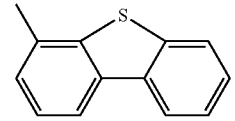 | 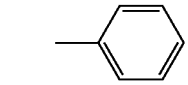 |
| D2536 | — | — | 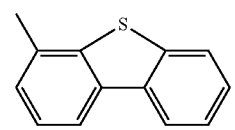 | 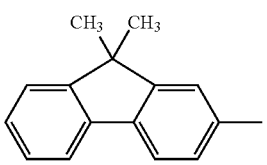 |
| D2537 | — | — | 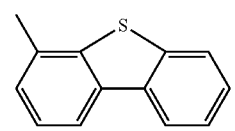 | 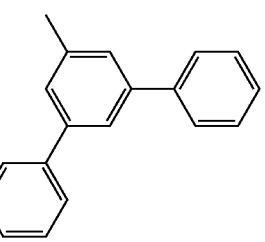 |
TABLE 106
| compound | $R_1$ | $R_3$ | $R_5$ | $R_6$ | $R_7$ | $R_8$ | $R_9$ | $R_{10}$ | $L_1$ | $L_2$ | $L_3$ | $Ar_1$ | $Ar_2$ |
|---|---|---|---|---|---|---|---|---|---|---|---|---|---|
| D2538 | H | H | H | H | H | H | H | H | — | — | — | 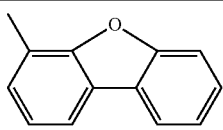 | 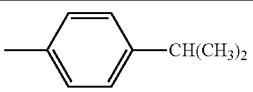 |
| D2539 | H | H | H | H | H | H | H | H | — | — | — | 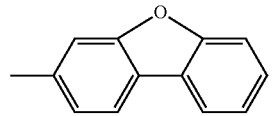 | 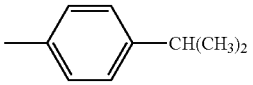 |
| D2540 | H | H | H | H | H | H | H | H | — | — | — | 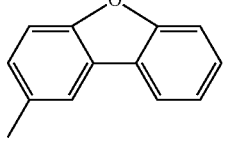 | 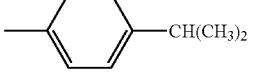 |
| D2541 | H | H | H | H | H | H | H | H | — | — | — | 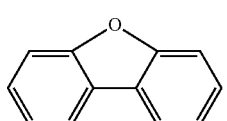 | 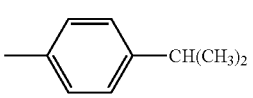 |
| D2542 | H | H | H | H | H | H | H | H | — | — | — | 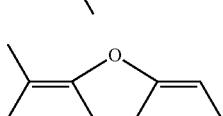 | 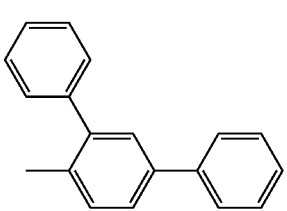 |

TABLE 106-continued

| compound | R$_1$ | R$_3$ | R$_5$ | R$_6$ | R$_7$ | R$_8$ | R$_9$ | R$_{10}$ | L$_1$ | L$_2$ | L$_3$ | Ar$_1$ | Ar$_2$ |
|---|---|---|---|---|---|---|---|---|---|---|---|---|---|
| D2543 | H | H | H | H | H | H | H | H | — | — | — | methyl-dibenzofuran | methyl-biphenyl-phenyl |
| D2544 | H | H | H | H | H | H | H | H | — | — | — | methyl-dibenzofuran | methyl-biphenyl-phenyl |
| D2545 | H | H | H | H | H | H | H | H | — | — | — | methyl-dibenzofuran | methyl-biphenyl-phenyl |

The specific examples of the aromatic amine derivative are the compounds having R$_2$ and R$_4$ in the same structure represented by the formula (2a), however, not limited thereto. The aromatic amine derivative may be a compound having R$_2$ and R$_4$ in different structures.

In the aromatic amine derivative according to the exemplary embodiment, R$_2$ and R$_5$ in the formula (1a) are preferably represented by the formula (2a). At this instance, the aromatic amine derivative has a structure represented by the following formula (1H).

[Formula 56]

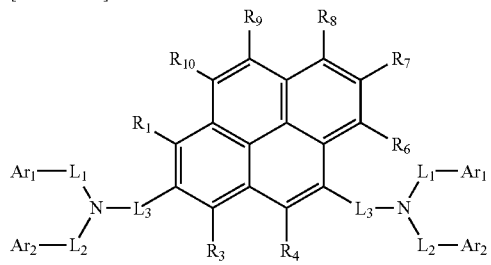

(1H)

Specific examples of the aromatic amine derivative according to the exemplary embodiment are aromatic amine derivatives described in Tables 107 to 111 for R$_1$, R$_3$, R$_4$, R$_6$ to R$_{10}$, L$_1$ to L$_3$, and Ar$_1$ to Ar$_2$ in the formula (1H). Note that "—" in L$_1$ to L$_3$ of the tables represents a single bond. Moreover, in L$_1$ to L$_3$ and Ar$_1$ to Ar$_2$ in the tables, a line extending outward from the cyclic structure and having no chemical formula (e.g., CH$_3$, Ph, CN, benzene ring) at an end of the line represents a single bond, not a methyl group. For instance, in the following compound D2601, Ar$_1$ has a single bond at a position 4 of a dibenzofuran ring. In short, Ar$_1$ represents a 4-dibenzofuranyl group. Likewise, Ar$_2$ represents a phenyl group.

TABLE 107

| compound | R$_1$ | R$_3$ | R$_5$ | R$_6$ | R$_7$ | R$_8$ | R$_9$ | R$_{10}$ | L$_1$ | L$_2$ | L$_3$ | Ar$_1$ | Ar$_2$ |
|---|---|---|---|---|---|---|---|---|---|---|---|---|---|
| D2601 | H | H | H | H | H | H | H | H | — | — | — | dibenzofuran | phenyl |

TABLE 107-continued
| compound | R₁ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D2602 | H | H | H | H | H | H | H | H | — | — | — | 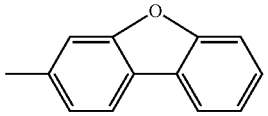 | 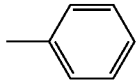 |
| D2603 | H | H | H | H | H | H | H | H | — | — | — | 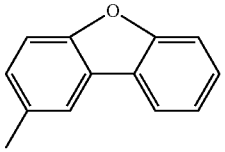 | 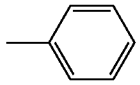 |
| D2604 | H | H | H | H | H | H | H | H | — | — | — | 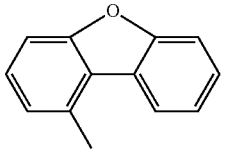 | 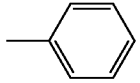 |
| D2605 | H | H | H | H | H | H | H | H | — | — | — | 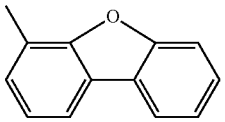 | 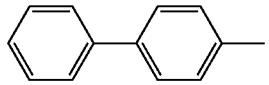 |
| D2606 | H | H | H | H | H | H | H | H | — | — | — | 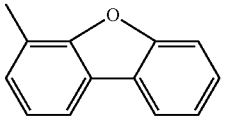 | 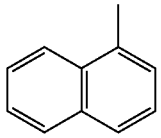 |
| D2607 | H | H | H | H | H | H | H | H | — | — | — | 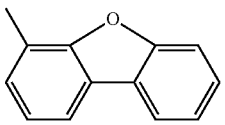 | 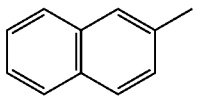 |
TABLE 108
| compound | R₁ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D2608 | H | H | H | H | H | H | H | H | — | — | — | 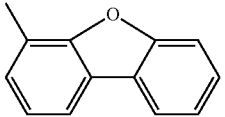 | 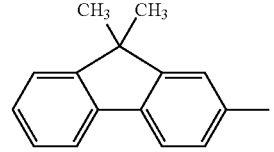 |
| D2609 | H | H | H | H | H | H | H | H | — | — | — | 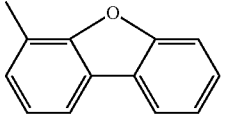 | 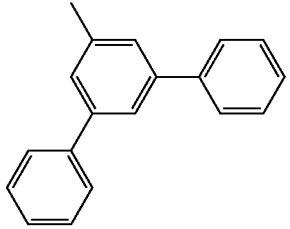 |

TABLE 108-continued
| compound | R₁ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D2610 | H | H | H | H | H | H | H | H | — | — | — | 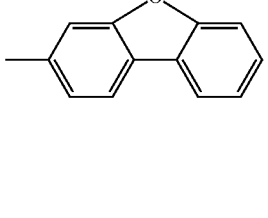 | 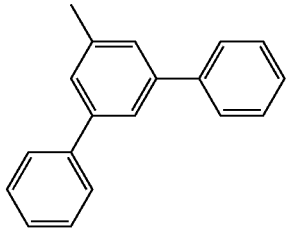 |
| D2611 | H | H | H | H | H | H | H | H | — | — | — | 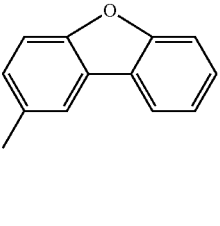 | 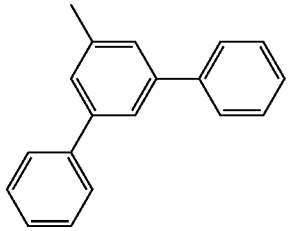 |
| D2612 | H | H | H | H | H | H | H | H | — | — | — | 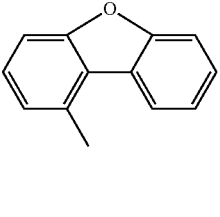 | 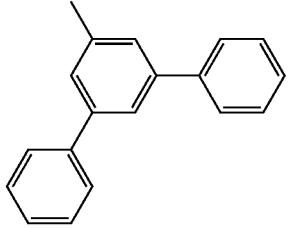 |
| D2613 | H | H | H | H | H | H | H | H | — | — | — | 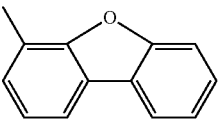 |  |
| D2614 | H | H | H | H | H | H | H | H | — | — | — | 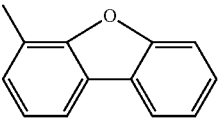 | 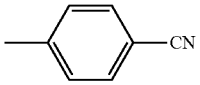 |
| D2615 | H | H | H | H | H | H | H | H | — | — | — | 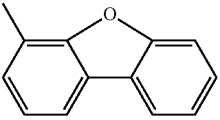 | 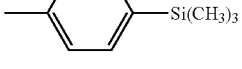 |
TABLE 109
| compound | R₁ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D2616 | H | H | H | H | H | H | H | H | — | — | — | 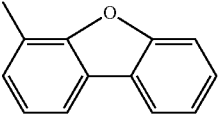 | 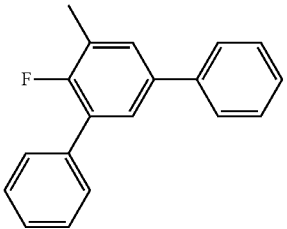 |

US 9,640,773 B2
299                                                                           300
TABLE 109-continued
| compound | R$_1$ | R$_3$ | R$_5$ | R$_6$ | R$_7$ | R$_8$ | R$_9$ | R$_{10}$ | L$_1$ | L$_2$ | L$_3$ | Ar$_1$ | Ar$_2$ |
|---|---|---|---|---|---|---|---|---|---|---|---|---|---|
| D2617 | H | H | H | H | H | H | H | H | — | — | — | 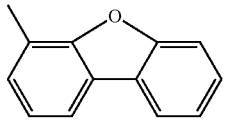 | 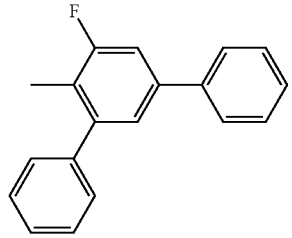 |
| D2618 | H | H | H | H | H | H | H | H | — | — | — | 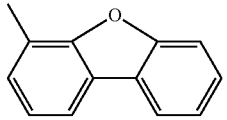 | 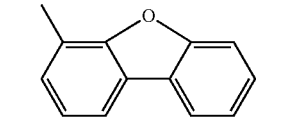 |
| D2619 | H | H | H | H | H | H | H | H | — | — | — | 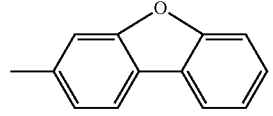 | 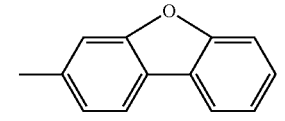 |
| D2620 | H | H | H | H | H | H | H | H | — | — | — | 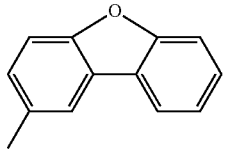 | 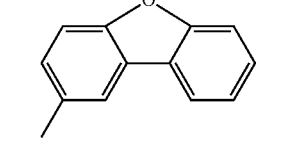 |
| D2621 | H | H | H | H | H | H | H | H | — | — | — | 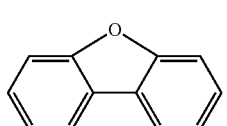 | 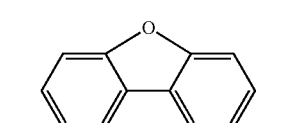 |
| D2622 | H | H | H | H | H | H | H | H | — | — | — | 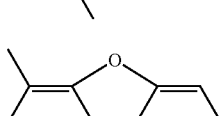 | 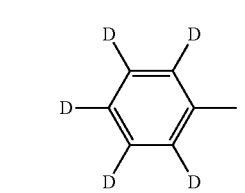 |
| D2623 | H | H | H | H | H | H | H | H | — | — | — | 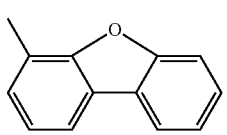 | 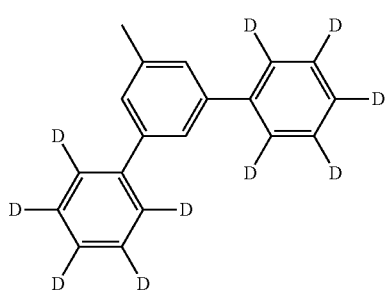 |
| D2624 | H | H | H | H | H | H | H | H | — | — | — | 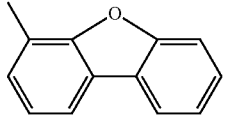 | 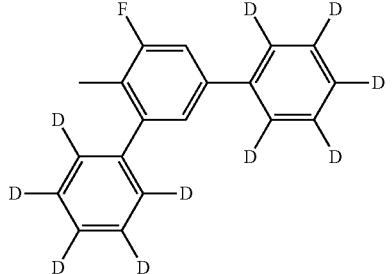 |

TABLE 109-continued
| compound | R₁ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D2625 | H | H | H | H | H | H | H | H | — | — | — | 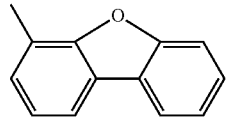 | 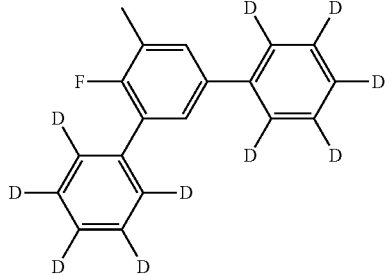 |
TABLE 110
| compound | R₁ | R₃ | R₅ | R₆ | R₇ | R₈ | R₉ | R₁₀ | L₁ |
|---|---|---|---|---|---|---|---|---|---|
| D2626 | H | H | H | H | H | H | H | H | — |
| D2627 | H | H | H | H | H | H | H | H | — |
| D2628 | H | H | H | H | H | H | H | H | 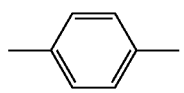 |
| D2629 | H | H | H | H | H | H | H | H | 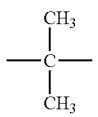 |
| D2630 | H | H | H | H | H | H | H | H | — |
| D2631 | H | H | H | H | H | H | H | H | — |
| D2632 | H | H | H | H | H | H | H | H | 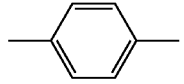 |
| D2633 | H | H | H | H | H | H | H | H | 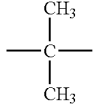 |
| D2634 | H | H | H | H | H | H | H | H | — |
| D2635 | H | H | H | H | H | H | H | H | — |
| D2636 | H | H | H | H | H | H | H | H | — |
| D2637 | H | H | H | H | H | H | H | H | — |
| compound | L₂ | L₃ | Ar₁ | Ar₂ |
|---|---|---|---|---|
| D2626 | — | — | 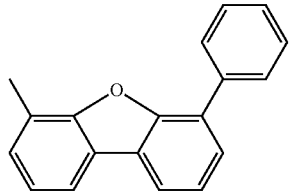 | 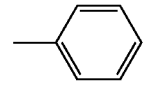 |
| D2627 | — | — | 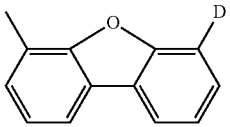 | 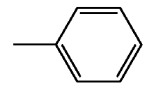 |

US 9,640,773 B2
TABLE 110-continued
| | | | | |
|---|---|---|---|---|
| D2628 | — | — | 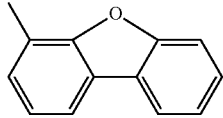 | 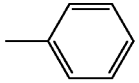 |
| D2629 | — | — | 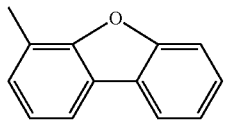 | 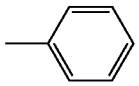 |
| D2630 |  | — | 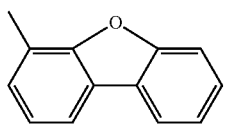 | 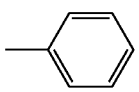 |
| D2631 | — |  | 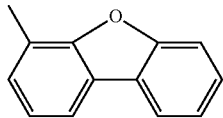 | 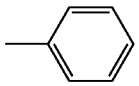 |
| D2632 |  | — | 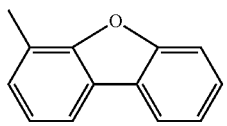 | 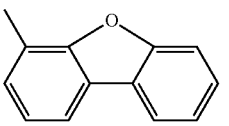 |
| D2633 | 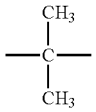 | — | 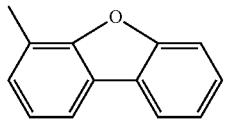 | 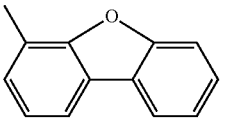 |
| D2634 | — |  | 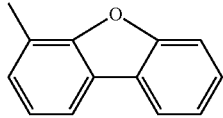 | 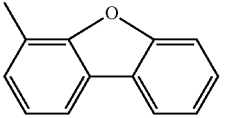 |
| D2635 | — | — | 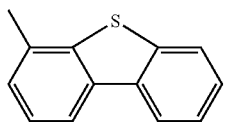 | 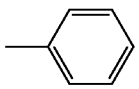 |
| D2636 | — | — | 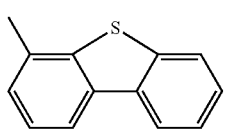 | 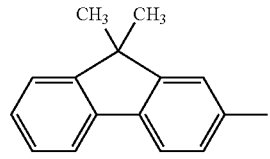 |
| D2637 | — | — | 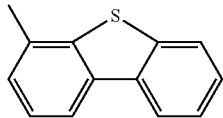 | 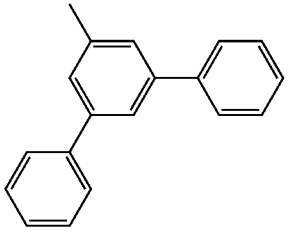 |

TABLE 111
| compound | R₁ | R₃ | R₅ | R₆ | R₇ | R₈ | R₉ | R₁₀ | L₁ | L₂ | L₃ | Ar₁ | Ar₂ |
|---|---|---|---|---|---|---|---|---|---|---|---|---|---|
| D2538 | H | H | H | H | H | H | H | H | — | — | — | 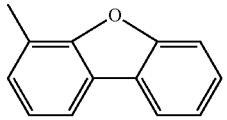 | 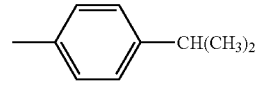 |
| D2639 | H | H | H | H | H | H | H | H | — | — | — | 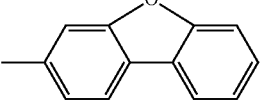 | 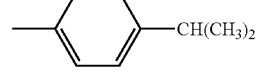 |
| D2540 | H | H | H | H | H | H | H | H | — | — | — | 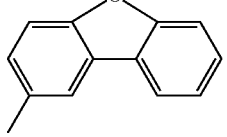 | 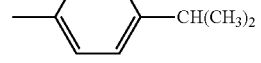 |
| D2641 | H | H | H | H | H | H | H | H | — | — | — | 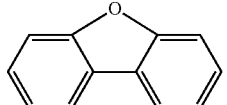 | 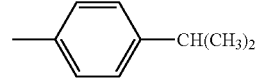 |
| D2642 | H | H | H | H | H | H | H | H | — | — | — | 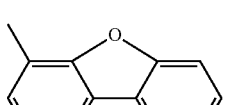 | 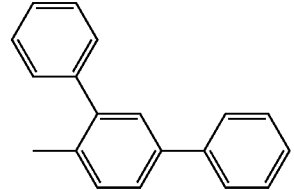 |
| D2643 | H | H | H | H | H | H | H | H | — | — | — | 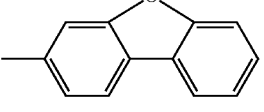 | 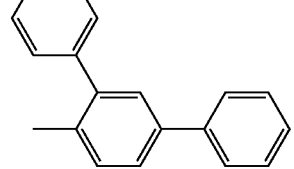 |
| D2644 | H | H | H | H | H | H | H | H | — | — | — | 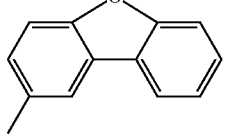 | 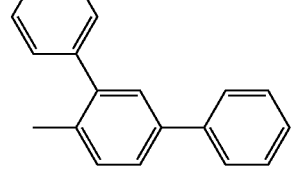 |
| D2645 | H | H | H | H | H | H | H | H | — | — | — | 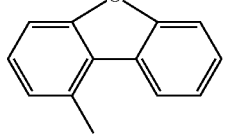 | 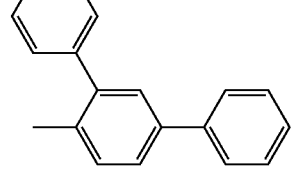 |

The specific examples of the aromatic amine derivative are the compounds having $R_2$ and $R_5$ in the same structure represented by the formula (2a), however, not limited thereto. The aromatic amine derivative may be a compound having $R_2$ and $R_5$ in different structures.

In the aromatic amine derivative according to the exemplary embodiment, $R_2$ and $R_7$ in the formula (1a) are preferably represented by the formula (2a). At this instance, the aromatic amine derivative has a structure represented by the following formula (1J).

[Formula 57]

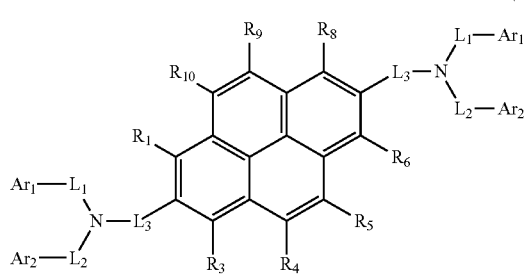

(1J)

Specific examples of the aromatic amine derivative according to the exemplary embodiment are aromatic amine derivatives described in Tables 112 to 139 for $R_1$, $R_3$ to $R_6$, $R_8$ to $R_{10}$, $L_1$ to $L_3$, and $Ar_1$ to $Ar_2$ in the formula (1J). Note that "—" in $L_1$ to $L_3$ of the tables represents a single bond. Moreover, in $L_1$ to $L_3$ and $Ar_1$ to $Ar_2$ in the tables, a line extending outward from the cyclic structure and having no chemical formula (e.g., $CH_3$, Ph, CN, benzene ring) at an end of the line represents a single bond, not a methyl group. For instance, in the following compound D2701, $Ar_1$ has a single bond at a position 4 of a dibenzofuran ring. In short, $Ar_1$ represents a 4-dibenzofuranyl group. Likewise, $Ar_2$ represents a phenyl group.

TABLE 112

| compound | $R_1$ | $R_3$ | $R_4$ | $R_5$ | $R_6$ | $R_8$ | $R_9$ | $R_{10}$ | $L_1$ | $L_2$ | $L_3$ | $Ar_1$ | $Ar_2$ |
|---|---|---|---|---|---|---|---|---|---|---|---|---|---|
| D2701 | H | H | H | H | H | H | H | H | — | — | — | dibenzofuranyl | phenyl |
| D2702 | H | H | H | H | H | H | H | H | — | — | — | dibenzofuranyl | phenyl |
| D2703 | H | H | H | H | H | H | H | H | — | — | — | dibenzofuranyl | phenyl |
| D2704 | H | H | H | H | H | H | H | H | — | — | — | dibenzofuranyl | phenyl |
| D2705 | H | H | H | H | H | H | H | H | — | — | — | dibenzofuranyl | biphenyl |
| D2706 | H | H | H | H | H | H | H | H | — | — | — | dibenzofuranyl | biphenyl |

TABLE 112-continued
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2707 | H | H | H | H | H | H | H | H | — | — | — | 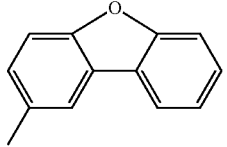 | 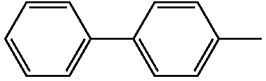 |
| D2708 | H | H | H | H | H | H | H | H | — | — | — | 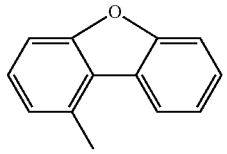 | 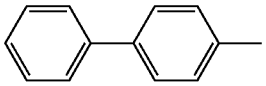 |
TABLE 113
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2709 | H | H | H | H | H | H | H | H | — | — | — | 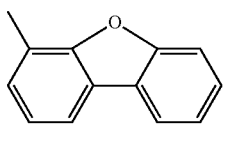 | 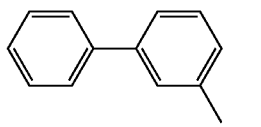 |
| D2710 | H | H | H | H | H | H | H | H | — | — | — | 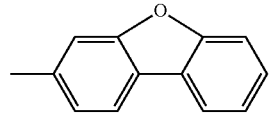 | 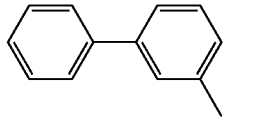 |
| D2711 | H | H | H | H | H | H | H | H | — | — | — | 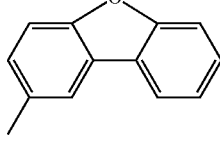 | 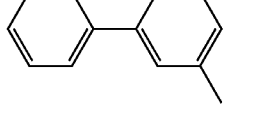 |
| D2712 | H | H | H | H | H | H | H | H | — | — | — | 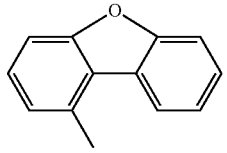 | 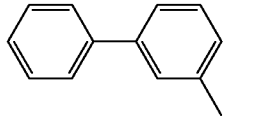 |
| D2713 | H | H | H | H | H | H | H | H | — | — | — | 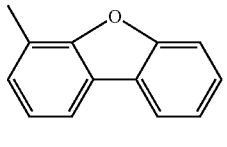 | 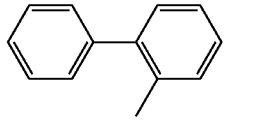 |
| D2714 | H | H | H | H | H | H | H | H | — | — | — | 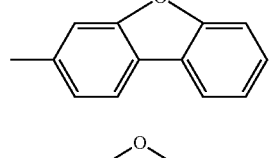 | 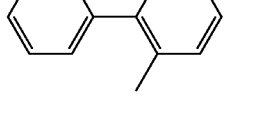 |
| D2715 | H | H | H | H | H | H | H | H | — | — | — | 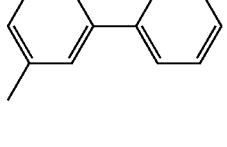 | 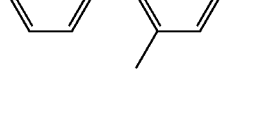 |

TABLE 113-continued
| compound | R1 | R3 | R4 | R5 | R6 | R8 | R9 | R10 | L1 | L2 | L3 | Ar1 | Ar2 |
|---|---|---|---|---|---|---|---|---|---|---|---|---|---|
| D2716 | H | H | H | H | H | H | H | H | — | — | — | 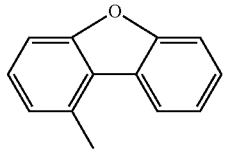 | 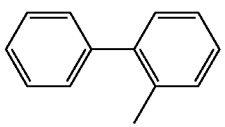 |
TABLE 114
| compound | R1 | R3 | R4 | R5 | R6 | R8 | R9 | R10 | L1 | L2 | L3 | Ar1 | Ar2 |
|---|---|---|---|---|---|---|---|---|---|---|---|---|---|
| D2717 | H | H | H | H | H | H | H | H | — | — | — | 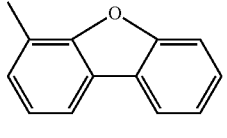 | 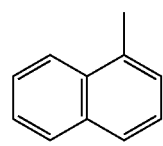 |
| D2718 | H | H | H | H | H | H | H | H | — | — | — | 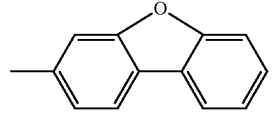 | 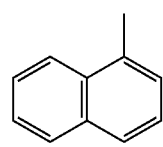 |
| D2719 | H | H | H | H | H | H | H | H | — | — | — | 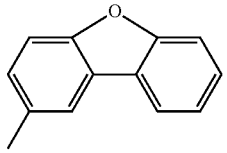 | 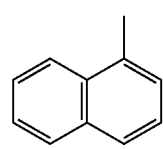 |
| D2720 | H | H | H | H | H | H | H | H | — | — | — | 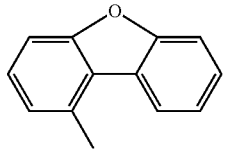 | 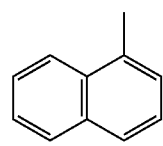 |
| D2721 | H | H | H | H | H | H | H | H | — | — | — | 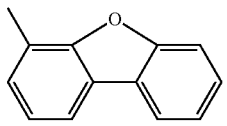 | 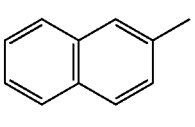 |
| D2722 | H | H | H | H | H | H | H | H | — | — | — | 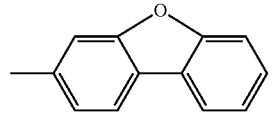 | 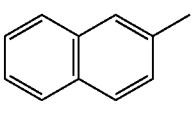 |
| D2723 | H | H | H | H | H | H | H | H | — | — | — | 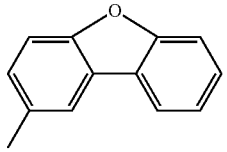 | 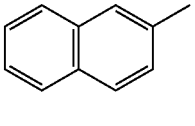 |
| D2724 | H | H | H | H | H | H | H | H | — | — | — | 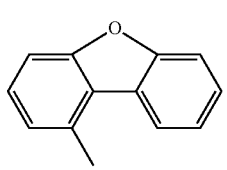 | 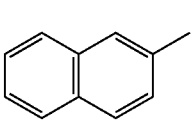 |

TABLE 115
| compound | R1 | R3 | R4 | R5 | R6 | R8 | R9 | R10 | L1 | L2 | L3 | Ar1 | Ar2 |
|---|---|---|---|---|---|---|---|---|---|---|---|---|---|
| D2725 | H | H | H | H | H | H | H | H | — | — | — | 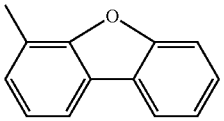 | 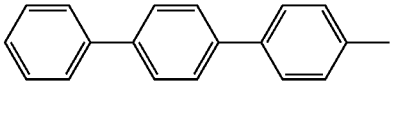 |
| D2726 | H | H | H | H | H | H | H | H | — | — | — | 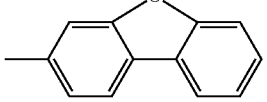 | 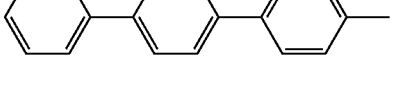 |
| D2727 | H | H | H | H | H | H | H | H | — | — | — | 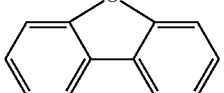 | 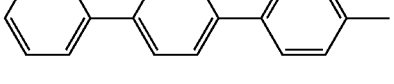 |
| D2728 | H | H | H | H | H | H | H | H | — | — | — | 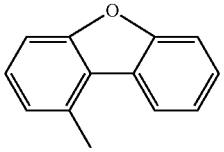 | 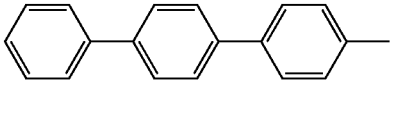 |
| D2729 | H | H | H | H | H | H | H | H | — | — | — | 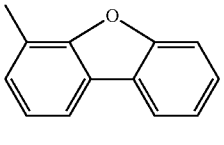 | 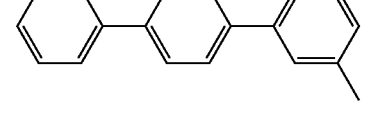 |
| D2730 | H | H | H | H | H | H | H | H | — | — | — | 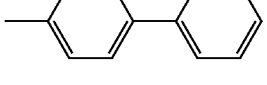 | 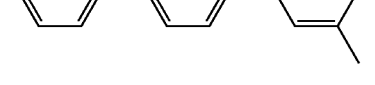 |
| D2731 | H | H | H | H | H | H | H | H | — | — | — | 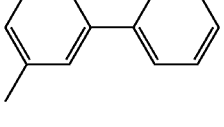 | 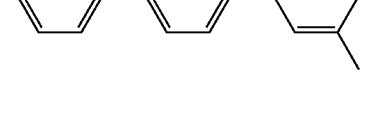 |
| D2732 | H | H | H | H | H | H | H | H | — | — | — | 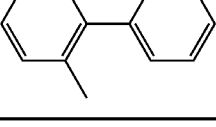 | 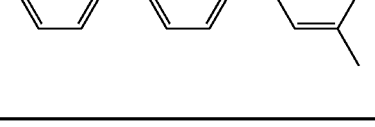 |
TABLE 116
| compound | R1 | R3 | R4 | R5 | R6 | R8 | R9 | R10 | L1 | L2 | L3 | Ar1 | Ar2 |
|---|---|---|---|---|---|---|---|---|---|---|---|---|---|
| D2733 | H | H | H | H | H | H | H | H | — | — | — | 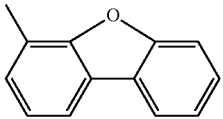 | 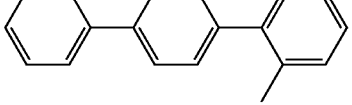 |

TABLE 116-continued
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2734 | H | H | H | H | H | H | H | H | — | — | — | 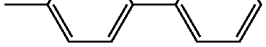 | 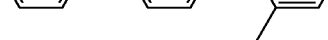 |
| D2735 | H | H | H | H | H | H | H | H | — | — | — | 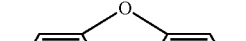 | 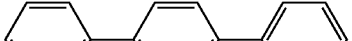 |
| D2736 | H | H | H | H | H | H | H | H | — | — | — |  |  |
| D2737 | H | H | H | H | H | H | H | H | — | — | — | 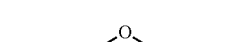 | 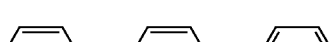 |
| D2738 | H | H | H | H | H | H | H | H | — | — | — | 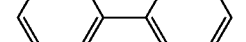 | 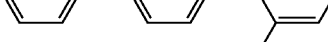 |
| D2739 | H | H | H | H | H | H | H | H | — | — | — |  |  |
| D2740 | H | H | H | H | H | H | H | H | — | — | — |  | 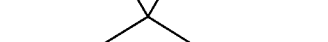 |
TABLE 117
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2741 | H | H | H | H | H | H | H | H | — | — | — | 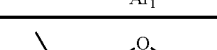 | 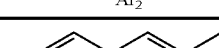 |
| D2742 | H | H | H | H | H | H | H | H | — | — | — | 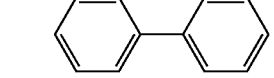 | 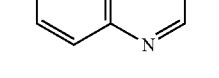 |

TABLE 117-continued
| compound | R1 | R3 | R4 | R5 | R6 | R8 | R9 | R10 | L1 | L2 | L3 | Ar1 | Ar2 |
|---|---|---|---|---|---|---|---|---|---|---|---|---|---|
| D2743 | H | H | H | H | H | H | H | H | — | — | — | 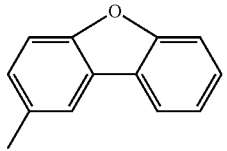 | 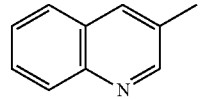 |
| D2744 | H | H | H | H | H | H | H | H | — | — | — | 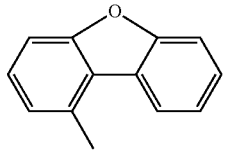 | 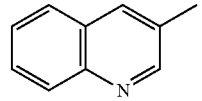 |
TABLE 118
| compound | R1 | R3 | R4 | R5 | R6 | R8 | R9 | R10 | L1 | L2 | L3 | Ar1 | Ar2 |
|---|---|---|---|---|---|---|---|---|---|---|---|---|---|
| D2745 | H | H | H | H | H | H | H | H | — | — | — | 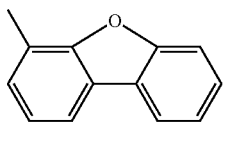 | 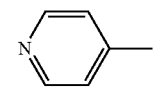 |
| D2746 | H | H | H | H | H | H | H | H | — | — | — | 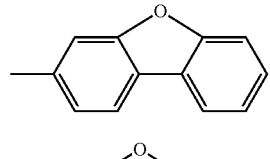 | 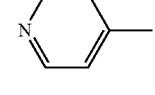 |
| D2747 | H | H | H | H | H | H | H | H | — | — | — | 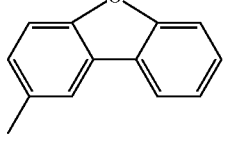 | 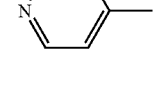 |
| D2748 | H | H | H | H | H | H | H | H | — | — | — | 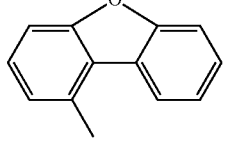 | 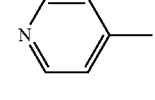 |
| D2749 | H | H | H | H | H | H | H | H | — | — | — | 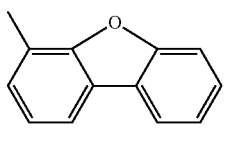 | 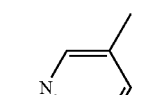 |
| D2750 | H | H | H | H | H | H | H | H | — | — | — | 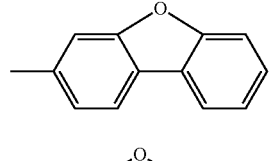 | 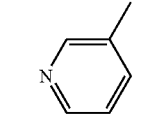 |
| D2751 | H | H | H | H | H | H | H | H | — | — | — | 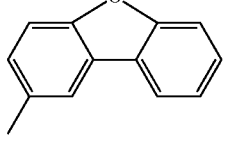 | 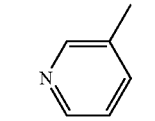 |

TABLE 118-continued
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2752 | H | H | H | H | H | H | H | H | — | — | — | 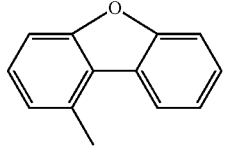 | 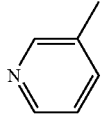 |
TABLE 119
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2753 | H | H | H | H | H | H | H | H | — | — | — | 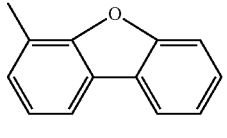 | 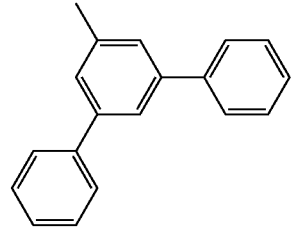 |
| D2754 | H | H | H | H | H | H | H | H | — | — | — | 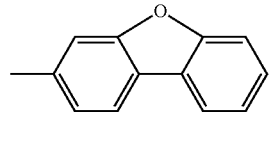 | 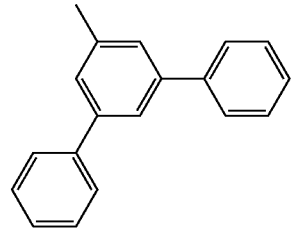 |
| D2755 | H | H | H | H | H | H | H | H | — | — | — | 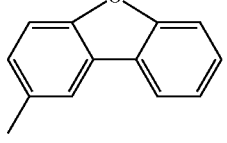 | 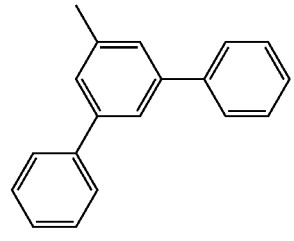 |
| D2756 | H | H | H | H | H | H | H | H | — | — | — | 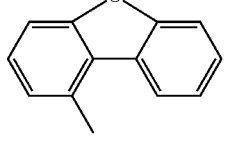 | 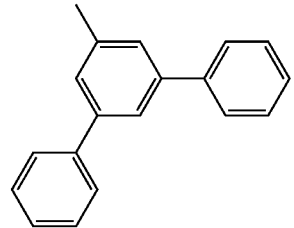 |
| D2757 | H | H | H | H | H | H | H | H | — | — | — | 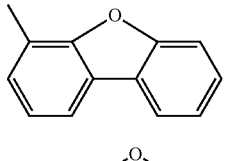 | 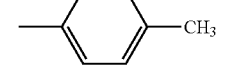 |
| D2758 | H | H | H | H | H | H | H | H | — | — | — | 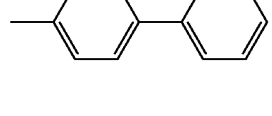 | 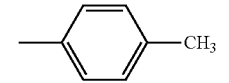 |

TABLE 119-continued
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2759 | H | H | H | H | H | H | H | H | — | — | — | 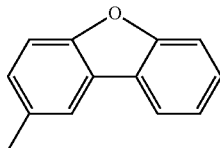 | 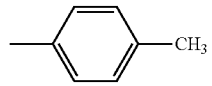 |
| D2760 | H | H | H | H | H | H | H | H | — | — | — | 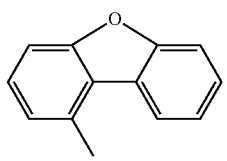 | 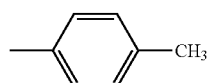 |
TABLE 120
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2761 | H | H | H | H | H | H | H | H | — | — | — | 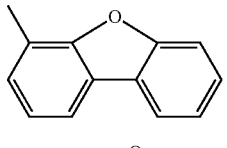 |  |
| D2762 | H | H | H | H | H | H | H | H | — | — | — | 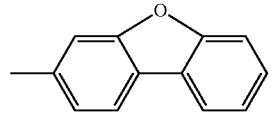 |  |
| D2763 | H | H | H | H | H | H | H | H | — | — | — | 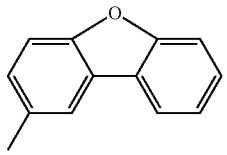 |  |
| D2764 | H | H | H | H | H | H | H | H | — | — | — | 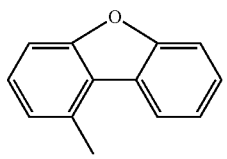 | 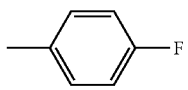 |
| D2765 | H | H | H | H | H | H | H | H | — | — | — | 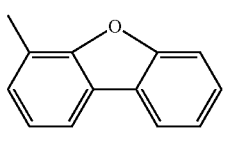 | 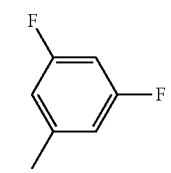 |
| D2766 | H | H | H | H | H | H | H | H | — | — | — | 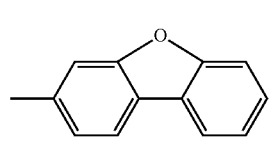 | 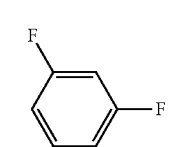 |
| D2767 | H | H | H | H | H | H | H | H | — | — | — | 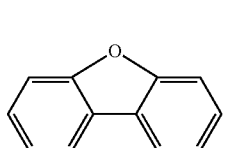 | 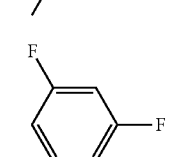 |

TABLE 120-continued
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2768 | H | H | H | H | H | H | H | H | — | — | — | 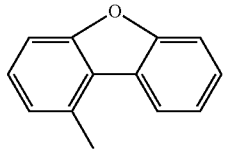 | 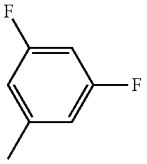 |
| D2769 | H | H | H | H | H | H | H | H | — | — | — | 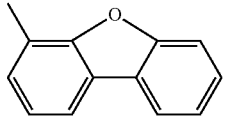 | 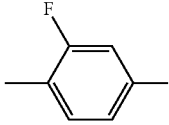 |
| D2770 | H | H | H | H | H | H | H | H | — | — | — | 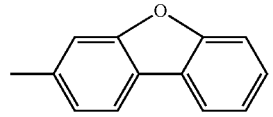 | 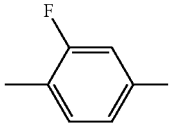 |
| D2771 | H | H | H | H | H | H | H | H | — | — | — | 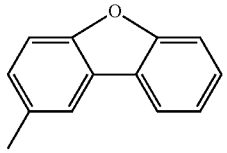 | 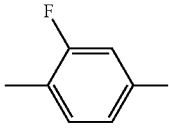 |
| D2772 | H | H | H | H | H | H | H | H | — | — | — | 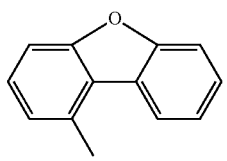 | 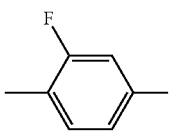 |
TABLE 121
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2773 | H | H | H | H | H | H | H | H | — | — | — | 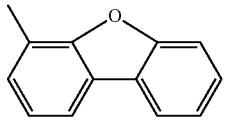 |  |
| D2774 | H | H | H | H | H | H | H | H | — | — | — | 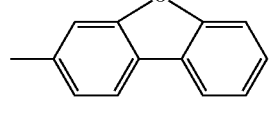 | 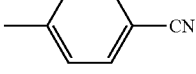 |
| D2775 | H | H | H | H | H | H | H | H | — | — | — | 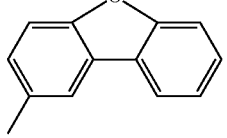 | 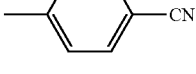 |
| D2776 | H | H | H | H | H | H | H | H | — | — | — | 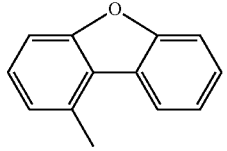 | 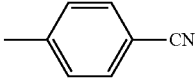 |

TABLE 121-continued
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2777 | H | H | H | H | H | H | H | H | — | — | — | 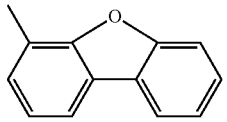 | 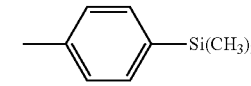 |
| D2778 | H | H | H | H | H | H | H | H | — | — | — | 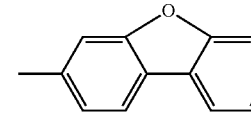 | 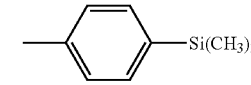 |
| D2779 | H | H | H | H | H | H | H | H | — | — | — | 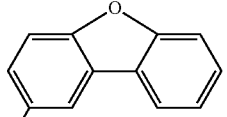 | 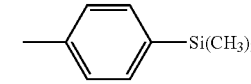 |
| D2780 | H | H | H | H | H | H | H | H | — | — | — | 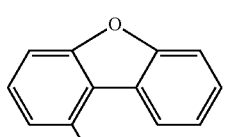 | 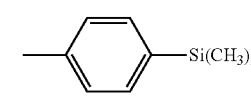 |
| D2781 | H | H | H | H | H | H | H | H | — | — | — | 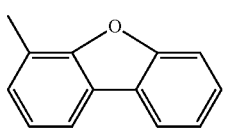 |  |
| D2782 | H | H | H | H | H | H | H | H | — | — | — | 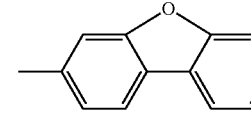 |  |
| D2783 | H | H | H | H | H | H | H | H | — | — | — | 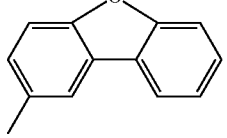 | 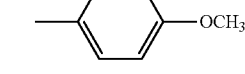 |
| D2784 | H | H | H | H | H | H | H | H | — | — | — | 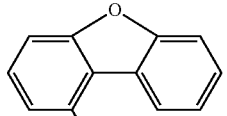 |  |
TABLE 122
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2785 | H | H | H | H | H | H | H | H | — | — | — | 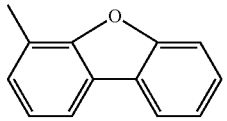 | 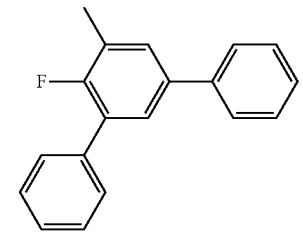 |

TABLE 122-continued
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2786 | H | H | H | H | H | H | H | H | — | — | — | 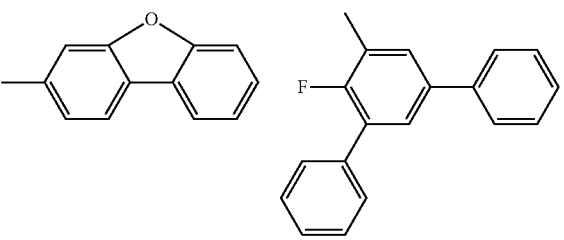 | 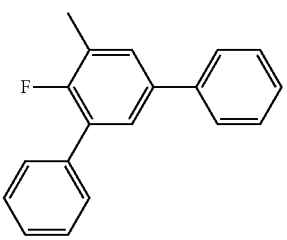 |
| D2787 | H | H | H | H | H | H | H | H | — | — | — | 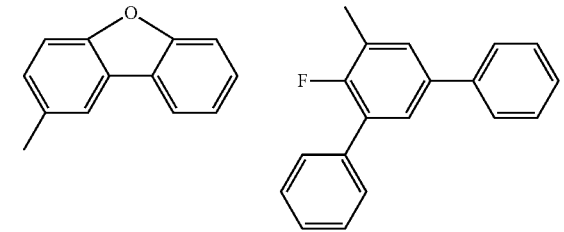 | 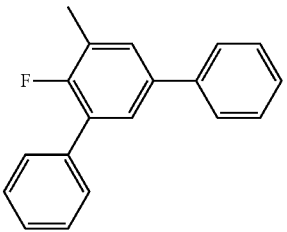 |
| D2788 | H | H | H | H | H | H | H | H | — | — | — | 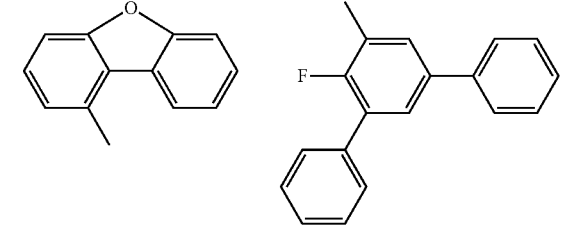 | 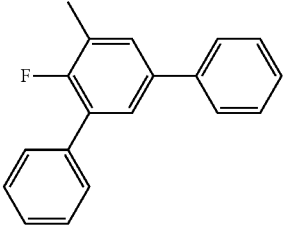 |
| D2789 | H | H | H | H | H | H | H | H | — | — | — | 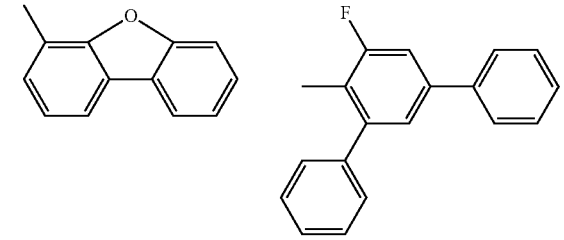 | 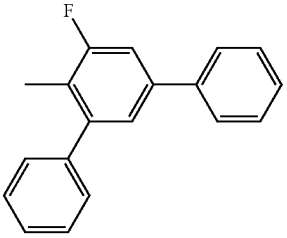 |
| D2790 | H | H | H | H | H | H | H | H | — | — | — | 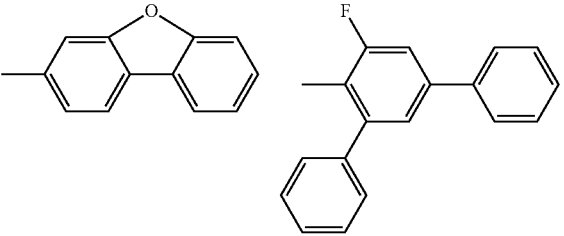 | 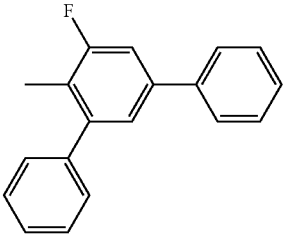 |
| D2791 | H | H | H | H | H | H | H | H | — | — | — | 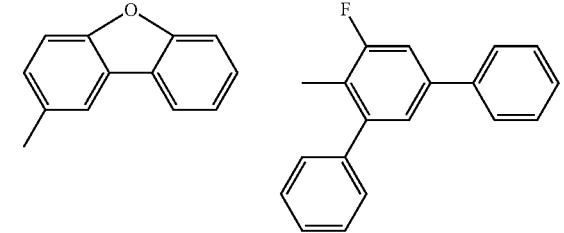 | 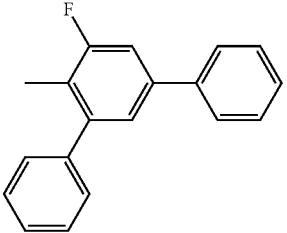 |

TABLE 122-continued
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2792 | H | H | H | H | H | H | H | H | — | — | — | 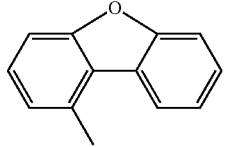 | 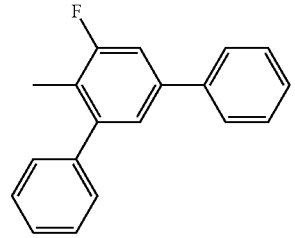 |
TABLE 123
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2793 | H | H | H | H | H | H | H | H | — | — | — | 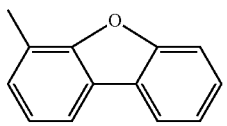 | 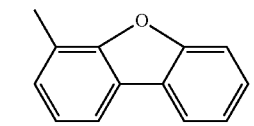 |
| D2794 | H | H | H | H | H | H | H | H | — | — | — | 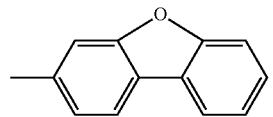 | 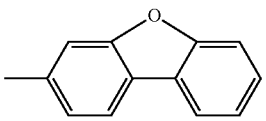 |
| D2795 | H | H | H | H | H | H | H | H | — | — | — | 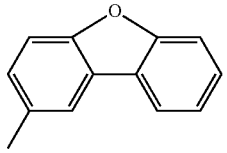 | 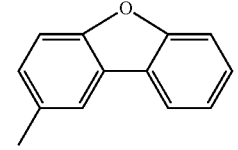 |
| D2796 | H | H | H | H | H | H | H | H | — | — | — | 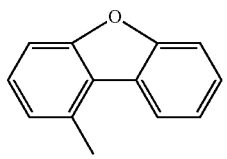 | 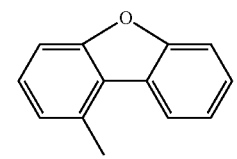 |
TABLE 124
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2797 | H | H | H | H | H | H | H | H | — | — | — | 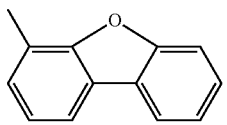 | 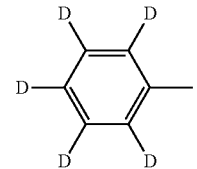 |
| D2798 | H | H | H | H | H | H | H | H | — | — | — | 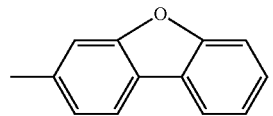 | 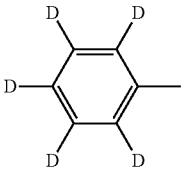 |

TABLE 124-continued
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2799 | H | H | H | H | H | H | H | H | — | — | — | 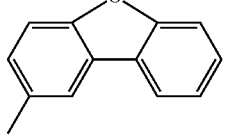 | 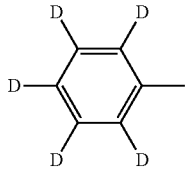 |
| D2800 | H | H | H | H | H | H | H | H | — | — | — | 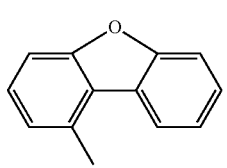 | 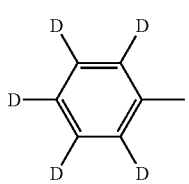 |
TABLE 125
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2801 | H | H | H | H | H | H | H | H | — | — | — | 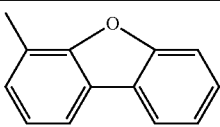 | 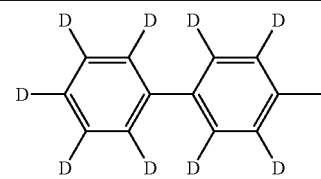 |
| D2802 | H | H | H | H | H | H | H | H | — | — | — | 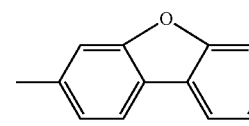 | 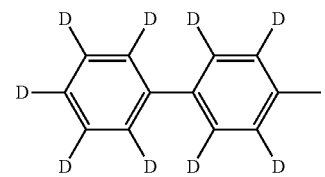 |
| D2803 | H | H | H | H | H | H | H | H | — | — | — | 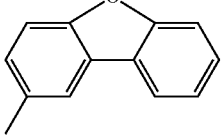 | 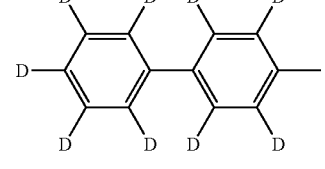 |
| D2804 | H | H | H | H | H | H | H | H | — | — | — | 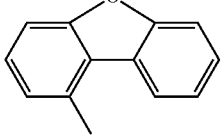 | 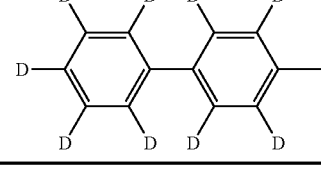 |
TABLE 126
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2805 | H | H | H | H | H | H | H | H | — | — | — | 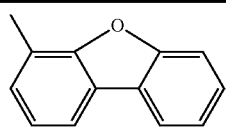 | 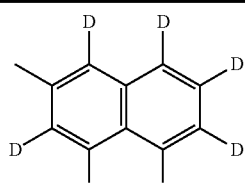 |

TABLE 126-continued
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2806 | H | H | H | H | H | H | H | H | — | — | — | 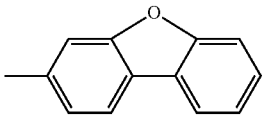 | 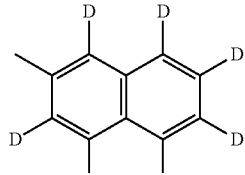 |
| D2807 | H | H | H | H | H | H | H | H | — | — | — | 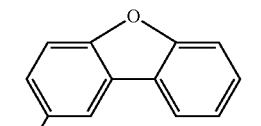 | 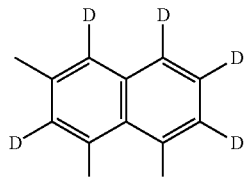 |
| D2808 | H | H | H | H | H | H | H | H | — | — | — | 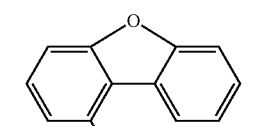 | 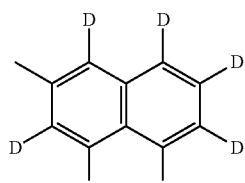 |
TABLE 127
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2809 | H | H | H | H | H | H | H | H | — | — | — | 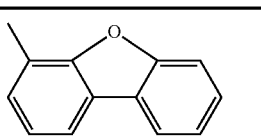 | 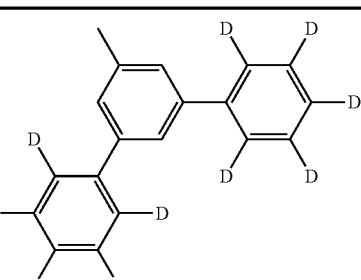 |
| D2810 | H | H | H | H | H | H | H | H | — | — | — | 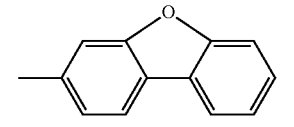 | 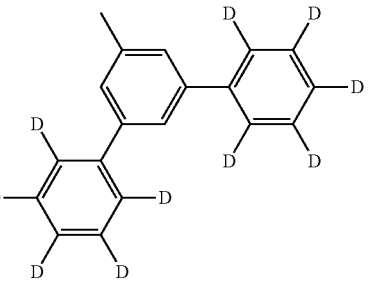 |
| D2811 | H | H | H | H | H | H | H | H | — | — | — | 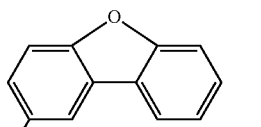 | 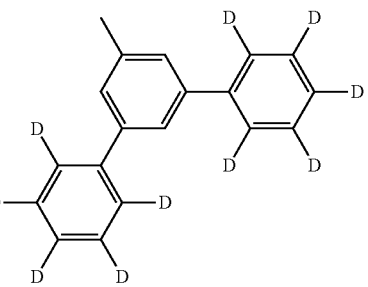 |

TABLE 127-continued
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2812 | H | H | H | H | H | H | H | H | — | — | — | 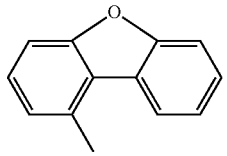 | 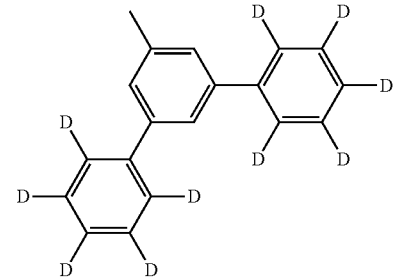 |
TABLE 128
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2813 | H | H | H | H | H | H | H | H | — | — | — | 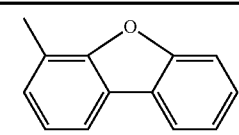 | 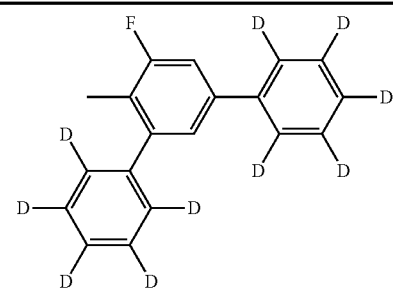 |
| D2814 | H | H | H | H | H | H | H | H | — | — | — | 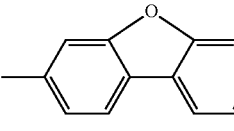 | 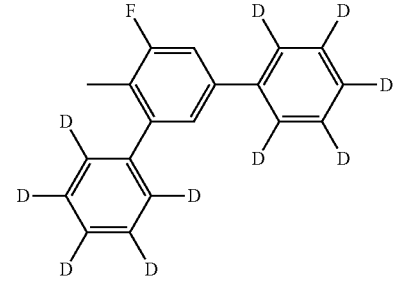 |
| D2815 | H | H | H | H | H | H | H | H | — | — | — | 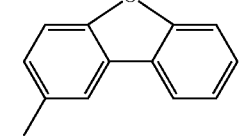 | 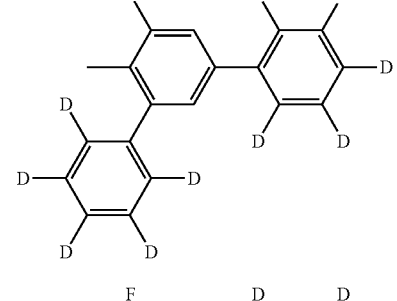 |
| D2816 | H | H | H | H | H | H | H | H | — | — | — | 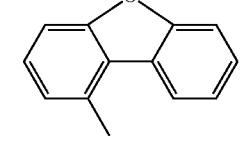 | 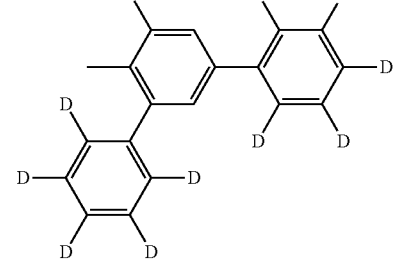 |

TABLE 129
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2817 | H | H | H | H | H | H | H | H | — | — | — | 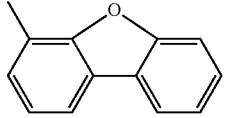 | 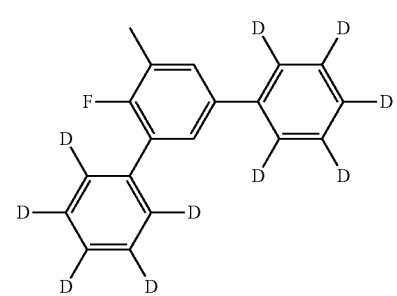 |
| D2818 | H | H | H | H | H | H | H | H | — | — | — | 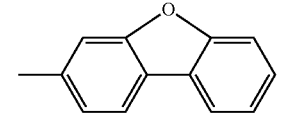 | 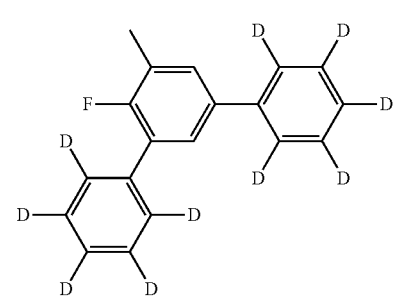 |
| D2819 | H | H | H | H | H | H | H | H | — | — | — | 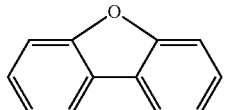 | 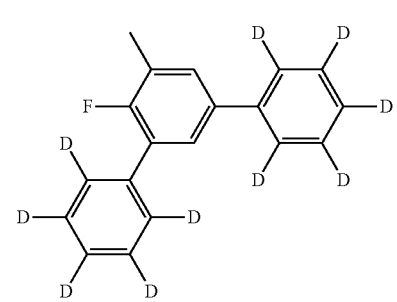 |
| D2820 | H | H | H | H | H | H | H | H | — | — | — | 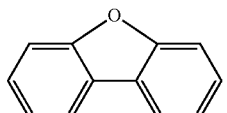 | 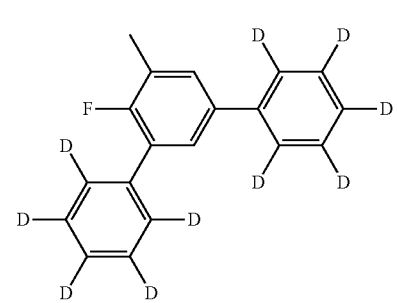 |
TABLE 130
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2821 | H | H | H | H | H | H | H | H | — | — | — | 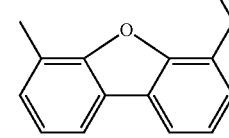 |  |

TABLE 130-continued

| compound | R$_1$ | R$_3$ | R$_4$ | R$_5$ | R$_6$ | R$_8$ | R$_9$ | R$_{10}$ | L$_1$ | L$_2$ | L$_3$ | Ar$_1$ | Ar$_2$ |
|---|---|---|---|---|---|---|---|---|---|---|---|---|---|
| D2822 | H | H | H | H | H | H | H | H | — | — | — | methyl-dibenzofuran-phenyl | phenyl |
| D2823 | H | H | H | H | H | H | H | H | — | — | — | methyl-dibenzofuran-phenyl | phenyl |
| D2824 | H | H | H | H | H | H | H | H | — | — | — | methyl-dibenzofuran-phenyl | phenyl |
| D2825 | H | H | H | H | H | H | H | H | — | — | — | dimethyl-dibenzofuran | phenyl |
| D2826 | H | H | H | H | H | H | H | H | — | — | — | dimethyl-dibenzofuran | phenyl |

TABLE 131

| compound | R$_1$ | R$_3$ | R$_4$ | R$_5$ | R$_6$ | R$_8$ | R$_9$ | R$_{10}$ | L$_1$ | L$_2$ | L$_3$ | Ar$_1$ | Ar$_2$ |
|---|---|---|---|---|---|---|---|---|---|---|---|---|---|
| D2827 | H | H | H | H | H | H | H | H | — | — | — | methyl-dibenzofuran-tert-butyl | phenyl |
| D2828 | H | H | H | H | H | H | H | H | — | — | — | methyl-dibenzofuran-tert-butyl | phenyl |

TABLE 131-continued
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2829 | H | H | H | H | H | H | H | H | — | — | — | 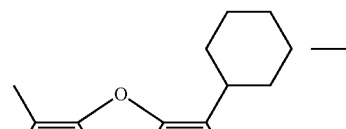 |  |
| D2830 | H | H | H | H | H | H | H | H | — | — | — | 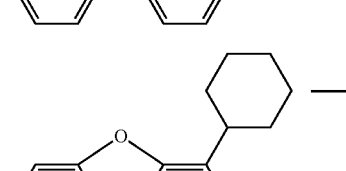 |  |
TABLE 132
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2831 | H | H | H | H | H | H | H | H | — | — | — | 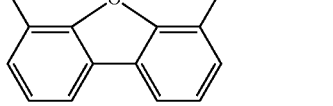 |  |
| D2832 | H | H | H | H | H | H | H | H | — | — | — | 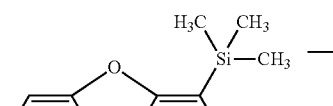 | 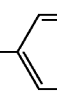 |
| D2833 | H | H | H | H | H | H | H | H | — | — | — | 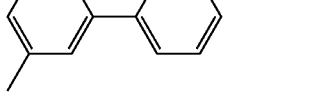 |  |
| D2834 | H | H | H | H | H | H | H | H | — | — | — | 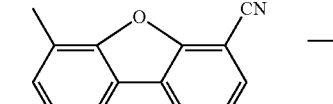 | 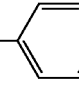 |
| D2835 | H | H | H | H | H | H | H | H | — | — | — | 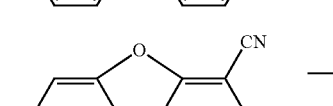 | 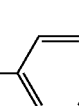 |
| D2836 | H | H | H | H | H | H | H | H | — | — | — | 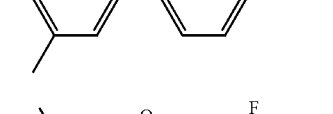 |  |

TABLE 132-continued
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2837 | H | H | H | H | H | H | H | H | — | — | — | 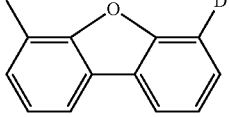 | 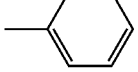 |
| D2838 | H | H | H | H | H | H | H | H | — | — | — | 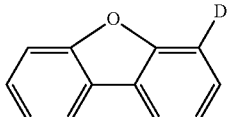 | 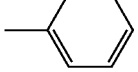 |
TABLE 133
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2839 | H | H | H | H | H | H | H | H |  | — | — | 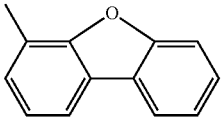 | 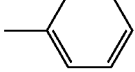 |
| D2840 | H | H | H | H | H | H | H | H | 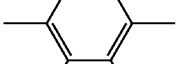 | — | — | 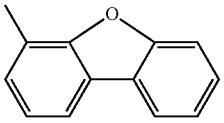 | 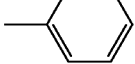 |
| D2841 | H | H | H | H | H | H | H | H |  | — | — | 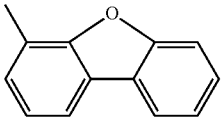 | 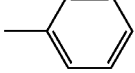 |
| D2842 | H | H | H | H | H | H | H | H | 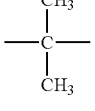 | — | — | 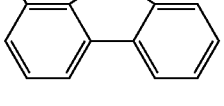 | 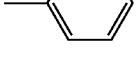 |
| D2843 | H | H | H | H | H | H | H | H | — | 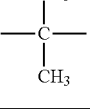 | — | 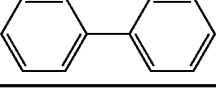 | 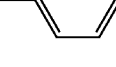 |
TABLE 134
| compound | R₁ | R₃ | R₄ | R₅ | R₆ | R₈ | R₉ | R₁₀ | L₁ | L₂ |
|---|---|---|---|---|---|---|---|---|---|---|
| D2844 | H | H | H | H | H | H | H | H | — | — |
| D2845 | H | H | H | H | H | H | H | H | — | — |
| D2846 | H | H | H | H | H | H | H | H | — | — |
| D2847 | H | H | H | H | H | H | H | H | 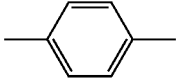 | 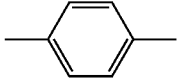 |
| D2848 | H | H | H | H | H | H | H | H | 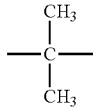 | 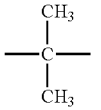 |

TABLE 134-continued

| D2849 | H | H | H | H | H | H | H | H | — | — |

| compound | L₃ | Ar₁ | Ar₂ |
|---|---|---|---|
| D2844 | ![p-phenylene] | ![dibenzofuran-4-yl] | ![phenyl] |
| D2845 | ![1,4-naphthylene] | ![dibenzofuran-4-yl] | ![phenyl] |
| D2846 | ![pyrimidine-2,5-diyl] | ![dibenzofuran-4-yl] | ![phenyl] |
| D2847 | — | ![dibenzofuran-4-yl] | ![dibenzofuran-4-yl] |
| D2848 | — | ![dibenzofuran-4-yl] | ![dibenzofuran-4-yl] |
| D2849 | ![p-phenylene] | ![dibenzofuran-4-yl] | ![dibenzofuran-4-yl] |

TABLE 135

| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2850 | H | H | H | H | H | H | H | H | — | — | — | ![dibenzothiophen-4-yl] | ![phenyl] |
| D2851 | H | H | H | H | H | H | H | H | — | — | — | ![dibenzothiophen-3-yl] | ![phenyl] |
| D2852 | H | H | H | H | H | H | H | H | — | — | — | ![dibenzothiophen-2-yl] | ![phenyl] |
| D2853 | H | H | H | H | H | H | H | H | — | — | — | ![dibenzothiophen-1-yl] | ![phenyl] |

TABLE 135-continued
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2854 | H | H | H | H | H | H | H | H | — | — | — | 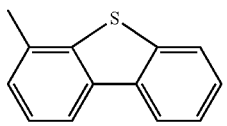 | 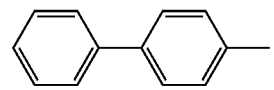 |
| D2855 | H | H | H | H | H | H | H | H | — | — | — | 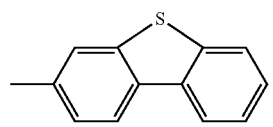 | 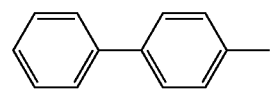 |
| D2856 | H | H | H | H | H | H | H | H | — | — | — | 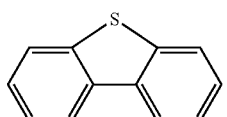 | 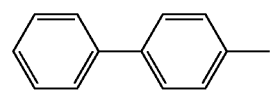 |
| D2857 | H | H | H | H | H | H | H | H | — | — | — | 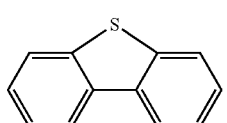 | 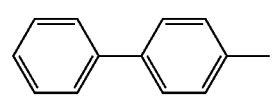 |
TABLE 136
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2858 | H | H | H | H | H | H | H | H | — | — | — | 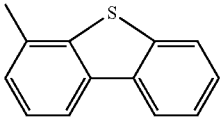 | 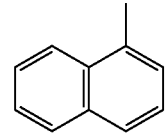 |
| D2859 | H | H | H | H | H | H | H | H | — | — | — | 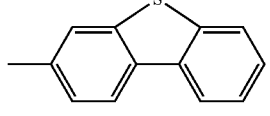 | 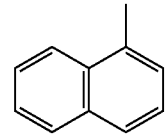 |
| D2860 | H | H | H | H | H | H | H | H | — | — | — | 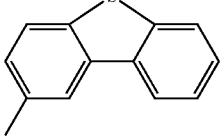 | 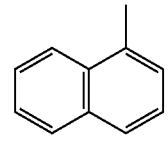 |
| D2861 | H | H | H | H | H | H | H | H | — | — | — | 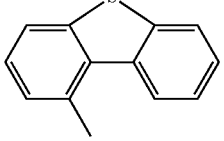 | 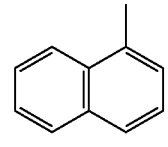 |
| D2862 | H | H | H | H | H | H | H | H | — | — | — | 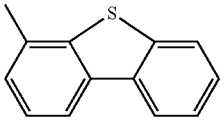 | 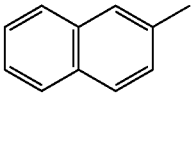 |

TABLE 136-continued

| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2863 | H | H | H | H | H | H | H | H | — | — | — | dibenzothiophene | naphthyl |
| D2864 | H | H | H | H | H | H | H | H | — | — | — | dibenzothiophene | naphthyl |
| D2865 | H | H | H | H | H | H | H | H | — | — | — | dibenzothiophene | naphthyl |
| D2866 | H | H | H | H | H | H | H | H | — | — | — | dibenzothiophene | terphenyl |
| D2867 | H | H | H | H | H | H | H | H | — | — | — | dibenzothiophene | terphenyl |
| D2868 | H | H | H | H | H | H | H | H | — | — | — | dibenzothiophene | terphenyl |
| D2869 | H | H | H | H | H | H | H | H | — | — | — | dibenzothiophene | terphenyl |

TABLE 137

| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2870 | H | H | H | H | H | H | H | H | — | — | — | dibenzothiophene | 9,9-dimethylfluorenyl |
| D2871 | H | H | H | H | H | H | H | H | — | — | — | dibenzothiophene | 9,9-dimethylfluorenyl |

TABLE 137-continued
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2872 | H | H | H | H | H | H | H | H | — | — | — | 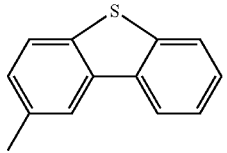 | 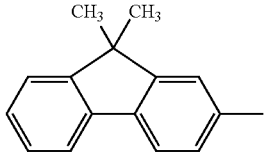 |
| D2873 | H | H | H | H | H | H | H | H | — | — | — | 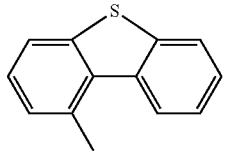 | 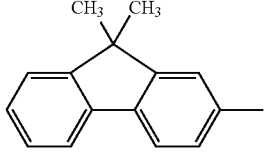 |
| D2874 | H | H | H | H | H | H | H | H | — | — | — | 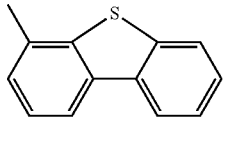 | 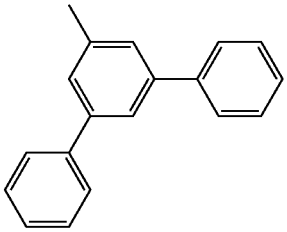 |
| D2875 | H | H | H | H | H | H | H | H | — | — | — | 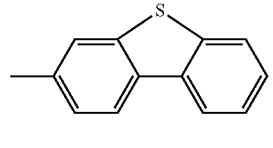 | 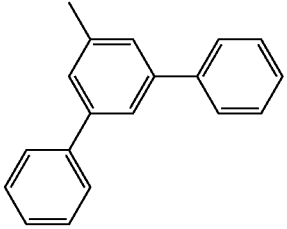 |
| D2876 | H | H | H | H | H | H | H | H | — | — | — | 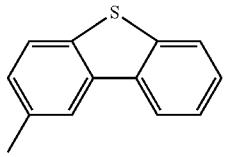 | 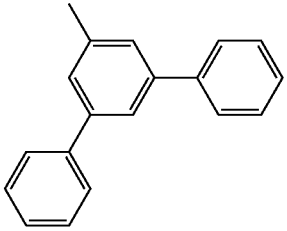 |
| D2877 | H | H | H | H | H | H | H | H | — | — | — | 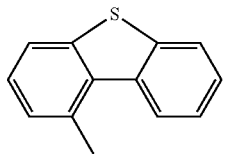 | 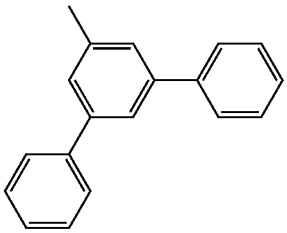 |
TABLE 138
| compound | R₁ | R₃ | R₄ | R₅ | R₆ | R₈ | R₉ | R₁₀ | L₁ | L₂ | L₃ | Ar₁ | Ar₂ |
|---|---|---|---|---|---|---|---|---|---|---|---|---|---|
| D2878 | H | H | H | H | H | H | H | H | — | — | — | 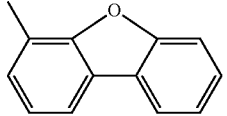 | 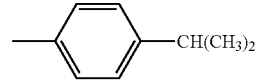 |

TABLE 138-continued
| compound | R$_1$ | R$_3$ | R$_4$ | R$_5$ | R$_6$ | R$_8$ | R$_9$ | R$_{10}$ | L$_1$ | L$_2$ | L$_3$ | Ar$_1$ | Ar$_2$ |
|---|---|---|---|---|---|---|---|---|---|---|---|---|---|
| D2879 | H | H | H | H | H | H | H | H | — | — | — | 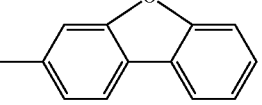 | 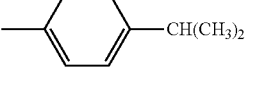 |
| D2880 | H | H | H | H | H | H | H | H | — | — | — | 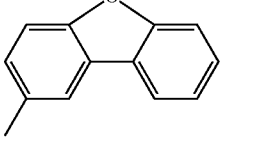 | 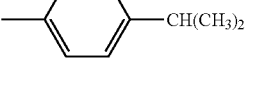 |
| D2881 | H | H | H | H | H | H | H | H | — | — | — | 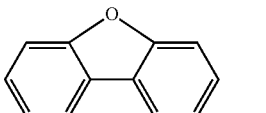 | 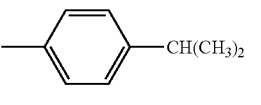 |
| D2882 | H | H | H | H | H | H | H | H | — | — | — | 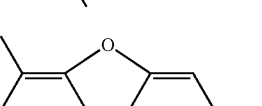 | 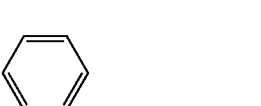 |
| D2883 | H | H | H | H | H | H | H | H | — | — | — | 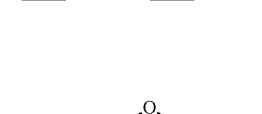 | 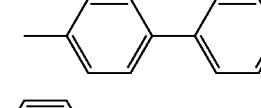 |
| D2884 | H | H | H | H | H | H | H | H | — | — | — | 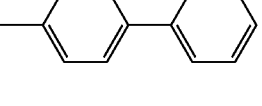 | 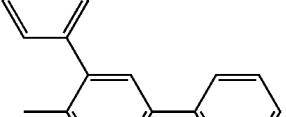 |
| D2885 | H | H | H | H | H | H | H | H | — | — | — | 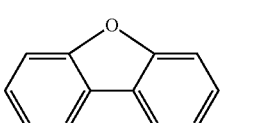 |  |
TABLE 139
| compound | R$_1$ | R$_3$ | R$_4$ | R$_5$ | R$_6$ | R$_8$ | R$_9$ | R$_{10}$ | L$_1$ | L$_2$ | L$_3$ |
|---|---|---|---|---|---|---|---|---|---|---|---|
| D2886 | 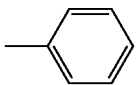 | H | H | H | 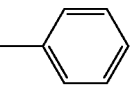 | H | H | H | — | — | — |
| D2887 | 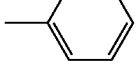 | H | H | H | 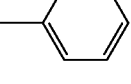 | H | H | H | — | — | — |

TABLE 139-continued
| compound | | | | | | | | | | | |
|---|---|---|---|---|---|---|---|---|---|---|---|
| D2888 | 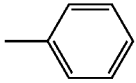 | H | H | H | 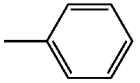 | H | H | H | — | — | — |
| D2889 | 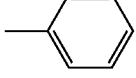 | H | H | H | 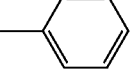 | H | H | H | — | — | — |
| D2890 | 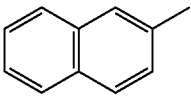 | H | H | H | 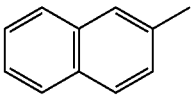 | H | H | H | — | — | — |
| D2891 | 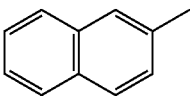 | H | H | H | 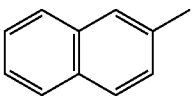 | H | H | H | — | — | — |
| D2892 | 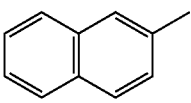 | H | H | H | 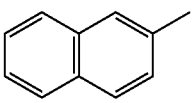 | H | H | H | — | — | — |
| D2893 | 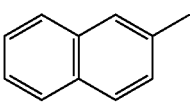 | H | H | H | 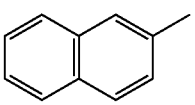 | H | H | H | — | — | — |
| compound | Ar₁ | Ar₂ |
|---|---|---|
| D2886 | 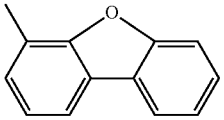 | 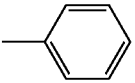 |
| D2887 | 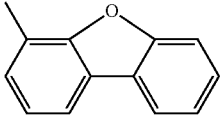 | 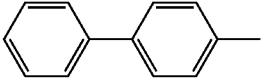 |
| D2888 | 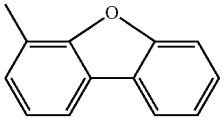 | 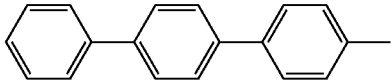 |
| D2889 | 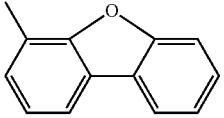 | 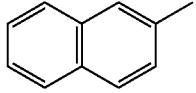 |
| D2890 | 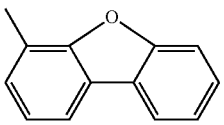 | 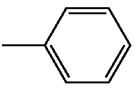 |
| D2891 | 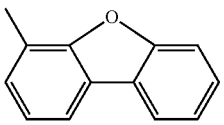 | 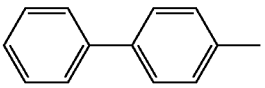 |
| D2892 | 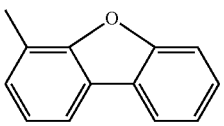 | 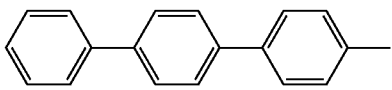 |

TABLE 139-continued

D2893 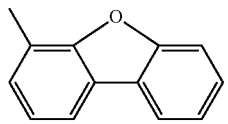 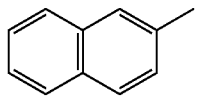

The specific examples of the aromatic amine derivative are the compounds having $R_2$ and $R_7$ in the same structure represented by the formula (2a), however, not limited thereto. The aromatic amine derivative may be a compound having $R_2$ and $R_7$ in different structures.

Organic-EL-Device Material

The aromatic amine derivative according to the second exemplary embodiment of the invention is usable as an organic-EL-device material. The organic-EL-device material according to the exemplary embodiment may be composed solely of the aromatic amine derivative according to the second exemplary embodiment, or alternatively, may contain another compound in addition to the aromatic amine derivative according to the second exemplary embodiment. The organic-EL-device material containing the aromatic amine derivative according to the second exemplary embodiment is exemplarily usable as a dopant material.

The organic-EL-device material containing the aromatic amine derivative according to the second exemplary embodiment and another compound is exemplified by an organic-EL-device material containing the aromatic amine derivative according to the second exemplary embodiment and an anthracene derivative represented by the formula (20).

Moreover, an organic-EL-device material containing the aromatic amine derivative according to the second exemplary embodiment and a pyrene derivative represented by the formula (30) in place of the anthracene derivative is usable as the organic-EL-device material according to the second exemplary embodiment.

Furthermore, an organic-EL-device material containing the aromatic amine derivative according to the second exemplary embodiment, the anthracene derivative represented by the formula (20) and the pyrene derivative represented by the formula (30) is usable as the organic-EL-device material according to the second exemplary embodiment.

Organic EL Device

The organic EL device according to the second exemplary embodiment includes an organic compound layer between the cathode and the anode.

The aromatic amine derivative according to the second exemplary embodiment is contained in the organic compound layer. The organic compound layer is formed using the organic-EL-device material containing the aromatic amine derivative according to the second exemplary embodiment.

The organic compound layer has at least one layer of an organic thin-film layer formed of an organic compound. At least one layer of the organic thin-film layer contains the aromatic amine derivative according to the second exemplary embodiment singularly or as a component of a mixture. The organic thin-film layer may contain an inorganic compound.

The at least one layer of the organic thin-film layer is an emitting layer. Accordingly, the organic compound layer may be provided by a single emitting layer. Alternatively, the organic compound layer may be provided by layers applied in a known organic EL device such as a hole injecting layer, a hole transporting layer, an electron injecting layer, an electron transporting layer, a hole blocking layer and an electron blocking layer. When the organic thin-film layer is provided by plural layers, the aromatic amine derivative according to the exemplary embodiment is contained singularly or as a component of a mixture in at least one of the layers.

The emitting layer preferably contains the aromatic amine derivative according to the second exemplary embodiment. In this arrangement, the emitting layer may be formed of the aromatic amine derivative alone. Alternatively, the emitting layer may contain the aromatic amine derivative as a host material or a dopant material.

The organic EL device according to the second exemplary embodiment is formed in the same manner as in the first exemplary embodiment except for using the aromatic amine derivative according to the second exemplary embodiment in place of the aromatic amine derivative according to the first exemplary embodiment.

Modifications of Embodiment(s)

It should be noted that the invention is not limited to the above exemplary embodiment but may include any modification and improvement as long as such modification and improvement are compatible with the invention.

For instance, in the organic EL device of the invention, the emitting layer may contain at least one of the luminescent material, doping material, hole injecting material, hole transporting material, and electron injecting material in addition to at least one of the aromatic amine derivatives represented by formulae (1) and (1a). Moreover, in order to improve stability against the temperature, humidity, atmosphere and the like of the organic EL device obtained by the invention, a protection layer can be provided on a surface of the device, or the entire device can be protected by silicone oil, resins and the like.

An arrangement of the organic EL device is not particularly limited to the arrangement of the organic EL device 1 shown in FIG. 1. For instance, an electron blocking layer may be provided to the emitting layer adjacent to the anode while a hole blocking layer may be provided to the emitting layer adjacent to the cathode.

The emitting layer is not limited to a single layer, but may be provided by laminating a plurality of emitting layers. When the organic EL device has the plurality of emitting layers, at least one of the emitting layers preferably contains the aromatic amine derivative of the invention. In this instance, the other emitting layer(s) may be a fluorescent-emitting layer including a fluorescent material, or a phosphorescent-emitting layer including a phosphorescent material.

Moreover, when the organic EL device includes the plurality of emitting layers, the plurality of emitting layers may be adjacent to each other, or may be laminated on each other via a layer other than the emitting layers (e.g., a charge generating layer).

EXAMPLES

Next, the invention will be described in further detail by exemplifying Example(s) and Comparative(s). However, the invention is not limited by the description of Example(s).

Synthesis of Compounds

Synthesis Example 1

Synthesis of Compound 1

A synthesis scheme of a compound 1 is shown below.

[Formula 58]

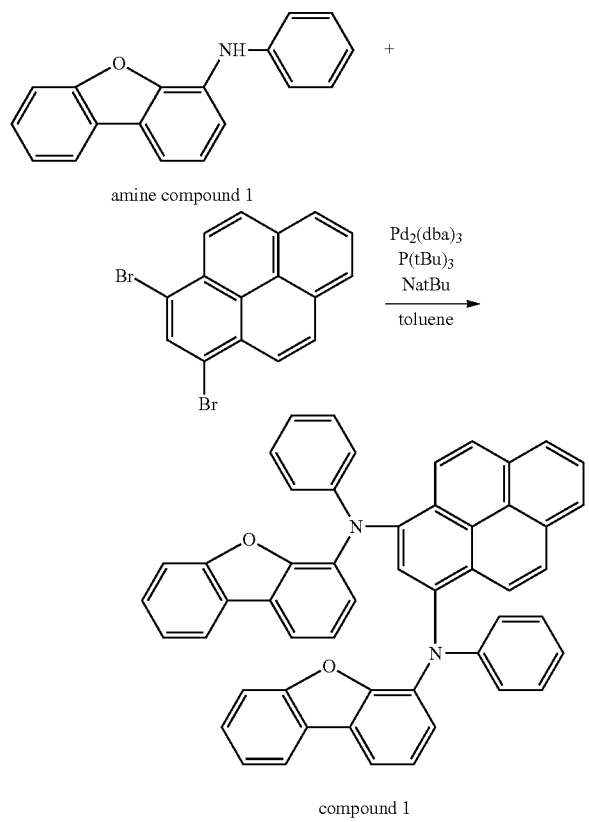

Synthesis Example 1

Synthesis of Compound 1

In an argon gas stream, into a 300-mL eggplant flask, an amine compound 1 (5.7 g, 22 mmol), 1,3-dibromopyrene (3.6 g, 10 mmol), sodium tert-butoxide (2 g), tris(dibenzylideneacetone)dipalladium(0)[Pd$_2$(dba)$_3$] (550 mg), tri-tert-butylphosphine (115 mg), and dehydrated toluene (100 mL) were put and reacted at 85 degrees C. for seven hours. After the reaction, the reaction solution was filtrated. The obtained crude product was purified by silica-gel chromatography (an eluent: toluene). After the purification, the obtained solid was recrystallized with toluene. After the recrystallization, the obtained solid was dried under reduced pressure to provide 4 g of the compound 1. The compound 1 corresponds to the compound D1. The obtained compound 1 was analyzed by FD-MS (Field Desorption Mass Spectrometry). Analysis results are shown below.

FDMS, calcd for $C_{52}H_{32}N_2O_2$=716. found m/z=716 (M+).

Synthesis Examples 2 to 13

Synthesis Examples 2 to 13 were conducted in the same manner as in Synthesis Example 1 except that the amine compound 1 was replaced by the following amine compounds 2 to 13. As a result, the following compounds 2 to 13 were obtained.

Table 140 shows a correspondence relationship between the used amine compounds and the obtained aromatic amine derivative in each of Synthesis Examples.

TABLE 140

| Synthesis Examples | Amine Compounds | Aromatic Amine Derivatives |
|---|---|---|
| 1 | Amine compound 1 | Compound 1 (Compound D1) |
| 2 | Amine compound 2 | Compound 2 (Compound D178) |
| 3 | Amine compound 3 | Compound 3 (Compound D73) |
| 4 | Amine compound 4 | Compound 4 (Compound D77) |
| 5 | Amine compound 5 | Compound 5 (Compound D61) |
| 6 | Amine compound 6 | Compound 6 (Compound D13) |
| 7 | Amine compound 7 | Compound 7 (Compound D9) |
| 8 | Amine compound 8 | Compound 8 (Compound D53) |
| 9 | Amine compound 9 | Compound 9 (Compound D182) |
| 10 | Amine compound 10 | Compound 10 (Compound D93) |
| 11 | Amine compound 11 | Compound 11 (Compound D37) |
| 12 | Amine compound 12 | Compound 12 (Compound D3) |
| 13 | Amine compound 13 | Compound 13 (Compound D150) |

[Formula 59]

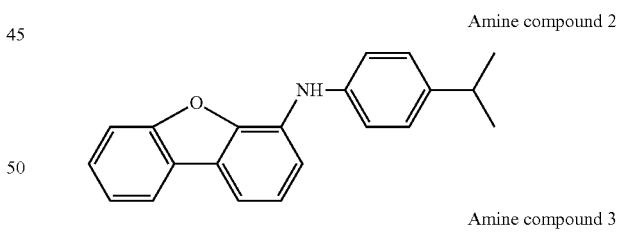

Amine compound 2

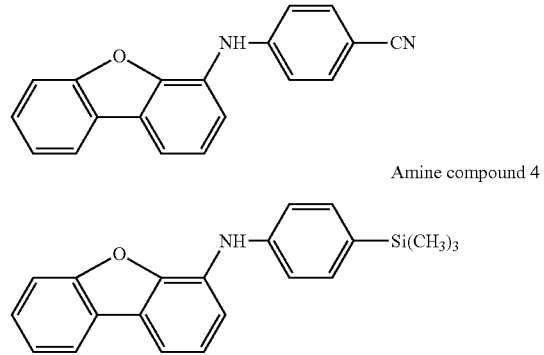

Amine compound 3

Amine compound 4

Amine compound 5
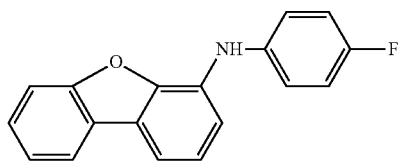
Amine compound 6
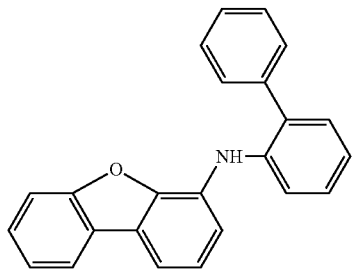
Amine compound 7
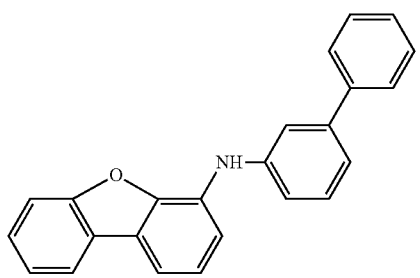
Amine compound 8
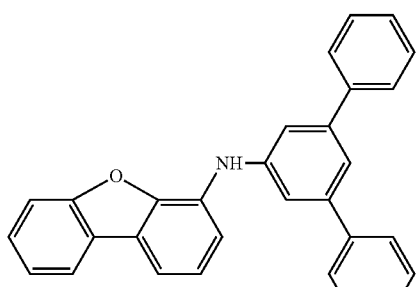
Amine compound 9
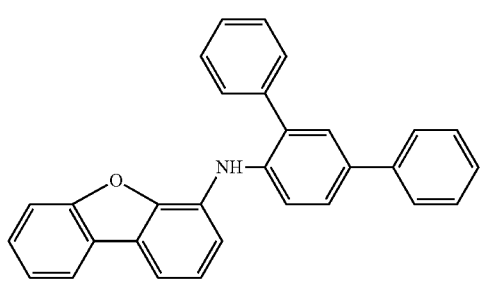
Amine compound 10
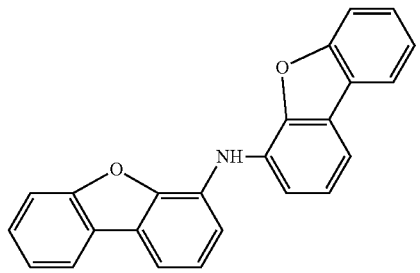
Amine compound 11
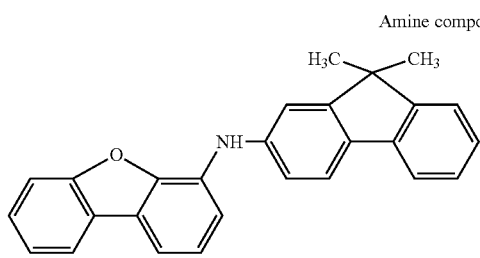
Amine compound 12
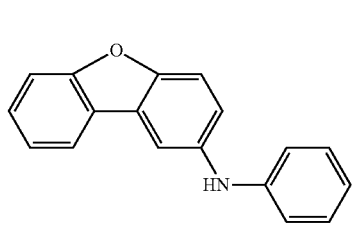
Amine compound 13
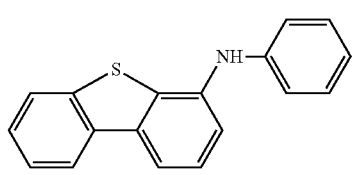
[Formula 60]
Compound 2
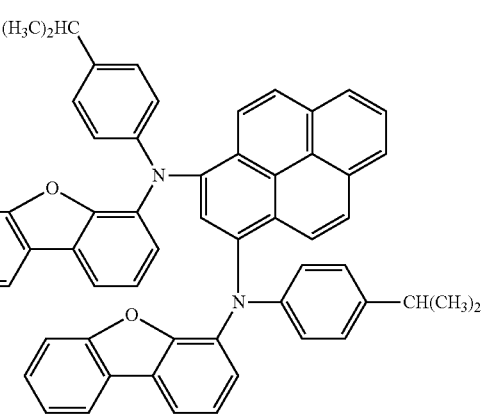

Compound 3
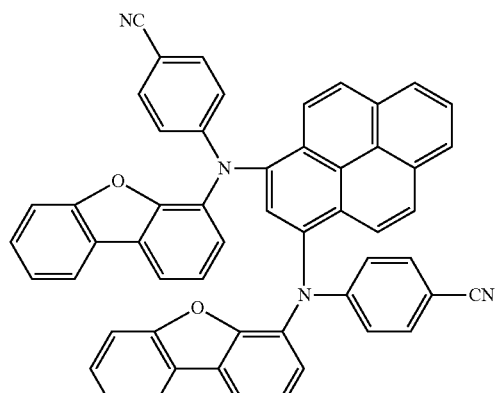
Compound 4
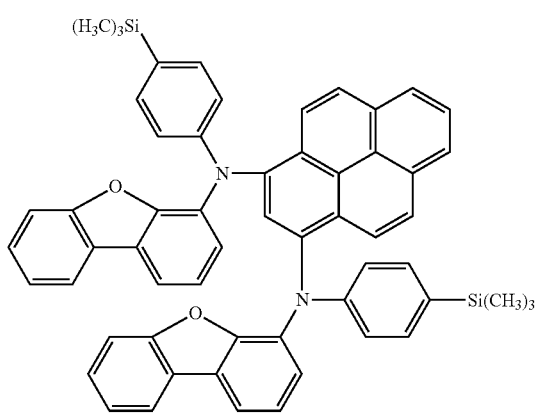
Compound 5
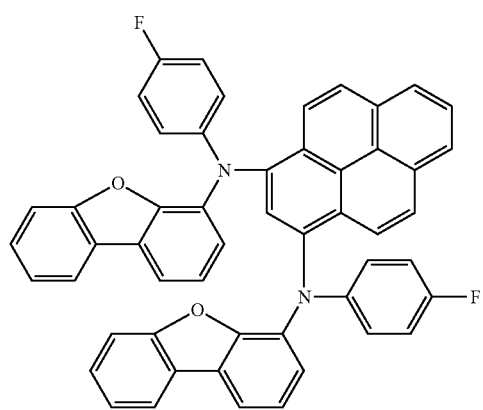
Compound 6
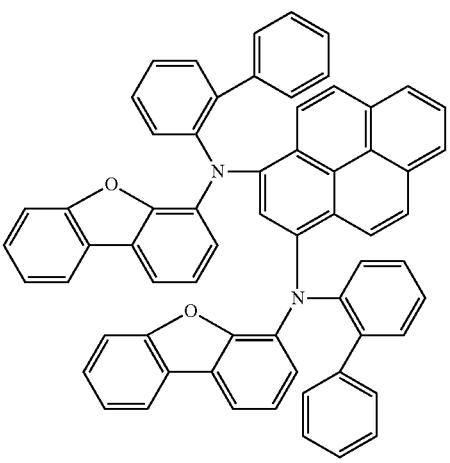
Compound 7
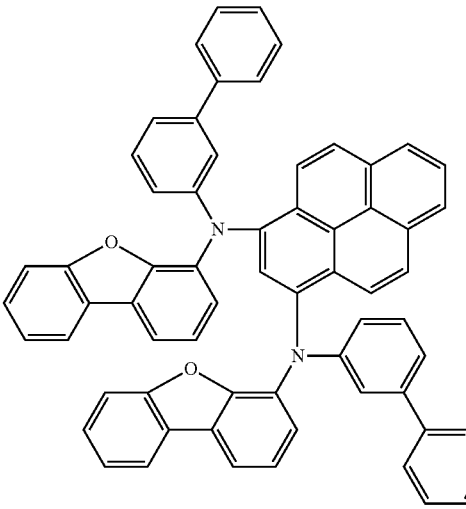
Compound 8
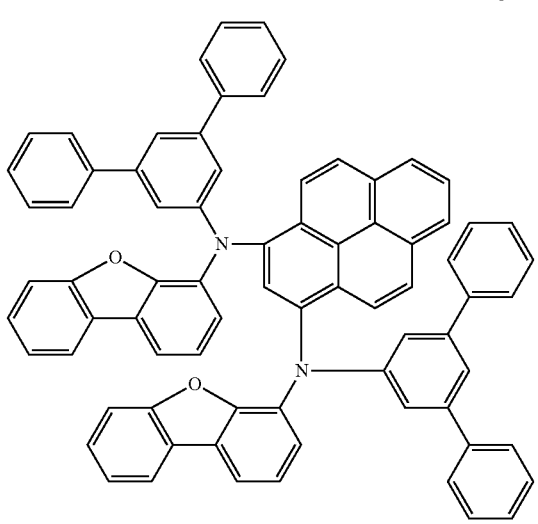

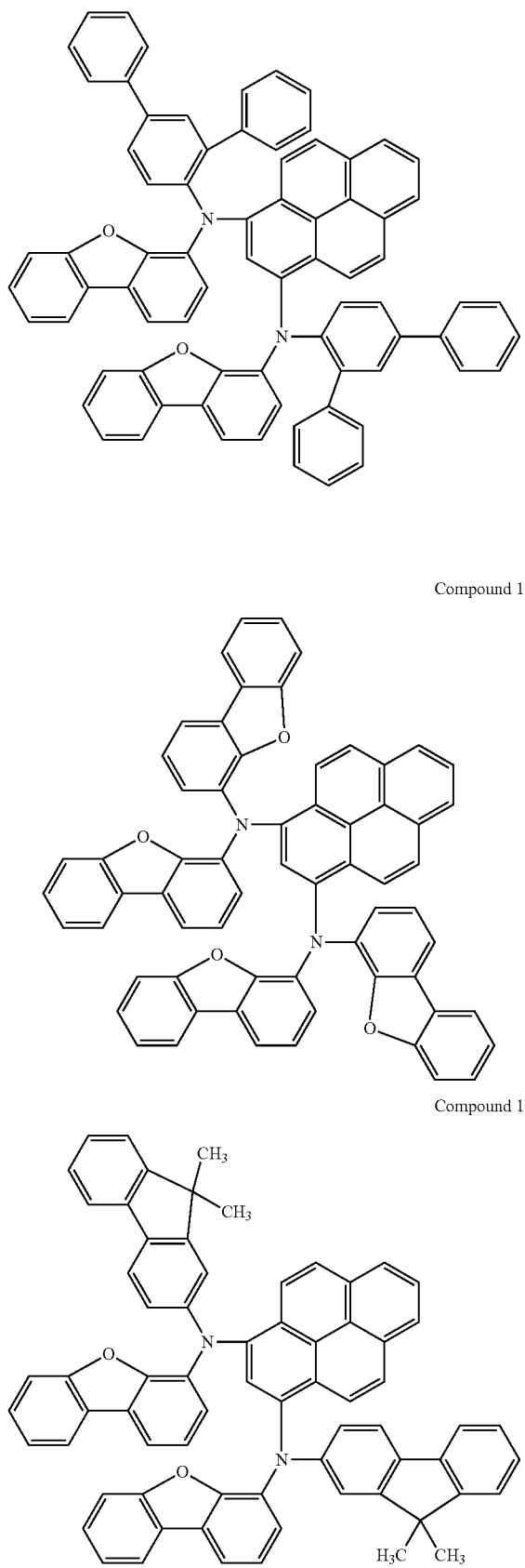

Compound 9

Compound 10

Compound 11

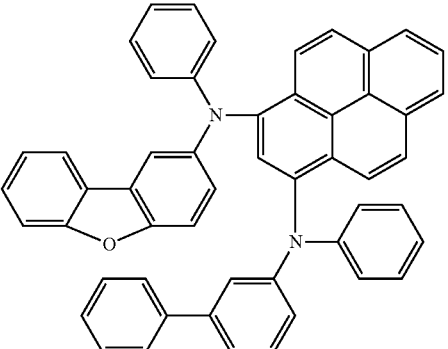

Compound 12

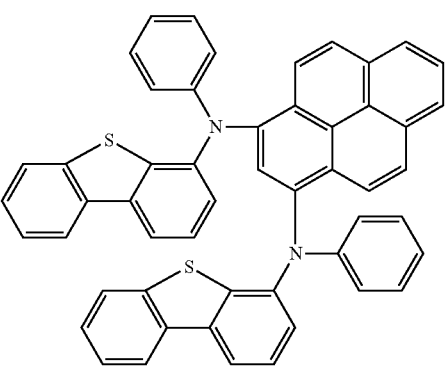

Compound 13

Synthesis Example 14

Synthesis of Compound 14

Synthesis Example 14 was conducted in the same manner as in Synthesis Example 1 except that 1,3-dibromopyrene was replaced by 1,8-dibromopyrene. As a result, the following compound 14 was obtained.

Synthesis Examples 15 to 26

Synthesis Examples 15 to 26 were conducted in the same manner as in Synthesis Example 14 except that the amine compound 1 was replaced by the amine compounds 2 to 13. As a result, the following compounds 15 to 26 were obtained.

Table 141 shows a correspondence relationship between the used amine compounds and the obtained aromatic amine derivative in each of Synthesis Examples.

TABLE 141

| Synthesis Examples | Amine Compounds | Aromatic Amine Derivatives |
| --- | --- | --- |
| 14 | Amine compound 1 | Compound 14 (Compound D1501) |
| 15 | Amine compound 2 | Compound 15 (Compound D1678) |
| 16 | Amine compound 3 | Compound 16 (Compound D1573) |
| 17 | Amine compound 4 | Compound 17 (Compound D1577) |
| 18 | Amine compound 5 | Compound 18 (Compound D1561) |
| 19 | Amine compound 6 | Compound 19 (Compound D1513) |
| 20 | Amine compound 7 | Compound 20 (Compound D1509) |
| 21 | Amine compound 8 | Compound 21 (Compound D1553) |
| 22 | Amine compound 9 | Compound 22 (Compound D1682) |

TABLE 141-continued
| Synthesis Examples | Amine Compounds | Aromatic Amine Derivatives |
|---|---|---|
| 23 | Amine compound 10 | Compound 23 (Compound D1593) |
| 24 | Amine compound 11 | Compound 24 (Compound D1537) |
| 25 | Amine compound 12 | Compound 25 (Compound D1503) |
| 26 | Amine compound 13 | Compound 26 (Compound D1650) |
[Formula 61]
Compound 14
Compound 15
Compound 16
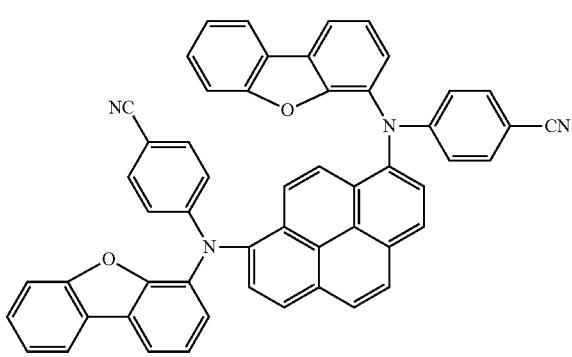
Compound 17
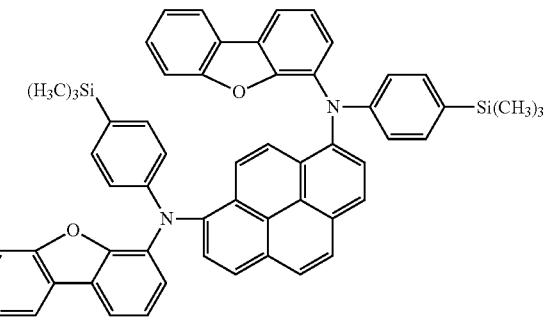
Compound 18
Compound 19
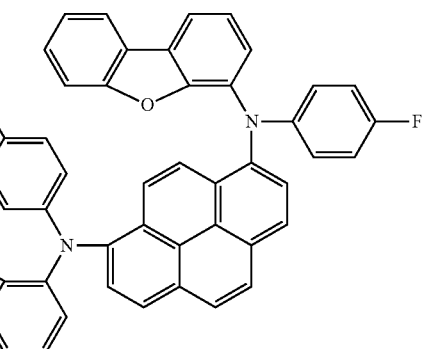
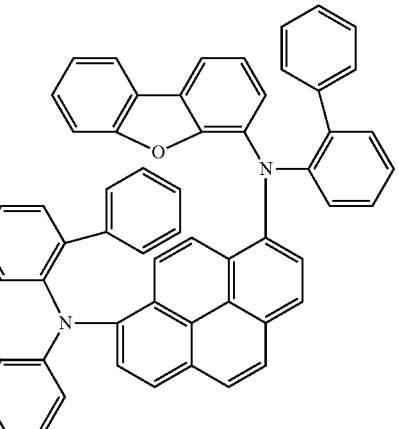
Compound 20
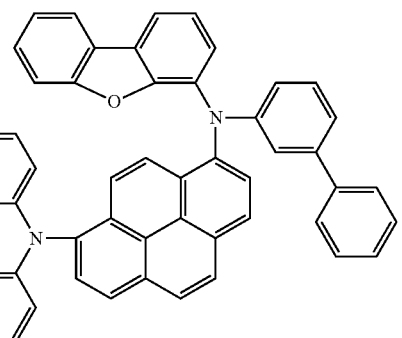

Compound 21
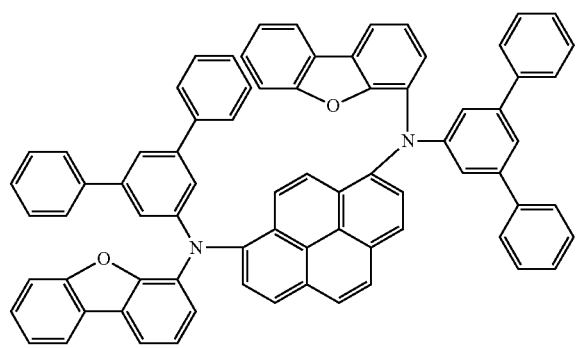
Compound 22
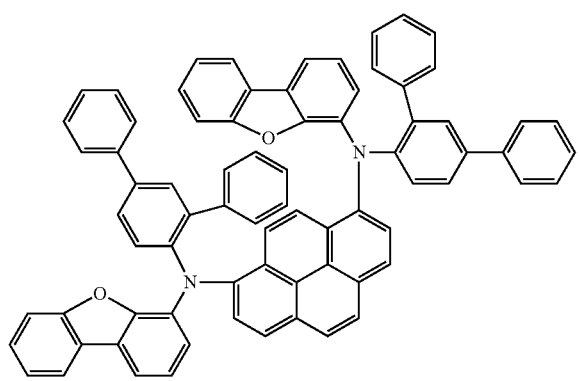
Compound 23
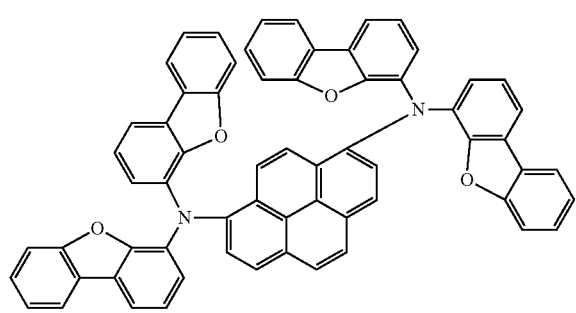
Compound 24
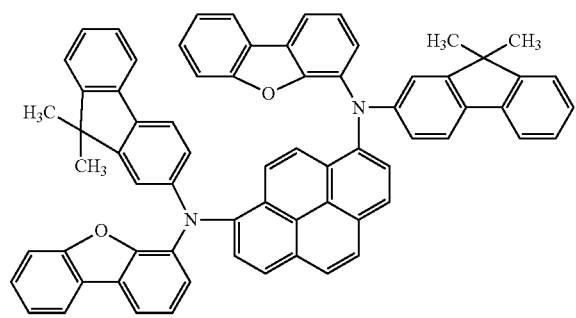
Compound 25
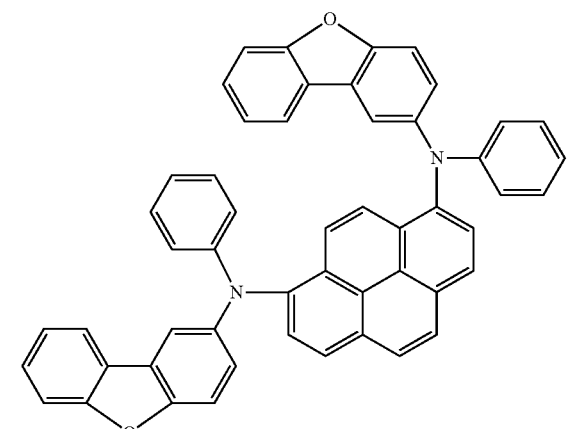
Compound 26
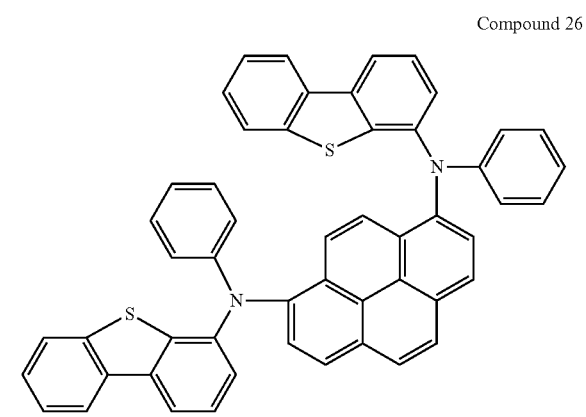 [SMILES: c1ccc(N(c2ccc3ccc4ccc(N(c5ccccc5)c5cccc6c5sc5ccccc56)c5ccc2c3c45)c2cccc3c2sc2ccccc23)cc1]
Synthesis Example 27
Synthesis of Compound 27
A synthesis scheme of a compound 27 is shown below.
[Formula 62]
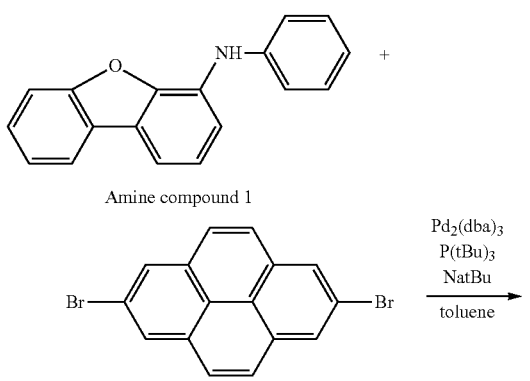

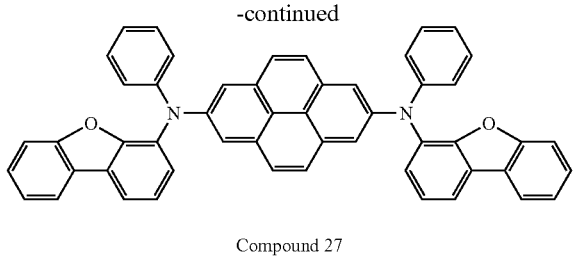

Compound 27

In an argon gas stream, into a 300-mL eggplant flask, the amine compound 1 (5.7 g, 22 mmol), 2,7-dibromopyrene (3.6 g, 10 mmol), sodium tert-butoxide (2 g), tris(dibenzylideneacetone)dipalladium(0)[$Pd_2(dba)_3$] (550 mg), tri-tert-butylphosphine (115 mg), and dehydrated toluene (100 mL) were put and reacted at 85 degrees C. for seven hours.

After the reaction, the reaction solution was filtrated. The obtained crude product was purified by silica-gel chromatography (an eluent: toluene). After the purification, the obtained solid was recrystallized with toluene. After the recrystallization, the obtained solid was dried under reduced pressure to provide 3.5 g of the compound 27. The compound 27 corresponds to the compound D2701. The obtained compound 27 was analyzed by FD-MS (Field Desorption Mass Spectrometry). Analysis results are shown below.

FDMS, calcd for $C_{52}H_{32}N_2O_2$=716. found m/z=716 (M+).

Synthesis Examples 28 to 39

Synthesis of Compounds 28 to 39

Synthesis Examples 28 to 39 were conducted in the same manner as in Synthesis Example 27 except that the amine compound 1 was replaced by the amine compounds 2 to 13. As a result, the following compounds 28 to 39 were obtained.

Table 142 shows a correspondence relationship between the used amine compounds and the obtained aromatic amine derivative in each of Synthesis Examples.

TABLE 142

| Synthesis Examples | Amine Compounds | Aromatic Amine Derivatives |
|---|---|---|
| 27 | Amine compound 1 | Compound 27 (Compound D2701) |
| 28 | Amine compound 2 | Compound 28 (Compound D2878) |
| 29 | Amine compound 3 | Compound 29 (Compound D2773) |
| 30 | Amine compound 4 | Compound 30 (Compound D2777) |
| 31 | Amine compound 5 | Compound 31 (Compound D2761) |
| 32 | Amine compound 6 | Compound 32 (Compound D2713) |
| 33 | Amine compound 7 | Compound 33 (Compound D2709) |
| 34 | Amine compound 8 | Compound 34 (Compound D2753) |
| 35 | Amine compound 9 | Compound 35 (Compound D2882) |
| 36 | Amine compound 10 | Compound 36 (Compound D2793) |
| 37 | Amine compound 11 | Compound 37 (Compound D2737) |
| 38 | Amine compound 12 | Compound 38 (Compound D2703) |
| 39 | Amine compound 13 | Compound 39 (Compound D2850) |

[Formula 63]

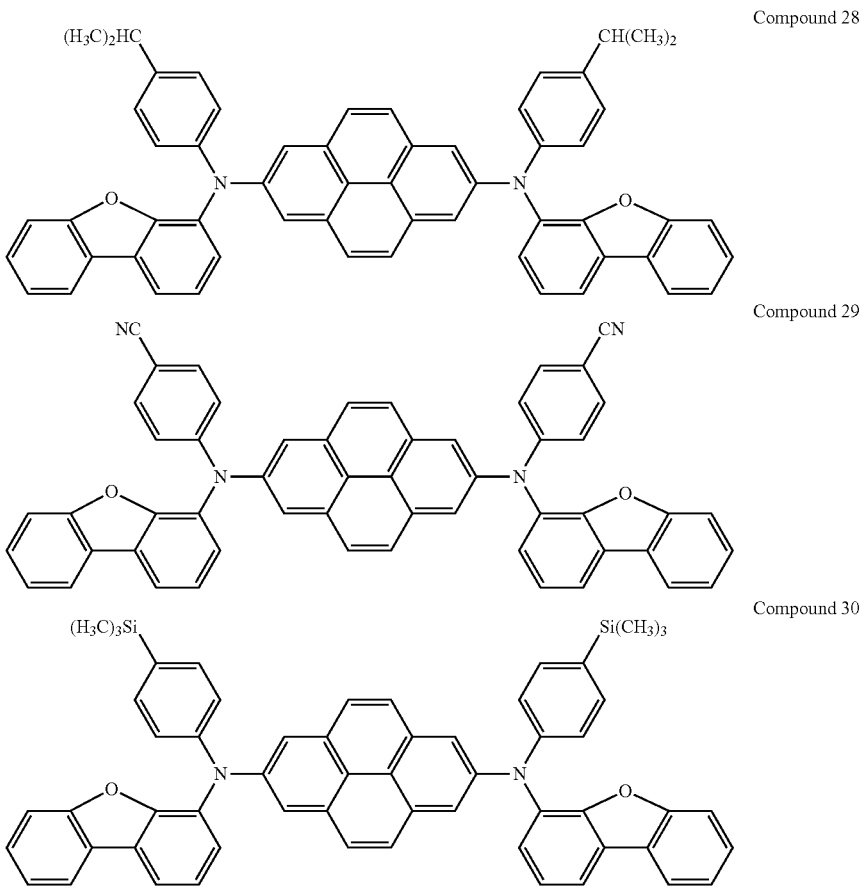

-continued
Compound 31
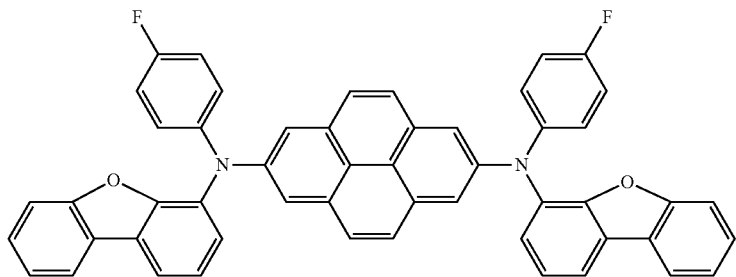
Compound 32
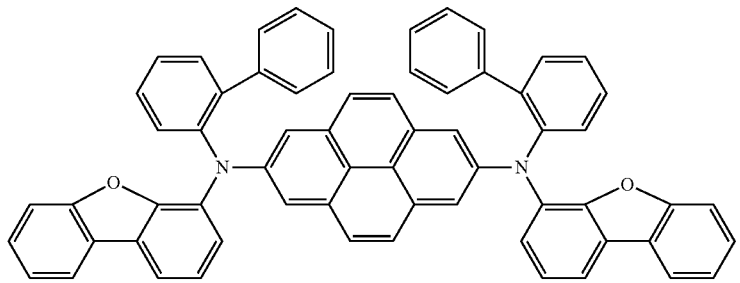
Compound 33
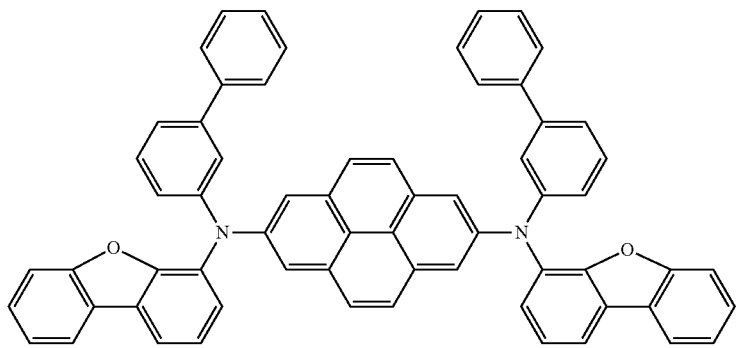
Compound 34
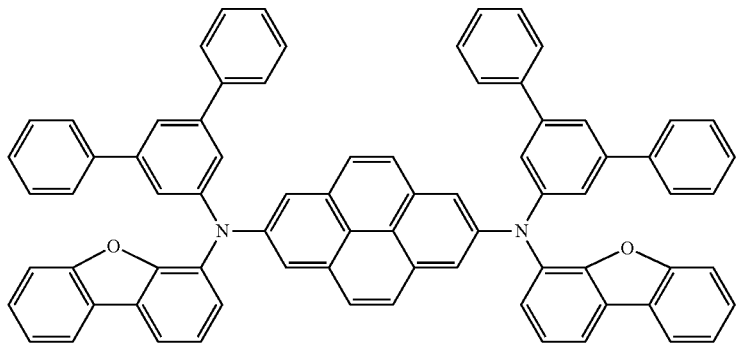
Compound 35
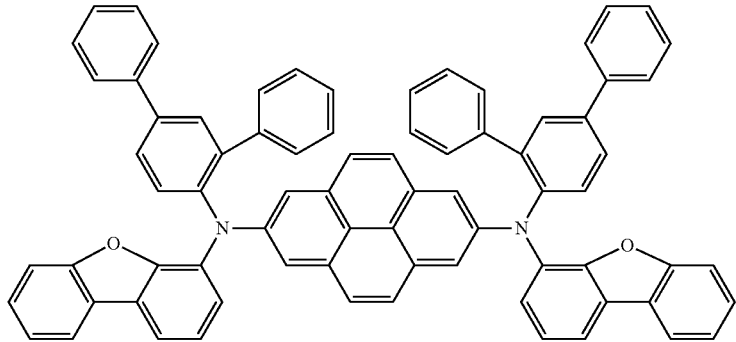

-continued

Compound 36

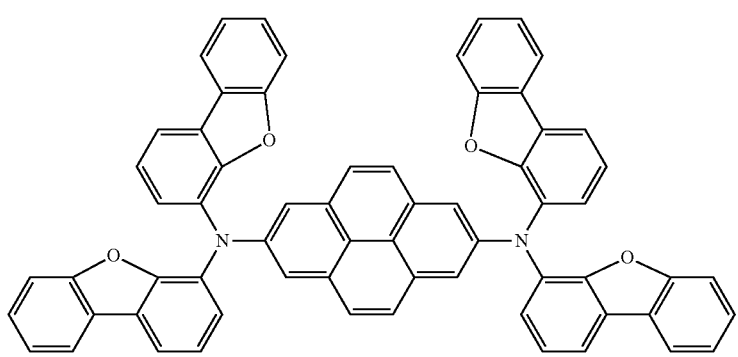

Compound 37

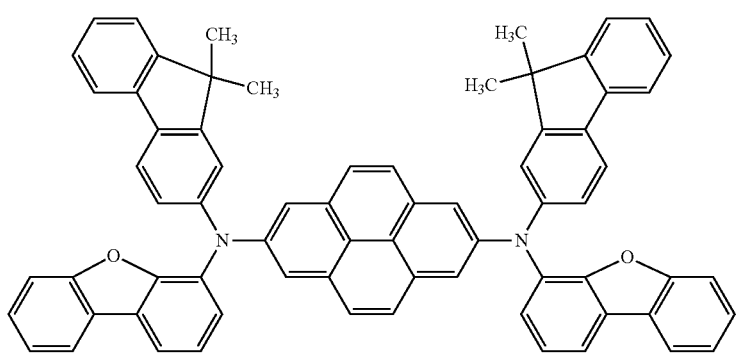

Compound 38

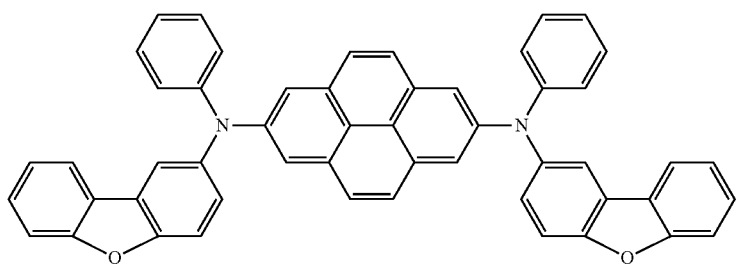

Compound 39

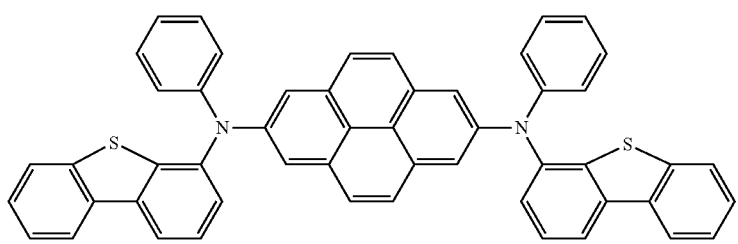

Manufacturing of Organic EL Device

Example 1

A 120 nm-thick transparent electrode formed of indium tin oxide was formed on a glass substrate having a size of 25 mm×75 mm×1.1 mm. The transparent electrode served as the anode.

Subsequently, the glass substrate was irradiated and washed with ultraviolet ray and ozone, and then was set in vacuum deposition equipment.

Firstly, N',N'''-bis[4-(diphenylamino)phenyl]-N',N'''-diphenylbiphenyl-4,4'-diamine was deposited on the transparent electrode of the glass substrate to form a 60-nm thick hole injecting layer.

Next, N,N,N',N'-tetrakis(4-biphenyl)-4,4'-benzidine was deposited on the hole injecting layer to form a 20-nm thick hole transporting layer.

Next, the anthracene derivative EM2 (the host material) and the compound 1 (the dopant material) were co-deposited on the hole transporting layer at a mass ratio of 40:2 to form a 40-nm thick emitting layer.

Next, tris(8-hydroxyquinolinate)aluminium was deposited on the emitting layer to form a 20-nm thick electron injecting layer.

Next, lithium fluoride was deposited on the electron injecting layer to form a 1-nm thick film.

Next, aluminium was deposited on the lithium-fluoride film to form a 150-nm thick film. The aluminum film and the lithium-fluoride film served as the cathode.

Thus, the organic EL device of Example 1 was prepared.

When the organic EL device of Example 1 was driven at a current density of 10 mA/cm², blue emission was observed. Thus, it was verified that the compound 1 was useful as the organic-EL-device material.

Examples 2 to 26

Organic EL devices of Examples 2 to 26 were prepared in the same manner as in Example 1 except that the compound 1 (the dopant material) of the organic EL device of Example 1 was replaced by the compounds 2 to 26, respectively.

Example 27

An organic EL device of Example 27 was prepared in the same manner as in the organic EL device of Example 1 except that the anthracene derivative EM2 (the host material) of the organic EL device of Example 1 was replaced by the anthracene derivative EM367.

Examples 28 to 52

Organic EL devices of Examples 28 to 52 were prepared in the same manner as the organic EL device of Example 27 except that the compound 1 (the dopant material) of the organic EL device of Example 27 was replaced by the compounds 2 to 26, respectively.

The organic EL devices of Examples 2 to 52 were driven at a current density of 10 mA/cm² in the same manner as the organic EL device of Example 1. As a result, in all of the organic EL devices of Examples 2 to 52, blue emission was observed. Thus, it was verified that the compounds 1 to 26 were useful as the organic-EL-device material.

Manufacturing of Organic EL Device

Example 53

A 120 nm-thick transparent electrode formed of indium tin oxide was formed on a glass substrate having a size of 25 mm×75 mm×1.1 mm. The transparent electrode served as the anode.

Subsequently, the glass substrate was irradiated and washed with ultraviolet ray and ozone, and then was set in vacuum deposition equipment.

Firstly, N',N'''-bis[4-(diphenylamino)phenyl]-N',N'''-diphenylbiphenyl-4,4'-diamine was deposited on the transparent electrode of the glass substrate to form a 60-nm thick hole injecting layer.

Next, N,N,N',N'-tetrakis(4-biphenyl)-4,4'-benzidine was deposited on the hole injecting layer to form a 20-nm thick hole transporting layer.

Next, the anthracene derivative EM2 (the host material) and the compound 27 (the dopant material) were co-deposited on the hole transporting layer at a mass ratio of 40:2 to form a 40-nm thick emitting layer.

Next, tris(8-hydroxyquinolinate)aluminium was deposited on the emitting layer to form a 20-nm thick electron injecting layer.

Next, lithium fluoride was deposited on the electron injecting layer to form a 1-nm thick film.

Next, aluminium was deposited on the lithium-fluoride film to form a 150-nm thick film. The aluminum film and the lithium-fluoride film served as the cathode.

Thus, the organic EL device of Example 53 was prepared.

When the organic EL device of Example 53 was driven at a current density of 10 mA/cm², blue emission was observed. Thus, it was verified that the compound 27 was useful as the organic-EL-device material.

Examples 54 to 65

Organic EL devices of Examples 54 to 65 were prepared in the same manner as in Example 53 except that the compound 27 (the dopant material) of Example 53 was replaced by the compounds 28 to 39, respectively.

Example 66

An organic EL device of Example 66 was prepared in the same manner as in Example 53 except that the anthracene derivative EM2 (the host material) of Example 53 was replaced by the anthracene derivative EM367.

Examples 67 to 78

Organic EL devices of Examples 67 to 78 were prepared in the same manner as in Example 66 except that the compound 27 (the dopant material) of Example 66 was replaced by the compounds 28 to 39, respectively.

The organic EL devices of Examples 54 to 78 were driven at a current density of 10 mA/cm² in the same manner as the organic EL device of Example 53. As a result, in all of the organic EL devices of Examples 54 to 78 blue emission was observed. Thus, it was verified that the compounds 27 to 39 were useful as the organic-EL-device material.

The aromatic amine derivative of the invention is exemplified by one exhibiting blue emission in Examples, but not limited thereto. An aromatic amine derivative in which an aryl group and the like are directly bonded to a pyrene ring can emit green light. For instance, such an aromatic amine derivative is exemplified by the above compounds D186 to D193 and D2886 to D2893.

The invention claimed is:

1. An aromatic amine derivative represented by a formula (1):

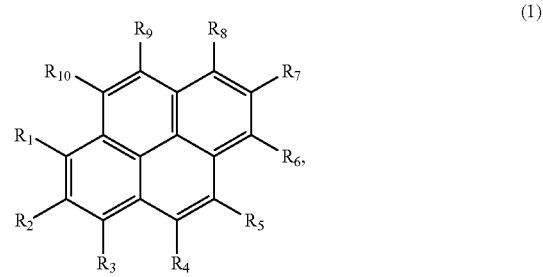

(1)

wherein:
$R_1$ is represented by a formula (2);
any one of $R_2$ to $R_5$ and $R_7$ to $R_{10}$ is represented by the formula (2), and the remaining ones of $R_2$ to $R_5$ and $R_7$ to $R_{10}$ each independently represent: a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms; and $R_6$ represents: a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms;

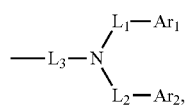

(2)

wherein:

$L_1$, $L_2$ and $L_3$ each independently represent a single bond, a divalent residue of a substituted or unsubstituted aryl group having 6 to 30 ring carbon atoms, or a divalent residue of a substituted or unsubstituted heterocyclic group having 5 to 30 ring atoms;

$Ar_1$ is a monovalent substituent having a partial structure represented by a formula (3):

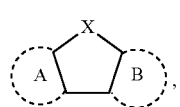

(3)

wherein:

X represents an oxygen atom or a sulfur atom; and

A and B represent a six-membered ring; the six-membered ring represented by A and B is optionally fused with another ring; and $Ar_2$ represents a substituted or unsubstituted aryl group having 6 to 30 ring carbon atoms, a substituted or unsubstituted heterocyclic group having 5 to 30 ring atoms, or a monovalent substituent having a partial structure represented by the formula (3).

2. The aromatic amine derivative according to claim 1, wherein $R_1$ and $R_3$ are represented by the formula (2).

3. The aromatic amine derivative according to claim 1, wherein $R_1$ and $R_8$ are represented by the formula (2).

4. The aromatic amine derivative according to claim 1, wherein the monovalent substituent having the partial structure represented by the formula (3) is a monovalent residue represented by a formula (4):

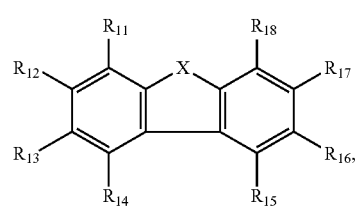

(4)

wherein:

X represents an oxygen atom or a sulfur atom;

$R_{11}$ to $R_{18}$ each independently represent a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms, with the proviso that, in the formula (2); when $Ar_1$ is a monovalent residue of the formula (4), one of $R_{11}$ to $R_{18}$ is a single bond to be bonded to $L_1$; and when $Ar_e$ is a monovalent residue of the formula (4), one of $R_{11}$ to $R_{18}$ is a single bond to be bonded to $L_2$; and at least one combination of $R_{11}$ and $R_{12}$, $R_{12}$ and $R_{13}$, $R_{13}$ and $R_{14}$, $R_{15}$ and $R_{16}$, $R_{16}$ and $R_{17}$, and $R_{17}$ and $R_{18}$ optionally forms a saturated or unsaturated ring.

5. An organic electroluminescence device comprising:

a cathode;

an anode; and an organic compound layer interposed between the cathode and the anode, wherein the organic compound layer comprises the aromatic amine derivative according to claim 1.

6. The organic electroluminescence device according to claim 5, wherein the organic compound layer comprises a plurality of organic thin-film layers comprising an emitting layer, and wherein at least one of the plurality of organic thin-film layers comprises the aromatic amine derivative.

7. The organic electroluminescence device according to claim 6, wherein at least one of the plurality of organic thin-film layers comprises the aromatic amine derivative and an anthracene derivative represented by a formula (20):

(20)

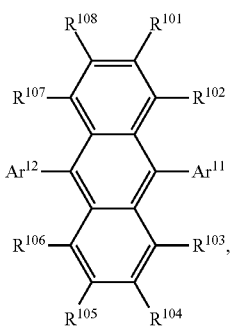

wherein:
Ar$^{11}$ and Ar$^{12}$ each independently represent a substituted or unsubstituted monocyclic group having 5 to 30 ring atoms, a substituted or unsubstituted fused ring group having 10 to 30 ring atoms, or a group provided by combining the monocyclic group and the fused ring group; and R$^{101}$ to R$^{108}$ each independently represent a hydrogen atom, a halogen atom, a cyano group, a substituted or unsubstituted monocyclic group having 5 to 30 ring atoms, a substituted or unsubstituted fused ring group having 10 to 30 ring atoms, a group provided by combining the monocyclic group and the fused ring group, a substituted or unsubstituted alkyl group having 1 to 30 carbon atoms, a substituted or unsubstituted cycloalkyl group having 3 to 30 ring carbon atoms, a substituted or unsubstituted alkoxy group having 1 to 30 carbon atoms, a substituted or unsubstituted aralkyl group having 7 to 30 carbon atoms, a substituted or unsubstituted aryloxy group having 6 to 30 ring carbon atoms, or a substituted or unsubstituted silyl group.

8. The organic electroluminescence device according to claim 7, wherein, in the formula (20), Ar$^{11}$ and Ar$^{12}$ are each independently a substituted or unsubstituted fused ring group having 10 to 30 ring atoms.

9. The organic electroluminescence device according to claim 7, wherein, in the formula (20), one of Ar$^{11}$ and Ar$^{12}$ is a substituted or unsubstituted monocyclic group having 5 to 30 ring atoms, and the other of Ar$^{11}$ and Ar$^{12}$ is a substituted or unsubstituted fused ring group having 10 to 30 ring atoms.

10. The organic electroluminescence device according to claim 9, wherein, in the formula (20), Ar$^{12}$ is selected from a naphthyl group, phenanthryl group, benzoanthryl group and dibenzofuranyl group, and Ar$^{11}$ is an unsubstituted phenyl group or a phenyl group substituted by at least one of the substituted or unsubstituted monocyclic group having 5 to 30 ring atoms and the substituted or unsubstituted fused ring group having 10 to 30 ring atoms.

11. The organic electroluminescence device according to claim 9, wherein, in the formula (20), A$^{12}$ is a substituted or unsubstituted fused ring group having 10 to 30 ring atoms and Ar$^{11}$ is an unsubstituted phenyl group.

12. The organic electroluminescence device according to claim 7, wherein, in the formula (20), Ar$^{11}$ and Ar$^{12}$ are each independently a substituted or unsubstituted monocyclic group having 5 to 30 ring atoms.

13. The organic electroluminescence device according to claim 12, wherein, in the formula (20), Ar$^{11}$ and Ar$^{12}$ are each independently a substituted or unsubstituted phenyl group.

14. The organic electroluminescence device according to claim 13, wherein, in the formula (20), Ar$^{11}$ is an unsubstituted phenyl group and Ar$^{12}$ is a phenyl group having at least one of the substituted or unsubstituted monocyclic group having 5 to 30 ring atoms and the substituted or unsubstituted fused ring group having 10 to 30 ring atoms as a substituent.

15. The organic electroluminescence device according to claim 13, wherein, in the formula (20), Ar$^{11}$ and Ar$^{12}$ are each independently a phenyl group having at least one of the substituted or unsubstituted monocyclic group having 5 to 30 ring atoms and the substituted or unsubstituted fused ring group having 10 to 30 ring atoms as a substituent.

16. The aromatic amine derivative according to claim 1, wherein R$_1$ is represented by the formula (2), and
wherein any one of R$_3$, R$_4$, R$_5$, R$_8$, R$_9$ and R$_{10}$ is represented by the formula (2).

17. The aromatic amine derivative according to claim 1, wherein R$_1$ is represented by the formula (2), and
wherein any one of R$_3$ and R$_8$ is represented by the formula (2).

18. The aromatic amine derivative according to claim 4, wherein the monovalent residue of the formula (4) is represented by a formula (4A), (4B), (4C), or (4D):

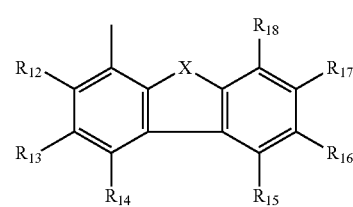

(4A)

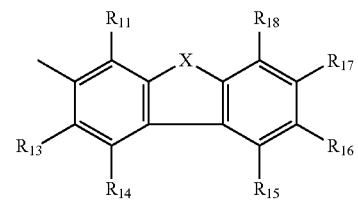

(4B)

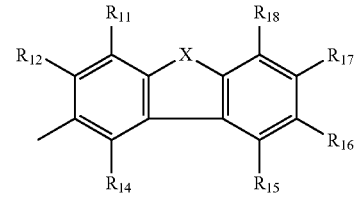

(4C)

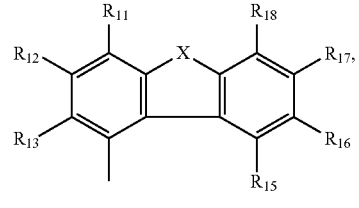

(4D)

wherein:
R$_{11}$ to R$_{18}$ each independently represent a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms; and at least one combination of $R_{11}$ and $R_{12}$, $R_{12}$ and $R_{13}$, $R_{13}$ and $R_{14}$, $R_{15}$ and $R_{16}$, $R_{16}$ and $R_{17}$, and $R_{17}$ and $R_{18}$ optionally forms a saturated or unsaturated ring.

19. The aromatic amine derivative according to claim 4, wherein the monovalent residue of the formula (4) is represented by a formula (4A):

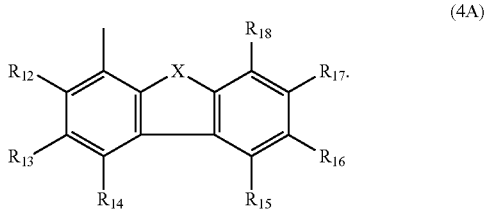

(4A)

wherein:

$R_{12}$ to $R_{18}$ each independently represent a hydrogen atom, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 30 ring carbon atoms, a substituted or unsubstituted alkoxy group having 1 to 30 carbon atoms, a substituted or unsubstituted aralkyl group having 6 to 30 ring carbon atoms, or a substituted or unsubstituted aryloxy group having 6 to 30 ring carbon atoms; and at least one combination of $R_{12}$ and $R_{13}$, $R_{13}$ and $R_{14}$, $R_{15}$ and $R_{16}$, $R_{16}$ and $R_{17}$, and $R_{17}$ and $R_{18}$ optionally forms a saturated or unsaturated ring.

20. The aromatic amine derivative according to claim 4, wherein $R_1$ is represented by the formula (2), and any one of $R_3$ and $R_8$ is represented by the formula (2).

21. The aromatic amine derivative according to claim 18, wherein $R_1$ is represented by the formula (2), and any one of $R_3$ and $R_8$ is represented by the formula (2).

22. The aromatic amine derivative according to claim 21, wherein X represents an oxygen atom.

23. The aromatic amine derivative according to claim 4, wherein any one of $R_1$ and $R_3$ is represented by the formula (2).

24. The aromatic amine derivative according to claim 18, wherein any one of $R_1$ and $R_3$ is represented by the formula (2).

25. The aromatic amine derivative according to claim 24, wherein X represents an oxygen atom.

26. An organic electroluminescence device comprising:
a cathode;
an anode; and
an organic compound layer interposed between the cathode and the anode,
wherein the organic compound layer comprises the aromatic amine derivative according to claim 2.

* * * * *